United States Patent
Webber et al.

(10) Patent No.: US 6,548,494 B1
(45) Date of Patent: Apr. 15, 2003

(54) TRICYCLIC INHIBITORS OF POLY(ADP-RIBOSE) POLYMERASES

(75) Inventors: Stephen Evan Webber, San Diego, CA (US); Donald James Skalitzky, San Diego, CA (US); Jayashree Girish Tikhe, San Diego, CA (US); Robert Arnold Kumpf, Encinitas, CA (US); Joseph Timothy Marakovits, Encinitas, CA (US); Brian Walter Eastman, San Diego, CA (US)

(73) Assignee: Agouron Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 09/653,184

(22) Filed: Aug. 31, 2000

Related U.S. Application Data

(60) Provisional application No. 60/152,142, filed on Aug. 31, 1999.

(51) Int. Cl.⁷ ................ C07D 487/06; A61K 31/5517; A61P 35/00
(52) U.S. Cl. ................ 514/220; 540/496; 540/499
(58) Field of Search ................ 540/496, 499; 514/220

(56) References Cited

U.S. PATENT DOCUMENTS

| | | | |
|---|---|---|---|
| 3,642,820 A | * 2/1972 | Hester et al. | 260/326.5 B |
| 3,734,919 A | * 5/1973 | Hester et al. | 260/239.3 T |
| 3,883,590 A | 5/1975 | Schmerling | 260/588 |
| 3,900,477 A | 8/1975 | Philipp et al. | 260/288 |
| 3,950,343 A | 4/1976 | Philipp et al. | 260/288 |
| 3,978,066 A | 8/1976 | Philipp et al. | 260/288 |
| 4,910,193 A | 3/1990 | Buchheit | 514/216 |
| 5,272,143 A | 12/1993 | Benson et al. | 514/215 |
| 5,342,946 A | 8/1994 | Hamilton | 546/23 |
| 5,587,384 A | 12/1996 | Zhang et al. | 514/309 |
| 5,589,483 A | 12/1996 | West | 514/310 |
| 5,659,082 A | 8/1997 | Flitter et al. | 564/166 |
| 5,756,510 A | 5/1998 | Griffin et al. | 514/261 |
| 5,756,548 A | 5/1998 | Flitter et al. | 514/616 |

FOREIGN PATENT DOCUMENTS

| | | |
|---|---|---|
| DE | 2056215 | 5/1972 |
| GB | 1052390 | 12/1966 |
| GB | 2 297 089 | 7/1996 |
| JP | 57 144286 | 9/1982 |
| JP | 64 34988 | 2/1989 |
| WO | WO 95/09159 | 4/1995 |
| WO | WO 95/24379 | 9/1995 |
| WO | WO 95/26186 | 10/1995 |
| WO | WO 97/04771 | 2/1997 |
| WO | WO 97/19934 | 6/1997 |
| WO | WO 98/33802 | 8/1998 |
| WO | WO 98/51307 | 11/1998 |
| WO | WO 98/51308 | 11/1998 |
| WO | WO 99/11622 | 3/1999 |
| WO | WO 99/11623 | 3/1999 |
| WO | WO 99/11624 | 3/1999 |
| WO | WO 99/11628 | 3/1999 |
| WO | WO 99/11644 | 3/1999 |
| WO | WO 99/11645 | 3/1999 |
| WO | WO 99/11649 | 3/1999 |
| WO | WO 99/59973 | 11/1999 |
| WO | WO 99/59975 | 11/1999 |

OTHER PUBLICATIONS

Gatta et al. (Chim. Ther. (1973), 8(4), 455–8).*
Breslin et al. (J. Med. Chem. (1995), 38(5), 771–93).*
Kukla et al. (J. Med. Chem. (1991), 34(11), 3187–97).*
Geneste et al. (Eur. J. Med. Chem.—Chim. Ther. (1978), 13(1), 53–9).*
Haerter et al. (Chimia (1976), 30(2), 50–2).*
Choi, D., "At the scene of ischemic brain injury: Is PARP a perp?", *Nature Medicine* 3(*10*), 1073–1074 (1997).
Pullen et al., "Chiral separation retention mechanisms in high–performance liquid chromatography using bare silica stationary phase and β–cyclodextrin as a mobile phase additive," *Journal of Chromatography A*, 691, 187–193 (1995).
Pullen et al., "Direct Determination of Substituted Azepinoindole Enantiomers in Rat Plasma Using Silica Stationary Phase and β–Cyclodextrin as a Mobile Phase Additive," *Analytical Chem.* 67, 1903–1906 (1995).
Naidong et al., "Sterospecific determinations of (±)–DU–124884 and its metabolites (±)–KC–9048 in human plasma by liquid chromatography," *J. Pharm. And Biomed. Analysis* 14, 325–337 (1996).
Bowes et al., "Effects of inhibitors of the activity of poly – (ADP-ribose) synthetase on the liver injury caused by ischaemia–reperfusion: a comparison with radical scavengers," *Brit. J. of Phrmacology 124*, 1254–1260 (1998).
Eliasson et al., "Poly(ADP–ribose) polymerase gene disruption renders mice resistant to cerebral ischemia," *Nature Medicine* 3(*10*), 1089–1095 (1997).

(List continued on next page.)

*Primary Examiner*—Bruck Kifle
(74) *Attorney, Agent, or Firm*—Karl Neidert; Bryan C. Zielinski; Peter Richardson

(57) ABSTRACT

Compounds of the formula shown below are poly(ADP-ribosyl)transferase inhibitors:

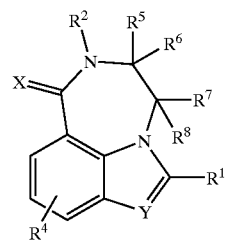

Such compounds are useful as therapeutics in treating cancers and in ameliorating the effects of stroke, head trauma, and neurodegenerative disease.

13 Claims, No Drawings

OTHER PUBLICATIONS

Ananthanarayanan et al., "3,4–Bridged Indoles: Part II—Synthesis of 6–Keto–I,5–dihydro–4,5–diazepino [6,5, 4–cd]indoles & 3,4–Disubstituted Indoles as 5–HT Antagonists," *Indian J Chem 15B*, 710–714 (1997).

Somei et al., The Chemistry of Indoles XLIV. Synthetic Study Directed toward 3,4,5,6–Tetrahydro–1H–azepino[5,4,3–cd]indoles, *Chem. Pharm. Bull.* 36(3), 1162–1168 (1988).

Clark et al., "1,9–Alkano–Bridged 2,3,4,5–Tetrahydro–1H–3–benzazepines with Affinity for the $a_2$–Adrenoceptor and the 5–$HT_{1A}$ Receptor," *J. Med. Chem.* 33, 633–641 (1990).

Santangelo et al., "A Convenient Synthesis of 9–Hydroxy–3,4,5,6–Tetrahydro–1H–azepino [5,4,3–cd]Indole from 7–Methoxyindole," *Synth. Communications* 23(19), 2717–2725 (1993).

Tentori et al., "Role of Wild–Type p53 on the Antineoplastic Activity of Temozolomide Alone or Combined with Inhibitors of Poly(ADP–Ribose) Polymerase," *J. Pharmacology and Experimental Therapeutics* 285(2), 884–893 (1998).

Endres et al., "Protective effects of 5–iodo–6–amino–1,2–benzopyrone, an inhibitor of poly(ADP–ribose) synthetase against peroxynitrite–induced glial damage and stroke development," Euro. J. Pharmacology 351, 377–382 (1998).

Pennisi, E., "A Possible New Partner for Telomerase," *Science* 282, 1395,1397 (1998).

Smith et al., "Tankyrase, a Poly(ADP–Ribose) Polymerase at Human Telomeres," *Science* 282, 1484–1487 (1998).

Bowman et al., "Potentiation of anti–cancer agent cytotoxicity by the potent poly(ADP–ribose) polymerase inhibitors NU1025 and NU 1064," *Brit. J. Cancer* 78(10), 1269–1277 (1998).

Denny et al., "Potential Antitumor Agents. 59. Structure–Activity Relationships for 2–Phenylbenzimidazole–4–carboxamides, a New Class of "Minimal" DNA–Intercalating Agents Which May Not Act via Topoisomerase," *J. Med. Chem.* 33, 814–819 (1990).

Kubo et al., "Nonpeptide Angiotensin II Receptor Antagonists. Synthesis and Biological Activity of Benzimidazoles," *J. Med. Chem.* 36, 1772–1784 (1993).

Schneller et al., "Synthesis of proximal–Benzoguanine and a Simplified Synthesis of proximal–Benzohypoxanthine," *J. Org. Chem.* 51, 4067–4070 (1986).

Babiychuk et al., "Higher plants possess two structurally different poly(ADP–ribose) polymerases," *The Plant Journal* 15(5), 635–645 (1998).

Kawamura et al., "An Alternative Form of Poly(ADP–Ribose) Polymerase in *Drosophila melanogaster* and Its Ectopic Expression in Rat–1 Cells," *Biochem. And Biophys. Res. Commun.* 251, 35–40 (1998).

Demerson et al., "Pyrrolo[4,3,2–de]isoquinolines with Central Nervous System and Antihypertensive Activities," *J. Med. Chem.* 17(11), 1140–1145 (1974).

de Murcia et al., "Poly(ADP–ribose) polymerase: a molecular nick–sensor," *TIBS* 19, 172–176 (1994).

Bowes et al., "Inhibitors of the activity of poly(ADP–ribose) synthetase reduce the cell death caused by hydrogen peroxide in human cardiac myoblasts," *Brit. J. Pharmacology* 124, 1760–1766 (1998).

Mahajan et al., "Purification and cDNA Cloning of Maize Poly(ADP)–Ribose Polymerase," *Plant Physiol.* 118, 895–905 (1998).

Horning et al., "Isocarbostyrils, II. The Conversion of 2–Methyl–4acyl–5–nitroisocarbostyrils to 2–Substituted Indole–4–carboxylic Acids," *Canadian J. Chem.* 49, 2797–2802 (1971).

Zhang, "PARP inhibition: a novel approach to treat ischemia/reperfusion and inflammation related injuries," Emerging Drugs: *The Prospect for Improved Medicines* (1999), Ashley Publications Ltd.

Zingarelli et al., "Protection against myocardial ischemia and reperfusion injury by 3–aminobenzamide, an inhibitor of poly (ADP–ribose) synthetase," *Cardiovascular Research* (1997), 36:205–215).

Love et al., "Neuronal accumulation of poly(ADP–ribose) after brain ischaemia," *Neuropathology and Applied Neurobiology* (1999), 25:98–103.

Endres et al., "Ischemic Brain Injury is Mediated by the Activation of Poly(ADP–Ribose)Polymerase," *J. Cerbral Blood Flow Metab.* (1997), 17:1143–1151.

Zhang, "PARP Inhibition Results in Substantial Neuroprotection in Ceregral Ischemia." *Cambridge Healthtech Institute's Conference on Acute Neuronal Injury New Therapeutic Opportunities*, Sep. 23–24, 1998, Las Vegas, Nevada.

Cosi et al., "Poly(ADP–Ribose) Polymerase Revisited: A New Role for an Old Enzyme: PARP Involvement in Neurodegeneration and PARP Inhibitors as Possible Neuroprotective Agents," Ann. N.Y. Acad. Sci., (1997), 825:366–379.

Mandir et al., "Poly(ADP–ribose) plymerase activation mediates 1–methyl–4–phenyl–1,2,3,–tetrahydropyridine (MPTP)–induced parkinsonism", Proc. Natl. Acad. Sci. USA 96 (1999) pp. 5774–5779.

Saldeen et al., "Nicotinamide–induced apoptosis in insulin producing cells is associated with cleavage of poly(ADP–ribose) polymerase," *Mol. Cellular Endocrinal.* (1998), 139:99–107.

Pieper et al., "Poly (ADP–ribose) polymerase, nitric oxide, and cell death," *Trends Pharmacolog. Sci.* (1999), 20:171–181.

Burkart et al., "Mice lacking the poly(ADP–ribose) polymerase gene are resistant to pancreatic beta–cell destruction and diabetes development induced by streptozocin," *Nature Medicine* (1999), 5:314–319.

Szabo et al., "Protective effect of an inhibitor of poly(ADP–ribose) synthetase in collagen–induced arthritis," *Portland Press Proc.* (1998), 15:280–281.

Szabo, "Role of Poly(ADP–ribose) Synthetase in Inflammation and Ischaemia–Reperfusion" TIPS (1998), vol. 19, pp. 287–297.

Banasik et al. "Specific Inhibitors of Poly(ADP–Ribose) Synthetase and Mono(ADP–Ribosyl) transferase," *J. Biol. Chem.* (1992) 267:1569–1575).

Suto et al. "Dihydroisoquinolinones: The Design and Synthesis of a New Series of Potent Inhibitors of Poly(ADP–ribose) Polymerase," *Anti–Cancer Drug Design* (1991), 7, 107–117.

Griffin et al. Resistance–Modifying Agents. 5. Synthesis and Biological Properties of Quinazoline Inhibitors of the DNA Repair Enzyme Poly(ADP–ribose) Polymerase (PARP) J. Med. Chem (1998) 41:5247–5256.

Hayashi, et al. Induction of hepatic poly(ADP–ribose) polymerase by peroxisome proliferators, non–genotoxic hepatocarcinogens, Cancer Letters 127 (1998) 1–7.

Griffin, Roger J. "Novel Potent Inhibitors of the DNA Repair Enzyme Poly(ADP–ribose) polymerase (PARP)" Anti–Cancer Drug Design (1995), 10, pp. 507–514.

Simonin. Frederic "Identification of Potential Active–Site Residues in the Human Poly(ADP–ribose) Polymerase" The Journal of Biological Chemistry. vol. 268, No. 12, Apr. 25, 1993, pp. 8529–8535.

Marsischky, Gerald "Role of Glutamic Acid 988 of Human Pol–ADP–ribose Polymerase in Polymer Formation" The Journal of Biological Chemistry. vol. 270, No. 7, Feb. 17, 1995, pp. 3247–3254.

Sculley, Michael "The Determination of Kinetic Constants Governing the Slow, Tight–Binding Inhibition of Enzyme–Catalysed Reactions" Biochimica et Biophysica Acta 874 (1986) pp. 44–53.

Kamenka, Jean–Marc et al., "Syntheses en Serie de la Ceto 6 imidazo [4,5,1–ij] quinoleine" Chem. 10, 459 (1973).

Higgins, Jerry, "Benzimidazole Polymers from Aldehydes and Tetraamines" Journal of Polymer Science, Part A–1, vol. 8, 171–177 (1970).

Imai, Yoshio, "Facile Synthesis of 2H–1,2,4–Benzothiadiazine 1,1–Dioxides and 4–Oxo–3,4–dihydroquinazolines from 2–Aminobenzenesulfonamide or 2–Aminobenzamide and Aldehydes in the Presence of Sodium Hydrogen Sulfite" Synthesis (Jan. 1981), pp. 35–36.

Ackerly, Norman, "A Novel Approach to Dual–Acting Thromboxane Receptor Antagonist/Synthase Inhibitors Based on the Link of 1,3–Dioxane–Thromboxane Receptor Antagonists and –Thromboxane Synthase Inhibitors" Journal of Med. Chem. 1995, 38, pp. 1608–1628.

Hester, Jackson, "Pyrrolo [3,2,1–jk][1,4] benzodiazepines and Pyrrolo [1,2,3–ef][1,5] benzodiazepines Which Have Central Nervous System Activity " Journal of Medicinal Chemistry, 1970, vol. 13, No. 5, pp. 827–835.

Breslin, Henry, "Synthesis and Anti–HIV–1 Activity of 4,5,6,7–Tetrahydro–5–methylimidazo–[4,5,1–jk][1,4] benzodiazepin–2(1H)–one (TIBO) Derivatives" Journal of Medicinal Chemistry, 1995, vol. 38, No. 5, pp. 771–793.

Marx, Thomas, "Chirale Porphyrine mit C–verknüpften Menthyl–Resten" Liebigs Ann. Chem., 1992, pp 183–185.

Ito, Yoshikatsu, "Photochemistry of Meta–Substituted and Para–Substituted Aromatic Polycarbonyl Compounds" J. Org. Chem., 1985, 50, pp. 2893–2904.

Norris, James et. al., "The Reactivity of Atoms and Groups in Organic Compounds. XIX. The Relative Reactivities of the Chlorine Atoms in Certain Derivatives of Benzoyl Chloride" Journal of American Chemical Society, (1939), 61:1418–1420.

Szabo, Csaba, "Protection against peroxynitrite–induced fibroblast injure and arthritis development by inhibition of poly(ADP–ribose) synthase" Medical Sciences, vol. 95, Issue 7, 3867–3872, Mar. 21, 1998.

Szabo, et al., "Protection against Peroxynitnite–induced Fibroblast injury & Arthritis Development by inhibition of poly (ADP–riblse) synthetase". Proc. Natl. Acad. Sci. USA (1998), 95(7): 3867–72.

Maryanott, et al., J. Med Chem. 38, 16 (1995) p. 28.

Butler, et al. "Novel Pharmacological Activity of a Series of Substituted Pyridines"; Journal of Med. Chem. 1971, vol. 14, No. 7; 575–579.

Segel, Enzyme Kinetics Behavior & Analysis of Rapid Equilibrium & steady–state enzyme system, John Wiley & Sons, Inc., New York (1975) 100–125.

* cited by examiner

TRICYCLIC INHIBITORS OF POLY(ADP-RIBOSE) POLYMERASES

CROSS-REFERENCE TO RELATED APPLICATIONS

This application claims the benefit of U.S. Provisional Application No. 60/152,142, filed Aug. 31, 1999.

FIELD OF THE INVENTION

The invention pertains to compounds that inhibit poly (ADP-ribose) polymerases, thereby retarding the repair of damaged DNA strands, and to methods of preparing such compounds. The invention also relates to the use of such compounds in pharmaceutical compositions and therapeutic treatments useful for potentiation of anti-cancer therapies, inhibition of neurotoxicity consequent to stroke, head trauma, and neurodegenerative diseases, and prevention of insulin-dependent diabetes.

BACKGROUND OF THE INVENTION

Poly(ADP-ribose) polymerases (PARPs), nuclear enzymes found in almost all eukaryotic cells, catalyze the transfer of ADP-ribose units from nicotinamide adenine dinucleotide (NAD$^+$) to nuclear acceptor proteins, and are responsible for the formation of protein-bound linear and branched homo-ADP-ribose polymers. Activation of PARP and resultant formation of poly(ADP-ribose) are induced by DNA strand breaks, e.g., after exposure to chemotherapy, ionizing radiation, oxygen free radicals, or nitric oxide (NO). The acceptor proteins of poly(ADP-ribose), including histones, topoisomerases, DNA and RNA polymerases, DNA ligases, and Ca$^{2+}$- and Mg$^{2+}$-dependent endonucleases, are involved in maintaining DNA integrity.

Because this cellular ADP-ribose transfer process is associated with the repair of DNA strand breakage in response to DNA damage caused by radiotherapy or chemotherapy, it can contribute to the resistance that often develops to various types of cancer therapies. Consequently, inhibition of PARP may retard intracellular DNA repair and enhance the antitumor effects of cancer therapy. Indeed, in vitro and in vivo data show that many PARP inhibitors potentiate the effects of ionizing radiation or cytotoxic drugs such as DNA methylating agents. Thus, inhibitors of the PARP enzyme are useful as adjunct cancer chemotherapeutics.

PARP inhibitors are additionally useful in therapy of cardiovascular diseases. Ischemia, a deficiency of oxygen and glucose in a part of the body, can be caused by an obstruction in the blood vessel supplying that area or a massive hemorrhage. Two severe forms, heart attack and stroke, are major killers in the developed world. Cell death results directly and also occurs when the deprived area is reperfused. PARP inhibitors are being developed to treat ischemia/reperfusion injuries. See, e.g., Zhang, "PARP inhibition: a novel approach to treat ischemia/reperfusion and inflammation-related injuries," *Emerging Drugs: The Prospect for Improved Medicines* (1999), Ashley Publications Ltd. Inhibition of PARP has been shown to protect against myocardial ischemia and reperfusion injury (Zingarelli et al., "Protection against myocardial ischemia and reperfusion injury by 3-aminobenzamide, an inhibitor of poly (ADP-ribose) synthetase," *Cardiovascular Research* (1997), 36:205–215).

Inhibitors of the PARP enzyme are also useful inhibitors of neurotoxicity consequent to stroke, head trauma, and neurodegenerative diseases. After brain ischemia, the distribution of cells with accumulation of poly(ADP-ribose), that is, the areas where PARP was activated, correspond to the regions of ischemic damage (Love et al., "Neuronal accumulation of poly(ADP-ribose) after brain ischaemia," *Neuropathology and Applied Neurobiology* (1999), 25:98–103). It has been shown that inhibition of PARP promotes resistance to brain injury after stroke (Endres et al., "Ischemic Brain Injury is Mediated by the Activation of Poly(ADP-Ribose)Polymerase," *J. Cerebral Blood Flow Metab.* (1997), 17:1143–1151; Zhang, "PARP Inhibition Results in Substantial Neuroprotection in Cerebral Ischemia," *Cambridge Healthtech Institute's Conference on Acute Neuronal Injury: New Therapeutic Opportunities*, Sep. 18–24, 1998, Las Vegas, Nev.).

The activation of PARP by DNA damage is believed to play a role in the cell death consequent to head trauma and neurodegenerative diseases, as well as stroke. DNA is damaged by excessive amounts of NO produced when the NO synthase enzyme is activated as a result of a series of events initiated by the release of the neurotransmitter glutamate from depolarized nerve terminals (Cosi et al., "Poly(ADP-Ribose) Polymerase Revisited: A New Role for an Old Enzyme: PARP Involvement in Neurodegeneration and PARP Inhibitors as Possible Neuroprotective Agents," *Ann. N.Y. Acad. Sci.* (1997), 825:366–379). Cell death is believed to occur as a result of energy depletion as NAD$^+$ is consumed by the enzyme-catalyzed PARP reaction.

Parkinson's disease is an example of a neurodegenerative condition whose progression may be prevented by PARP inhibition. Mandir et al. have demonstrated that mice that lack the gene for PARP are "dramatically spared" from the effects of exposure to 1-methyl-4-phenyl-1,2,3,6-tetrahydropyridine (MPTP), a neurotoxin that causes parkinsonism in humans and animals (Mandir et al., "Poly (ADP-ribose) polymerase activation mediates 1-methyl-4-phenyl-1,2,3,6-tetrahydropyridine (MPTP)-induced parkinsonism," *Proc. Natl. Acad. Sci. USA* (1999), 96:5774–5779). MPTP potently activates PARP exclusively in dopamine-containing neurons of the substantia nigra, the part of the brain whose degeneration is associated with development of parkinsonism. Hence, potent PARP inhibitors may slow the onset and development of this crippling condition.

Furthermore, inhibition of PARP should be a useful approach for treatment of conditions or diseases associated with cellular senescence, such as skin aging, through the role of PARP in the signaling of DNA damage. See, e.g., U.S. Pat. No. 5,589,483.

PARP inhibition is also being studied at the clinical level to prevent development of insulin-dependent diabetes mellitus in susceptible individuals (Saldeen et al., "Nicotinamide-induced apoptosis in insulin producing cells in associated with cleavage of poly(ADP-ribose) polymerase," *Mol. Cellular Endocrinol.* (1998), 139:99–107). In models of Type I diabetes induced by toxins such as streptozocin and alloxan that destroy pancreatic islet cells, it has been shown that knock-out mice lacking PARP are resistant to cell destruction and diabetes development (Pieper et al., "Poly (ADP-ribose) polymerase, nitric oxide, and cell death," *Trends Pharmacolog. Sci.* (1999), 20:171–181; Burkart et al., "Mice lacking the poly(ADP-ribose) polymerase gene are resistant to pancreatic beta-cell destruction and diabetes development induced by streptozocin," *Nature Medicine* (1999), 5:314–319). Administration of nicotinamide, a weak PARP inhibitor and a free-radical scavenger, prevents development of diabetes in a spontaneous autoimmune diabetes model, the non-obese, diabetic mouse (Pieper et al., ibid.). Hence, potent and specific PARP inhibitors may be useful as diabetes-prevention therapeutics.

PARP inhibition is also an approach for treating inflammatory conditions such as arthritis (Szabo et al., "Protective effect of an inhibitor of poly(ADP-ribose) synthetase in collagen-induced arthritis," *Portland Press Proc.* (1998), 15:280–281; Szabo, "Role of Poly(ADP-ribose) Synthetase in Inflammation," *Eur. J. Biochem.* (1998), 350(1):1–19; Szabo et al., "Protection Against Peroxynitrite-induced Fibroblast Injury and Arthritis Development by Inhibition of Poly(ADP-ribose) Synthetase," *Proc. Natl. Acad. Sci. USA* (1998), 95(7):3867–72).

The PARP family of enzymes is extensive. It has recently been shown that tankyrases, which bind to the telomeric protein TRF-1, a negative regulator of telomere length maintenance, have a catalytic domain that is strikingly homologous to PARP and have been shown to have PARP activity in vitro. It has been proposed that telomere function in human cells is regulated by poly(ADP-ribosyl)ation. PARP inhibitors have utility as tools to study this function. Further, as a consequence of regulation of telomerase activity by tankyrase, PARP inhibitors should have utility as agents for regulation of cell life-span, e.g., for use in cancer therapy to shorten the life-span of tumor cells, or as anti-aging therapeutics, since telomere length is believed to be associated with cell senescence.

Various competitive inhibitors of PARP have been described. For example, Banasik et al. ("Specific Inhibitors of Poly(ADP-Ribose) Synthetase and Mono(ADP-Ribosyl) transferase," *J. Biol. Chem.* (1992) 267:1569–1575) examined the PARP-inhibiting activity of over one hundred compounds, the most potent of which were 4-amino-1,8-naphthalimide, 6(5H)-phenanthridone, 2-nitro-6(5H)-phenanthridone, and 1,5-dihydroxyisoquinoline. Griffin et al. reported the PARP-inhibiting activity for certain benzamide compounds (U.S. Pat. No. 5,756,510; see also "Novel Potent Inhibitors of the DNA Repair Enzyme Poly(ADP-ribose)polymerase (PARP)," *Anti-Cancer Drug Design* (1995), 10:507–514), benzimidazole compounds (International Publication No. WO 97/04771), and quinalozinone compounds (International Publication No. WO 98/33802). Suto et al. reported PARP inhibition by certain dihydroisoquinoline compounds ("Dihydroisoquinolines: The Design and Synthesis of a New Series of Potent Inhibitors of Poly(ADP-ribose) Polymerase," *Anti-Cancer Drug Design* (1991), 7:107–117). Griffin et al. have reported other PARP inhibitors of the quinazoline class ("Resistance-Modifying Agents. 5. Synthesis and Biological Properties of Quinazoline Inhibitors of the DNA Repair Enzyme Poly(ADP-ribose) Polymerase (PARP)," *J. Med. Chem.* (1998) 41:5247–5256). International Publication Nos. WO 99/11622, WO 99/11623, WO 99/11624, WO 99/11628, WO 99/11644, WO 99/11645, and WO 99/11649 describe various PARP-inhibiting compounds. Furthermore, certain tricyclic PARP inhibitors are described in commonly owned U.S. Provisional Application No. 60/115,431, filed Jan. 11, 1999, in the name of Webber et al., the disclosure of which is incorporated by reference herein.

Nonetheless, there is still a need for small-molecule compounds that are active PARP inhibitors, especially those that have physical, chemical, and pharmacokinetic properties desirable for therapeutic applications.

SUMMARY OF THE INVENTION

Thus, an object of the invention is to discover small-molecule PARP-inhibiting compounds. Another object is to discover such compounds having properties advantageous for therapeutic uses.

The compounds of the general formula I have been discovered to be effective PARP inhibitors:

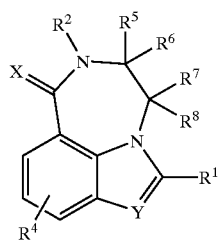

(I)

wherein:
X is O or S;
Y is N or $CR^3$, where $R^3$ is: H;
halogen;
cyano;
an optionally substituted alkyl, alkenyl, alkynyl, cycloalkyl, heterocycloalkyl, aryl, or heteroaryl group (e.g., unsubstituted or substituted with one or more substituents selected from halogen, hydroxy, nitro, cyano, and amino, and alkoxy, alkyl, aryl, and heteroaryl groups unsubstituted or substituted with one or more substituents selected from halogen, hydroxy, nitro, cyano, and optionally substituted amino and ether groups (such as O-aryl)); or
—C(W)—$R^{20}$, where W is O or S, and $R^{20}$ is: H; OH; an optionally substituted alkyl, alkenyl, alkynyl, cycloalkyl, heterocycloalkyl, aryl, heteroaryl, O-alkyl, or O-aryl group (e.g., unsubstituted or substituted with one or more substituents selected from halogen, hydroxy, cyano, nitro, and amino, and alkyl and aryl groups unsubstituted or substituted with one or more substituents selected from halo, hydroxy, nitro, cyano, and amino); or $NR^{27}R^{28}$, where $R^{27}$ and $R^{28}$ are each independently H; OH; an optionally substituted alkyl, alkenyl, alkynyl, cycloalkyl, heterocycloalkyl, aryl, or heteroaryl group (e.g., unsubstituted or substituted with one or more substituents selected from alkyl, alkenyl, alkynyl, cycloalkyl, heterocycloalkyl, aryl, and heteroaryl groups unsubstituted or substituted with one or more substituents selected from halogen, hydroxy, nitro, cyano, amino, trifluoromethyl, alkyl and aryl groups);
—$CR^{29}$=N—$R^{30}$, where $R^{29}$ is H or an optionally substituted amino (e.g., dialkylamino), alkyl, alkenyl, alkynyl, cycloalkyl, heterocycloalkyl, aryl, heteroaryl, group. (e.g., unsubstituted or substituted with one or more substituents selected from halogen, hydroxy, cyano, nitro, and amino, and alkyl and aryl groups unsubstituted or substituted with one or more substituents selected from halogen, hydroxy, nitro, cyano, and amino), salkyl, sakyl, O-alkyl, or O-aryl and $R^{30}$ is H, OH, an optionally substituted alkyl, alkenyl, alkynyl, cycloalkyl, heterocycloalkyl, aryl, heteroaryl, O-alkyl, or O-aryl group (e.g., unsubstituted or substituted with one or more substituents selected from halogen, hydroxy, cyano, nitro, and amino, and alkyl and aryl groups unsubstituted or substituted with one or more substituents selected from halogen, hydroxy, nitro, cyano, and amino), or $NR^{31}R^{32}$, where $R^{31}$ and $R^{32}$ are each independently H, OH, or an optionally substituted alkyl, alkenyl, alkynyl, cycloalkyl, heterocycloalkyl, aryl, or heteroaryl group (e.g., unsubstituted or substituted with one or more substituents selected from alkyl, alkenyl, alkynyl, cycloalkyl, heterocycloalkyl, aryl, and heteroaryl groups unsubstituted or substituted with one or more substituents selected from halogen, hydroxy, nitro, cyano, amino, trifluoromethyl, alkyl and aryl groups);

$R^1$ is H;

halogen;

cyano;

an optionally substituted alkyl, alkenyl, alkynyl, cycloalkyl, heterocycloalkyl, aryl, or heteroaryl group (e.g., unsubstituted or substituted with one or more substituents selected from halogen, hydroxy, cyano, nitro, and amino, and alkyl, alkenyl, alkynyl, cycloalkyl, heterocycloalkyl, alkoxy, aryl, aryloxy, heteroaryl, and heteroaryloxy groups unsubstituted or substituted with one or more substituents selected from halogen, hydroxy, nitro, cyano, amino, lower alkoxy, trifluoromethyl, and alkylcarbonyl);

$C(O)R^{12}$, where $R^{12}$ is: H; an optionally substituted alkyl, alkenyl, alkynyl, cycloalkyl, heterocycloalkyl, aryl, or heteroaryl group (e.g., unsubstituted or substituted with one or more substituents selected from halogen, hydroxy, cyano, nitro, and amino, and alkyl and aryl groups unsubstituted or substituted with one or more substituents selected from halogen, hydroxy, nitro, cyano, and amino); or $OR^{19}$ or $NR^{21}R^{22}$, where $R^{19}$, $R^{21}$ and $R^{22}$ are each independently H or an optionally substituted alkyl, alkenyl, alkynyl, cycloalkyl, heterocycloalkyl, aryl, or heteroaryl group (e.g., unsubstituted or substituted with one or more substituents selected from alkyl, alkenyl, alkynyl, cycloalkyl, heterocycloalkyl, aryl, and heteroaryl groups unsubstituted or substituted with one or more substituents selected from halogen, hydroxy, nitro, cyano, amino, trifluoromethyl, alkyl and aryl groups);

$OR^{13}$, where $R^{13}$ is: H; an optionally substituted alkyl, alkenyl, alkynyl, cycloalkyl, heterocycloalkyl, aryl, or heteroaryl group (e.g., unsubstituted or substituted with one or more substituents selected from halogen, hydroxy, cyano, nitro, and amino, and alkyl and aryl groups unsubstituted or substituted with one or more substituents selected from halogen, hydroxy, nitro, cyano, and amino);

$S(O)_nNR^{16}$, where n is 0, 1 or 2, and $R^{16}$ is: H; an optionally substituted alkyl, alkenyl, alkynyl, cycloalkyl, heterocycloalkyl, aryl, or heteroaryl group (e.g., unsubstituted or substituted with one or more substituents selected from halogen, hydroxy, cyano, nitro, and amino, and alkyl and aryl groups unsubstituted or substituted with one or more substituents selected from halogen, hydroxy, nitro, cyano, and amino); or $NR^{23}R^{24}$, where $R^{23}$ and $R^{24}$ are each independently H or an optionally substituted alkyl, alkenyl, alkynyl, cycloalkyl, heterocycloalkyl, aryl, or heteroaryl group (e.g., unsubstituted or substituted with one or more substituents selected from alkyl, alkenyl, alkynyl, cycloalkyl, heterocycloalkyl, aryl, and heteroaryl groups unsubstituted or substituted with one or more substituents selected from halogen, hydroxy, nitro, cyano, amino, trifluoromethyl, alkyl and aryl groups); or $NR^{17}R^{18}$, where $R^{17}$ and $R^{18}$ are each independently: H; an optionally substituted alkyl, alkenyl, alkynyl, cycloalkyl, heterocycloalkyl, aryl, or heteroaryl group (e.g., unsubstituted or substituted with one or more substituents selected from alkyl, alkenyl, alkynyl, cycloalkyl, heterocycloalkyl, aryl, and heteroaryl groups unsubstituted or substituted with one or more substituents selected from halogen, hydroxy, nitro, cyano, amino, trifluoromethyl, alkyl and aryl groups); $C(O)—R^{20}$ where $R^{20}$ is: H, OH, an optionally substituted alkyl, alkenyl, alkynyl, cycloalkyl, heterocycloalkyl, aryl, heteroaryl, O-alkyl, or O-aryl group (e.g., unsubstituted or substituted with one or more substituents selected from halogen, hydroxy, cyano, nitro, and amino, and alkyl and aryl groups unsubstituted or substituted with one or more substituents selected from halo, hydroxy, nitro, cyano, and amino); or $NR^{27}R^{28}$, where $R^{27}$ and $R^{28}$ are each independently H; OH; an optionally substituted alkyl, alkenyl, alkynyl, cycloalkyl, heterocycloalkyl, aryl, or heteroaryl group (e.g., unsubstituted or substituted with one or more substituents selected from alkyl, alkenyl, alkynyl, cycloalkyl, heterocycloalkyl, aryl, and heteroaryl groups unsubstituted or substituted with one or more substituents selected from halogen, hydroxy, nitro, cyano, amino, trifluoromethyl, alkyl and aryl groups); or $S(O)_2NR^{25}N^{26}$, where $R^{25}$ and $R^{26}$ are each independently H or an optionally substituted alkyl, alkenyl, alkynyl, cycloalkyl, heterocycloalkyl, aryl, or heteroaryl group (e.g., unsubstituted or substituted with one or more substituents selected from alkyl, alkenyl, alkynyl, cycloalkyl, heterocycloalkyl, aryl, and heteroaryl groups unsubstituted or substituted with one or more substituents selected from halogen, hydroxy, nitro, cyano, amino, trifluoromethyl, alkyl and aryl groups);

$R^2$ is H or alkyl;

$R^4$ is H, halogen or alkyl;

$R^5$, $R^6$, $R^7$, and $R^8$ are each independently selected from:

H;

an optionally substituted alkyl, alkenyl, alkynyl, cycloalkyl, heterocycloalkyl, aryl, or heteroaryl group (e.g., unsubstituted or substituted with one or more substituents selected from halogen, hydroxy, nitro, and amino, and alkoxy, alkyl, and aryl groups unsubstituted or substituted with one or more substituents selected from halogen, hydroxy, nitro, cyano, and optionally substituted amino and ether groups (such as O-aryl)); and —$C(O)$—$R^{50}$, where $R^{50}$ is: H; an optionally substituted alkyl, alkenyl, alkynyl, cycloalkyl, heterocycloalkyl, aryl, or heteroaryl group (e.g., unsubstituted or substituted with one or more substituents selected from halogen, hydroxy, nitro, and amino, and alkyl and aryl groups unsubstituted or substituted with one or more substituents selected from halogen, hydroxy, nitro, and amino); or $OR^{51}$ or $NR^{52}R^{53}$, where $R^{51}$, $R^{52}$ and $R^{53}$ are each independently H or an optionally substituted alkyl, alkenyl, alkynyl, cycloalkyl, heterocycloalkyl, aryl, or heteroaryl group (e.g., unsubstituted or substituted with one or more substituents selected from alkyl, alkenyl, alkynyl, cycloalkyl, heterocycloalkyl, aryl, and heteroaryl groups unsubstituted or substituted with one or more substituents selected from halogen, hydroxy, nitro, and amino, and alkyl and aryl groups unsubstituted or substituted with one or more substituents selected from halogen, hydroxy, nitro, and optionally substituted amino groups);

where when Y is $CR^3$, $R^1$, $R^2$, $R^3$, $R^4$, $R^5$, $R^6$, $R^7$, and $R^8$ are not all H.

The invention is also directed to pharmaceutically acceptable salts, prodrugs, active metabolites, and solvates of compounds of formula I.

Preferably, the compounds of formula I have a PARP-inhibiting activity corresponding to a $K_i$ of 10 μM or less in the PARP enzyme inhibition assay.

The present invention is also directed to pharmaceutical compositions each comprising an effective PARP-inhibiting amount of an agent selected from compounds of formula I and their pharmaceutically acceptable salts, prodrugs, active metabolites, and solvates, in combination with a pharmaceutically acceptable carrier therefor.

The present invention is also directed to a method of inhibiting PARP enzyme activity, comprising contacting the enzyme with an effective amount of a compound of formula I or a pharmaceutically acceptable salt, prodrug, active metabolite, or solvate thereof. The invention is also directed to therapeutic methods comprising inhibiting ARP enzyme activity in the relevant tissue of a patient by administering a compound of formula I or a pharmaceutically acceptable salt, prodrug, active metabolite, or solvate thereof.

Other embodiments, objects and advantages of the invention will become apparent from the following detailed description.

DETAILED DESCRIPTION AND PREFERRED EMBODIMENTS OF THE INVENTION

PARP-Inhibiting Agents

In accordance with a convention used in the art, the symbol

is used in structural formulas herein to depict the bond that is the point of attachment of the moiety or substituent to the core or backbone structure. In accordance with another convention, in some structural formulae herein the carbon atoms and their bound hydrogen atoms are not explicitly depicted, e.g.,

represents a methyl group,

represents an ethyl group,

represents a cyclopentyl group, etc.

As used herein, the term "alkyl" means a branched- or straight-chained (linear) paraffinic hydrocarbon group (saturated aliphatic group) having from 1 to 16 carbon atoms in its chain, which may be generally represented by the formula $C_kH_{2k+1}$, where k is an integer of from 1 to 10. Examples of alkyl groups include methyl, ethyl, n-propyl, isopropyl, n-butyl, isobutyl, t-butyl, pentyl, n-pentyl, isopentyl, neopentyl, and hexyl, and the simple aliphatic isomers thereof. A "lower alkyl" is intended to mean an alkyl group having from 1 to 4 carbon atoms in its chain.

The term "alkenyl" means a branched- or straight-chained olefinic hydrocarbon group (unsaturated aliphatic group having one or more double bonds) containing 2 to 10 carbons in its chain. Exemplary alkenyls include ethenyl, 1-propenyl, 2-propenyl, 1-butenyl, 2-butenyl, isobutenyl, and the various isomeric pentenyls and hexenyls (including both cis and trans isomers).

The term "alkynyl" means a branched or straight-chained hydrocarbon group having one or more carbon-carbon triple bonds and from 2 to 10 carbon atoms in its chain. Exemplary alkynyls include ethynyl, propynyl, 1-butynyl, 2-butynyl, and 1-methyl-2-butynyl.

The term "carbocycle" refers to a saturated, partially saturated, unsaturated, or aromatic, monocyclic or fused or non-fused polycyclic, ring structure having only carbon ring atoms (no heteroatoms, i.e., non-carbon ring atoms). Exemplary carbocycles include cycloalkyl, aryl, and cycloalkyl-aryl groups.

The term "heterocycle" refers to a saturated, partially saturated, unsaturated, or aromatic, monocyclic or fused or non-fused polycyclic, ring structure having one or more heteroatoms selected from nitrogen, oxygen and sulfur. Exemplary heterocycles include heterocycloalkyl, heteroaryl, and heterocycloalkyl-heteroaryl groups.

A "cycloalkyl group" is intended to mean a non-aromatic monovalent, monocyclic or fused polycyclic, ring structure having a total of from 3 to 18 carbon ring atoms (but no heteroatoms). Exemplary cycloalkyls include cyclopropyl, cyclobutyl, cyclopentyl, cyclopentenyl, cyclohexyl, cycloheptyl, adamantyl, phenanthrenyl, and like groups.

A "heterocycloalkyl group" is intended to mean a non-aromatic monovalent, monocyclic or fused polycyclic, ring structure having a total of from 3 to 18 ring atoms, including 1 to 5 heteroatoms selected from nitrogen, oxygen, and sulfur. Illustrative examples of heterocycloalkyl groups include pyrrolidinyl, tetrahydrofuryl, piperidinyl, piperazinyl, morpholinyl, thiomorpholinyl, aziridinyl, and like groups.

The term "aryl" means an aromatic monocyclic or fused polycyclic ring structure having a total of from 4 to 18 ring carbon atoms (no heteroatoms). Exemplary aryl groups include phenyl, naphthyl, anthracenyl, and the like.

A "heteroaryl group" is intended to mean an aromatic monovalent, monocyclic or fused polycyclic, ring structure having from 4 to 18 ring atoms, including from 1 to 5 heteroatoms selected from nitrogen, oxygen, and sulfur. Illustrative examples of heteroaryl groups include pyrrolyl, thienyl, oxazolyl, pyrazolyl, thiazolyl, furyl, pyridinyl, pyrazinyl, triazolyl, tetrazolyl, indolyl, quinolinyl, quinoxalinyl, and the like.

An "amine" or "amino group" is intended to mean the radical —$NH_2$, and "optionally substituted" amines refers to —$NH_2$ groups wherein none, one or two of the hydrogens is replaced by a suitable substituent. Disubstituted amines may have substituents that are bridging, i.e., form a heterocyclic ring structure that includes the amine nitrogen. An "alkylamino group" is intended to mean the radical —$NHR_a$, where $R_a$ is an alkyl group. A "dialkylamino group" is intended to mean the radical —$NR_aR_b$, where $R_a$ and $R_b$ are each independently an alkyl group.

The term "optionally substituted" is intended to indicate that the specified group is unsubstituted or substituted by one or more suitable substituents, unless the optional substituents are expressly specified, in which case the term indicates that the group is unsubstituted or substituted with the specified substituents. Unless indicated otherwise (e.g., by indicating that a specified group is unsubstituted), the various groups defined above may be generally unsubstituted or substituted (i.e., they are optionally substituted) with one or more suitable substituents.

The term "substituent" or "suitable substituent" is intended to mean any substituent for a group that may be recognized or readily selected by the artisan, such as through routine testing, as being pharmaceutically suitable. Illustrative examples of suitable substituents include hydroxy, halogen (F, Cl, I, or Br), oxo, alkyl, acyl, sulfonyl, mercapto, nitro, alkylthio, alkoxy, cycloalkyl, heterocycloalkyl, aryl, heteroaryl, carboxy, amino (primary, secondary, or tertiary), carbamoyl, aryloxy, heteroaryloxy, arylthio, heteroarylthio, and the like (e.g., as illustrated by the exemplary compounds described herein).

Preferred optional substituents for alkyl and aryl groups in the compounds of the invention include halogens and aryl groups. Substituted alkyl groups include perfluoro-substituted alkyls, and optional substituents for alkyl and aryl moieties include halogen; lower alkyl optionally substituted by —OH, —NH$_2$, or halogen; —OH; —NO$_2$; —CN; —CO$_2$H; O-lower alkyl; aryl; —O-aryl; aryl-lower alkyl; —OCHF$_2$; —CF$_3$; —OCF$_3$; —CO$_2$R$^a$, —CONR$^a$R$^b$, —OCH$_2$CONR$^a$R$^b$, —NR$^a$R$^b$, —SO$_2$R$^a$R$^b$, where R$_a$ and R$_b$ are each independently H, lower alkyl, or aryl; and the like. Aryl moieties may also be optionally substituted by two substituents forming a bridge, for example —O—(CH$_2$)$_z$—O—, where z is an integer of 1, 2, or 3.

A "prodrug" is intended to mean a compound that is converted under physiological conditions or by solvolysis, or metabolically, to a specified compound that is pharmaceutically active.

An "active metabolite" is intended to mean a pharmacologically active product produced through metabolism in the body of a specified compound. Metabolic products of a given compound may be identified using techniques generally known in the art for determining metabolites and assaying them for their activity using techniques such as those described below.

Prodrugs and active metabolites of a compound may be identified using routine techniques known in the art. See, e.g., Bertolini, G. et al., *J. Med. Chem.*, 40, 2011–2016 (1997); Shan, D. et al., *J. Pharm. Sci.*, 86 (7), 765–767; Bagshawe K., *Drug Dev. Res.*, 34, 220–230 (1995); Bodor, N., *Advances in Drug Res.*, 13, 224–331 (1984); Bundgaard, H., *Design of Prodrugs* (Elsevier Press 1985); and Larsen, I. K., *Design and Application of Prodrugs*, Drug Design and Development (Krogsgaard-Larsen et al., eds., Harwood Academic Publishers, 1991).

A "solvate" is intended to mean a pharmaceutically acceptable solvate form of a specified compound that retains the biological effectiveness of such compound. Examples of solvates include compounds of the invention in combination with water, isopropanol, ethanol, methanol, DMSO, ethyl acetate, acetic acid, or ethanolamine.

A "pharmaceutically acceptable salt" is intended to mean a salt that retains the biological effectiveness of the free-acid or base form of the specified compound and that is pharmaceutically suitable. Examples of pharmaceutically acceptable salts include sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycollates, tartrates, methancsulfonates, propanesulfonates, naphthalene-1-sulfonates, naphthalene-2-sulfonates, and mandelates.

If an inventive compound is a base, a desired salt may be prepared by any suitable method known in the art, including treatment of the free base with: an inorganic acid, such as hydrochloric acid, hydrobromic acid, sulfuric acid, nitric acid, phosphoric acid, and the like; or with an organic acid, such as acetic acid, maleic acid, succinic acid, mandelic acid, fumaric acid, malonic acid, pyruvic acid, oxalic acid, glycolic acid, salicylic acid, pyranosidyl acid such as glucuronic acid or galacturonic acid; alpha-hydroxy acid such as citric acid or tartaric acid; amino acid such as aspartic acid or glutamic acid; aromatic acid such as benzoic acid or cinnamic acid; sulfonic acid such as p-toluenesulfonic acid or ethanesulfonic acid; or the like.

If an inventive compound is an acid, a desired salt may be prepared by any suitable method known in the art, including treatment of the free acid with an inorganic or organic base, such as an amine (primary, secondary, or tertiary), an alkali metal or alkaline earth metal hydroxide, or the like. Illustrative examples of suitable salts include: organic salts derived from amino acids such as glycine and arginine; ammonia; primary, secondary, and tertiary amines; and cyclic amines, such as piperidine, morpholine, and piperazine; as well as inorganic salts derived from sodium, calcium, potassium, magnesium, manganese, iron, copper, zinc, aluminum, and lithium.

In the case of compounds, salts, or solvates that are solids, it is understood by those skilled in the art that the inventive compounds, salts, and solvates may exist in different crystalline or polymorph forms, all of which are intended to be within the scope of the present invention and specified formulas.

In some cases, the inventive compounds will have chiral centers. When chiral centers are present, the inventive compounds may exist as single stereoisomers, racemates, and/or mixtures of enantiomers and/or diastereomers. All such single stereoisomers, racemates, and mixtures thereof are intended to be within the broad scope of the generic structural formulae (unless otherwise indicated). Preferably, however, the inventive compounds are used in essentially optically pure form (as generally understood by those skilled in the art, an optically pure compound is one that is enantiomerically pure). Preferably, the compounds of the invention are at least 90% of the desired single isomer (80% enantiomeric excess), more preferably at least 95% (90% e.e.), even more preferably at least 97.5% (95% e.e.), and most preferably at least 99% (98% e.e.).

The tautomeric forms of the compounds of formula I are also intended to be covered by the depicted general formula. For example, when R$^1$ is OH or SH and Y is N, the tautomeric forms of formula I are available.

Preferred R$^1$ groups for compounds of formula I include unsubstituted, mono- and di-substituted aryl and heteroaryl groups; and alkyl groups unsubstituted or substituted with optionally substituted aryl or heteroaryl groups. Also preferred are compounds wherein R$^1$ is: C(O)R$^{12}$, where R$^{12}$ is alkyl or NR$^{21}$, R$^{22}$; or S(O)$_n$R$^{16}$, where R$^{16}$ is H or alkyl and n is 0, 1, or 2 (the sulfur atom is partially or fully oxidized).

$R^2$ is preferably H or lower alkyl. $R^4$ is preferably H or halogen. $R^5$, $R^6$, $R^7$, and $R^8$ are each preferably H or an optionally substituted alkyl or acyl group.

In other preferred embodiments of the formula I, $R^1$ is optionally substituted aryl or heteroaryl; $R^2$ is H; $R^4$ is H or halogen; $R^5$, $R^6$, $R^7$, and $R^8$ are each H; and X is oxygen.

In other preferred embodiments of formula I, $R^1$ is OH or SH, and Y is N. More preferably, such compounds are the tautomers of formula I represented by formula II, where Z is O or S, $R^9$ is H or alkyl, and all other variables have the definitions given above:

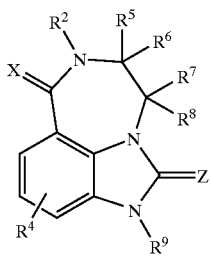

(II)

In preferred embodiments of formula II, $R^2$ and $R^9$ are each independently H or methyl, $R^4$ is H or halogen, $R^5$, $R^6$, $R^7$, and $R^8$ are each H, and X is oxygen.

In further preferred embodiments, the PARP-inhibiting compounds are represented by formula III:

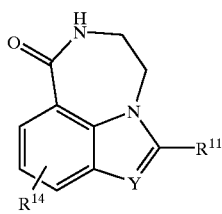

(III)

wherein:

Y is as defined above;

$R^{11}$ is an aryl or heteroaryl group unsubstituted or substituted with one or more substituents selected from halogen, hydroxy, nitro, and amino, and alkyl, aryl, heteroaryl, alkoxy, aryloxy, and heteroaryloxy groups unsubstituted or substituted with one or more substituents selected from halogen, hydroxy, lower alkoxy, cyano, nitro, and amino; and $R^{14}$ is H or halogen.

In preferred embodiments of formula III, $R^{11}$ is mono- or di-substituted phenyl.

Preferred species of the invention include:

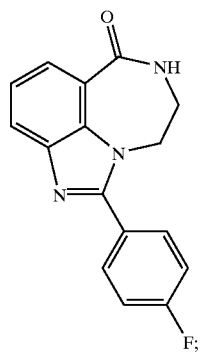

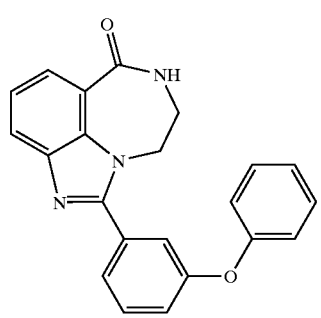

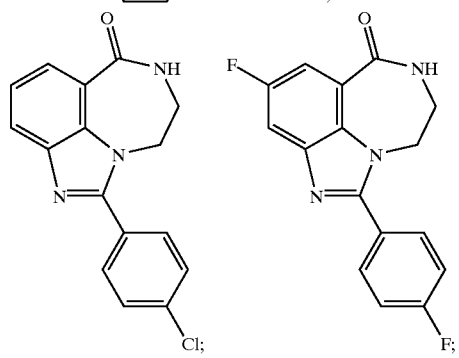

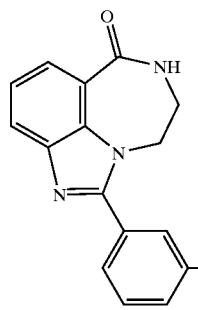

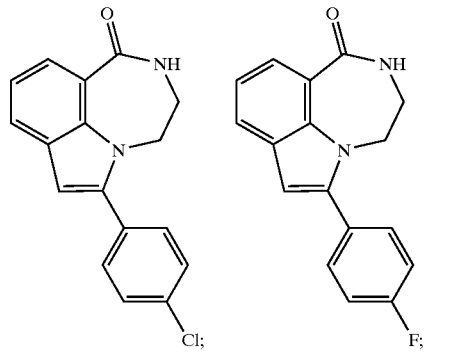

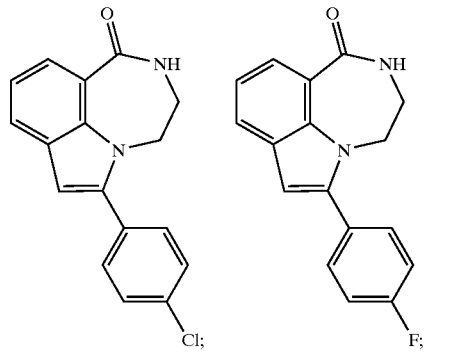

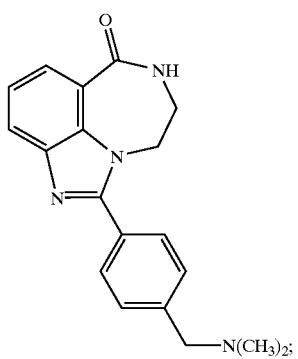
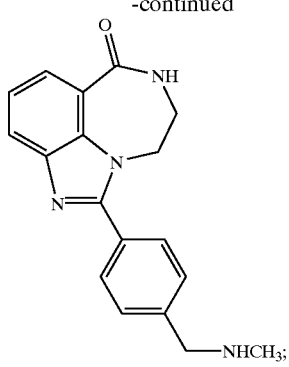
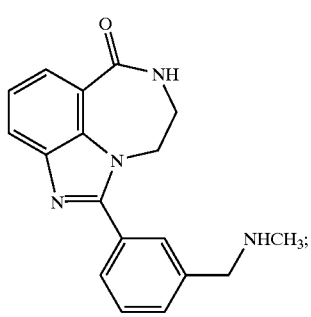
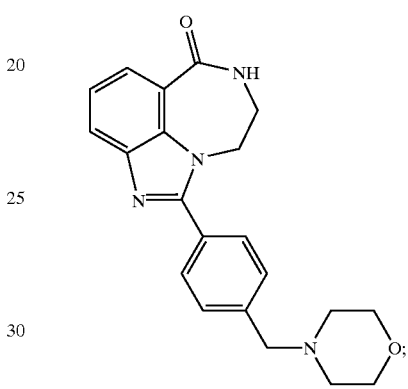
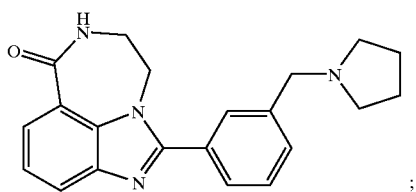
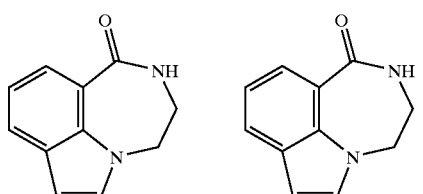
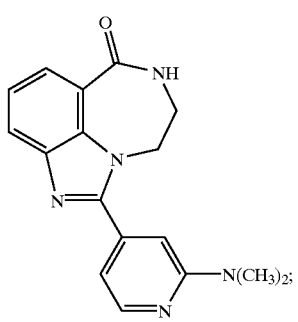
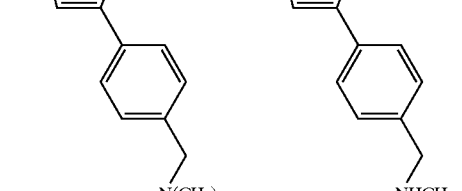
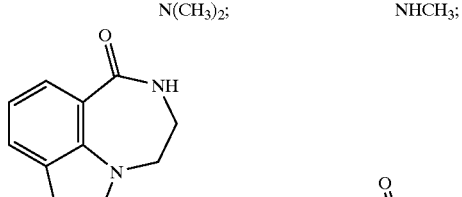
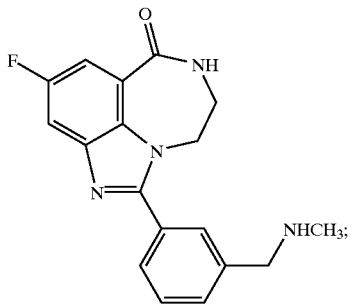
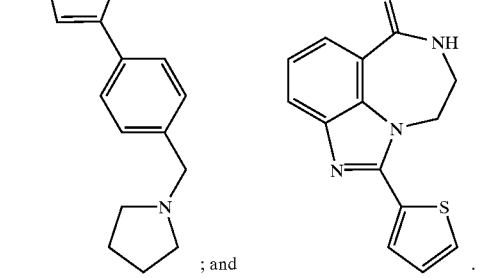

Especially preferred species are described in the Examples as Examples 2, 6, 8, 14, 34, 37, 58, 59, 75, 82, 98, 99, 119, 129, 130, 132, 134, 137, 141, 142, 148, 149, 170, 171, 177, 184, 186, 197, 203, 207, 210, 211, 212, 223, 233, 245 and 246.

Pharmaceutical Methods and Compositions

The invention is also directed to a method of inhibiting PARP enzyme activity, comprising contacting the enzyme with an effective amount of a compound of formula I, II, or III, or a pharmaceutically acceptable salt, prodrug, active metabolite, or solvate thereof (collectively, "agents"). For example, PARP activity may be inhibited in mammalian tissue by administering such an agent.

"Treating" or "treatment" is intended to mean mitigating or alleviating an injury is or a disease condition in a mammal, such as a human, that is mediated by the inhibition of PARP activity, such as by potentiation of anti-cancer therapies or inhibition of neurotoxicity consequent to stroke, head trauma, and neurodegenerative diseases. Types of treatment include: (a) as a prophylactic use in a mammal, particularly when the mammal is found to be predisposed to having the disease condition but not yet diagnosed as having it; (b) inhibition of the disease condition; and/or (c) alleviation, in whole or in part, of the disease condition.

The invention also provides therapeutic interventions appropriate in disease or injury states where PARP activity is deleterious to a patient. For example, the tricyclic compounds of the invention are useful for treating cancer, inflammation, the effects of heart attack, stroke, head trauma and neurodegenerative disease, and diabetes.

One treatment method involves improving the effectiveness of a cytotoxic drug and/or radiotherapy administered to a mammal in the course of therapeutic treatment, comprising administering to the mammal an effective amount of a PARP-inhibiting agent (compound, pharmaceutically acceptable salt, prodrug, active metabolite, or solvate) in conjunction with administration of the cytotoxic drug (e.g., topotecan, irinotecan, temozolimide) and/or radiotherapy. The agents of the invention preferably have a cytotoxicity potentiation activity corresponding to a $PF_{50}$ of greater than I in the cytotoxicity potentiation assay.

The PARP-inhibiting agents may also be advantageously used in a method for reducing neurotoxicity consequent to stroke, head trauma, and neurodegenerative diseases in a mammal by administering a therapeutically effective amount of an inventive agent to the mammal.

The PARP-inhibiting agents of the invention may also be used in a method for delaying the onset of cell senescence associated with skin aging in a human, comprising administering to fibroblast cells in the human an effective PARP-inhibiting amount of an agent.

Further, the agents may also be used in a method for helping prevent the development of insulin-dependent diabetes mellitus in a susceptible individual, comprising administering a therapeutically effective amount of an agent.

Additionally, the agents may also be employed in a method for treating an inflammatory condition in a mammal, comprising administering a therapeutically effective amount of an agent to the mammal.

Moreover, the agents may also be used in a method for treating cardiovascular disease in a mammal, comprising administering to the mammal a therapeutically effective amount of a PARP-inhibiting agent. More particularly, a therapeutic intervention method provided by the present invention is a cardiovascular therapeutic method for protecting against myocardial ischemia and reperfusion injury in a mammal, comprising administering to the mammal an effective amount of a compound of formula I, II, or III or a pharmaceutically acceptable salt, prodrug, active metabolite, or solvate thereof.

The activity of the inventive agents as inhibitors of PARP activity may be measured by any of the suitable methods known or available in the art, including by in vivo and in vitro assays. An example of a suitable assay for activity measurements is the PARP enzyme inhibition assay described herein.

Administration of the compounds of the formula I, II, or III and their pharmaceutically acceptable prodrugs, salts, active metabolites, and solvates may be performed according to any of the generally accepted modes of administration available in the art. Illustrative examples of suitable modes of administration include intravenous, oral, nasal, parenteral, topical, transdermal, and rectal delivery. Oral and intravenous delivery are preferred.

An inventive agent may be administered as a pharmaceutical composition in any pharmaceutical form recognizable to the skilled artisan as being suitable. Suitable pharmaceutical forms include solid, semisolid, liquid, or lyophilized formulations, such as tablets, powders, capsules, suppositories, suspensions, liposomes, and aerosols. Pharmaceutical compositions of the invention may also include suitable excipients, diluents, vehicles, and carriers, as well as other pharmaceutically active agents (including other PARP-inhibiting agents), depending upon the intended use.

Acceptable methods of preparing suitable pharmaceutical forms of the compositions are generally known or may be routinely determined by those skilled in the art. For example, pharmaceutical preparations may be prepared following conventional techniques of the pharmaceutical chemist involving steps such as mixing, granulating, and compressing when necessary for tablet forms, or mixing, filling, and dissolving the ingredients as appropriate to give the desired products for intravenous, oral, parenteral, topical, intravaginal, intranasal, intrabronchial, intraocular, intraaural, and/or rectal administration.

Solid or liquid pharmaceutically acceptable carriers, diluents, vehicles, or excipients may be employed in the pharmaceutical compositions. Illustrative solid carriers include starch, lactose, calcium sulphate dihydrate, terra alba, sucrose, talc, gelatin, pectin, acacia, magnesium stearate, and stearic acid. Illustrative liquid carriers include syrup, peanut oil, olive oil, saline solution, and water. The carrier or diluent may include a suitable prolonged-release material, such as glyceryl monostearate or glyceryl distearate, alone or with a wax. When a liquid carrier is used, the preparation may be in the form of a syrup, elixir, emulsion, soft gelatin capsule, sterile injectable liquid (e.g., solution), or a nonaqueous or aqueous liquid suspension.

A dose of the pharmaceutical composition contains at least a therapeutically effective amount of a PARP-inhibiting agent (i.e., a compound of formula I, II, or III, or a pharmaceutically acceptable salt, prodrug, active metabolite, or solvate thereof), and preferably contains one or more pharmaceutical dosage units. The selected dose may be administered to a mammal, for example, a human patient, in need of treatment of a condition mediated by inhibition of PARP activity, by any known or suitable method of administering the dose, including: topically, for example, as an ointment or cream; orally; rectally, for example, as a suppository; parenterally by injection; or continuously by intravaginal, intranasal, intrabronchial, intraaural, or intraocular infusion. A "therapeutically effective amount" is intended to mean the amount of an agent that, when administered to a mammal in need thereof, is sufficient to effect treatment for injury or disease condition mediated by inhibition of PARP activity. The amount of a given agent of the invention that will be therapeutically effective will vary depending upon factors such as the particular agent, the disease condition and the severity thereof, the identity of the mammal in need thereof, which amount may be routinely determined by artisans.

It will be appreciated that the actual dosages of the PARP-inhibiting agents used in the pharmaceutical compositions of this invention will be selected according to the properties of the particular agent being used, the particular composition formulated, the mode of administration and the particular site, and the host and condition being treated. Optimal dosages for a given set of conditions can be ascertained by those skilled in the art using conventional dosage-determination tests. For oral administration, e.g., a dose that may be employed is from about 0.001 to about 1000 mg/kg body weight, with courses of treatment repeated at appropriate intervals.

Synthetic Processes

The PARP-inhibiting agents of the invention may be synthesized according to the processes described below, such as the one of the following general processes.

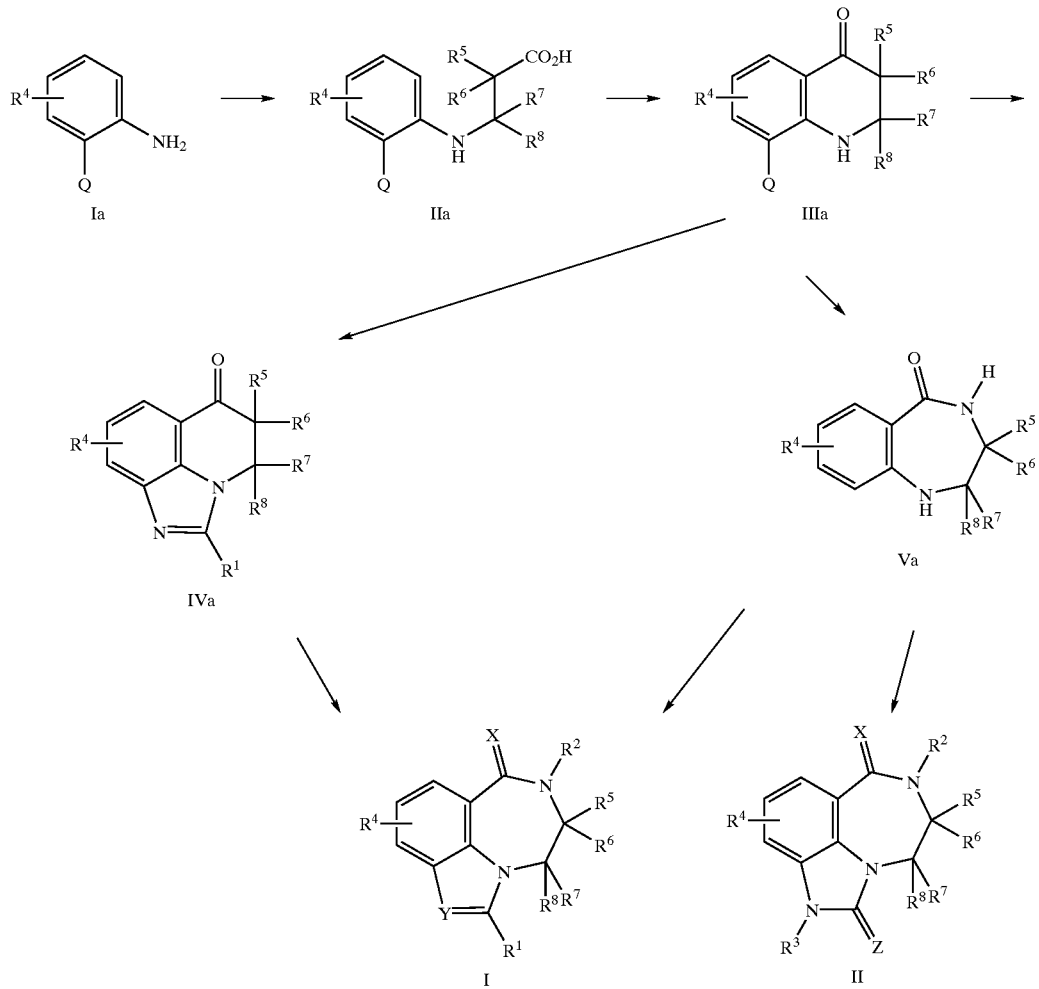

General Process A

In this process, an ortho-substituted-aniline (Ia) is alkylated to an N-substituted intermediate (IIa), which can be further converted to cyclic ketone (IIIa). The ketone (IIIa) can be transformed to a compound of formula I via alternative routes. When Q is a nitro group, it can be reduced to the corresponding amine and further used in a reaction with an acid chloride to provide tricyclic ketone intermediate (IVa). Ring expansion of (IVa) yields a tricyclic amide with formula I (Y=N, X=O), which may be further derivatized. A more preferred and alternative route for the conversion of a ketone (IIIa) to I (Y=N) or II (Z=O, S) involves first performing the ring expansion step to yield intermediate amide (Va), followed by reduction of the nitro group and cyclization with an acid chloride, aldehyde, or any reagent used to form a urea or thiourea. The product formed may also be further derivatized. For intermediate (IIIa) when Q is an appropriate leaving group, however, it can be transformed to an acetylene derivative (Va) where Q is C≡C—$R_1$, which is further converted to I (Y=CH). The product formed may also be further derivatized.

General Process B

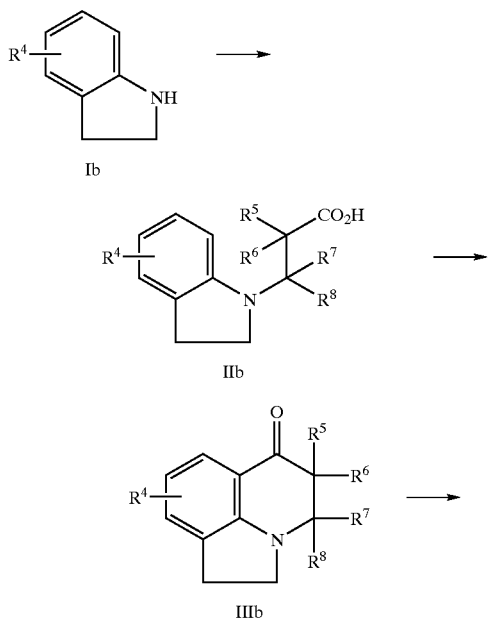

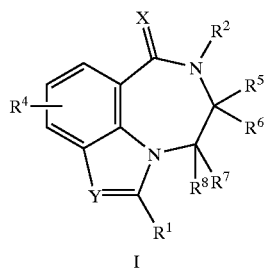

Under this reaction scheme, an indoline (Ib) is alkylated to the N-substituted intermediate (IIb), which is further converted to tricyclic ketone (IIIb). The tricyclic ketone (IIIb) is exposed to conditions for ring expansion and oxidized to yield compounds of formula I (Y=CH), which may be further derivatized.

General Process C

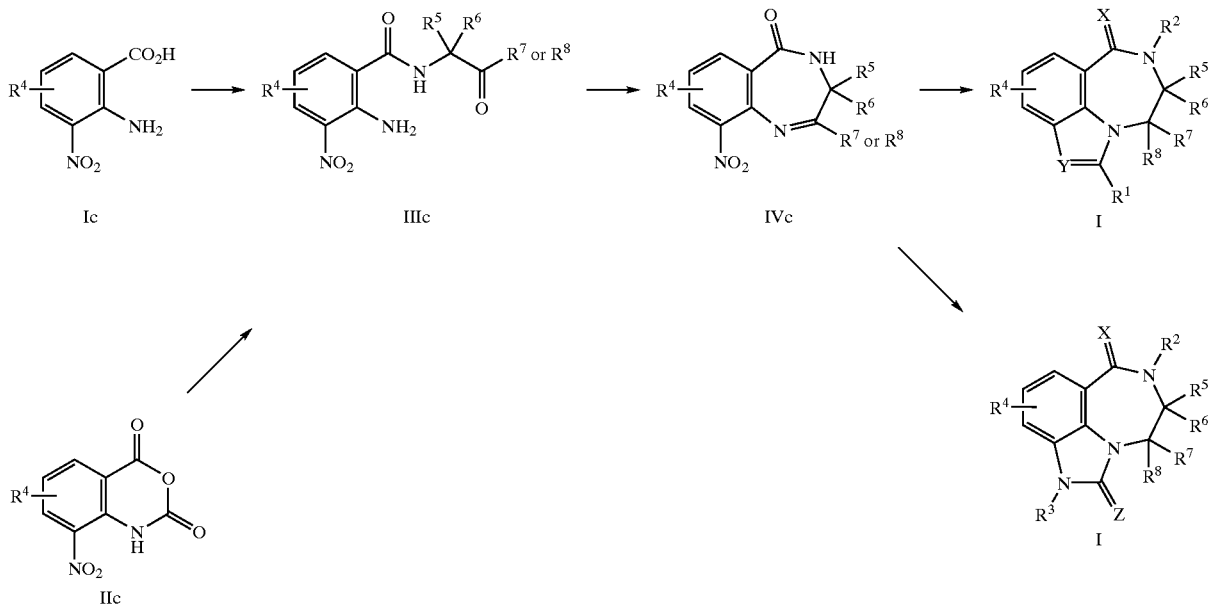

In this process, a nitro-anthranilic acid (Ic) or nitro-isotoic anhydride (IIc) is transformed to an intermediate amino acylbenzamide (IIIc). This intermediate is further transformed to the ortho-nitro cyclic imine (IVc). The imine and nitro functionalities are concomitantly reduced followed by cyclization with an acid chloride, aldehyde, or reagent used to form a urea or thiourea yielding compounds of formula I (Y=N) or II (Z=O, S).

General Process D

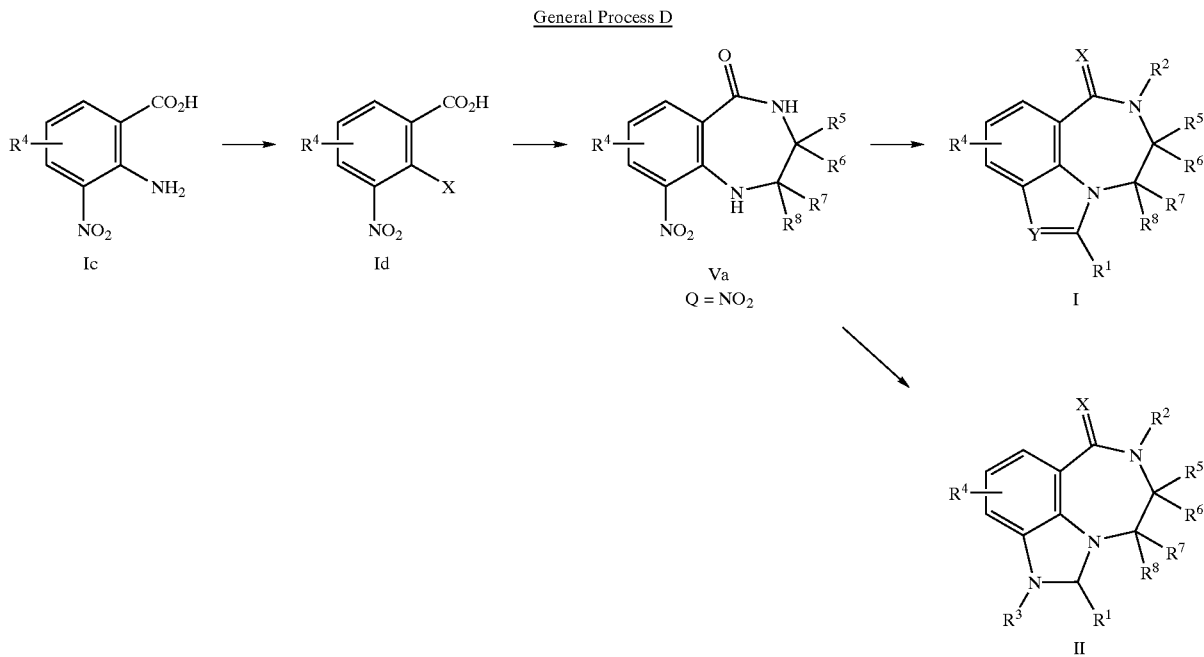

Compounds of formula I (Y=N) or II (Z=O, S) can also be prepared via an alternative route from intermediate Va (Q=NO$_2$). Nitro-anthranilic acid (Ic) is first converted to nitro-benzoic acid ester (Id), where X is a halide or an appropriate leaving group, followed by cyclization to Va with an appropriate ethylenediamine.

More particularly, the following reaction schemes are useful in the preparation of the illustrated compounds of the invention.

Scheme 1

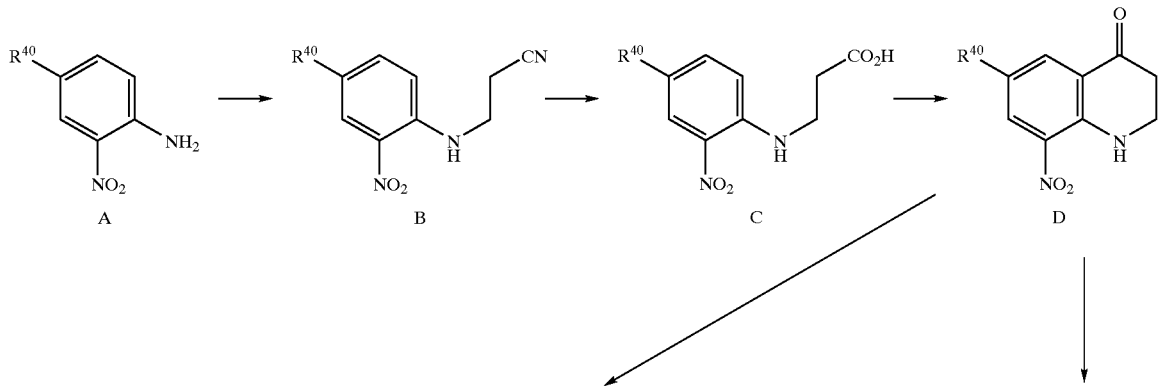

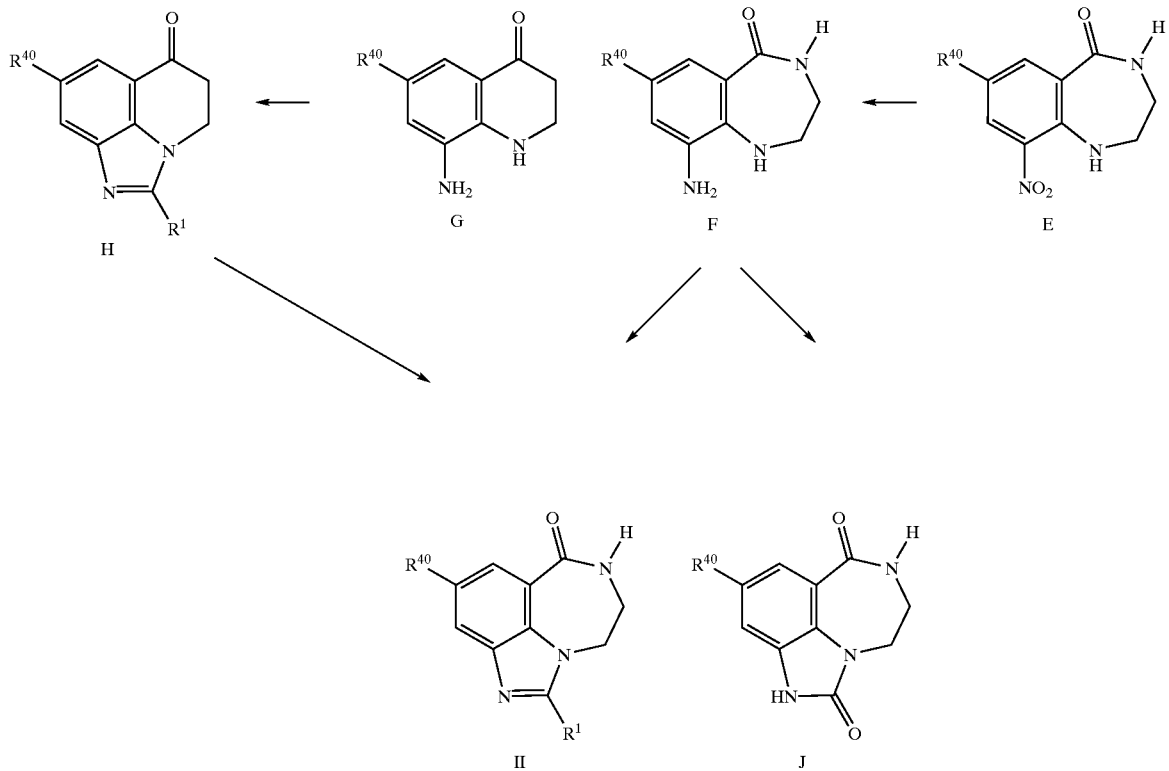

In this scheme, 2-nitroaniline A ($R^{40}$=H, F) is N-alkylated with acrylonitrile to yield B. The nitrile group of B is hydrolyzed to carboxylic acid C, which is subjected to Friedel-Craft-type intramolecular cyclization conditions to form ketone D. Nitro-ketone D is reduced to the diamino-ketone G, which undergoes cyclization to H ($R^1$=aryl, alkyl) when exposed to an acid chloride or aldehyde. Tricyclic ketone H can be transformed via a Schmidt-type reaction with $NaN_3$ and acid to tricyclic lactam I. Alternatively and preferable, nitro-ketone D is first transformed to tricylic lactam E via the Schmidt reaction, reduced to diamino-lactam F, and further exposed to an acid chloride, aldehyde, $CS_2$, thiophosgene, thiocarbonyl diimidazole or equivalent reagent to form I ($R^1$=aryl, alkyl, SH). Diamino-lactam F may also be converted to tricyclic lactam J when exposed to phosgene, carbonyl diimidazole or equivalent reagent. In all cases, I may be optionally modified at $R^1$.

Scheme 1a
Alternative Route to intermediate E

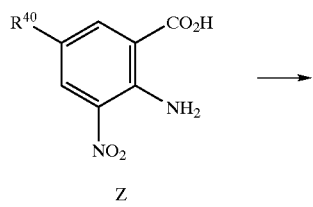

In this scheme, 3-nitroanthranilic acid Z ($R^{40}$=H) is converted to methyl ester FF ($R^{40}$=H). Diazotization of the amino group of FF ($R^{40}$=H) and halogenation transforms it into bromide GG ($R^{40}$=H). The cyclic lactam E ($R^{40}$=H) is formed by displacement of the bromide and subsequent cyclization with ethylene diamine.

Scheme 2

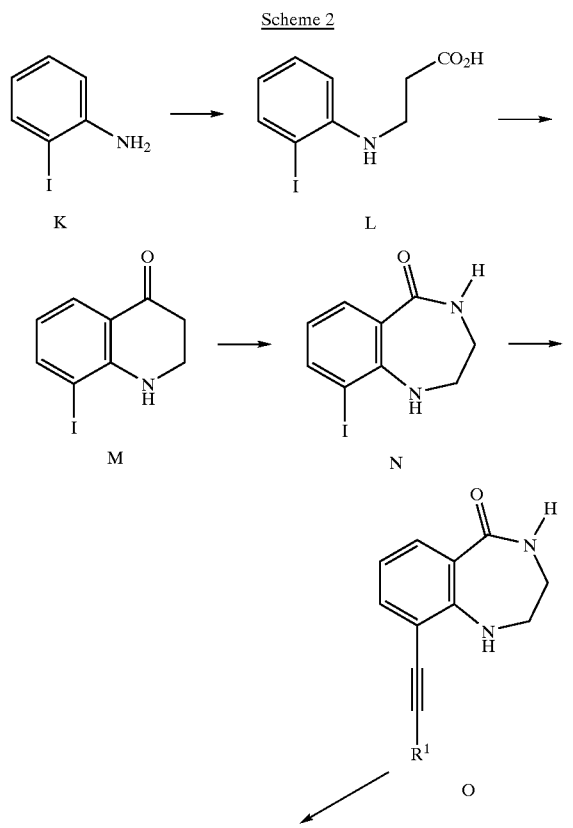

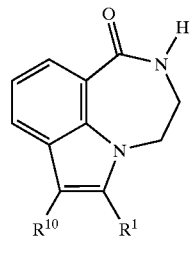

Here, 2-iodoaniline K is N-alkylated with β-propiolactone to yield L, which is subjected to Friedel-Craft-type intramolecular cyclization conditions to form ketone M. Iodo-ketone M is transformed to iodo-lactam N via a Schmidt-type reaction with $NaN_3$ and acid. Intermediate N is converted to the corresponding substituted acetylene O, is where $R^1$ is aryl, alkyl, H or —Si(alkyl)$_3$, using a metal-catalyzed reaction, typically employing both palladium and copper(I). Tricyclic lactam P is formed by further exposing acetylene O to a metal-catalyzed reaction, typically using palladium. P is optionally modified at $R^1$ and $R^{10}$.

Scheme 3

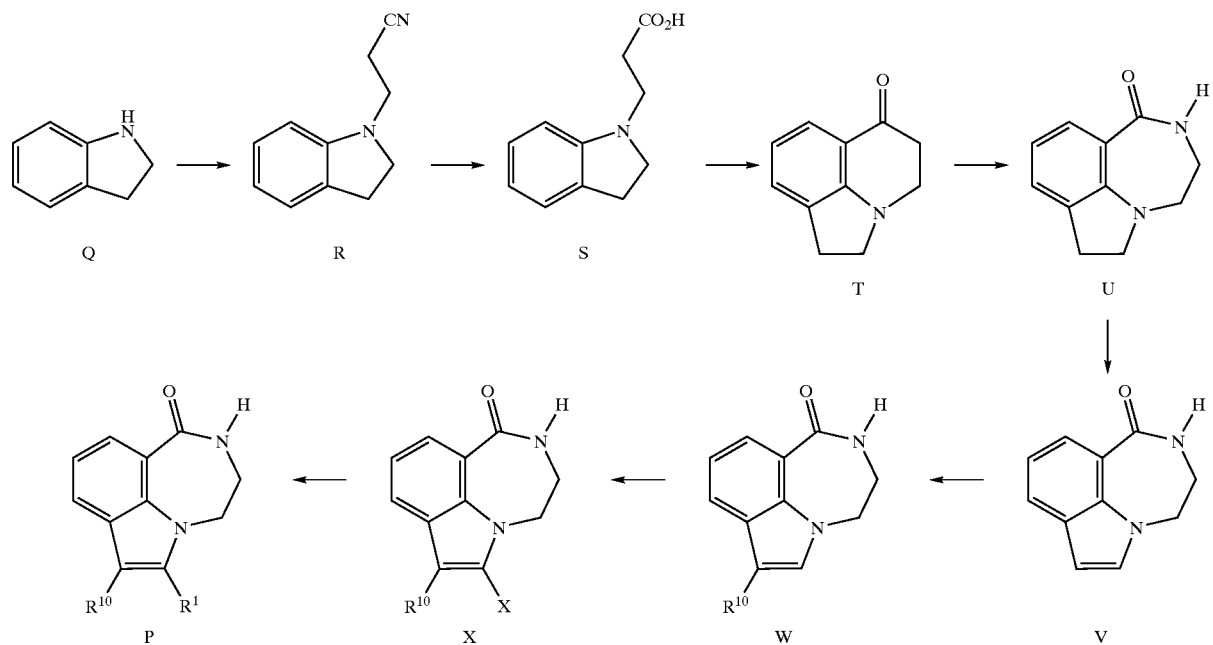

In this scheme, indoline Q is N-alkylated with acrylonitrile to yield R. The nitrile group of R is hydrolyzed to carboxylic acid S, which is subjected to Friedel-Craft-type intramolecular cyclization conditions to form ketone T.

Tricyclic ketone T is exposed to Schmidt-type ring-expansion reaction conditions with NaN$_3$ and acid to form tricyclic lactam U. Intermediate U is oxidized to produce V, which can then be further modified. For example, V can be halogenated or formylated to W, where $R^{10}$=I, CHO. In all cases W is optionally modified at $R^{10}$. Product W may also be halogenated to product X, where the formula variable X is iodine. Product X can be transformed via a metal-catalyzed reaction (typically with palladium as catalyst) into a number of different tricyclic lactams P where $R^1$ is aryl, etc. P may be optionally modified at $R^1$ and $R^{10}$.

protic solvent signals as follows: CHCl$_3$=7.26 ppm; DMSO=2.49 ppm; C$_6$HD$_5$=7.15 ppm. Peak multiplicities are designated as follows: s=singlet; d=doublet; dd=doublet of doublets; t=triplet; q=quartet; br=broad resonance; and m=multiplet. Coupling constants are given in Hertz (Hz). Infrared absorption (IR) spectra were obtained using a Perkin-Elmer 1600 series or a Midac Corporation FTIR spectrometer. Elemental microanalyses were performed by Atlantic Microlab Inc. (Norcross, Ga.) or Galbraith Laboratories (Nashville, Tenn.), and gave results for the elements stated within ±0.4% of the theoretical values. Flash column Scheme 4

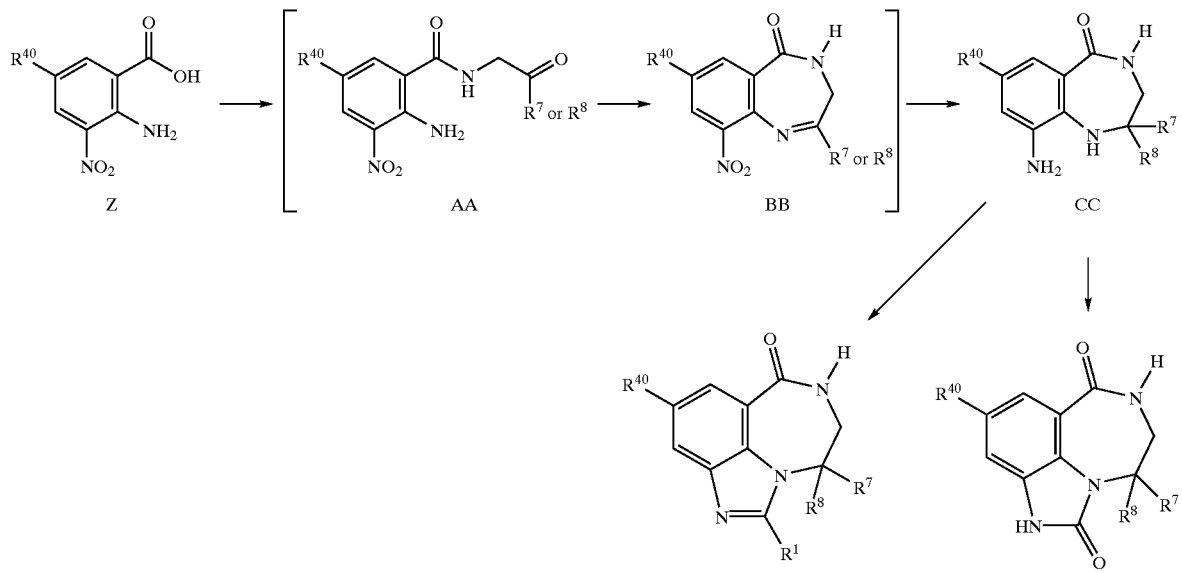

In this scheme, 3-nitroanthranilic acid Z ($R^{40}$=H) is converted sequentially to intermediate amide AA and cyclic imine BB, which are usually not isolated, but further subjected to hydrogenation to form cyclic diamino-lactam CC where $R^7$ or $R^8$ is H, alkyl, or aryl. When CC (one of $R^7$ and $R^8$ must be H) is further exposed to an acid chloride, aldehyde, CS$_2$, thiophosgene, thiocarbonyl diimidazole or equivalent reagent, tricyclic lactam DD is formed ($R^1$=aryl, alkyl, SH; $R^7$ or $R^8$=H, alkyl, or aryl.). Diamino-lactam CC may also be converted to tricyclic lactam EE when exposed to phosgene, carbonyl diimidazole or equivalent reagent. In all cases DD and EE are optionally modified at $R^1$, $R^7$, and/or $R^8$.

EXAMPLES

The invention is further illustrated by reference to the following specific examples. Unless otherwise indicated, all percentages and parts are by weight, and all temperatures are in degrees Celsius. In the following examples, the structures of the compounds were confirmed by one or more of the following: proton magnetic resonance spectroscopy, infrared spectroscopy, elemental microanalysis, mass spectrometry, thin layer chromatography, high performance liquid chromatography, and melting point.

Proton magnetic resonance ($^1$H NMR) spectra were determined using a 300 megahertz Tech-Mag, Bruker Avance 300DPX, or Bruker Avance 500 DRX spectrometer operating at a field strength of 300 or 500 megahertz (MHz). Chemical shifts are reported in parts per million (ppm, δ) downfield from an internal tetramethylsilane standard. Alternatively, $^1$H NMR spectra were referenced to residual chromatography was performed using Silica gel 60 (Merck Art 9385). Analytical thin layer chromatography (TLC) was performed using precoated sheets of Silica 60 F$_{254}$ (Merck Art 5719). Analytical HPLC was performed using a Hewlett Packard (HP) Series 1100 Quaternary system, equipped with an HP 1100 variable wavelength detector set at 254 nm; sensitivity 0.02 to 50 AUFS. A Pheomenex Prodigy 5 ODS (3) column (250 mm×4.6 mm; 5 μm) was used. Typically, a gradient mobile phase starting with 90% H$_2$O with 0.1% TFA, 10% CH$_3$CN with 0.1% TFA up to 20 minutes (min), then 35% H$_2$O with 0.1% TFA, 65% CH$_3$CN with 0.1% TFA up to 25 min, then 10% H$_2$O with 0.1% TFA, 90% CH$_3$CN with 0.1% TFA thereafter was used. Flow rate=1 mL/min. Preparative HPLC was performed using a Gilson Model 806 Manometric module, equipped with a Gilson 811c dynamic mixer, two Gilson Model 306 pumps, a Gilson 215 liquid handler, and a Gilson Model 119 UV/visible detector set at 214 or 220 and 254 nm; sensitivity 0.02 to 50 AUFS. A Metasil AQ C18 column (250 mm×212 mm; 10 μm) was used. Typically a gradient mobile phase, starting with 90% H$_2$O with 0.1% TFA, 10% CH$_3$CN with 0.1% TFA up to 2 min, then reaching 35% H$_2$O with 0.1% TFA, 65% CH$_3$CN with 0.1% TFA after 22 min or 90% 0.1M NH$_4$OAc, 10% CH$_3$CN up to 2 min, then reaching 100% CH$_3$CN after 22 min, was used. Flow rate=25 mL/min. Melting points (mp) were determined on a MelTemp apparatus and are uncorrected. All reactions were performed in septum-sealed flasks under a slight positive pressure of argon, unless otherwise noted. All commercial solvents were reagent-grade or better and used as supplied.

The following abbreviations may be used herein: Et$_2$O (diethyl ether); DMF (N,N-dimethylformamide); DMSO (dimethylsulfoxide); MeOH (methanol); EtOH (ethanol); EtOAc (ethyl acetate); THF (tetrahydrofuran); Ac (acetyl); Me (methyl); Et (ethyl); and Ph (phenyl).

Example 1

1-Phenyl-8,9-dihydro-7H-2,7,9a-triaza-benzo[cd]azulen-6-one

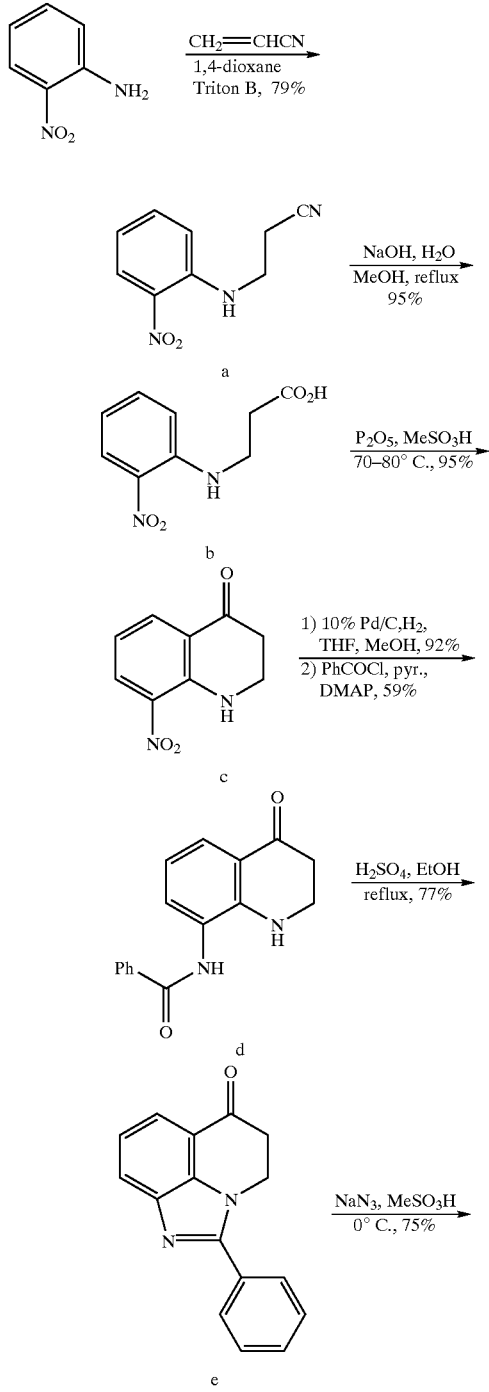

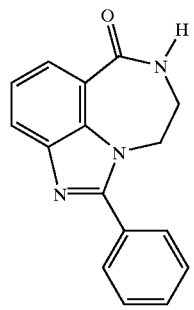

(a) Intermediate a—3-(2-Nitrophenylamino)-propionitrile (Maryanoff et al., *J. Med. Chem.* 38, 16 (1995)):

2-Nitroaniline (22.4 g, 159 mmol) was dissolved in 1,4-dioxane (160 mL). Acrylonitrile (12.68 mL, 190 mmol) was added to the reaction flask followed by 0.50 mL of benzyltrimethylammonium hydroxide, 40 wt. % solution in methanol (Triton B). The slightly exothermic reaction was allowed to stir for 1 hour (h), after which the solvent was removed in vacuo. The crude solid was triturated with $Et_2O$ to remove some of the dark color. The product was recrystallized with EtOAc to give 24.07 g (79% yield) of an orange solid: mp=112–115° C. (Lit. 109–112° C. (Kamenka et al., *J. Heterocycl. Chem.* 10, 459 (1973); German Patent Publication DE 2056215)); $R_f$=0.18 (30% EtOAc/hexanes); $^1H$ NMR ($CDCl_3$) δ 2.77 (t, 2H, J=7.0 Hz), 3.76 (q, 2H, J=6.8 Hz), 6.78–6.81 (m, 1H), 6.88 (d, 1H, J=8.5 Hz), 7.52–7.55 (m, 1H), 8.21 (br, 1H), 8.25 (dd, 1H, J=8.6, 1.5 Hz).

(b) Intermediate b—3-(2-Nitrophenylamino)-propionic Acid (Kamenka et al., *J. Heterocycl. Chem.* 10, 459 (1973)):

3-(2-Nitrophenylamino)-propionitrile a (25.45 g, 133.12 mmol) was dissolved in MeOH (250 mL). A 10%-solution of NaOH (250 mL) was added, and the reaction mixture was refluxed for 3.5 h. The MeOH was removed in vacuo, and the residue was dissolved in $H_2O$ and acidified to a pH=2–3 with 10% HCl. The resulting precipitate was filtered off and washed with $H_2O$ and dried overnight under vacuum. The product (26.47 g, 95%) was obtained as a yellow solid: mp=146–147° C. (Lit.=144–145° C.); $^1H$ NMR ($CDCl_3$) δ 2.81 (t, 2H, J=6.7 Hz), 3.69–3.72 (m, 2H), 6.70–6.73 (m, 1H), 6.91 (d, 1H, J=8.6 Hz), 7.48–7.51 (m, 1H), 8.21 (dd, 1H, J=8.6, 1.5 Hz).

(c) Intermediate c—8-Nitro-2,3-dihydro-1H-quinolin-4-one (Kamenka et al., *J. Heterocycl. Chem.* 10, 459 (1973)):

3-(2-Nitrophenylamino)-propionic acid b (26.89 g, 127.93 mmol) was added into a flask containing stirred Eaton's Reagent ($P_2O_5$, 7.5 wt. % in methanesulfonic acid) (562 g, 375 mL). The reaction mixture was heated to 70–80° C. for 1.5 h, then cooled to ambient temperature, after which ice was added. The product was extracted with EtOAc, and the organic phase was washed with $H_2O$ and brine, dried ($MgSO_4$), and concentrated. The residue was dissolved in hot benzene and filtered through paper to remove some white solids. The volume of solvent was reduced until the product began to crystallize. The solids were filtered and washed with $Et_2O$, yielding 11.41 g (46%): mp=150–152° C. (Lit.=144–145° C.); $R_f$=0.26 (30% EtOAc/hexanes); $^1H$ NMR ($CDCl_3$) δ 2.83 (t, 2H, J=7.0 Hz), 3.80–3.85 (m, 2H), 6.76–6.81 (m, 1H), 8.21–8.24 (m, 1H), 8.35 (br, 1H), 8.41 (dd, 1H, J=8.4, 1.5 Hz).

(d) Intermediate d—N-(4-Oxo-1,2,3,4-tetrahydroquinolin-8-yl)benzamide:

8-Nitro-2,3-dihydro-1H-quinolin-4-one c (0.39 g, 2.05 mmol) was dissolved in THF (5 mL) and MeOH (13 mL) and placed under an argon atmosphere. To this solution 10% Pd/C (0.06 g) was added, and the flask was evacuated and placed twice under a hydrogen atmosphere. The reaction mixture was stirred at ambient temperature overnight. The catalyst was filtered off, and the solvent removed in vacuo. The residue was dissolved in 1,4-dioxane (15 mL) and a solution of 4M HCl/dioxane (1.07 mL) was added and stirred for 5 min. The solvent was removed in vacuo, and the residual solids triturated with Et$_2$O. These solids were filtered off and washed with additional Et$_2$O to give 0.44 g (92%) of the diamine intermediate, which was used without further purification. The diamine (0.41 g, 1.76 mmol) was dissolved in pyridine (9 mL), and 4-dimethylaminopyridine (0.02 g, 0.18 mmol) was added followed by benzoyl chloride (0.23 mL, 1.94 mmol). The reaction mixture was stirred overnight at room temperature (rt), at which time the solvent was removed in vacuo. Toluene was added and the solution was reconcentrated under vacuum to remove any residual pyridine. The solid residue was dissolved in CH$_2$Cl$_2$, and washed with water and brine, followed by drying over MgSO$_4$. Filtration and removal of solvent gave the crude product, which was purified by flash silica gel chromatography (30–70% EtOAc/hexanes) yielding 0.28 g (59%) of a gold-colored solid. A small analytical sample was recrystallized (MeOH/EtOAc): mp=232–234° C.; R$_f$=0.13 (50% EtOAc/hexanes); IR(KBr) 1657, 1607, 1516 cm$^{-1}$; $^1$H NMR (DMSO-d$_6$) δ 2.51–2.59 (m, 2H), 3.44–3.49 (m, 2H), 6.42 (br, 1H), 6.63–6.68 (m, 1H), 7.34–7.37 (m, 1H), 7.50–7.63 (m, 4H), 8.02–8.05 (m, 2H), 9.72 (s, 1H). LRMS (M+H) 267.

(e) Intermediate e—2-Phenyl-4,5-dihydro-imidazo-[4,5,1-ij]quinolin-6-one:

Anilide intermediate d (0.032 g, 0.12 mmol) was dissolved in EtOH (2.5 mL). Concentrated H$_2$SO$_4$ (0.13 mL) was added, and the reaction mixture was stirred at reflux for 45 min. The mixture was poured into an EtOAc/sat. NaHCO$_3$ solution. The organic phase was separated and washed with H$_2$O and brine, dried over MgSO$_4$, filtered and concentrated in vacuo. The residue was purified by flash silica gel chromatography (3–10% EtOAc/hexanes) to give 0.23 g (77%) of a white solid: mp=114–118° C.; R$_f$=0.16 (30% EtOAc/hexanes); IR(KBr) 1690, 1609, 1457 cm$^{-1}$; $^1$H NMR (DMSO-d$_6$) δ 3.10 (t, 2H, J=6.9 Hz), 4.78 (t, 2H, J=6.9 Hz), 7.36–7.38 (m, 1H), 7.58–7.61 (m, 4H), 7.96–7.98 (m, 3H). LRMS (M$^+$) 248.

(f) Preparation of Title Compound:

Methanesulfonic acid (5 mL) was added to a flask containing intermediate e (0.14 g, 0.55 mmol) at 0° C. The ice bath was removed, and NaN$_3$ (0.05 g, 0.72 mmol) was added portionwise while carefully keeping nitrogen gas evolution under control. The reaction mixture was stirred at rt for 1 h, at which time it was poured onto ice. The pH of the solution was brought to 8.5 with 10% aqueous (aq) NaOH. The product was extracted three times with EtOAc, the organic layers were combined and dried (MgSO$_4$), and the solvent was removed. The product was purified by flash silica gel chromatography (50–75% EtOAc/hexanes) to give 0.108 g (75%) of a white solid: mp=255–257° C.; R$_f$=0.13 (90% EtOAc/hexanes); IR (KBr) 1661, 1478 cm$^{-1}$; $^1$H NMR (DMSO-d$_6$) δ 3.52–3.53 (m, 2H), 4.45–4.46 (m, 2H), 7.34–7.37 (m, 1H), 7.57–7.60 (m, 3H), 7.85–7.91 (m, 4H), 8.43 (t, 1H, J=5.6 Hz). HRMS calcd for C$_{16}$H$_{13}$N$_3$O 263.1059 (M$^+$), found 263.1068. Anal. (C$_{16}$H$_{13}$N$_3$O) C, H, N.

Example 2

1-(4-Fluoro-phenyl)-8,9-dihydro-7H-2,7,9a-triaza-benzo[cd]azulen-6-one

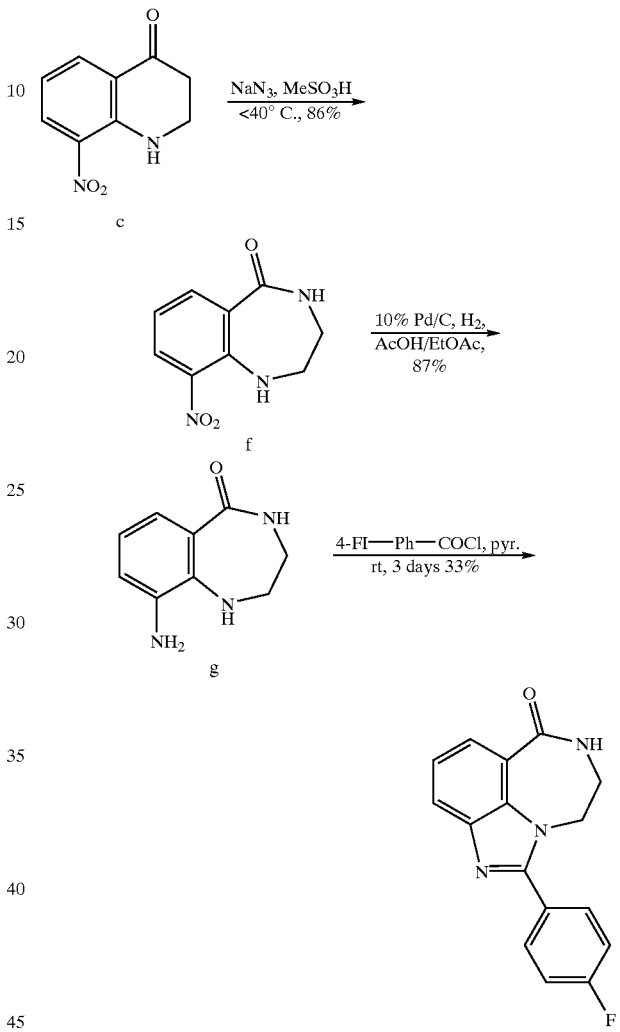

(a) Intermediate f—9-Nitro-1,2,3,4-tetrahydro-benzo[e][1,4]diazepin-5-one

Intermediate c, 8-nitro-2,3-dihydro-1H-quinolin-4-one (1.96 g, 10.2 mmol), was added portionwise to a flask containing stirred methanesulfonic acid (50 mL), while keeping the temperature below 40° C. with a water bath. NaN$_3$ (0.86 g, 13.24 mmol) was carefully added in small portions, maintaining the temperature below 40° C. and keeping the nitrogen gas evolution under control. The reaction mixture was stirred at rt an additional 1 h and then poured onto ice. The pH of the mixture was adjusted to 10 with 10% aq NaOH, and the resulting solids were filtered off and washed with H$_2$O to give 1.46 g of crude product. The aqueous phase was extracted twice with EtOAc, and the organic layers were combined, dried (MgSO$_4$) and filtered, and the solvent was removed to provide an additional 0.57 g of crude product. The combined material was purified by flash silica gel chromatography (20% EtOAc/CHCl$_3$) to give 1.80 g (86%) of an orange solid: mp=190–192° C.; R$_f$=0.11

(40% EtOAc/CHCl$_3$); IR (KBr) 1653, 1603, 1262 cm$^{-1}$; $^1$H NMR (DMSO-d$_6$) δ 3.33–3.35 (m, 2H), 3.61–3.64 (m, 2H), 6.72–5 6.75 (m, 1H), 8.12–8.14 (m, 1H), 8.20–8.22 (m, 1H), 8.38 (s, 1H), 8.68 (s, 1H). LRMS (M$^+$) 207. Anal. (C$_9$H$_9$N$_3$O$_3$) C, H, N.

(b) Title Compound:

In a Parr shaker bottle, intermediate f, 9-nitro-1,2,3,4-tetrahydro-benzo[e][1,4]diazepin-5-one (3.0 g, 14 mmol), was dissolved in EtOAc (70 mL) and glacial acetic acid (30 mL). To this solution was added 10% Pd/C (0.60 g) and the reaction mixture was placed in a Parr hydrogenation apparatus under a hydrogen atmosphere at 50 psi. After shaking for 12 h, the catalyst was filtered off and washed with AcOH and EtOAc. Solvents were removed under vacuum. EtOAc was added to the residue and the product precipitated. The solids were washed with EtOAc. A is second crop was obtained from the EtOAc washes. The resulting solids were filtered and dried to give 2.24 g (87%) of the intermediate diamine g (9-amino-1,2,3-tetrahydro-benzo[e][1,4]diazepin-5-one) as a brown solid, which was used without further purification. The diamine g (0.22 g, 1.27 mmol) was dissolved in pyridine (7 mL), and 4-fluorobenzoyl chloride (0.17 mL, 1.40 mmol) was added. The reaction mixture was stirred at rt for 3 days, at which time the solvent was removed in vacuo. The resultant residue was subjected to flash silica gel chromatography (60–90% EtOAc/hexanes) to give 0.12 g (33%) of a white solid: mp=264–266° C.; R$_f$=0.13 (90% EtOAc/hexanes); IR (KBr) 1653, 1601, 1480, 1223 cm$^{-1}$; $^1$H NMR (DMSO-d$_6$) δ 3.52–3.53 (m, 2H), 4.43–4.44 (m, 2H), 7.34–7.37 (m, 1H), 7.41–7.44 (m, 2H), 7.86–7.93 (m, 4H), 8.44 (t, 1H, J=5.6 Hz). HRMS calcd for C$_{16}$H$_{12}$N$_3$OF 281.0964 (M$^+$), found 281.0963. Anal. (C$_{16}$H$_{12}$N$_3$OF) C, H, N.

Alternative Method for Preparation of Intermediate f:

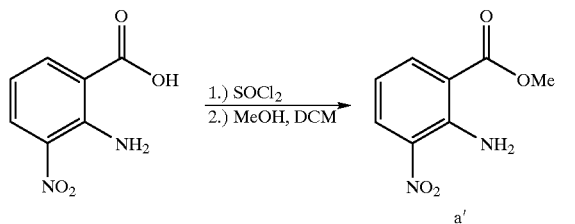

(c) Intermediate a'—2-Amino-3-nitro-benzoic Acid Methyl Ester:

2-Amino-3-nitro-benzoic acid (6.30 g, 34.6 mmol) was converted to the corresponding acid chloride by refluxing in neat thionyl chloride. After removal of excess thionyl chloride and drying under vacuum, the crude acid chloride was suspended in 100 mL of CH$_2$Cl$_2$ and cooled to 0° C. A solution of 20 mL of MeOH in 20 mL of CH$_2$Cl$_2$ was added slowly via addition funnel. The reaction was allowed to stir overnight while warming to rt. The solution was then concentrated and purified by column chromatography to give 5.40 g (78%) of product as a yellow solid. (An alternative method involves Fisher esterification. The acid can be dissolved in an appropriate amount of MeOH, cooled to 0° C. and saturated with HCl gas. The reaction is then heated to reflux until the ester is formed.)

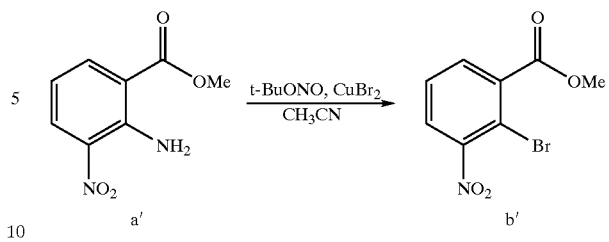

(d) Intermediate b'—2-Bromo-3-nitro-benzoic Acid Methyl Ester:

2-Amino-3-nitro-benzoic acid methyl ester (5.00 g, 25.5 mmol) and copper(II) bromide (6.80 g, 30.5 mmol) were dissolved in 125 mL acetonitrile at 0° C. To this solution was added 4.5 mL tert-butyl nitrite (37.8 mmol). The reaction, after stirring overnight and warming to 23° C., was poured into 200 mL 10% HCl and extracted 4 times with Et$_2$O. The combined organic layers were washed with 10% HCl, water and saturated brine, dried (MgSO$_4$), filtered and concentrated in vacuo to give 6.00 g (90%) of product as a light-yellow solid, which was used without further purification: IR (KBr) 1736, 1529, 1429, 1363, 1292, 1275, 1211, 1138, 1035, 976, 885, 814, 767, 733, 706 cm$^{-1}$; $^1$H NMR (CDCl$_3$) δ 3.98 (s, 3H), 7.53 (t, 1H, J=7.7 Hz), 7.77 (d, 1H, J=7.7 Hz), 7.86 (d, 1H, J=7.7 Hz). Anal. (C$_8$H$_6$BrNO$_4$) C, H, N.

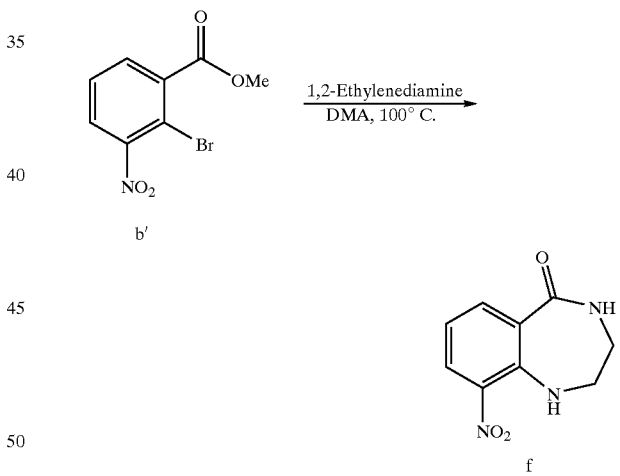

(e) 9-Nitro-1,2,3,4-tetrahydro-benzo[e][1,4]diazepin-5-one (Intermediate f):

2-Bromo-3-nitro-benzoic acid methyl ester (0.50 g, 1.92 mmol) and 1,2-ethylenediamine (250 μL, 3.74 mmol) was dissolved in 5 mL of DMA. The solution was heated to 100° C. overnight. The reaction was then cooled to room temperature and poured into 200 mL of 1M NaH$_2$PO$_4$ and placed in the freezer for 4 h. The resulting orange-red solid was collected by filtration to give 256 mg (1.23 mmol, 64% yield) of product. The aqueous layer was still highly colored and the presence of product was confirmed by HPLC. This solution was then extracted with $CH_2Cl_2$ (3×150 mL). The organic layers were dried ($MgSO_4$), filtered, concentrated and purified by column chromatography using a gradient of 2.5% to 5% $MeOH/CH_2Cl_2$ as eluent to give an additional 125 mg (0.60 mmol, 31% yield) of product.

Example 3

1-Pyridin-4-yl-8,9-dihydro-7H-2,7,9a-triaza-benzo[cd]azulen-6-one

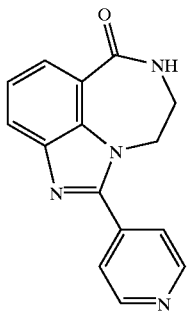

The diamine intermediate g (0.088 g, 0.50 mmol) described above was dissolved in pyridine (5 mL). Isonicotinoyl chloride hydrochloride (0.093 g, 0.50 mmol) was added, and the reaction mixture was stirred overnight at rt. The solvent was removed in vacuo. Toluene was added to the residue and concentrated under vacuum; this was repeated to remove traces of pyridine. The residue was dissolved in 4:1 $CHCl_3/iPrOH$ and washed with 0.5N $Na_2CO_3$. The aqueous phase was separated and reextracted three times with 4:1 $CHCl_3/iPrOH$, and the organic layers were combined, dried ($MgSO_4$), filtered and concentrated under vacuum. The residue was subjected to silica gel chromatography (5–10% MeOH/EtOAc) to provide 0.055 g (42%) of a tan solid: mp=269° C. (dec); $R_f$=0.13 (20% MeOH/EtOAc); IR (KBr) 1653, 1609, 1472 $cm^{-1}$; $^1H$ NMR (DMSO-$d_6$) δ 3.54–3.55 (m, 2H), 4.51–4.52 (m, 2H), 7.38–7.42 (m, 1H), 7.86–7.87 (m, 2H), 7.91–7.93 (m, 1H), 7.95–7.97 (m, 1H), 8.47 (t, 1H, J=5.6 Hz), 8.79–8.80 (m, 2H). HRMS calcd for $C_{15}H_{12}N_4O$ 264.2022 ($M^+$), found 264.1008. Anal. ($C_{15}H_{12}N_4O \cdot 0.25\ H_2O$) C, H, N.

The compounds of Examples 4–6, 8–11, 14, and 66–68 described below were synthesized from intermediate g and the appropriate acid chloride in a manner analogous to that described above in Example 2 for the preparation of 1-(4-fluoro-phenyl)-8,9-dihydro-7H-2,7,9a-triaza-benzo[cd]azulen-6-one. The compounds of Examples 7, 12, and 15–17 were synthesized from intermediate g and the appropriate acid chloride in a manner like that described above in Example 3 for the preparation of 1-pyridin-4-yl-8,9-dihydro-7H-2,7,9a-triaza-benzo[cd]azulen-6-one.

Example 4

1-(3,4-Difluoro-phenyl)-8,9-dihydro-7H-2,7,9a-triaza-benzo[cd]azulen-6-one

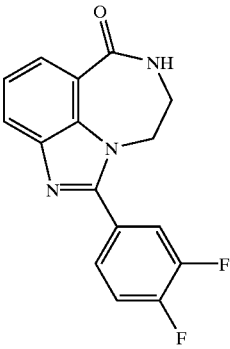

The reaction was carried out at room temperature (rt); the reaction time was 72 h to yield a white solid (55%): mp=245–247° C.; $R_f$=0.18 (90% EtOAc/hexanes); IR (KBr) 1665, 1497 $cm^{-1}$; $^1H$ NMR (DMSO-$d_6$) δ 3.53–3.54 (m, 2H), 4.46–4.47 (m, 2H), 7.36–7.39 (m, 1H), 7.64–7.68 (m, 1H), 7.70–7.73 (m, 1H), 7.88–7.92 (m, 2H), 7.94–7.98 (m, 1H), 8.46 (t, 1H, J=5.7 Hz). HRMS calcd for $C_{16}H_{11}N_3OF_2$ 299.0870 ($M^+$), found 299.0857. Anal. ($C_{16}H_{11}N_3OF_2$) C, H, N.

Example 5

1-(2-Chloro-phenyl)-8,9-dihydro-7H-2,7,9a-triaza-benzo[cd]azulen-6-one

The reaction temperature was held at 75° C.; reaction time was 72 h to yield a white solid (50%): mp=253–255° C.; $R_f$=0.16 (90% EtOAc/hexanes); IR (KBr) 1665, 1468, 1389 $cm^{-1}$; $^1H$ NMR (DMSO-$d_6$) δ 3.54–3.58 (m, 2H), 4.09–4.12 (m, 2H), 7.36–7.42 (m, 1H), 7.52–7.72 (m, 4H), 7.91–7.95 (m, 2H), 8.43 (t, 1H, J=5.5 Hz). HRMS calcd for $C_{16}H_{12}N_3OCl$ 297.0668 ($M^+$), found 297.0677. Anal. ($C_{16}H_{12}N_3OCl \cdot 0.25\ H_2O$) C, H, N.

Example 6

1-(3-Phenoxy-phenyl)-8,9-dihydro-7H-2,7,9a-triaza-benzo[cd]azulen-6-one

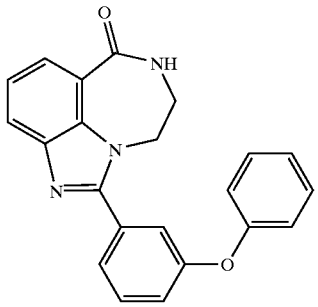

(a) 3-Phenoxybenzoyl Chloride:

This compound was prepared as generally described in (Patent Publication No. GB 1052390). To 3-phenoxybenzoic acid (1.95 g, 9.10 mmol) dissolved in $CH_2Cl_2$ (45 mL) was added oxalyl chloride (0.89 mL, 10.01 mmol) followed by a drop of DMF. The reaction mixture was stirred overnight at rt and the solvent was removed in vacuo. The residue was taken up in $Et_2O$, and the liquid was carefully decanted away from any remaining solid. The $Et_2O$ was evaporated and the resulting crude product was purified by short path vacuum distillation (bp=139° C./3 mm Hg) to give 1.12 g (53%) of a clear liquid: IR (neat) 1755, 1584 $cm^{-1}$; $^1$H NMR ($CDCl_3$) δ 7.02–7.05 (m, 2H), 7.16–7.21 (m, 1H), 7.29–7.33 (m, 1H), 7.37–7.49 (m, 3H), 7.70–7.71 (m, 1H), 7.84–7.87 (m, 1H).

(b) Title Compound:

The reaction was carried out at room temperature; reaction time was 72 h to yield a cream-colored solid (49%): mp=216–219° C.; $R_f$=0.29 (90% EtOAc/hexanes); IR (KBr) 1661, 1456, 1219 $cm^{-1}$; $^1$H NMR (DMSO-$d_6$) δ 3.52–3.53 (m, 2H), 4.45–4.47 (m, 2H), 7.11–7.13 (m, 2H), 7.18–7.22 (m, 2H), 7.33–7.36 (m, 1H), 7.42–7.45 (m, 3H), 7.57–7.61 (m, 2H), 7.85–7.89 (m, 2H), 8.43 (t, 1H, J=5.7 Hz). HRMS calcd for $C_{22}H_{17}N_3O_2$ 355.1321 ($M^+$), found 355.1308. Anal. ($C_{22}H_{17}N_3O_2$) C, H, N.

Example 7

1-Pyridin-3-yl-8,9-dihydro-7H-2,7,9a-triaza-benzo[cd]azulen-6-one

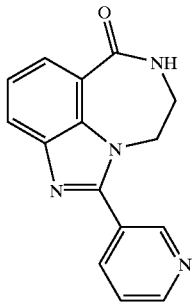

The reaction was carried out at room temperature; reaction time was 72 h to yield a cream-colored solid (67%): mp=250° C. (dec); $R_f$=0.16 (20% MeOH/EtOAc); IR (KBr) 1663, 1385, 1310 $cm^{-1}$; $^1$H NMR (DMSO-$d_6$) δ 3.54–3.56 (m, 2H), 4.48–4.49 (m, 2H), 7.39 (t, 1H, J=7.7 Hz), 7.62 (dd, 1H, J=8.1, 5.0 Hz), 7.90 (dd, 1H, J=7.8, 1.0 Hz), 7.94 (dd, 1H, J=7.9, 1.9 Hz), 8.28 (dt, 1H, J=7.9, 1.9 Hz), 8.46 (t, 1H, J=5.7 Hz), 8.75 (dd, 1H, J=4.9, 1.3 Hz), 9.05 (d, 1H, J=1.9 Hz). HRMS calcd for $C_{15}H_{12}N_4O$ 264.1011 ($M^+$), found 264.1013. Anal. ($C_{15}H_{12}N_4O \cdot 0.4H_2O$) C, H, N.

Example 8

1-Thiophen-2-yl-8,9-dihydro-7H-2,7,9a-triaza-benzo[cd]azulen-6-one

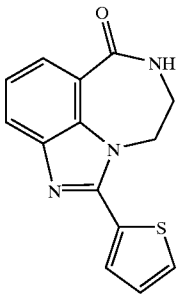

The reaction was carried out at room temperature; reaction time was 72 h to yield a white solid (63%): mp=247–250° C.; $R_f$=0.21 (5% MeOH/$CHCl_3$); IR (KBr) 1661, 1474, 737 $cm^{-1}$; $^1$H NMR (DMSO-$d_6$) δ 3.59–3.60 (m, 2H), 4.56–4.57 (m, 2H), 7.29 (dd, 1H, J=5.0, 3.8 Hz), 7.35 (t, 1H, J=7.8 Hz), 7.72 (d, 1H, J=3.7 Hz), 7.84–7.87 (m, 3H), 8.45 (t, 1H, J=5.6 Hz). HRMS calcd for $C_{14}H_{11}N_3OS$ 269.0622 ($M^+$), found 269.0627. Anal. ($C_{14}H_{11}N_3OS$) C, H, N.

Example 9

1-Naphthalen-1-yl-8,9-dihydro-7H-2,7,9a-triaza-benzo[cd]azulen-6-one

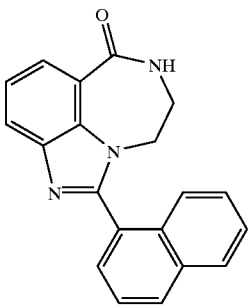

The reaction was carried out at 70° C.; reaction time was 72 h to yield a white solid (53%): mp=223–225° C. (dec); $R_f$=0.18 (90% EtOAc/hexanes); IR (KBr) 1659, 1464, 1312 $cm^{-1}$; $^1$H NMR (DMSO-$d_6$) δ 3.52–3.54 (m, 2H), 4.11–4.12 (m, 2H), 7.41 (t, 1H, J=7.8 Hz), 7.53–7.64 (m, 2H), 7.67–7.72 (m, 1H), 7.81 (dd, 1H, J=7.1, 1.2 Hz), 7.89 (d, 1H, J=8.3 Hz), 7.96 (dt, 2H, J=7.7, 1.0 Hz), 8.06–8.09 (m, 1H), 8.17 (d, 1H, J=8.2 Hz), 8.40 (t, 1H, J=5.7 Hz). HRMS calcd for $C_{20}H_{15}N_3O$ 313.1215 ($M^+$), found 313.1204. Anal. ($C_{20}H_{15}N_3O$) C, H, N.

Example 10

1-(3-Trifluoromethyl-phenyl)-8,9-dihydro-7H-2,7,9a-triaza-benzo[cd]azulen-6-one

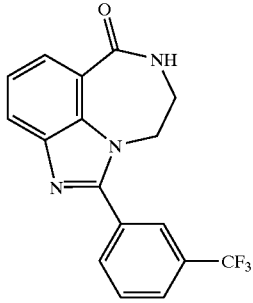

The reaction was carried out at room temperature; reaction time was 72 h to yield a light-gray solid (53%): mp=250–252° C.; $R_f$=0.18 (90% EtOAc/hexanes); IR (KBr) 1669, 1393, 1325 cm$^{-1}$; $^1$H NMR (DMSO-d$_6$) δ 3.53–3.54 (m, 2H), 4.48–4.49 (m, 2H), 7.34 (t, 1H, J=7.8 Hz), 7.80–7.86 (m, 1H), 7.92 (ddd, 1H, J=8.5, 8.0, 1.1 Hz), 7.94–7.95 (m, 1H), 7.96–7.97 (m, 1H), 8.16–8.19 (m, 2H), 8.47 (t, 1H, J=5.7 Hz). HRMS calcd for $C_{17}H_{12}N_3OF_3$ 331.0932 (M$^+$), found 331.0944. Anal. ($C_{17}H_{12}N_3OF_3$) C, H, N.

Example 11

1-Naphthalen-2-yl-8,9-dihydro-7H-2,7,9a-triaza-benzo[cd]azulen-6-one

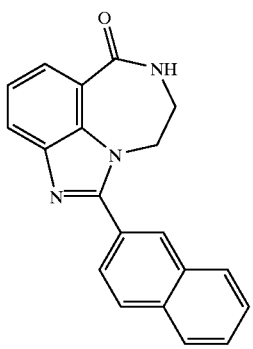

The reaction was carried out at room temperature; reaction time was 72 h to yield a white solid (32%): mp=259–261° C.; $R_f$=0.16 (90% EtOAc/hexanes); IR (KBr) 1659, 1466, 1395, 1308 cm$^{-1}$; $^1$H NMR (DMSO-d$_6$) δ 3.55–3.57 (m, 2H), 4.57–4.59 (m, 2H), 7.38 (t, 1H, J=7.8 Hz), 7.62–7.65 (m, 2H), 7.89 (dd, 1H, J=7.7, 1.1 Hz), 7.94 (dd, 1H, J=7.9, 1.1 Hz), 7.99–8.05 (m, 2H), 8.08–8.13 (m, 2H), 8.45–8.46 (m, 1H), 8.49 (t, 1H, J=5.7 Hz). HRMS calcd for $C_{20}H_{15}N_3O$ 313.1215 (M$^+$), found 313.1221. Anal. ($C_{20}H_{15}N_3O \cdot 0.15H_2O$) C, H, N.

Example 12

1-Pyridin-2-yl-8,9-dihydro-7H-2,7,9a-triaza-benzo[cd]azulen-6-one

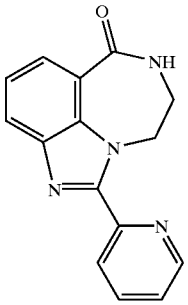

The reaction was carried out at room temperature; reaction time was 72 h to yield a tan solid (52%): mp=249–250° C.; $R_f$=0.26 (10% MeOH/EtOAc); IR (KBr) 1659, 1605, 1443 cm$^{-1}$; $^1$H NMR (DMSO-d$_6$) δ 3.57–3.62 (m, 2H), 4.60–5.20 (br, 2H), 7.39 (t, 1H, J=7.8 Hz), 7.55 (ddd, 1H, J=7.7, 4.9, 1.2 Hz), 7.92–7.96 (m, 2H), 8.03 (dt, 1H, J=7.7, 1.8 Hz), 8.29–8.32 (m, 1H), 8.45 (t, 1H, J=5.5 Hz), 8.75–8.77 (m, 1H). HRMS calcd for $C_{15}H_{12}N_4O$ 264.1011 (M$^+$), found 264.1001. Anal. ($C_{15}H_{12}N_4O$) C, H, N.

Example 13

1-Isoxazol-5-yl-8,9-dihydro-7H-2,7,9a-triaza-benzo[cd]azulen-6-one

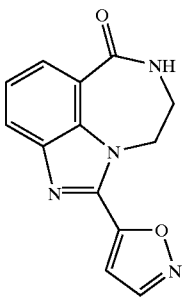

The reaction was carried out at room temperature; reaction time was 72 h to yield a white solid (21%): mp=226° C. (dec); $R_f$=0.08 (5% MeOH/CHCl$_3$); IR (KBr) 1661, 1466, 1379 cm$^{-1}$; $^1$H NMR (DMSO-d$_6$) δ 3.61–3.66 (m, 2H), 4.65–4.67 (m, 2H), 7.28 (d, 1H, J=2.0 Hz), 7.41–7.46 (m, 1H), 7.95–7.97 (m, 1H), 7.98–7.80 (m, 1H), 8.50 (t, 1H, J=5.7 Hz), 8.90 (d, 1H, J=2.0 Hz). HRMS calcd for $C_{13}H_{10}N_4O_2$ 254.0804 (M$^+$), found 254.0798. Anal. ($C_{13}H_{10}N_4O_2$) C, H, N.

Example 14

1-(4-Chloro-phenyl)-8,9-dihydro-7H-2,7,9a-triaza-benzo[cd]azulen-6-one

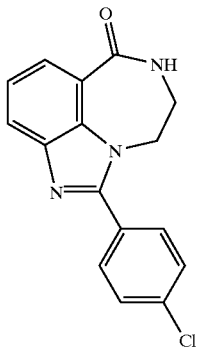

The reaction was carried out at room temperature; reaction time was 72 h to yield an off-white solid (47%): mp=272–274° C.; $R_f$=0.26 (90% EtOAc/hexanes); IR (KBr) 1663, 1597, 1464, 1408 cm$^{-1}$; $^1$H NMR (DMSO-d$_6$) δ 3.52–3.54 (m, 2H), 4.44–4.46 (m, 2H), 7.37 (t, 1H, J=7.8 Hz), 7.64–7.66 (m, 2H), 7.86–7.92 (m, 4H), 8.44–8.47 (m, 1H). HRMS calcd for $C_{16}H_{12}N_3OCl$ 297.0669 (M$^+$), found 297.0667. Anal. ($C_{16}H_{12}N_3OCl$) C, H, N.

Example 15

1-(2-Chloropyridin-4-yl)-8,9-dihydro-7H-2,7,9a-triaza-benzo[cd]azulen-6-one

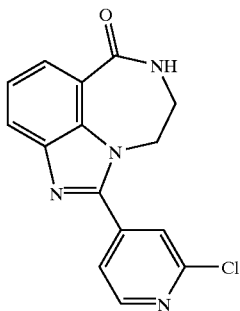

The reaction was carried out at room temperature; reaction time was 72 h to yield a yellow solid (47%): mp=265° C. (dec); $R_f$=0.20 (5% MeOH/EtOAc); IR (KBr) 1661, 1607, 1464, 1399 cm$^{-1}$; $^1$H NMR (DMSO-d$_6$) δ 3.35–3.39 (m, 2H), 3.54–3.55 (m, 2H), 7.39–7.44 (m, 1H), 7.89–7.98 (m, 4H), 8.50 (t, 1H, J=5.8 Hz), 8.63 (d, 1H, J=5.2 Hz). HRMS calcd for $C_{15}H_{11}N_4OCl$ 298.0621 (M$^+$), found 298.0617. Anal. ($C_{15}H_{11}N_4OCl$·0.25 H$_2$O) C, H, N.

Example 16

1-[3-(Pyridin-3-yloxy)-phenyl]-8,9-dihydro-7H-2,7,9a-triaza-benzo[cd]azulen-6-one

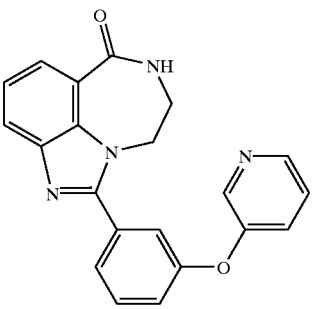

(a) 3-(Pyridin-3-yloxy)-benzoic Acid-hydrochloride Salt:

A solution of methyl 3-(pyridin-3-yloxy)benzoate (Butler et al., *J. Med. Chem.* 24, 346 (1981), 0.229 g, 1.0 mmol) in 6N HCl (2 mL) was refluxed for 18 h. The solution was concentrated under high vacuum and dried at 60° C. under vacuum to give 0.244 g (97%) of a tan solid: mp=208–210° C.; $^1$H NMR (DMSO-d$_6$) δ 7.46 (m, 1H), 7.60 (m, 2H), 7.83 (m, 2H), 7.98 (m, 1H), 8.60 (dd, 1H, J=5.1, 0.9 Hz), 8.70 (d, 1H, J=2.6 Hz), 9.30–11.90 (br, 2H). Anal. ($C_{12}H_{10}NO_3Cl$) C, H, N.

(b) 3-(Pyridin-3-yloxy)-benzoyl Chloride:

This acid chloride was prepared from the HCl salt of 3-(pyridin-3-yloxy)-benzoic as described above for 3-phenoxybenzoyl chloride, except the product was not purified (99%, white solid): IR (KBr) 1751 cm$^{-1}$; $^1$H NMR (CDCl$_3$) δ 7.45–7.49 (m, 1H), 7.66–7.72 (m, 1H), 7.86–7.92 (m, 2H), 7.97–8.01 (m, 1H), 8.12–8.15 (m, 1H), 8.39–8.40 (m, 1H), 8.53–8.55 (m, 1H).

(c) Title Compound:

The reaction was carried out at room temperature; reaction time was 72 h to yield a white solid (55%): mp=223–225° C.; $R_f$=0.18 (10% MeOH/EtOAc); IR (KBr) 1665, 1571, 1460 cm$^{-1}$; $^1$H NMR (CDCl$_3$) δ 3.52–3.53 (m, 2H), 4.45–4.48 (m, 2H), 7.27–7.38 (m, 2H), 7.44–7.68 (m, 5H), 7.85–7.91 (m, 2H), 8.41–8.48 (m, 3H). HRMS calcd for $C_{21}H_{16}N_4O_2$ 356.1273 (M$^+$), found 356.1263. Anal. ($C_{21}H_{16}N_4O_2$·0.25 H$_2$O) C, H, N.

Example 17

1-[3-(Pyridin-4-yloxy)-phenyl]-8,9-dihydro-7H-2,7,9a-triaza-benzo[cd]azulen-6-one

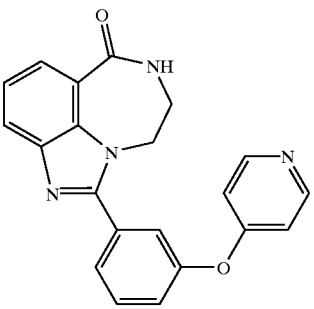

(a) Methyl 3-(Pyridyn-4-yloxy)benzoate (Butler et al., *J. Med. Chem.* 14, 575 (1971):

A solution of 4-[3-(trifluoromethyl)phenoxy]pyridine[1] (1.89 g, 7.9 mmol) in concentrated H$_2$SO$_4$ (5.4 mL) was heated to 120° C. for 16 h. The reaction mixture was cooled to rt and carefully poured into MeOH (200 mL). This solution was refluxed for 2 h. The solution was then concentrated under vacuum to half its volume and diluted with 350 mL of Et$_2$O. A large excess of solid NaHCO$_3$ was added portionwise with stirring, followed by solid Na$_2$CO$_3$. This suspension was stirred several hours until the pH was no longer acidic. The salts were filtered with the aid of Celite and the solution was concentrated. The turbid residue was taken up in CH$_2$Cl$_2$, dried (Na$_2$SO$_4$), filtered and reconcentrated to give 1.62 (89%) of pure product as a pale-brown oil: $^1$H NMR (DMSO-d$_6$) δ 3.84 (s, 3H), 6.96 (d, 2H, J=6.3 Hz), 7.49 (dd, 1H, J=8.1, 2.5 Hz), 7.64 (m, 2H), 7.87 (d, 1H, J=7.7 Hz), 8.49 (d, 2H, J=6.0 Hz).

(b) 3-(Pyridin-4-yloxy)-benzoic Acid-hydrochloride Salt:

A solution of methyl 3-(pyridyn-4-yloxy)benzoate (0.229 g, 1.0 mmol) in 6N HCl (2 mL) was refluxed for 18 h. The solution was concentrated under high vacuum and dried at 60° C. under vacuum to give 0.25 g (99%) of a white solid: mp=230–233° C.; $^1$H NMR (DMSO-d$_6$) δ 7.48 (d, 2H, J=6.9 Hz), 7.63 (m, 1H), 7.73 (t, 1H, J=8.0 Hz), 7.82 (s, 1H), 7.99 (d, 1H, J=7.8 Hz), 8.80 (d, 2H, J=7.2 Hz), 12.8–14.1 (br, 2H), Anal. (C$_{12}$H$_{10}$NO$_3$Cl) C, H, N.

(c) 3-(Pyridin-4-yloxy)-benzoyl Chloride:

This acid chloride was prepared from the HCl salt of 3-(pyridin-4-yloxy)-benzoic as described above for 3-phenoxybenzoyl chloride, except the product was not purified (99%, white solid): IR (KBr) 1736, 1709, 1501 cm$^{-1}$; $^1$H NMR (CDCl$_3$) δ 7.29–7.32 (m, 2H), 7.52–7.54 (m, 1H), 7.73–7.78 (m, 1H), 7.94 (s, 1H), 8.20–8.22 (m, 1H), 8.68–8.70 (m, 2H).

(d) Title Compound:

The reaction was carried out at room temperature; reaction time was 72 h to yield a white solid (52%): mp=245–247° C.; R$_f$=0.24 (15% MeOH/EtOAc); IR (KBr) 1661, 1576, 1264 cm$^{-1}$; $^1$H NMR (DMSO-d$_6$) δ 3.53–3.55 (m, 2H), 4.48–4.49 (m, 2H), 7.03 (d, 2H, J=6.2 Hz), 7.33–7.42 (m, 2H), 7.66–7.72 (m, 2H), 7.78–7.80 (m, 1H), 7.86–7.92 (m, 2H), 8.43–8.47 (m, 1H), 8.50 (d, 2H, J=6.2 Hz). HRMS calcd for C$_{21}$H$_{16}$N$_4$O$_2$ 356.1273 (M$^+$), found 356.1264. Anal. (C$_{21}$H$_{16}$N$_4$O$_2$) C, H, N.

Example 18

4-Fluoro-1-(4-fluoro-phenyl)-8,9-dihydro-7H-2,7,9a-triaza-benzo[cd]azulen-6-one

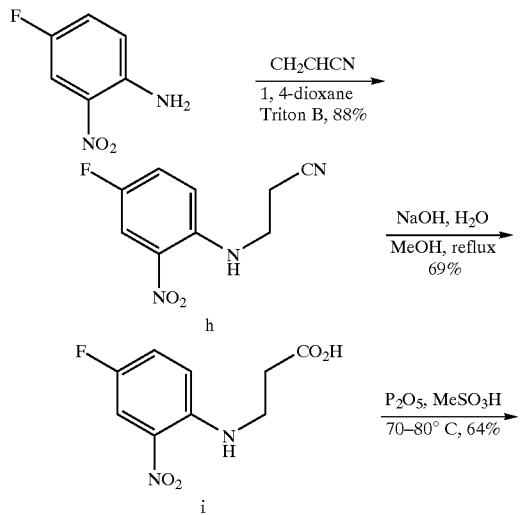

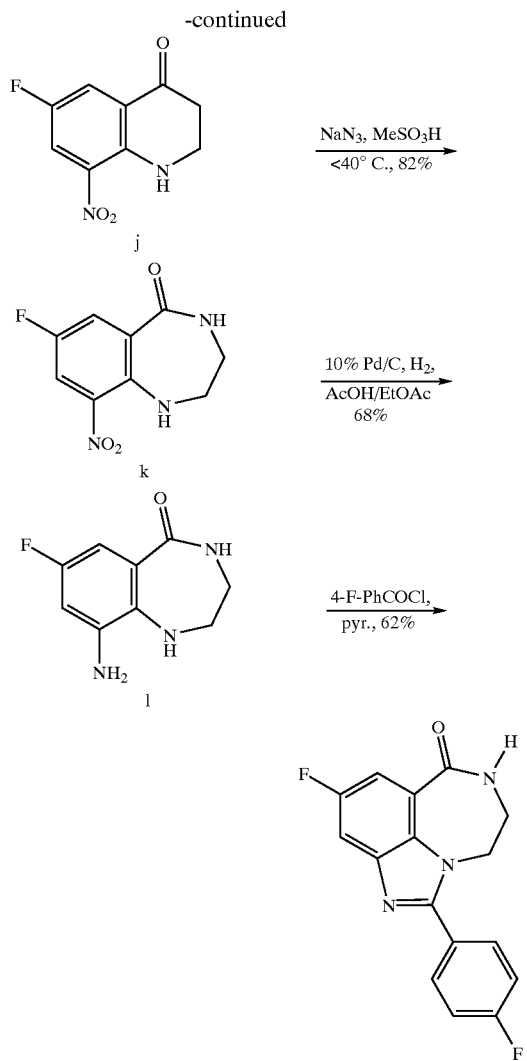

(a) Intermediate h—3-(4-Fluoro-2-nitrophenylamino)-propionitrile:

Using the procedure described to prepare intermediate a, 3-(4-fluoro-2-nitrophenylamino)-propionitrile was prepared in 88% yield from 4-fluoro-2-nitroaniline (3.17 g, 19.68 mmol), acrylonitrile (1.57 mL, 23.61 mmol), and Triton B (0.2 mL) as a brown crystalline solid: mp=140–142° C.; R$_f$=0.16 (30% EtOAc/hexanes); IR (KBr) 3380, 3117, 2955, 2251, 1526 cm$^{-1}$; $^1$H NMR (CDCl$_3$) δ 2.73–2.76 (m, 2H), 3.69–3.73 (m, 2H), 6.83–6.86 (m, 1H), 7.30–7.34 (m, 1H) 7.95 (dd, 1H, J=8.9, 3.0 Hz), 8.05 (br, 1H). Anal. (C$_9$H$_8$N$_3$O$_2$F) C, H, N.

(b) Intermediate i—3-(4-Fluoro-2-nitrophenylamino)-propionic Acid:

The desired compound was prepared by following the procedure to produce intermediate b using intermediate h, 3-(4-fluoro-2-nitrophenylamino)-propionitrile, to give 0.94 g (69%) of an orange-brown solid: mp=154–155° C.; IR (KBr) 3391, 1721, 1526 cm$^{-1}$; $^1$H NMR (CDCl$_3$) δ 2.76–2.79 (m, 2H), 3.64–3.68 (m, 2H), 6.85–6.88 (m, 1H), 7.28–7.30 (m, 1H), 7.91 (dd, 1H, J=9.0, 2.9 Hz), 8.07 (br, 1H). Anal. (C$_9$H$_9$N$_2$O$_4$) C, H, N.

(c) Intermediate j—6-Fluoro-8-nitro-2,3-dihydro-1H-quinolin-4-one:

Intermediate i (0.65 g, 2.84 mmol) was added to a flask containing stirring Eaton's Reagent (P$_2$O$_5$, 7.5 wt % in methanesulfonic acid) (11 mL). The reaction mixture was heated to 60° C. for 3.5 h, then cooled to rt, after which ice was added to the flask. The reaction mixture was then poured into water, and the solid product was filtered and washed with more water. The product was purified by flash silica gel chromatography (5–10% EtOAc/hexanes) to give 0.38 g (64%) of an orange solid: mp=155–157° C.; $R_f$=0.26 (30% EtOAc/hexanes); IR (KBr) 3389, 3057, 1692, 1514 cm$^{-1}$; $^1$H NMR (CDCl$_3$) δ 2.82 (t, 2H, J=7.1 Hz), 3.76–3.81 (m, 2H), 7.96 (dd, 1H, J=7.6, 3.2 Hz), 8.13 (dd, 1H, J=8.3, 3.2 Hz), 8.15 (br, 1H). Anal. (C$_9$H$_7$N$_2$O$_3$) C, H, N.

(d) Intermediate k—7-Fluoro-9-nitro-1,2,3,4-tetrahydro-benzo[e][1,4]diazepin-5-one:

The desired product was prepared by following the procedure to synthesize intermediate f, using intermediate j, 6-fluoro-8-nitro-2,3-dihydro-1H-quinolin-4-one, to give 0.33 g (82%) of a red-brown solid: mp=215–217° C.; $R_f$=0.11 (40% EtOAc/CHCl$_3$); IR (KBr) 1651, 1514, 1258, 1161 cm$^{-1}$; $^1$H NMR (DMSO-d$_6$) δ 3.29–3.36 (m, 2H), 3.59–3.63 (m, 2H), 7.98 (dd, 1H, J=9.5, 3.4 Hz), 8.10 (dd, 1H, J=8.4, 3.4 Hz), 8.52–8.56 (m, 2H). Anal. (C$_9$H$_8$N$_3$O$_3$F) C, H, N.

(e) Title Compound:

Using the procedure described above for preparation of intermediate g (Example 2), intermediate l was prepared in 68% yield from intermediate k. The title compound was then prepared from intermediate l and 4-fluorobenzoyl chloride using the procedure for Example 2 to give 0.096 g (62%) of a white solid: mp=284–287° C.; $R_f$=0.13 (90% EtOAc/hexanes); IR (KBr) 1661, 1603, 1485 cm$^{-1}$; $^1$H NMR (DMSO-d$_6$) δ 3.54–3.57 (m, 2H), 4.43–4.45 (m, 2H), 7.41–7.47 (m, 2H), 7.60 (dd, 1H, J=10.6, 2.6 Hz), 7.76 (dd, 1H, J=9.0, 2.6 Hz), 7.89–7.94 (m, 2H), 8.61 (t, 1H, J=5.6 Hz). HRMS calcd for C$_{16}$H$_{11}$N$_3$OF$_2$ 299.0870 (M$^+$), found 299.0858. Anal. (C$_{16}$H$_{11}$N$_3$OF$_2$) C, H, N.

Example 19

1-Phenylethyl-8,9-dihydro-7H-2,7,9a-triaza-benzo[cd]azulen-6-one

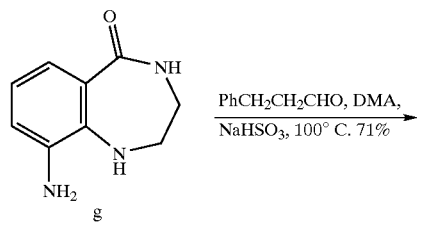

PhCH$_2$CH$_2$CHO, DMA,
NaHSO$_3$, 100° C. 71%

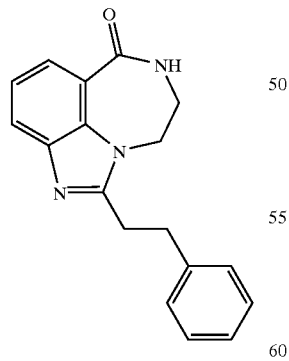

The title compound was prepared using a general procedure described previously (Higgins et al., *J. Polym. Sci. Part A-1* (1970), 8:171–177; Imai et al., *Synthesis* (1981), 35–36). Diamine intermediate g (0.048 g, 0.27 mmol) was dissolved in dimethylacetamide (DMA) (1.50 mL). Hydrocinnamaldehyde (90%, 0.039 mL, 0.27 mmol) was added to the DMA solution followed by sodium bisulfite (0.042 g, 0.40 mmol). The reaction mixture was heated to 100° C. for 1 h. The solvent was removed in vacuo, and the residue was dissolved in EtOAc/H$_2$O. The organic phase was separated, washed with brine, dried (MgSO$_4$), and concentrated. The residue was purified by flash silica gel chromatography (0–1% MeOH/EtOAc) to give 0.055 g (71%) of a white solid: mp=225–226° C.; $R_f$=0.26 (5% MeOH/EtOAc); IR (KBr) 1655, 1603, 1505, 1468 cm$^{-1}$; $^1$H NMR (DMSO-d$_6$) δ 3.07–3.18 (m, 4H), 3.48–3.49 (m, 2H), 4.15–4.30 (m, 2H), 7.18–7.23 (m, 1H), 7.26–7.28 (m, 5H), 7.76–7.81 (m, 2H), 8.31 (t, 1H, J=5.6 Hz). HRMS calcd for C$_{18}$H$_{17}$N$_3$O 291.1372 (M$^+$), found 291.1368. Anal. (C$_{18}$H$_{17}$N$_3$O·0.10H$_2$O) C, H, N.

The compounds of Examples 20–24, 30, 55–57, 61–65, 68, 73–74, and 78–80 were synthesized from intermediate g and the appropriate aldehyde in the manner described above in Example 4 for the preparation of 1-phenylethyl-8,9-dihydro-7H-2,7,9a-triaza-benzo[cd]azulen-6-one.

Example 20

1-Furan-2-yl-8,9-dihydro-7H-2,7,9a-triaza-benzo[cd]azulen-6-one

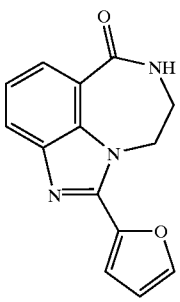

The title compound was isolated in 74% yield as a white solid: mp=278–279° C.; $R_f$=0.13 (90% EtOAc/hexanes); IR (KBr) 1655, 1464, 1437, 746 cm$^{-1}$; $^1$H NMR (DMSO-d$_6$) δ 3.58–3.63 (m, 2H), 4.59–4.62 (m, 2H), 6.79 (dd, 1H, J=3.5, 1.7 Hz), 7.25 (dd, 1H, J=3.5, 0.6 Hz), 7.35 (t, 1H, J=7.8 Hz), 8.02 (dd, 1H, J=1.7, 0.6 Hz), 8.45 (t, 1H, J=5.6 Hz). HRMS calcd for C$_{14}$H$_{11}$N$_3$O$_2$ 253.0851 (M$^+$), found 253.0852. Anal. (C$_{14}$H$_{11}$N$_3$O$_2$) C, H, N.

Example 21

1-Benzyl-8,9-dihydro-7H-2,7,9a-triaza-benzo[cd]azulen-6-one

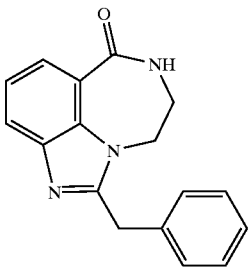

The title compound was isolated in 47% yield as a white solid: mp=226–228° C.; $R_f$=0.13 (90% EtOAc/hexanes); IR (KBr) 1661, 1468, 1316 cm$^{-1}$; $^1$H NMR (CDCl$_3$) δ 3.65–3.67 (m, 2H), 4.13–4.25 (m, 2H), 4.36 (s, 2H), 6.61–6.68 (m, 1H), 7.18–7.41 (m, 6H), 7.95–7.98 (m, 1H), 8.08–8.10 (m, 1H). HRMS calcd for $C_{17}H_{15}N_3O$ 277.1215 (M⁺), found 277.1203. Anal. ($C_{17}H_{15}N_3O$) C, H, N.

Example 22

1-tert-Butyl-8,9-dihydro-7H-2,7,9a-triaza-benzo[cd]azulen-6-one

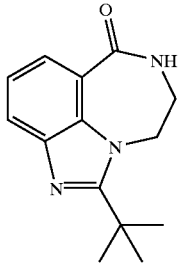

The title compound was isolated in 36% yield as a white solid: mp=246–248° C.; $R_f$=0.13 (EtOAc); IR (KBr) 1634, 1464, 1360 cm⁻¹; ¹H NMR (DMSO-$d_6$) δ 1.47 (s, 9H), 3.57–3.59 (m, 2H), 4.35–4.70 (br, 2H), 7.25 (t, 1H, J=7.8 Hz), 7.77 (dd, 1H, J=7.9, 1.1 Hz), 7.82 (dd, 1H, J=7.7, 1.1 Hz), 8.37 (t, 1H, J=5.7 Hz). HRMS calcd for $C_{14}H_{17}N_3O$ 243.1372 (M⁺), found 243.1371. Anal. ($C_{14}H_{17}N_3O$) C, H, N.

Example 23

1-Isobutyl-8,9-dihydro-7H-2,7,9a-triaza-benzo[cd]azulen-6-one

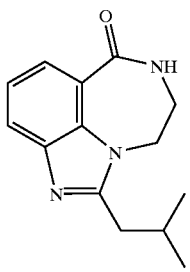

The title compound was isolated in 51% yield as a white solid: mp=211–212° C.; $R_f$=0.19 (5% MeOH/EtOAc); IR (KBr) 1659, 1474, 1404 cm⁻¹; ¹H NMR (DMSO-$d_6$) δ 0.96 (d, 6H, J=6.6 Hz), 2.15–2.18 (m, 1H), 2.73 (d, 2H, J=7.1 Hz), 3.54–3.58 (m, 2H), 4.35–4.40 (m, 2H), 7.25 (t, 1H, J=7.8 Hz), 7.75–7.80 (m, 2H), 8.33 (t, 1H, J=5.5 Hz). HRMS calcd for $C_{14}H_{17}N_3O$ 243.1372 (M⁺), found 243.1382. Anal. ($C_{14}H_{17}N_3O$) C, H, N.

Example 24

1-Cyclohexyl-8,9-dihydro-7H-2,7,9a-triaza-benzo[cd]azulen-6-one

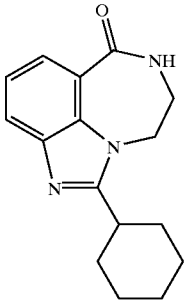

The title compound was isolated in 63% yield as an off-white solid: mp=265–266° C.; $R_f$=0.30 (5% MeOH/EtOAc); IR (KBr) 1657, 1462, 756 cm⁻¹; ¹H NMR (DMSO-$d_6$) δ 1.22–1.96 (m, 10H), 2.88–2.97 (m, 1H), 3.55–3.57 (m, 2H), 4.30–4.50 (m, 2H), 7.21–7.27 (m, 1H), 7.74–7.80 (m, 2H), 8.32 (t, 1H, J=5.5 Hz). HRMS calcd for $C_{16}H_{19}N_3O$ 269.1528 (M⁺), found 269.1531. Anal. ($C_{16}H_{19}N_3O \cdot 0.1 H_2O$) C, H, N.

Example 25

1-Phenyl-8,9-dihydro-7H-2,7,9a-triaza-benzo[cd]azulen-6-thione

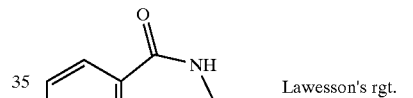

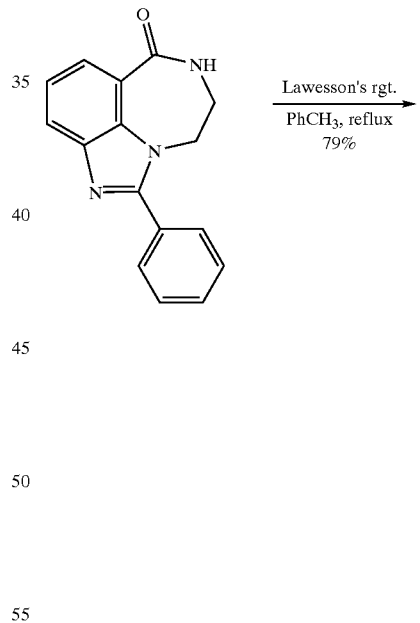

1-Phenyl-8,9-dihydro-7H-2,7,9a-triaza-benzo[cd]azulen-6-one (Example 1, 0.068 g, 0.26 mmol) was suspended in toluene (3 mL), and Lawesson's reagent (0.054 g, 0.13 mmol) was added. The reaction mixture was refluxed for 1 h. The solvent was removed in vacuo, and the crude product was subjected to flash silica gel chromatography (20–50% EtOAc/hexanes) to yield 0.057 g (79%) of a yellow solid: mp=224° C. (dec); $R_f$=0.21 (50% EtOAc/hexanes); IR (KBr) 1508, 1476, 1381, 1273 cm⁻¹; ¹H NMR (DMSO-$d_6$) δ 3.65–3.72 (m, 2H), 4.45–4.55 (m, 2H), 7.33–7.36 (m, 1H), 7.57–7.59 (m, 3H), 7.87–7.92 (m, 3H), 8.31–8.32 (m, 1H), 10.84 (t, 1H, J=5.9 Hz). HRMS calcd for $C_{16}H_{13}N_3S$ 279.0830 (M⁺), found 279.0835. Anal. ($C_{16}H_{13}N_3S \cdot 0.5\ H_2O$) C, H, N.

Example 26

8,9-Dihydro-2H 7H-2,7,9a-triaza-benzo[cd]azulen-1,6-dione

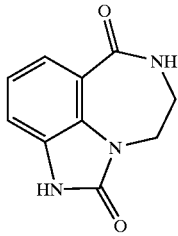

Diamine intermediate g (0.052 g, 0.29 mmol) was dissolved in DMF (3 mL), and 1,1'-carbonyldiimidazole (0.058 g, 0.36 mmol) was added. The stirred reaction mixture was heated to 100° C. for 24 h. An additional 0.048 g of carbonyldiimidazole was added with continued heating for another 24 h. The DMF was removed in vacuo, and the residue triturated and dissolved in EtOAc. The organic phase was washed with 10 mL of 10% aqueous HCl and separated. The aqueous phase was extracted four times with EtOAc. The combined extracts were dried ($MgSO_4$) and filtered, and the solvent was removed. The product was purified by flash silica gel chromatography (1% MeOH/EtOAc) to give 0.014 g (24%) of a white solid: mp=308–309° C. (dec); $R_f$=0.42 (20% MeOH/EtOAc); ¹H NMR (DMSO-d6) δ 3.44–3.49 (m, 2H), 3.86–3.89 (m, 2H), 7.05 (t, 1H, J=7.7 Hz), 7.14 (dd, 1H, J=7.6, 1.3 Hz), 7.55 (dd, 1H, J=7.9, 1.3 Hz), 8.29 (t, 1H, J=5.5 Hz), 11.12 (s, 1H). HRMS calcd for $C_{10}H_9N_3O_2$ 203.0695 (M⁺), found 203.0697. Anal. ($C_{10}H_9N_3O_2 \cdot 0.2\ H_2O$) C, H, N.

Example 27

7-Methyl-1-naphthalen-1-yl-8,9-dihydro-7H-2,7,9a-triaza-benzo[cd]azulen-6-one

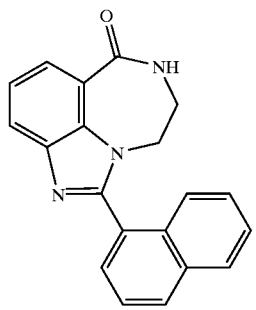

NaH, DMF, CH₃I
95%

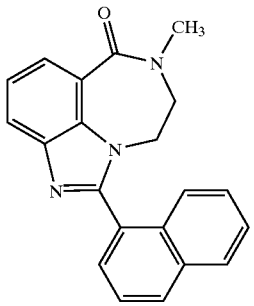

Sodium hydride (60% in mineral oil, 0.005 g, 0.13 mmol), washed free of mineral oil with hexanes, was suspended in DMF (1 mL). 1-Naphthalen-1-yl-8,9-dihydro-7H-2,7,9a-triaza-benzo[cd]azulen-6-one (Example 9, 0.035 g, 0.11 mmol) was added, and the reaction mixture was stirred for 15 minutes until gas evolution had ceased. Iodomethane (0.008 mL, 0.13 mmol) was added, and the reaction stirred at rt for 1 h. The solvent was removed in vacuo, and the residue purified by flash silica gel chromatography (50% EtOAc/hexanes) to give 0.035 g (95%) of a white solid: mp=126° C. (dec); $R_f$=0.30 (90% EtOAc/hexanes); ¹H NMR (DMSO-d6) δ 3.14 (s, 3H), 3.75–3.76 (m, 2H), 4.15–4.26 (m, 2H), 7.39–7.44 (m, 1H), 7.54–7.64 (m, 2H), 7.67–7.72 (m, 1H), 7.82–7.84 (m, 1H), 7.92–8.00 (m, 3H), 8.07–8.09 (m, 1H), 8.16–8.18 (m, 1H). HRMS calcd for $C_{21}H_{17}N_3O$ (M-H) 326.1293, found 326.1303. Anal. ($C_{21}H_{17}N_3O \cdot 0.2\ H_2O$) C, H, N.

Example 28

1-Mercapto-8,9-dihydro-7H-2,7,9a-triaza-benzo[cd]azulen-6-one

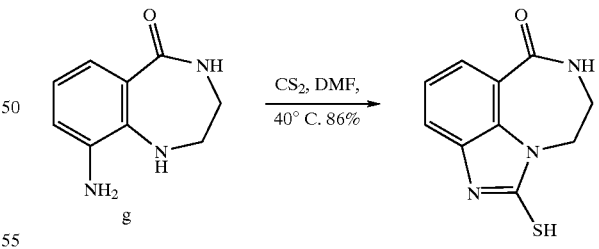

Diamine intermediate g (0.024 g, 0.13 mmol) was dissolved in DMF (0.5 mL). Carbon disulfide (1.0 mL) was added, and the reaction was heated to 40° C. for 3.5 h. The solvents were removed in vacuo to give the title compound (0.025 g, 86%): ¹H NMR (DMSO-d6) δ 3.54–3.55 (m, 2H), 3.80–4.80 (br, 2H), 7.25–7.30 (m, 1H), 7.35–7.37 (m, 1H), 7.74–7.76 (m, 1H), 8.44–8.48 (m, 1H), 13.08 (s, 1H). HRMS calcd for $C_{10}H_9N_3OS$ 219.0466 (M⁺), found 219.0469.

Example 29

1-Benzylsulfanyl-8,9-dihydro-7H-2,7,9a-triaza-benzo[cd]azulen-6-one

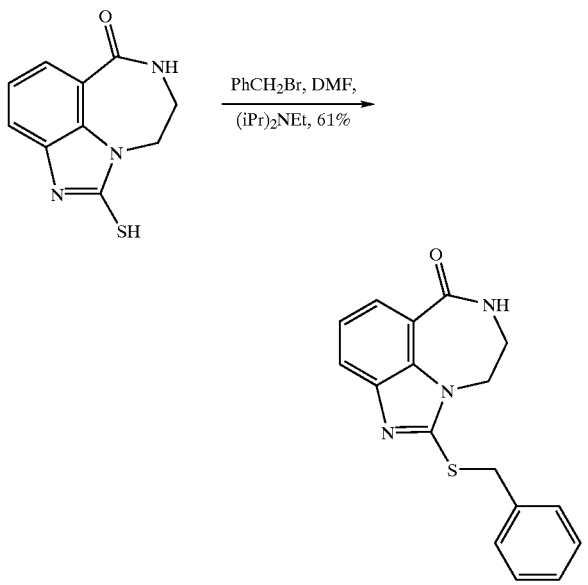

To 1-mercapto-8,9-dihydro-7H-2,7,9a-triaza-benzo[cd]azulen-6-one (0.026 g, 0.12 mmol, from Example 28 without further purification) suspended in DMF (1.0 mL) was added diisopropylethylamine (0.022 mL, 0.13 mmol) followed by dropwise addition of benzyl bromide (0.014 mL, 0.13 mmol). The reaction mixture gradually became homogeneous as stirring was continued at rt overnight. The solvent was removed in vacuo, and the residue purified by flash silica gel chromatography (50–60% EtOAc/hexanes) to give 0.023 g (61%) of a white solid: mp=189–191° C.; $R_f$=0.23 (75% EtOAc/hexanes); IR (KBr) 1651, 1462, 1445, 1356 cm$^{-1}$; $^1$H NMR (DMSO-$d_6$) δ 3.53–3.54 (m, 2H), 4.14–4.15 (m, 2H), 4.61 (s, 2H), 7.25–7.34 (m, 4H), 7.45–7.47 (m, 2H), 7.76–7.80 (m, 2H), 8.36 (t, 1H, J=5.5 Hz). HRMS calcd for $C_{17}H_{15}N_3OS$ 309.0936 (M$^+$), found 309.0933. Anal. ($C_{17}H_{15}N_3OS \cdot 0.3H_2O$) C, H, N.

Example 30

1-(3-[1,3]-Dioxan-2-yl-phenyl)-8,9-dihydro-7H-2,7,9a-triaza-benzo[cd]azulen-6-one

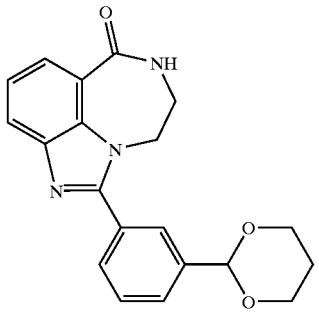

The title compound was prepared from 2-(3-formylphenyl)-1,3-dioxane (Ackerley et al., *J. Med. Chem* (1995), 38:1608) to give 0.20 g (52%) of a light-grey solid: mp=247° C. (dec); $R_f$=0.22 (5% MeOH/EtOAc); IR(KBr) 2361, 1653, 1472 cm$^{-1}$; $^1$H NMR (DMSO-$d_6$) δ 1.32–1.50 (m, 1H), 1.95–2.08 (m, 1H), 3.52–3.53 (m, 2H), 3.97 (ddd, 2H, J=12.1, 12.1, 2.1 Hz), 4.17 (dd, 2H, J=11.0, 5.1 Hz), 4.43–4.45 (m, 2H), 5.63 (s, 1H), 7.33–7.39 (m, 1H), 7.54–7.60 (m, 2H), 7.82–7.91 (m, 4H), 8.44 (t, 1H, J=5.5 Hz). Anal. ($C_{20}H_{19}N_3O_3$) C, H, N.

Example 31

3-(6-Oxo-6,7,8,9-tetrahydro-2,7,9a-triaza-benzo[cd]azulen-1-yl)-benzaldehyde

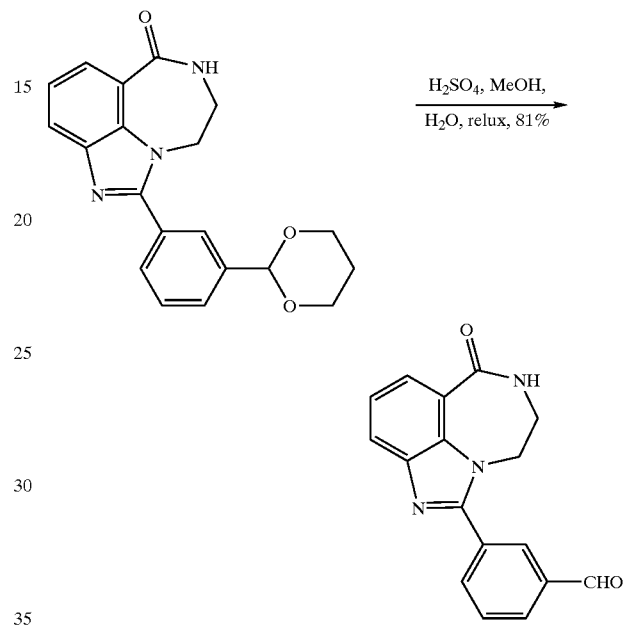

The dioxolane from Example 30 (1.96 g, 5.84 mmol) was dissolved in MeOH (58 mL) and water (58 mL). Concentrated sulfuric acid (1 mL) was added, and the reaction mixture was brought to reflux for 5 hours. The reaction was cooled to rt, and MeOH was removed in vacuo. The residue was diluted with saturated aqueous NaHCO$_3$, upon which the product came out of solution as a gum. The aqueous solution was decanted off, and the residue triturated with water. The water was decanted, and the residue was triturated with CHCl$_3$. The solvent was removed in vacuo, upon which the product solidified. The solids were triturated with EtOAc, filtered, washed with EtOAc, and dried overnight to give 1.23 g of a white crystalline solid. An additional 0.14 g of product had crystallized out of the aqueous phases upon standing overnight and was isolated to give a total yield of 81% of the aldehyde: $^1$H NMR (DMSO-$d_6$) δ 3.54–3.55 (m, 2H), 4.49–4.51 (m, 2H), 7.36–7.41 (m, 1H), 7.82 (t, 1H, J=7.6 Hz), 7.88–7.95 (m, 2H), 8.08–8.10 (m, 1H), 8.19–8.21 (m, 1H), 8.41 (s, 1H), 8.46–8.49 (m, 1H), 10.14 (s, 1H).

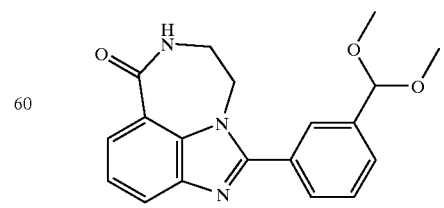

1-(3-Dimethoxymethyl-phenyl)-8,9-dihydro-7H-2,7,9a-triaza-benzo[cd]azulen-6-one (31a) was isolated during flash silica gel column chromatography as a by-product in the form of a white solid: mp=182–185° C.; $R_f$=0.15 (5% MeOH/CHCl$_3$); IR (KBr) 2361, 1653, 1458, 1091, 1046 cm$^{-1}$; $^1$H NMR (DMSO-d$_6$) δ 3.31 (s, 6H), 3.52–3.54 (m, 2H), 4.45–4.46 (m, 2H), 5.50 (s, 1H), 7.36 (t, 1H, J=7.8 Hz), 7.58–7.60 (m, 2H), 7.81–7.92 (m, 4H), 8.43–8.45 (m, 1H). HRMS calcd for C$_{19}$H$_{19}$N$_3$O$_3$ 337.1426 (M$^+$), found 337.1415. Anal. (C$_{19}$H$_{19}$N$_3$O$_3$) C, H, N, O.

Example 32

1-(3-Dimethylaminomethyl-phenyl)-8,9-dihydro-7H-2,7,9a-triaza-benzo[cd]azulen-6-one

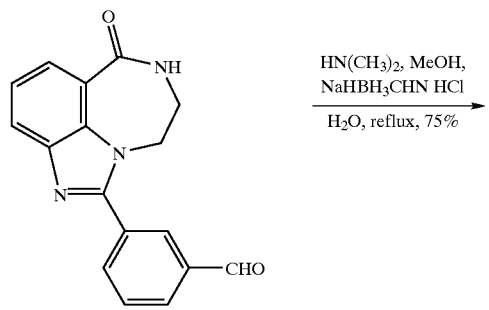

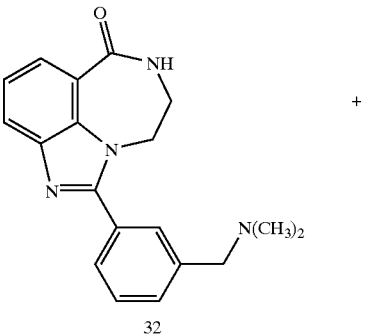

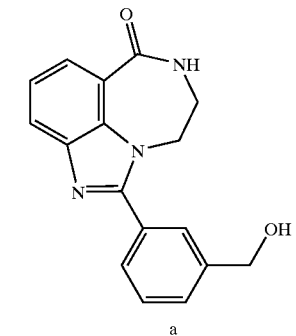

3-(6-Oxo-6,7,8,9-tetrahydro-2,7,9a-triaza-benzo[cd]azulen-1-yl)-benzaldehyde (from Example 31 without further purification, 0.24 g, 0.84 mmol) was suspended in MeOH (40 mL). Dimethylamine (2M in MeOH, 3.60 mL, 7.2 mmol) was added, upon which the starting material dissolved. To this solution was added a solution of NaBH$_3$CN (0.061 g, 0.92 mmol) and ZnCl$_2$ (0.063 g, 0.46 mmol) in MeOH (10 mL). The pH of the reaction mixture was adjusted to 6 with 2M HCl/MeOH (2.5 mL), and the mixture was stirred at rt for 3 h. Concentrated HCl (0.25 mL) was added and the MeOH was removed in vacuo. The residue was diluted with H$_2$O, and the pH adjusted to 10–11 with 10% NaOH. The product was extracted 3× with CHCl$_3$. The organic phases were combined, washed with H$_2$O and brine, dried (MgSO$_4$), and then concentrated in vacuo. The residue was purified by column chromatography (5% MeOH/CHCl$_3$) until the first product, the benzyl alcohol by-product eluted. The product was then eluted with 5% methanolic ammonia/CHCl$_3$ to give 0.20 g (75%) of compound 32 as a white solid: mp=192–194° C. (dec); $R_f$=0.10 (7% methanolic ammonia/CHCl$_3$); IR(KBr) 1651, 1464 cm$^{-1}$; $^1$H NMR (DMSO-d$_6$) δ 2.19 (s, 6H), 3.50 (s, 2H), 3.52–3.53 (m, 2H), 4.45–4.46 (m, 2H), 7.33–7.38 (m, 1H), 7.47–7.56 (m, 2H), 7.72–7.74 (m, 1H), 7.78 (s, 1H), 7.85–7.91 (m, 2H), 8.44 (t, 1H, J=5.5 Hz). HRMS calcd for C$_{19}$H$_{21}$N$_4$O 321.1715 (M$^+$H), found 321.1703. Anal. (C$_{19}$H$_{20}$N$_4$O.0.5 H$_2$O) C, H, N.

1-(3-Hydroxymethyl-phenyl)-8,9-dihydro-7H-2,7,9a-triaza-benzo[cd]azulen-6-one (32a) was isolated as a by-product to give a white solid (0.013 g, 5.5%): mp=275–278° C.; $R_f$=0.26 (10% MeOH/CHCl$_3$); IR (KBr) 1649, 1599, 1466, 1053 cm$^{-1}$; $^1$H NMR (DMSO-d$_6$) δ 3.46–3.53 (m, 2H), 4.44–4.46 (m, 2H), 4.61 (d, 2H, J=5.7 Hz), 5.32–5.36 (m, 1H), 7.33–7.38 (m, 1H), 7.51–7.56 (m, 2H), 7.70–7.72 (m, 1H), 7.81 (s, 1H), 7.85–7.91 (m, 2H), 8.43–8.47 (m, 1H). HRMS calcd for C$_{17}$H$_{15}$N$_3$O$_2$ 293.1164 (M$^+$), found 293.1168. Anal. (C$_{17}$H$_{15}$N$_3$O$_2$.0.5 H$_2$O) C, H, N.

Example 33

6-Phenyl-3,4-dihydro-2H-[1,4]diazepino[6,7,1-hi]indol-1-one

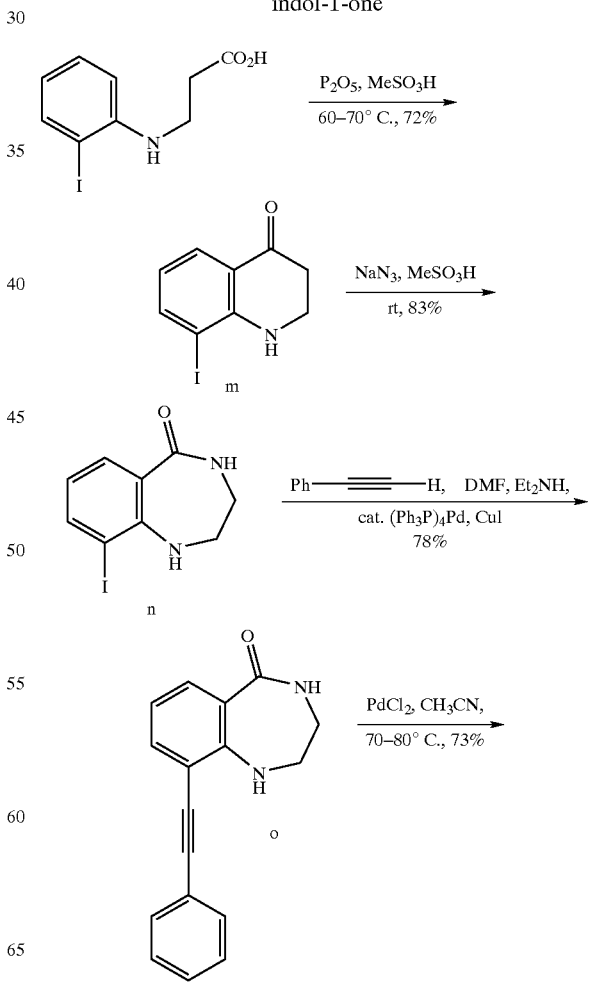

-continued

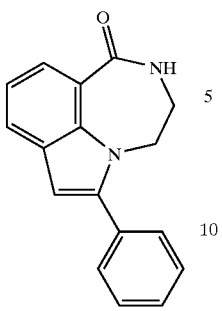

(a) Intermediate m—8-Iodo-2,3-dihydro-1H-quinolin-4-one:

A mixture of the 3-(2-iodophenylamino)-propionic acid (0.103 g, 0.354 mmol), prepared from the condensation of β-propiolactone and 2-iodoaniline according to the procedure of Bradley et al. (*JCS PI*, 2019 (1972)), in Eaton's reagent (2 mL) was heated between 60–70° C. for 3 h. After cooling the reaction mixture to rt, ice cold water was added. The solution was made basic (pH 12) with 50 wt. % NaOH and extracted with EtOAc several times. The combined organic extracts were dried over anhydrous $MgSO_4$ and concentrated to give 0.070 g (72%) of the product, which was used in the next step without further purification: $^1$H NMR ($CDCl_3$) δ 2.71 (t, 2H, J=6.0 Hz), 3.65 (t, 2H, J=6.0 Hz), 4.86 (bs, 1H), 6.50 (t, 1H, J=9.0 Hz), 7.79 (d, 1H, J=9.0 Hz), 7.85 (d, 1H, J=9.0 Hz).

(b) Intermediate n—9-Iodo-1,2,3,4-tetrahydro-benzo[e][1,4]diazepin-5-one:

To a solution of the ketone intermediate m (3.47 g, 12.7 mmol) in $CH_3SO_3H$ (50 mL) kept at rt was carefully and slowly added $NaN_3$ (1.074 g, 16.5 mmol) in portions. The reaction mixture was stirred at rt for 30 min. Upon completion of the reaction (as indicated by TLC), ice-cold water was added, and the mixture was made basic (pH 13) using 50 wt. % solution of NaOH, whereupon the product (3.05 g, 83%) precipitated. The solids were filtered, washed with water and dried: mp=182–184° C.; $^1$H NMR (DMSO-$d_6$) δ 3.25–3.27 (m, 2H), 3.48 (bs, 2H), 5.43 (bs, 1H), 6.41 (t, 1H, J=6.0 Hz), 7.73 (d, 1H, J=6.0 Hz), 7.80 (d, 1H, J=6.0 Hz), 8.15 (bs, 1H). LRMS ($M^+$) 288.

(c) Intermediate o—9-Phenylethynyl-1,2,3,4-tetrahydro-benzo[e][1,4]diazepin-5-one:

A mixture of the iodide intermediate n (0.144 g, 0.5 mmol), phenylacetylene (0.055 mL, 0.5 mmol), tetrakistriphenylphosphine palladium(0) (6 mg, 0.005 mmol), CuI (2 mg, 0.01 mmol), diethylamine (4 mL) and DMF (2 mL) was stirred at rt for 2 hours. The solvent was evaporated to dryness and the residue was taken up in water and extracted with EtOAc. The organic extract was dried over anhydrous $MgSO_4$, filtered and concentrated. The crude mixture was purified by flash silica gel chromatography eluting with a gradient of 0–3% MeOH in $CHCl_3$ to give 0.102 g (78%) of the desired product: IR (KBr) 3400, 3190, 3051, 1641, 1589, 1518, 1446, 1250, 756, 690 $cm^{-1}$; $^1$H NMR (DMSO-$d_6$) δ 3.27–3.29 (m, 2H), 3.53–3.56 (m, 2H), 6.26 (t, 1H, J=6.0 Hz), 6.61 (t, 1H, J=6.0 Hz), 7.40–7.47 (m, 4H), 7.62–7.65 (m, 2H), 7.80 (d, 1H, J=6.0 Hz), 8.13 (t, 1H, J=6.0 Hz). LRMS ($M^+$) 262.

(d) Title Compound:

To a clear solution of the acetylene intermediate o (0.08 g, 0.305 mmol) in $CH_3CN$ (10 mL) was added $PdCl_2$ (0.003 g, 0.0153 mmol) at rt. The reaction mixture was heated at a temperature between 70–80° C. for 3.5 h. Upon completion of the reaction (as indicated by TLC), the solvent was evaporated to dryness. The crude mixture was purified by flash silica gel chromatography eluting with a gradient of 0–3% MeOH in $CHCl_3$ to give 0.058 g (73%) of the desired product: $^1$H NMR (DMSO-$d_6$) δ 3.46–3.51 (m, 2H), 4.31–4.33 (m, 2H), 6.71 (s, 1H), 7.17 (t, 1H, J=9.0 Hz), 7.42–7.55 (m, 3H), 7.60–7.63 (m, 2H), 7.78 (d, 1H, J=9.0 Hz), 7.82 (d, 1H, J=9.0 Hz), 8.38 (t, 1H, J=6.0 Hz). HRMS calcd for $C_{17}H_{14}N_2O$ 262.1106 ($M^+$), found 262.1109. Anal. ($C_{17}H_{14}N_2O.0.1\ H_2O$) C, H, N.

Example 34

6-(4-Chlorophenyl)-3,4-dihydro-2H-[1,4]diazepino[6,7,1-hi]indol-1-one

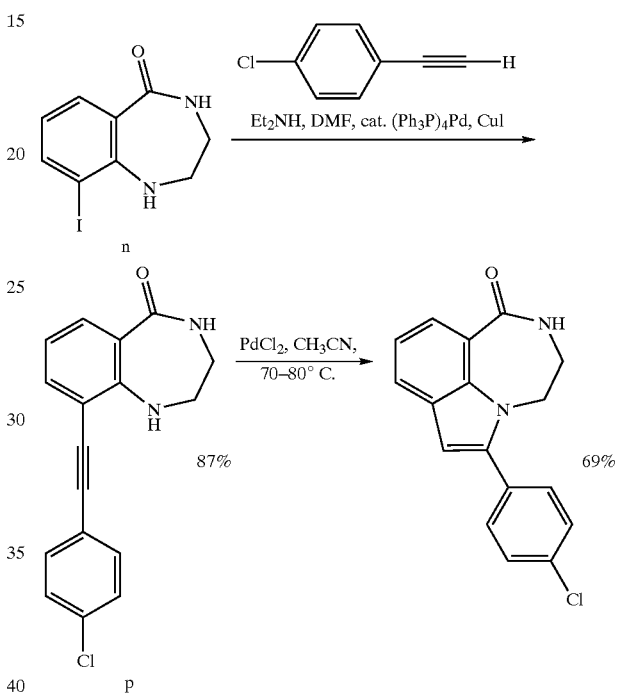

(a) Intermediate p—9-(4-Chlorophenylethynyl)-1,2,3,4-tetrahydro-benzo[e][1,4]diazepin-5-one:

Using the procedure described above for preparation of intermediate o, 1-chloro-4-ethynylbenzene and intermediate n, 9-iodo-1,2,3,4-tetrahydro-benzo[e][1,4]diazepin-5-one, were used to synthesize intermediate p (87%) as a yellow solid: mp 178–180° C.; $^1$H NMR (DMSO-$d_6$) δ 3.27–3.30 (m, 2H), 3.52–3.55 (m, 2H), 6.31 (t, 1H, J=6.0 Hz), 6.61 (t, 1H, J=6.0 Hz), 7.45 (d, 1H, J=6.0 Hz), 7.50 (d, 2H), J=9.0 Hz), 7.67 (d, 2H, J=9.0 Hz), 7.82 (d, 1H, J=6.0 Hz), 8.13 (t, 1H, J=6.0 Hz). LRMS 296 ($M^+$).

(b) 6-(4-Chlorophenyl)-3,4-dihydro-2H-[1,4]diazepino[6,7,1-hi]indol-1-one:

Using the procedure described above for preparation of 6-phenyl-3,4-dihydro-2H-[1,4]diazepino[6,7,1-hi]indol-1-one (Example 33), the title compound was synthesized from intermediate p in 69% yield as a pale-yellow solid: $^1$H NMR (DMSO-$d_6$) δ 3.47–3.50 (m, 2H), 4.29–4.32 (m, 2H), 6.74 (s, 1H), 7.18 (t, 1H, J=9.0 Hz), 7.58 (d, 2H, J=9.0 Hz), 7.65 (d, 2H, J=9.0 Hz), 7.80 (d, 2H, J=9.0 Hz), 7.83 (d, 2H, J=9.0 Hz), 8.39 (t, 1H, J=4.5 Hz). HRMS calcd for $C_{17}H_{13}N_2OCl$ ($M^+$) 296.0716, found 296.0715. Anal. ($C_{17}H_{13}N_2OCl$) C, H, N.

Example 35

6-(4-Methoxyphenyl)-3,4-dihydro-2H-[1,4]diazepino[6,7,1-hi]indol-1-one

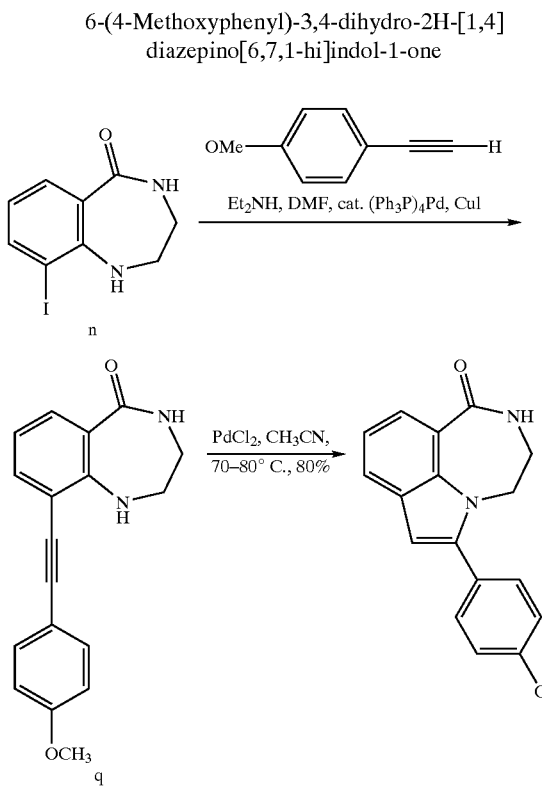

(a) Intermediate q—9-(4-Methoxyphenylethynyl)-1,2,3,4-tetrahydro-benzo[e][1,4]diazepin-5-one:

Using the procedure described above for preparation of intermediate o, 1-methoxy-4-ethynylbenzene and intermediate n, 9-iodo-1,2,3,4-tetrahydro-benzo[e][1,4]diazepin-5-one, were used to synthesize intermediate q in 80% yield as a yellow solid: mp 193–195° C.; $^1$H NMR (DMSO-d$_6$) δ 3.27–3.29 (m, 2H), 3.53–3.55 (m, 2H), 3.81 (s, 3H), 6.20 (br s, 1H), 6.60 (t, 1H, J=6.0 Hz), 6.98 (d, 2H, J=9.0 Hz), 7.41 (d, 1H, J=6.0 Hz), 7.57 (d, 2H, J=9.0 Hz), 7.79 (d, 1H, J=6.0 Hz), 8.11 (t, 1H, J=6.0 Hz). LRMS 292 (M$^+$).

(b) 6-(4-Methoxyphenyl)-3,4-dihydro-2H-[1,4]diazepino[6,7,1-hi]indol-1-one:

Using the procedure described above for preparation of 6-phenyl-3,4-dihydro-2H-[1,4]diazepino[6,7,1-hi]indol-1-one (Example 33), the title compound was synthesized from intermediate q in 84% yield as a pale-yellow solid: $^1$H NMR (DMSO-d$_6$) δ 3.48–3.50 (m, 2H), 4.27–4.30 (m, 2H), 6.60 (s, 1H), 7.07 (d, 2H, J=9.0 Hz), 7.15 (t, 1H, J=6.0 Hz), 7.54 (d, 2H, J=9.0 Hz), 7.75 (d, 1H, J=6.0 Hz), 7.79 (d, 1H, J=6.0 Hz), 8.36 (t, 1H, J=6.0 Hz). HRMS calcd for C$_{18}$H$_{16}$N$_2$O$_2$ (M$^+$) 292.1212, found 292.1218. Anal. (C$_{18}$H$_{16}$N$_2$O$_2$.0.1 H$_2$O) C, H, N.

Example 36

6-Phenethyl-3,4-dihydro-2H-[-1,4]diazepino[6,7,1-hi]indol-1-one

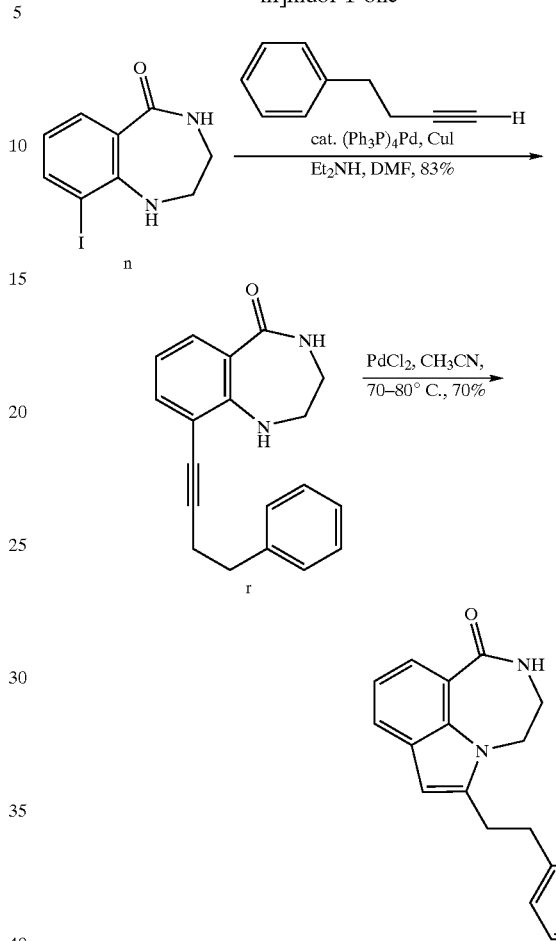

(a) Intermediate r—9-(4-Phenylbutynyl)-1,2,3,4-tetrahydro-benzo[e][1,4]diazepin-5-one:

Using the procedure described above for preparation of intermediate o, 4-phenyl-1-butyne and intermediate n, 9-iodo-1,2,3,4-tetrahydro-benzo[e][1,4]diazepin-5-one, were used to synthesize intermediate r which was obtained in 83% yield as a pale brown solid: mp=133–135° C.; $^1$H NMR (DMSO-d$_6$) δ 2.76–2.81 (m, 2H), 2.86–2.90 (m, 2H), 3.23–3.25 (m, 2H), 3.39–3.41 (m, 2H), 5.70 (bs, 1H), 6.53 (t, 1H, J=6.0 Hz), 7.23 (d, 1H, I=6.0 Hz), 7.31–7.35 (m, 5H), 7.69 (d, 1H, J=6.0 Hz), 8.07 (t, 1H, J=6.0 Hz); LRMS (M$^+$) 290.

(b) 6-Phenethyl-3,4-dihydro-2H-[1,4]diazepino[6,7,1-hi]indol-1-one

Using the procedure described above for preparation of 6-phenyl-3,4-dihydro-2H-[1,4]diazepino[6,7,1-hi]indol-1-one (Example 33), the title compound was synthesized from intermediate r and obtained in 70% yield as a pale yellow solid; $^1$H NMR (DMSO-d$_6$) δ 2.96–3.06 (m, 4H), 3.49–3.50 (m, 2H), 4.21 (bs, 2H), 6.37 (s, 1H), 7.07 (t, 1H, J=6.0 Hz), 7.18–7.29 (m, 5H), 7.65 (d, 1H, J=6.0 HZ), 7.74 (d, 1H, J=6.0 Hz), 8.26 (t, 1H, J=6.0 Hz); HRMS calcd. for C$_{19}$H$_{18}$N$_2$O (M$^+$) 290.1419, found 290.1421. Anal. (C$_{19}$H$_{18}$N$_2$O) C, H, N.

Example 37

6-(4-Fluorophenyl)-3,4-dihydro-2H-[1,4diazepino[6,7,1-hi]indol-1-one

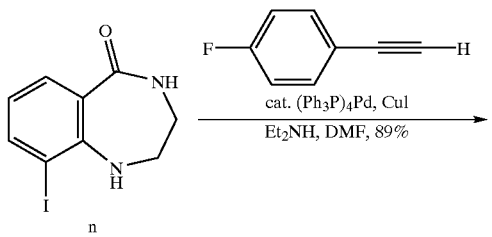

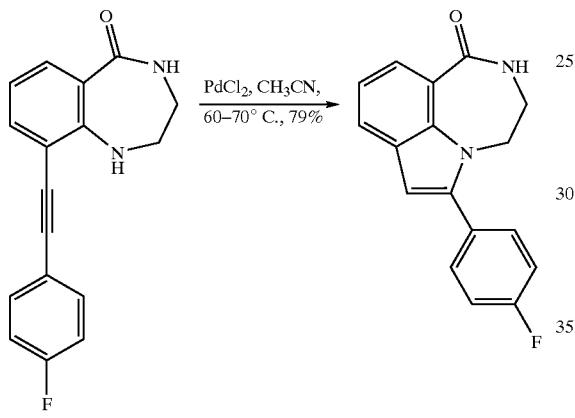

(a) Intermediate s—9-(4-Fluorophenylethynyl)-1,2,3,4-tetrahydro-benzo[e][1,4]diazepin-5-one:

Using the procedure described above for preparation of intermediate o, 1-fluoro-4-ethynylbenzene and intermediate n, 9-iodo-1,2,3,4-tetrahydro-benzo[e][1,4]diazepin-5-one, were used to synthesize intermediate s, which was obtained in 89% yield as a yellow solid: mp=160–162° C.; $^1$H NMR (DMSO-d$_6$) δ 3.27–3.30 (m, 2H), 3.52–3.55 (m, 2H), 6.27 (bs, 1H), 6.61 (t, 1H, J=6.0 Hz), 7.27 (t, 2H, J=9.0 Hz), 7.44 (d, 1H, J=6.0 Hz), 7.67–7.72 (m, 2H), 7.80 (d, 1H, J=6.0 Hz), 8.13 (t, 1H, J=6.0 Hz). LRMS (M$^+$) 280. Anal. (C$_{17}$H$_{13}$N$_2$OF. 0.1 H$_2$O) C, H, N.

(b) Title Compound:

Using a similar procedure to that described above for preparation of 6-phenyl-3,4-dihydro-2H-[1,4]diazepino[6,7,1-hi]indol-1-one (Example 33), the title compound was synthesized from intermediate s in 79% yield as a pale-yellow solid: $^1$H NMR (DMSO-d$_6$) δ 3.48–3.50 (m, 2H), 4.28–4.30 (m, 2H), 6.70 (s, 1H), 7.15 (t, 1H, J=6.0 Hz), 7.33–7.39 (m, 2H), 7.65 (d, 1H, J=6.0 Hz), 7.68 (d, 1H, J=6.0 Hz), 7.78 (d, 1H, J=6.0 Hz), 7.82 (d, 1H, J=6.0 Hz), 8.38 (t, 1H, J=6.0 Hz). HRMS calcd. for C$_{17}$H$_{13}$N$_2$OF (M$^+$) 280.1012, found 280.1002. Anal. (C$_{17}$H$_{13}$N$_2$OF) C, H, N.

Example 38

6-(4-Chloro-phenyl)-1-oxo-1,2,3,4-tetrahydro-[1,4]diazepino[6,7,1-hi]indole-7-carboxaldehyde

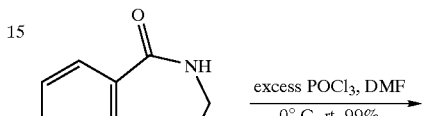

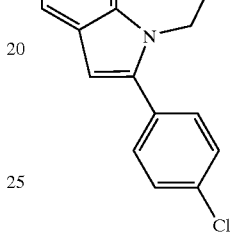

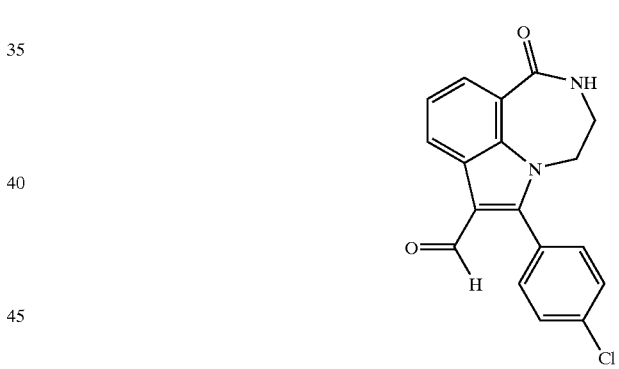

POCl$_3$ (0.3 mL, 3.19 mmol) was slowly added to DMF (3 mL) at 0° C. The mixture was stirred for 15 minutes and then was treated with a solution of 6-phenyl-3,4-dihydro-2H-[1,4]diazepino[6,7,1-hi]indol-1-one (Example 33, 0.070 g, 0.236 mmol) in DMF (2 mL). The reaction mixture was warmed to rt and stirred for 4 h. After removing all solvent, the residue was taken up in H$_2$O, made basic (pH 12–14) using 50% aqueous NaOH, whereupon the product precipitated. The product was filtered, washed with water several times and dried to yield 0.077 g (99%) of a pale-yellow solid: $^1$H NMR (DMSO-d$_6$) δ 3.41–3.52 (m, 2H), 4.20–4.22 (m, 2H), 7.43 (t, H, J=9.0 Hz), 7.68 (d, 2H, J=9.0 Hz), 7.74 (d, 2H, J=9.0 Hz), 8.00 (d, 1H, J=6.0 Hz), 8.47 (d, 1H, J=6.0 Hz), 8.51 (t, 1H, J=6.0 Hz), 9.65 (s, 1H). HRMS calcd. for C$_{18}$H$_{13}$N$_2$O$_2$Cl (M$^+$) 324.0665, found 324.0668. Anal. (C$_{18}$H$_{13}$N$_2$O$_2$Cl.0.25 H$_2$O) C, H, N.

Example 39

6-(4-Chloro-phenyl)-1-oxo-1,2,3,4-tetrahydro-[1,4]diazepino[6,7,1-hi]indole-7-carboxaldehyde Oxime

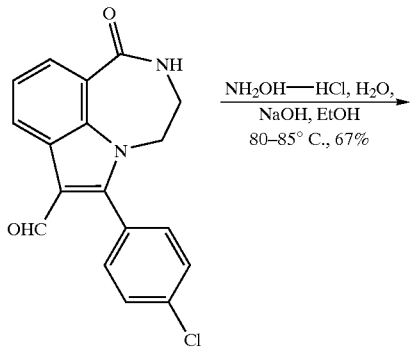

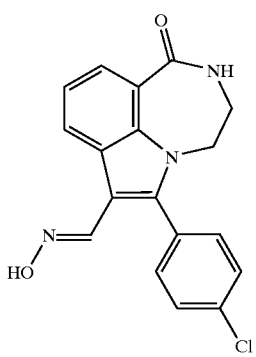

NH$_2$OH·HCl (0.027 g, 0.385 mmol) and NaOH (0.016 g, 0.385 mmol) were added to a suspension of the aldehyde 6-(4-chloro-phenyl)-1-oxo-1,2,3,4-tetrahydro-[1,4]diazepino[6,7,1-hi]indole-7-carboxaldehyde (Example 38, 0.050 g, 0.154 mmol) in EtOH (5 mL) and H$_2$O (0.5 mL). The reaction mixture was heated at 80–85° C. for 3 h, cooled to rt and evaporated to dryness. The residue was taken up in ice-cold H$_2$O, whereupon a pale-yellow solid precipitated. The solid was filtered, washed with H$_2$O and then purified by flash silica gel chromatography eluting with a gradient of 0–5% MeOH in CHCl$_3$ to give 0.035 g (67%) of the oxime: $^1$H NMR (DMSO-d$_6$) δ 3.40 (bs, 2H), 4.0–4.1 (m, 2H), 7.30 (t, 1H, J=9.0 Hz), 7.55 (d, 2H, J=9.0 Hz), 7.64 (d, 2H, J=9.0 Hz), 7.90 (s, 1H), 7.94 (d, 1H, J=9.0 Hz), 8.34 (d, 1H, J=9.0 Hz), 8.41 (t, 1H, J=6.0 Hz), 10.83 (s, 1H). HRMS calcd. for C$_{18}$H$_{14}$N$_3$O$_2$Cl (M$^+$+H) 340.0853, found 340.0862. Anal. (C$_{18}$H$_{14}$N$_3$O$_2$Cl · 0.75 CH$_2$Cl$_2$) C, H, N.

Example 40

6-Pyridin-2-yl-3,4-dihydro-2H-[1,4]diazepino[6,7,1-hi]indol-1-one

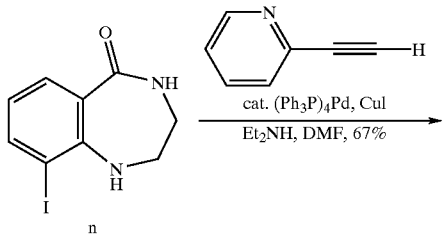

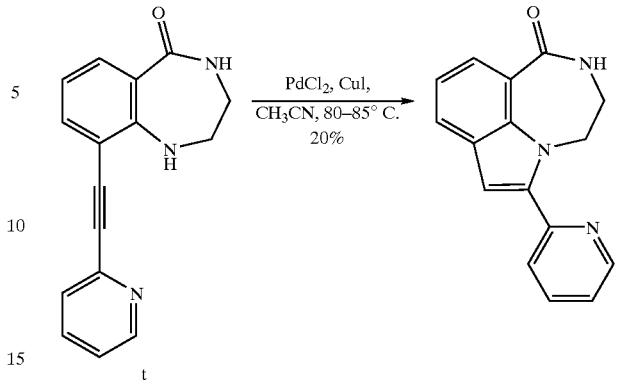

(a) Intermediate t-9-Pyridin-2-ylethynyl-1,2,3,4-tetrahydro-benzo[e][1,4]diazepin-5-one:

Using the procedure described above for preparation of intermediate o, 2-ethynylpyridine and intermediate n, 9-iodo-1,2,3,4-tetrahydro-benzo[e][1,4]diazepin-5-one, were used to synthesize intermediate t in 67% yield as a brown solid: mp=173–175° C.; $^1$H NMR (DMSO-d$_6$) δ 3.20–3.24 (m, 2H), 3.54–3.56 (m, 2H), 6.29 (t, 1H, J=6.0 Hz), 6.64 (t, 1H, J=6.0 Hz), 7.37–7.41 (m, 1H), 7.50 (d, 1H, J=6.0 Hz), 7.77 (d, 1H, J=9.0 Hz), 7.82–7.88 (m, 2H), 8.15 (t, 1H, J=6.0 Hz), 8.59 (d, 1H, J=6.0 Hz). LRMS (M$^+$) 263.

(b) Title Compound:

To a solution of the acetylene intermediate t (0.050 g, 0.190 mmol) in DMF (6 mL) was added CuI (0.003 g, 0.012 mmol) and PdCl$_2$ (0.005 g, 0.029 mmol) at rt. The reaction mixture was heated at 80–85° C. for 4 h. Upon completion of reaction (as indicated by TLC), the solvent was removed under vacuum and the crude residue was purified by flash silica gel chromatography eluting with a gradient of 0–3% MeOH in CHCl$_3$ to give 0.010 g (20%) of the product: $^1$H NMR (DMSO-d$_6$) δ 3.38–3.55 (m, 2H), 4.64 (bs, 2H), 7.06 (s, 1H), 7.19 (t, 1H, J=9.0 Hz), 7.37–7.41 (m, 1H), 7.82–7.96 (m, 4H), 8.38 (t, 1H, J=6.0 Hz), 8.70 (d, 1H, J=3.0 Hz). HRMS calcd. for C$_{16}$H$_{13}$N$_3$O (M$^+$) 263.1059, found 263.1062. Anal. (C$_{16}$H$_{13}$N$_3$O · 0.8 H$_2$O) C, H, N.

Comparison Example 41

3,4,6,7-Tetrahydro-2H-[1,4]diazepino[6,7,1-hi]indol-1-one

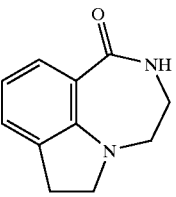

This known compound was prepared according to the literature procedure of Hester et al. and references cited therein (Hester et al., *J. Med. Chem.* 13, 827 (1970)): $^1$H NMR (DMSO-d$_6$) δ 2.92 (t, 2H, J=7.5 Hz), 3.29–3.31 (m, 4H), 3.47 (t, 2H, J=7.5 Hz), 6.49 (t, 1H, J=7.5 Hz), 7.04 (d, 1H, J=7.5 Hz), 7.49 (d, 1H J=7.5 Hz), 7.86 (bs, 1H). HRMS calcd for C$_{11}$H$_{12}$N$_2$O (M$^+$) 188.0950, found 188.0957. Anal. (C$_{11}$H$_{12}$N$_2$O) C, H, N.

Comparison Example 42

3,4-Dihydro-2H-[1,4]diazepino [6,7,1-hi]indol-1-one

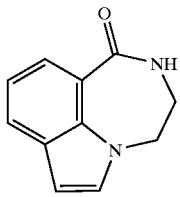

This known compound was prepared from 3,4,6,7-tetrahydro-2H-[1,4]diazepino[6,7,1-hi]indol-1-one (Example 41) according to the general procedure of Hester et al. and references cited therein (Hester et al., *J. Med. Chem.* 13, 827 (1970)): $^1$H NMR (DMSO-d$_6$) δ 3.52–3.56 (m, 2H), 4.31–4.36 (m, 2H), 6.53 (d, 1H, J=3.0 Hz), 7.11 (t, 1H, J=6.0 Hz), 7.38 (d, 1H, J=3.0 Hz), 7.70 (d, 1H, J=6.0 Hz), 7.80 (d, 1H, J=6.0 Hz), 8.30 (bs, 1H). LRMS (M$^+$) 186. Anal. (C$_{11}$H$_{10}$N$_2$O.0.05 H$_2$O) C, H, N.

Example 43

7-Iodo-3,4-dihydro-2H-[1,4]diazepino[6,7,1-hi]indol-1-one

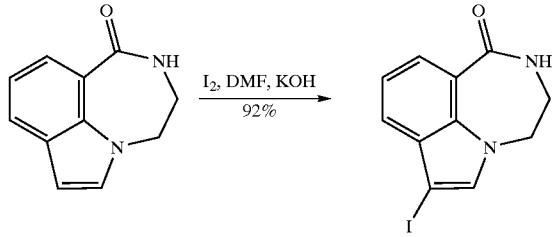

To a pale-yellow solution of 3,4-dihydro-2H-[1,4]diazepino[6,7,1-hi]indol-1-one (Example 42, 0.051 g, 0.274 mmol) in 5 mL DMF was added KOH (0.058 g, 1.03 mmol) and iodine (0.139 g, 0.548 mmol) at rt. The reaction mixture was stirred at rt overnight, at which time solvent was removed in vacuo. The residue was taken up in EtOAc and washed with 0.1% aq sodium bisulfite, H$_2$O and brine. The organic layer was dried over anhydrous MgSO$_4$, filtered and concentrated to give 0.078 g (92%) of a pale-yellow solid: $^1$H NMR (DMSO-d$_6$) δ 3.56–3.59 (m, 2H), 4.40 (m, 2H), 7.26 (t, 1H, J=7.5 Hz), 7.52 (d, 1H, J=7.5 Hz), 7.67 (s, 1H), 7.93 (d, 1H, J=7.5 Hz), 8.37 (t, 1H, J=5.3 Hz). HRMS calcd. for C$_{11}$H$_9$N$_2$OI (M$^+$) 311.9761, found 311.9776. Anal. (C$_{11}$H$_9$N$_2$OI) C, H, N.

Example 44

1-Oxo-1,2,3,4-tetrahydro-[1,4diazepino[6,7,1-hi] indole-7-carboxylic Acid Methyl Ester

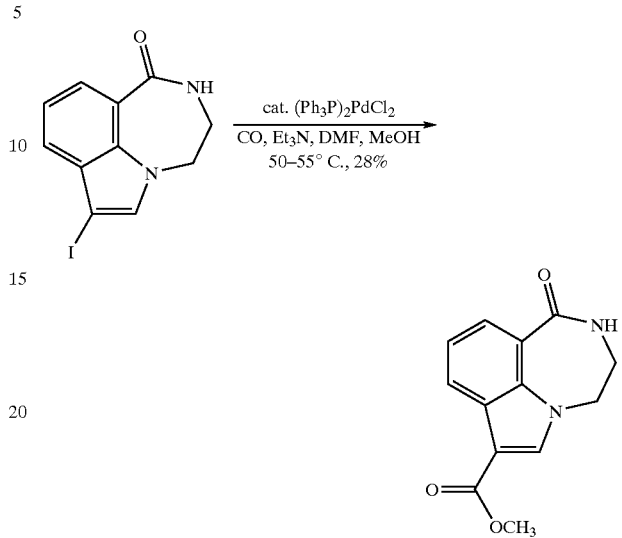

Triethylamine (0.11 mL, 0.747 mmol) was added to a mixture of 7-iodo-3,4-dihydro-2H-[1,4]diazepino[6,7,1-hi] indol-1-one (from Example 43 without further purification, 0.074 g, 0.37 mmol) and bistriphenylphosphine palladium chloride (8.4 mg, 0.012 mmol) in 8 mL MeOH and 3 mL DMF at rt. The reaction mixture was heated at 50–55° C. for 18 h under a CO atmosphere. The solvent was removed under vacuum, and the residue was taken up in EtOAc and washed with water. The organic layer was dried over anhydrous MgSO$_4$, filtered and concentrated to give a yellow solid, which was purified by flash silica gel chromatography eluting with a gradient of 0–3% MeOH in CHCl$_3$ to give 0.025 g (28%) of a white solid: $^1$H NMR (DMSO-d$_6$) δ 3.34–3.60 (m, 2H), 3.83 (s, 3H), 4.46 (bs, 2H), 7.36 (t, 1H, J=7.5 Hz), 7.95 (d, 1H, J=7.5 Hz), 8.23 (s, 1H), 8.27 (d, 1H, J=7.5 Hz), 8.40–8.50 (m, 1H). HRMS calcd. for C$_{13}$H$_{12}$N$_2$O$_3$ (M$^+$) 244.0848, found 244.0850. Anal. (C$_{13}$H$_{12}$N$_2$O$_3$.0.25 H$_2$O) C, H, N.

Example 45

1-Oxo-1,2,3,4-tetrahydro-[1,4]diazepino[6,7,1-hi] indole-7-carbaldehyde

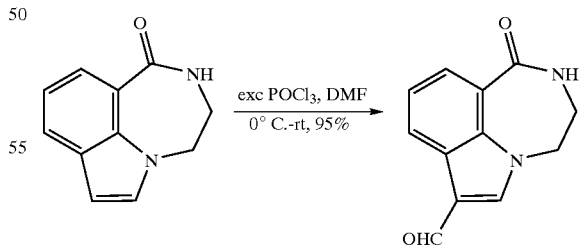

POCl$_3$ (16.37 g, 106.76 mmol) was slowly added to DMF (225 mL) at 0° C. The mixture was stirred for 15 minutes and then treated with a solution of 3,4-dihydro-2H-[1,4] diazepino[6,7,1-hi]indol-1-one (Example 42, 1.46 g, 7.85 mmol) in DMF (10 mL). The reaction mixture was warmed to rt and stirred for 17 h. After removing all solvent, the residue was taken up in H$_2$O, made basic (pH 12–14) using 50% aqueous NaOH and extracted with EtOAc several times. The organic layer was dried over anhydrous MgSO$_4$, filtered and concentrated to give 1.6 g (95%) of a pale-yellow solid: $^1$H NMR (DMSO-d$_6$) δ 3.58–3.61 (m, 2H), 4.48 (bs, 2H), 7.37 (t, 1H, J=7.5 Hz), 7.97 (d, 1H, J=7.5 Hz), 8.33–8.35 (m, 2H), 8.43–8.45 (m, 1H), 9.95 (s, 1H). HRMS calcd. for C$_{12}$H$_{10}$N$_2$O$_2$ (M$^+$) 214.0742, found 214.0737. Anal. (Cl$_2$H$_{10}$N$_2$O$_2$.0.1H$_2$O) C, H, N.

Example 46

1-Oxo-1,2,3,4-tetrahydro-[1,4]diazepino[6,7]-hi]indole-7-carbaldehyde Oxime

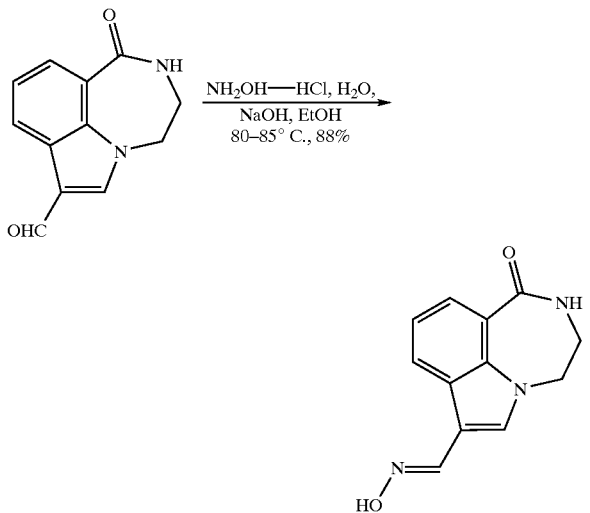

To a mixture of aldehyde 1-oxo-1,2,3,4-tetrahydro-[1,4]diazepino[6,7,1-hi]indole-7-carbaldehyde (from Example 45 without further purification, 0.050 g, 0.233 mmol) in EtOH (5 mL) and H$_2$O (0.5 mL) was added NH$_2$OH.HCl (0.041 g, 0.583 mmol) and NaOH (0.024 g, 0.583 mmol) at rt. The reaction mixture was heated at 80–85° C. for 2 days. The resulting suspension was filtered and the remaining white solid (0.047 g, 88%) was washed with water and dried: $^1$H NMR (DMSO-d$_6$) δ 3.56 (bs, 2H), 4.36 (bs, 2H), 7.23 (t, 1H, J=7.5 Hz), 7.68 (s, 1H), 7.90 (d, 1H, J=7.5 Hz), 8.21 (d, 1H, J=7.5 Hz), 8.26 (s, 1H), 8.33–8.35 (m, 1H), 10.66 (s, 1H). HRMS calcd for Cl$_2$H$_{11}$N$_3$O$_2$ (M$^+$) 229.0851, found 229.0843. Anal. (C$_{12}$H$_{11}$N$_3$O$_2$) C, H, N.

Example 47

(Z) and (E) 1-Oxo-1,2,3,4-tetrahydro-[1,4]diazepino[6,7,1-hi]indole-7-carbaldehyde O-Methyl-oxime

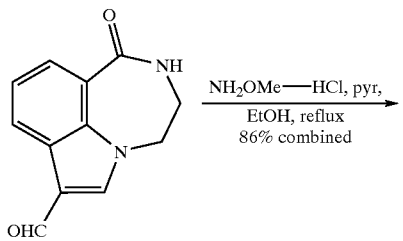

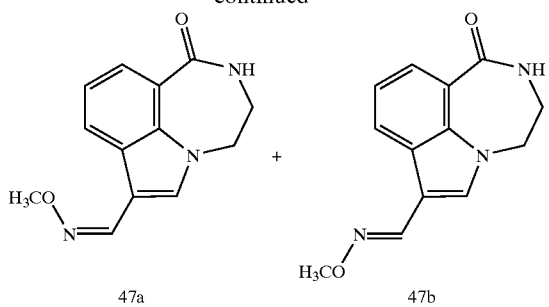

47a      47b

A solution of 1-oxo-1,2,3,4-tetrahydro-[1,4]diazepino[6,7,1-hi]indole-7-carbaldehyde (Example 45, 0.050 g, 0.234 mmol) and MeONH$_2$. HCl (0.020 g, 0.242 mmol) in EtOH (5 mL) and pyridine (5 mL) was refluxed for 20 h. The reaction mixture was then evaporated to dryness and the residue was taken up in H$_2$O and extracted with EtOAc several times. The combined organic layers were dried over anhydrous MgSO$_4$, filtered and concentrated. The residue was purified by flash silica gel chromatography eluting with a gradient of 0–1% MeOH in CHCl$_3$ to give 0.036 g (63%) of the (E) and 0.013 g (23%) of the (Z) isomers. (Z) isomer: $^1$H NMR (DMSO-d$_6$) δ 3.54–3.58 (m, 2H), 3.96 (s, 3H), 4.43 (bs, 2H), 7.27 (t, 1H, J=9.0 Hz), 7.89–7.92 (m, 2H), 8.14 (d, 1H, J=9.0 Hz), 8.21 (s, 1H), 8.35–8.39 (m, 1H). HRMS calcd for C$_{13}$H$_{13}$N$_3$O$_2$ (M$^+$) 243.1008, found 243.1020. Anal. (C$_{13}$H$_{13}$N$_3$O$_2$.0.1 H$_2$O.0.1 EtOAc) C, H, N. (E) isomer: $^1$H NMR (DMSO-d$_6$) δ 3.55 (bs, 2H), 3.87 (s, 3H), 4.37 (bs, 2H), 7.27 (t, 1H, J=7.5 Hz), 7.75 (s, 1H), 7.91 (d, 1H, J=7.5 Hz), 8.24 (d, 1H, J=7.5 Hz), 8.34–8.38 (m, 2H). HRMS calcd. for C$_{13}$H$_{13}$N$_3$O$_2$ (M$^+$) 243.1008, found 243.1016. Anal. (C$_{13}$H$_{13}$N$_3$O$_2$.0.25 H$_2$O) C, H, N.

Example 48

7-Hydroxymethyl-3,4-dihydro-2H-[1,4]diazepino[6,7,1-hi]indol-1-one

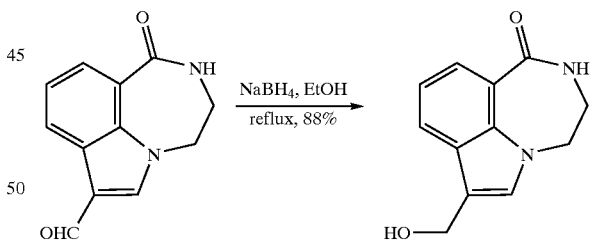

Sodium borohydride (0.018 g, 0.466 mmol) was added to a suspension of 1-oxo-1,2,3,4-tetrahydro-[1,4]diazepino[6,7,1-hi]indole-7-carbaldehyde (Example 45, 0.050 g, 0.233 mmol) in 15 mL EtOH. The reaction mixture was refluxed for 1.5 h, cooled to rt and the solvent was evaporated. The residue was partitioned between 1% aq NaOH and EtOAc. The organic extract was dried over anhydrous MgSO$_4$, filtered and evaporated to give a pale-yellow solid (88%): $^1$H NMR (DMSO-d$_6$) δ 3.52–3.55 (m, 2H), 4.31 (bs, 2H), 4.63 (d, 2H, J=5.0 Hz), 4.84 (t, 1H, J=5.0 Hz), 7.12 (t, 1H, J=7.5 Hz), 7.29 (s, 1H), 7.80–7.83 (m, 2H), 8.24–8.26 (m, 1H). HRMS calcd for C$_{12}$H$_{12}$N$_2$O$_2$ (M$^+$) 216.0899, found 216.0908. Anal. (C$_{12}$H$_{12}$N$_2$O$_2$.0.2H$_2$O) C, H, N.

Example 49

7-Methyl-3,4-dihydro-2H-[1,4]diazepino[6,7,1-hi]indol-1-one

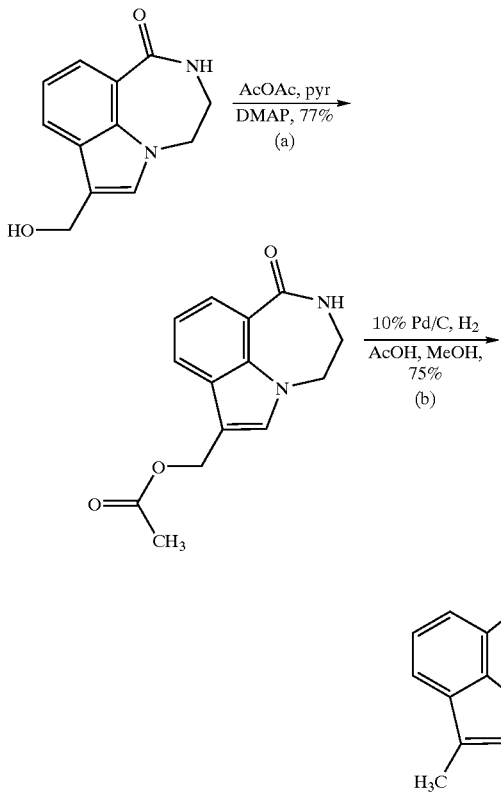

Example 50

6-(4-Fluoro-phenyl)-7-methyl-3,4-dihydro-2H-[1,4]diazepino[6,7,1-hi]indol-1-one

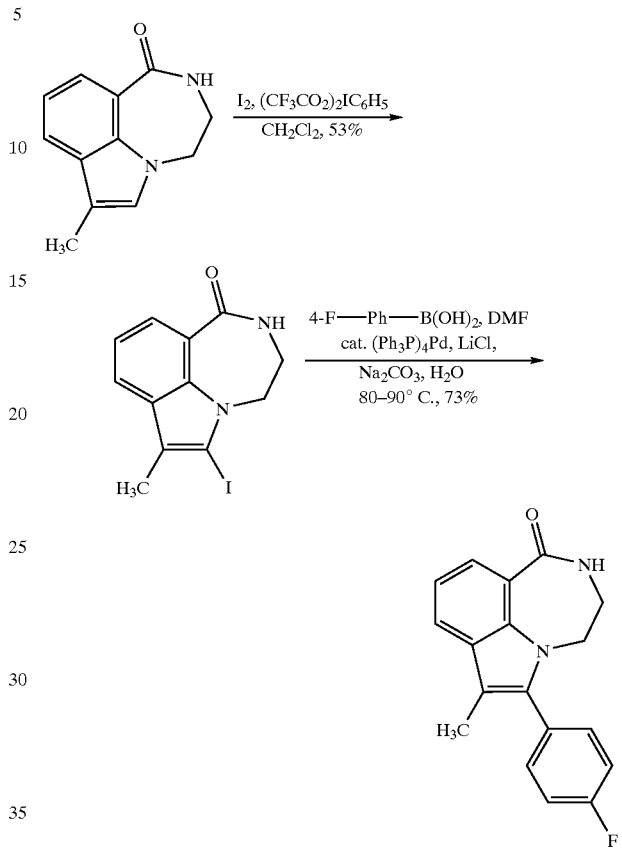

(a) Acetic acid-1-oxo-1,2,3,4-tetrahydro-[1,4]diazepino[6,7,1-hi]indole-7-ylmethyl Ester:

To a solution of alcohol 7-hydroxymethyl-3,4-dihydro-2H-[1,4]diazepino[6,7,1-hi]indol-1-one (Example 48, 1.007 g, 4.66 mmol) in acetic anhydride (1.1 mL, 11.65 mmol) and pyridine (25 mL) was added 4-dimethylaminopyridine (0.057 g, 0.466 mmol). The mixture was stirred for 15 h at rt and then concentrated under vacuum. The residue was purified by flash silica gel chromatography eluting with a gradient of 0–3% MeOH in $CHCl_3$ to give 0.925 g (77%) of the acetate product: $^1$H NMR (DMSO-$d_6$) δ 2.0 (s, 3H), 3.42–3.44 (bs, 2H), 4.23–4.25 (bs, 2H), 5.30 (s, 2H), 9.10 (t, 1H, J=7.5 Hz), 7.50 (s, 1H), 7.75 (d, 1H J=7.5 Hz), 7.85 (d, 1H, J=7.5 Hz), 8.30 (m, 1H).

(b) Title Compound:

Acetic acid-1-oxo-1,2,3,4-tetrahydro-[1,4]diazepino[6,7,1-hi]indole-7-ylmethyl ester (0.508 g, 1.97 mmol) was dissolved in MeOH (70 mL) and glacial AcOH (30 mL). To the solution was added 10% Pd/C (0.076 g) and the suspension was stirred under an atmosphere of $H_2$ for 4.5 h at rt. The black suspension was filtered and the filtrate was concentrated to give a white solid, which was purified by flash silica gel chromatography eluting with a gradient of 0–1% MeOH in $CHCl_3$ to give 0.296 g (75%) of the title compound: $^1$H NMR (DMSO-$d_6$) δ 2.52 (s, 3H), 3.51–3.54 (m, 2H), 4.27–4.28 (m, 2H), 7.11 (t, 1H, J=7.5 Hz), 7.15 (s, 1H), 7.69 (d, 1H, J=7.5 Hz), 7.81 (d, 1H, J=7.5 Hz), 8.22–8.24 (m, 1H). HRMS calcd. for $C_{12}H_{12}N_2O$ ($M^+$) 200.0950, found 200.0955. Anal. ($C_{12}H_{12}N_2O$) C, H, N.

(a) 6-Iodo-7-methyl-3,4-dihydro-2H-[1,4]diazepino[6,7,1hi]indol-1-one:

To a solution of 7-methyl-3,4-dihydro-2H-[1,4]diazepino[6,7,1-hi]indol-1-one (Example 49, 0.030 g, 0.150 mmol) in $CH_2Cl_2$ (5 mL) were added iodine (0.038 g, 0.150 mmol) and bistrifluoroacetoxyiodobenzene (0.077 g, 0.180 mmol). The reaction mixture was stirred at rt for 5 min. The reaction mixture was diluted with $CH_2Cl_2$ and washed with 10% $Na_2S_2O_3$. The organic layer was dried over anhydrous $MgSO_4$, filtered and concentrated. The residue was purified by flash silica gel chromatography eluting with a gradient of 0–1% MeOH in $CHCl_3$ to give 0.026 g (53%) of a pale-yellow solid: $^1$H NMR (DMSO-$d_6$) δ 2.20 (s, 3H), 3.33–3.35 (bs, 2H), 4.32–4.35 (bs, 2H), 7.10 (t, 1H, J=7.5 Hz), 7.60 (d, 1H, J=7.5 Hz), 7.80 (d, 1H J=7.5 Hz), 8.30 (bs, 1H).

(b) Title Compound:

To a solution of 6-iodo-7-methyl-3,4-dihydro-2H-[1,4]diazepino[6,7,1-hi]indol-1-one (0.061 g, 0.187 mmol) in DMF (5 mL) at rt was added 4-fluorobenzeneboronic acid (0.029 g, 0.206 mmol), $Na_2CO_3$ (0.050 g, 0.468 mmol) dissolved in minimum $H_2O$, LiCl (0.024 g, 0.561 mmol) and tetrakistriphenylphosphine palladium (0.011 g, 0.0094 mmol). The reaction mixture was stirred at 80–90° C. for 19 h, at which time the solvent was evaporated under vacuum. The residue was taken up in $H_2O$ and extracted with EtOAc several times. The combined organic layers were dried over anhydrous $MgSO_4$, filtered and concentrated to give a brown solid. This solid was subjected to flash silica gel chromatography eluting with a gradient of 0–1% MeOH in $CHCl_3$ to give 0.044 g (73%) of the product as an off-white solid: $^1$H NMR (DMSO-$d_6$) δ 2.77 (s, 3H), 3.74 (bs, 2H), 3.39–4.37 (m, 2H), 7.45 (t, 1H, J=7.5 Hz), 7.63–7.67 (m, 2H), 7.81–7.83 (m, 2H), 8.04 (d, 1H, J=7.5 Hz), 8.12 (d, 1H, J=7.5 Hz), 8.57–8.59 (m, 1H). HRMS calcd for $C_{18}H_{15}N_2OF$ (M$^+$) 294.1168, found 294.1175. Anal. ($C_{18}H_{15}N_2OF \cdot 0.1\ H_2O$) C, H, N.

Example 51

6-Phenyl-7-methyl-3,4-dihydro-2H-[1,4]diazepino[6,7,1-hi]indol-1-one

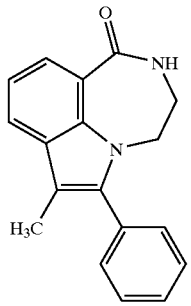

Using a procedure as described in Example 50(b), the title compound was synthesized from 6-iodo-7-methyl-3,4-dihydro-2H-[1,4]diazepino[6,7,1-hi]indol-1-one (Example 50(a)), and phenylboronic acid to give a white solid in 70% yield: $^1$H NMR (DMSO-d$_6$) δ 2.23 (s, 3H), 3.46 (bs, 2H), 4.13 (bs, 2H), 7.17 (t, 1H, J=7.5 Hz), 7.45–7.56 (m, 5H), 7.76 (d, 1H, J=7.5 Hz), 7.84 (d, 1H, J=7.5 Hz), 8.29–8.31 (m, 1H). LRMS (M$^+$) 276. Anal. ($C_{18}H_{16}N_2) \cdot 0.4\ H_2O$) C, H, N.

Example 52

6-(3-Trifluoromethyl-phenyl)-7-methyl-3,4-dihydro-2H-[1,4]diazepino[6,7,1-hi]indol-1-one

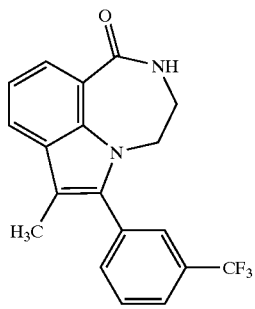

Using the procedure described in Example 50(b), the title compound was synthesized from 6-iodo-7-methyl-3,4-dihydro-2H-[1,4]diazepino[6,7,1-hi]indol-1-one (Example 50(a)) and 3-trifluoromethylphenylboronic acid in 81% yield after purification by preparative HPLC. A gradient mobile phase, starting with 90% 0.1M NH$_4$OAc, 10% CH$_3$CN up to 2 min, then reaching 100% CH$_3$CN after 22 min, was used. R$_f$=17.59 min. The title compound was obtained in the form of a white solid: $^1$H NMR (DMSO-d$_6$) δ 2.25 (s, 3H), 3.44–3.48 (m, 2H), 4.13–4.16 (m, 2H), 7.19 (t, 1H, J=7.5 Hz), 7.77–7.88 (m, 6H), 8.32–8.36 (m, 1H). HRMS calcd. for $C_{19}H_{15}N_2OF_3$ (M$^+$) 344.136, found 344.1136. Anal. HPLC R$_f$=14.9 min.

Example 53

(RS)-(±)-9-(4-Methoxy-phenyl)-8,9-dihydro-2H,7H-2,7,9a-triaza-benzo[cd]azulene-1,6-dione

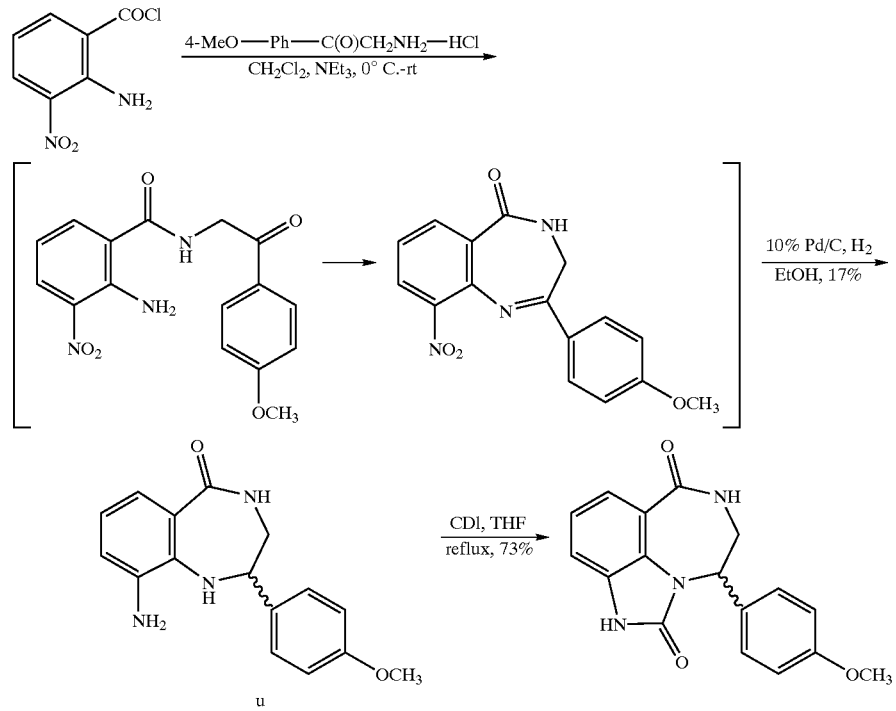

(a) Intermediate u-(RS)-(±)-9-Amino-2-(4-methoxy-phenyl)-1,2,3,4-tetrahydro-benzo[e][1,4]diazepin-5-one:

This intermediate was prepared according to the procedure of Breslin et a]., *J. Med. Chem.* (1995), 38:771–792. The acid chloride generated from 505 mg of 2-amino-3-nitrobenzoic acid (2.77 mmol) was treated with 558 mg of 2-amino-4'-methoxyacetophenone hydrochloride (2.77 mmol) and 715 mL Et$_3$N (5.54 mmol) at 0° C. in CH$_2$Cl$_2$. After stirring overnight and warming to rt, the reaction was diluted with CH$_2$Cl$_2$ and washed with saturated NaHCO$_3$, water and 1 N HCl. The organic layer was dried (MgSO$_4$), filtered and concentrated to give a yellow solid. The crude material was suspended in 150 mL EtOH containing 500 mg 10% Pd/C. This suspension was subjected to hydrogenation under H$_2$ at 60 psi for 48 h. An additional portion of 10% Pd/C was added after 24 h. The reaction mixture was then filtered through a pad of Celite® and concentrated. Purification by flash silica gel chromatography using a solvent system (40–50% CH$_3$CN/CH$_2$Cl$_2$) gave 140 mg (17%) of a yellow-orange solid: $^1$H NMR (CDCl$_3$) δ 3.35 (bs, 2H), 3.49–3.54 (m, 2H), 3.80 (s, 3H), 4.15 (bs, 1H), 4.70–4.75 (m, 1H), 6.58 (bt, 1H, J=6.0 Hz), 6.81 (t, 1H, J=7.8 Hz), 6.85–6.93 (m, 3H), 7.24–7.30 (m, 2H), 7.44 (dd, 1H, J=1.7, 7.8 Hz).

(b) Title Compound:

A solution containing 35 mg of intermediate u (0.12 mmol) and 40 mg of carbonyldiimidazole in 3 mL of THF was refluxed for 6 h. The reaction mixture was cooled to rt, concentrated and purified by flash silica gel chromatography using a gradient solvent system (2.5–5% MeOH/CH$_2$Cl$_2$) to give 27 mg (73%) of a yellow solid: IR (KBr) 3261, 2927, 1706, 1648, 1624, 1514, 1473, 1386, 1339, 1296, 1249, 1178, 1111, 1045, 1030, 756 cm$^{-1}$; $^1$H NMR (DMSO-d$_6$) δ 3.67–3.78 (m, 1H), 3.74 (s, 3H), 3.87–3.98 (m, 1H), 5.68 (d, 1H, J=3.7 Hz), 6.13–6.18 (m, 1H), 6.83 (d, 2H, J=8.7 Hz), 7.03 (d, 2H, J=8.7 Hz), 7.18–7.29 (m, 2H), 7.88 (dd, 1H, J=1.4, 7.8 H), 9.37 (bs, 1H). LRMS calcd for C$_{17}$H$_{15}$N$_3$O$_3$+H 310, found 310.

Example 54

(RS)-(±)-1-(4-Chloro-phenyl)-9-(4-methoxy-phenyl)-8,9-dihydro-7H-2,7,9a-triaza-benzo[cd]azulen-6-one

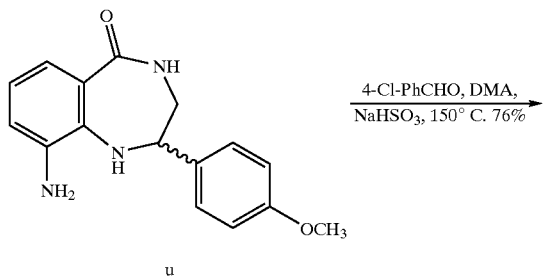

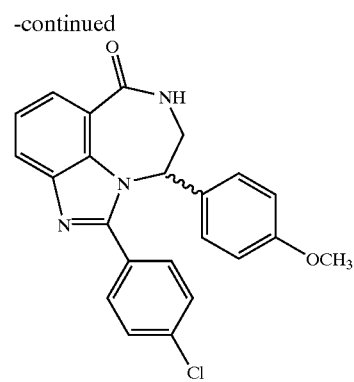

Following a reported procedure (Higgins et al., *J. Polym. Sci.* Part A-1 (1970), 8:171–177; Imai et al., Synthesis (1981), 35–36), a solution containing 92 mg of intermediate u (0.32 mmol), 54 mg of 4-chlorobenzaldehyde (0.38 mmol) and 48 mg of sodium bisulfite (0.46 mmol) in 3 mL of DMA was heated to 150° C. for 10 h. The reaction mixture was cooled to rt and poured into 200 mL of water. The resulting solid was filtered off and washed with water to give 98 mg (76%) of product as a yellow solid: IR (KBr) 3206, 3094, 2836, 1651, 1689, 1596, 1513, 1474, 1441, 1403, 1370, 1252, 1178, 1092, 1032, 1015, 1002, 843, 817, 755 cm$^{-1}$; $^1$H NMR (DMSO-d$_6$) δ 3.70–3.76 (m, 1H), 3.80 (s, 3H), 3.92–3.99 (m, 1H), 5.64 (d, 1H, J=4.3 Hz), 6.01–6.06 (m, 1 H), 6.87–7.00 (m, 4H), 7.32–7.55 (m, 5H), 8.09 (d, 1H, J=1.0, 8.0 Hz), 8.16 (d, 1H, J=1.0, 7.8 Hz); $^{13}$C NMR (DMSO-d$_6$) δ 46.90, 55.41, 61.82, 114.99, 116.92, 123.16, 124.52, 127.17, 127.42, 127.52, 129.03, 130.58, 131.01, 132.61, 137.00, 143.27, 153.62, 159.70, 168.76. LRMS calcd for C$_{23}$H$_{18}$ClN$_3$O$_2$ (M+H) 404, found 404. Anal. (C$_{23}$H$_{18}$ClN$_3$O$_2$.0.2 H$_2$O) C, H, N, Cl.

Example 55

(3-[1,3]Dioxolan-2-yl-phenyl)-8,9-dihydro-7H-2,7,9a-triaza-benzo[cd]azulen-6-one

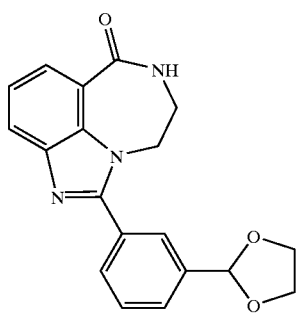

The title product was prepared from diamine g and 3-[1,3]dioxolan-2-yl-benzaldehyde (Marx et al, Liebig's Annalen der Chemie 3 . (1992), 183) using CH$_2$Cl$_2$ as described in Example 19, except using CH$_2$Cl$_2$ as the workup solvent, to give 3.10 g (81%) of an off-white solid: mp=223–225° C.; R$_f$=0.23 (5% MeOH/EtOAc); IR (KBr) 2361, 1653, 1635 1458 cm$^{-1}$; $^1$H NMR (DMSO-d$_6$) δ 3.52–3.53 (m, 2H), 3.96–4.12 (m, 4H), 4.45–4.46 (m, 2H), 5.85 (s, 1H), 7.36 (t, 1H, J=7.8 Hz), 7.58–7.65 (m, 2H), 7.86–7.93 (m, 4H), 8.45 (m, 1H). HRMS calcd for C$_{19}$H$_{17}$N$_3$O$_3$ 335.1270 (M$^+$), found 335.1278. Anal. (C$_{19}$H$_{17}$N$_3$O$_3$) C, H, N.

Example 56

1-(4-Diethoxymethyl-phenyl)-8,9-dihydro-7H-2,7,9a-triaza-benzo[cd]azulen-6-one

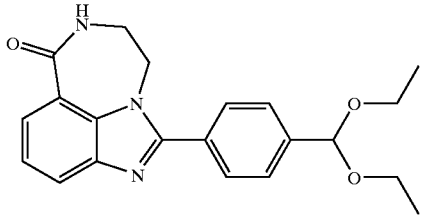

The title product was prepared in the manner described for Example 55 from terephthaldehyde-mono-diethyl acetal to give 1.19 g (77%) of a white solid: mp=213–215° C.; $R_f$=0.21 (90% EtOAc/hexanes); IR (KBr) 1660, 1605, 1481, 1307, 1055 cm$^{-1}$; $^1$H NMR (DMSO-d$_6$) δ 1.18 (t, 6H, J=7.0 Hz), 3.48–3.63 (m, 6H), 4.45–4.47 (m, 2H), 5.59 (s, 1H), 7.36 (t, 1H, J=7.8 Hz), 7.59 (d, 2H, J=8.2 Hz), 7.85–7.92 (m, 4H), 8.45 (t, 1H, J=5.7 Hz). HRMS calcd for $C_{21}H_{23}N_3O_3$ 365.1739 (M$^+$), found 365.1749. Anal. ($C_{21}H_{23}N_3O_3$) C, H, N.

Example 57

4-(6-Oxo-6,7,8,9-tetrahydro-2,7,9a-triaza-benzo[cd]azulen-1-yl)-benzaldehyde

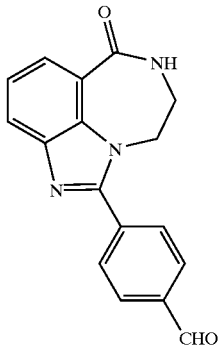

1-(3-Diethoxymethyl-phenyl)-8,9-dihydro-7H-2,7,9a-triaza-benzo[cd]azulen-6-one (0.79 g, 2.18 mmol) was dissolved in EtOH (22 mL) and water (22 mL). Concentrated sulfuric acid (0.5 mL) was added, and the reaction brought to reflux for 5 h. The reaction mixture was cooled to rt, and the EtOH removed in vacuo. The residue was diluted with saturated NaHCO$_3$, and the resulting solids were filtered and washed with water, then dried under vacuum overnight to produce 0.47 g (74%) of white solid: $^1$H NMR (DMSO-d$_6$) δ 3.54–3.55 (m, 2H), 4.50–4.51 (m, 2H), 7.39 (t, 1H, J=7.8 Hz), 7.88–7.96 (m, 2H), 8.09–8.10 (m, 4H), 8.46–8.50 (m, 1H), 10.13 (s, 1H).

Example 58

1-(4-Dimethylaminomethyl-phenyl)-8,9-dihydro-7H-2,7,9a-triaza-benzo[cd]azulen-6-one

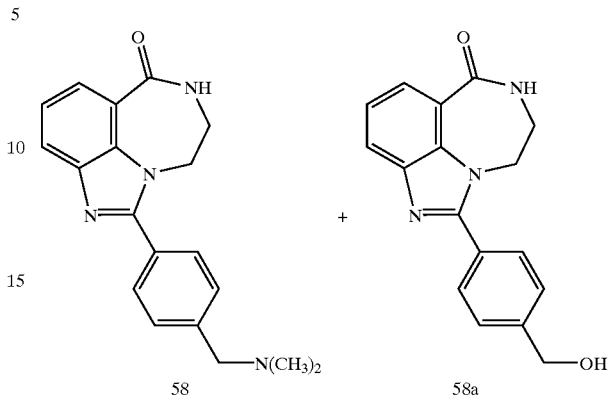

58   58a

Using the procedure described in Example 32, 0.37 g (71%) of 1-(4-dimethylaminomethyl-phenyl)-8,9-dihydro-7H-2,7,9a-triaza-benzo[cd]azulen-6-one (58) was prepared from 4-(6-oxo-6,7,8,9-tetrahydro-2,7,9a-triaza-benzo[cd]azulen-1-yl)-benzaldehyde as a white solid: mp=227–230° C.; $R_f$=0.16 (7% methanolic ammonia/CHCl$_3$); IR (KBr) 1663, 1603, 1478, 1308 cm$^{-1}$; $^1$H NMR (DMSO-d$_6$) δ 2.19 (s, 6H), 3.49 (s, 2H), 3.52–3.53 (m, 2H), 4.45–4.47 (m, 2H), 7.35 (t, 1H, J=7.8 Hz), 7.49 (d, 2H, J=8.2 Hz), 7.81–7.90 (m, 4H), 8.43–8.47 (m, 1H). HRMS calcd for $C_{19}H_{20}N_4O$ 320.1637 (M$^+$), found 320.1639. Anal. ($C_{19}H_{20}N_4O$) C, H, N.

As described in Example 32, 0.33 g (19%) of 1-(4-hydroxymethyl-phenyl)-8,9-dihydro-7H-2,7,9a-triaza-benzo[cd]azulen-6-one (58a) was isolated as a by-product in the preparation of 1-(4-dimethylaminomethyl-phenyl)-8,9-dihydro-7H-2,7,9a-triaza-benzo[cd]azulen-6-one as a white solid: mp=262–264° C.; $R_f$=0.32 (10% MeOH/CHCl$_3$); IR (KBr) 1651, 1470, 1310 cm$^{-1}$; $^1$H NMR (DMSO-d$_6$) δ 3.52–3.53 (m, 2H), 4.44–4.46 (m, 2H), 4.60 (d, 2H, J=5.7 Hz), 5.33–5.37 (m, 1H), 7.35 (t, 1H, J=7.8 Hz), 7.51 (d, 2H, J=8.2 Hz), 7.82 (d, 2H, J=8.2 Hz), 7.84–7.91 (m, 2H), 8.45 (t, 1H, J=5.7 Hz). HRMS calcd for $C_{17}H_{15}N_3O_2$ 293.1164 (M$^+$), found 293.1153. Anal. ($C_{17}H_{15}N_3O_2$) C, H, N.

Example 59

1-(3-Methylaminomethyl-phenyl)-8,9-dihydro-7H-2,7,9a-triaza-benzo[cd]azulen-6-one

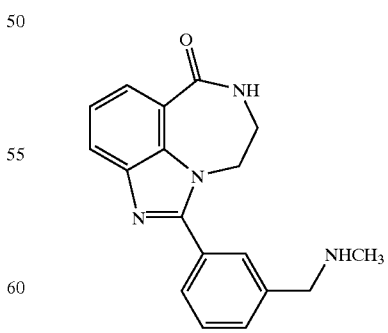

Using the procedure described in Example 32, 0.12 g (23%) of 1-(3-methylaminomethyl-phenyl)-8,9-dihydro-7H-2,7,9a-triaza-benzo[cd]azulen-6-one was prepared from 3-(6-oxo-6,7,8,9-tetrahydro-2,7,9a-triaza-benzo[cd]azulen- 1-yl)-benzaldehyde and methylamine as an amorphous white solid: mp=110° C. (dec); $R_f$=0.08 (10% methanolic ammonia/CHCl$_3$); IR (KBr) 1655, 1464, 1381, 1308 cm$^{-1}$; $^1$H NMR (DMSO-d$_6$) δ 2.31 (s, 3H), 3.52–3.53 (m, 2H), 3.79 (s, 2H), 4.45–4.47 (m, 2H), 7.36 (t, 1H, J=7.8 Hz), 7.52–7.53 (m, 2H), 7.71–7.75 (m, 1H), 7.83–7.91 (m, 3H), 8.46 (t, 1H, J=5.7 Hz). HRMS calcd for C$_{18}$H$_{17}$N$_4$O 305.1402 (M–H)$^+$, found 305.1416. Anal. (C$_{18}$H$_{18}$N$_4$O.0.75 H$_2$O) C, H, N.

Example 60

1-(3-Pyrrolidin-1-ylmethyl-phenyl)-8,9-dihydro-7H-2,7,9a-triaza-benzo[cd]azulen-6-one

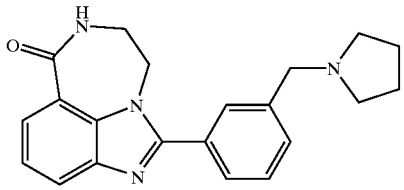

Using the procedure described in Example 32, 0.46 g (78%) of 1-(3-pyrrolidin-1-ylmethyl-phenyl)-8,9-dihydro-7H-2,7,9a-triaza-benzo[cd]azulen-6-one was prepared from 3-(6-oxo-6,7,8,9-tetrahydro-2,7,9a-triaza-benzo[cd]azulen-1-yl)-benzaldehyde and pyrrolidine as an amorphous off-white solid: mp=92° C. (dec); $R_f$=0.21 (10% methanolic ammonia/CHCl$_3$); IR (KBr) 1659, 1464, 1379, 1308 cm$^{-1}$; $^1$H NMR (DMSO-d$_6$) δ 1.69–1.71 (m, 4H), 2.47–2.50 (m, 4H), 3.52–3.53 (m, 2H), 3.68 (s, 2H), 4.45–4.46 (m, 2H), 7.35 (t, 1H, J=7.8 Hz), 7.48–7.55 (m, 2H), 7.70–7.73 (m, 1H), 7.79 (s, 1H), 7.85–7.91 (m, 2H), 8.42–8.46 (m, 11H). HRMS calcd for C$_{21}$H$_{21}$N$_4$O 345.1715 (M–H)$^+$, found 345.1719. Anal. (C$_{21}$H$_{22}$N$_4$O.0.2 H$_2$O) C, H, N.

Example 61

1-[3-(3-Trifluoromethyl-phenoxy)-phenyl]-8,9-dihydro-7H-2,7,9a-triaza-benzo[cd]azulen-6-one

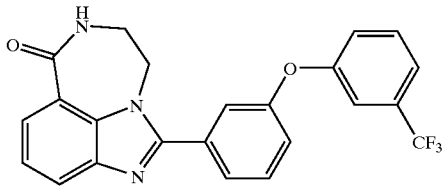

The title compound was prepared as described in Example 55 from 3-[3-(trifluoromethyl)phenoxyl]benzaldehyde to give 0.089 g (48%) of a white solid: mp=121–122° C.; $R_f$=0.21 (90% EtOAc/hexanes); IR (KBr) 1661, 1580, 1445, 1327, 1126 cm$^{-1}$; $^1$H NMR (DMSO-d$_6$) δ 3.52–3.53 (m, 2H), 4.46–4.48 (m, 2H), 7.29–7.44 (m, 4H), 7.53–7.56 (m, 2H), 7.61–7.71 (m, 3H), 7.85–7.91 (m, 2H), 8.45 (t, 1H, J=5.6 Hz). HRMS calcd for C$_{23}$H$_{17}$N$_3$O$_2$F$_3$ 424.1273 (M+H)$^+$, found 424.1277. Anal. (C$_{23}$H$_{16}$N$_3$O$_2$F$_3$.1.0 H$_2$O) C, H, N.

Example 62

1-[3-(4-Chlorophenoxy)-phenyl]-8,9-dihydro-7H-2,7,9a-triaza-benzo[cd]azulen-6-one

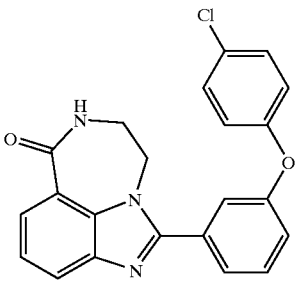

The title compound was prepared as described in Example 55 from 3-(4-chlorophenoxy)benzaldehyde, yielding 0.114 g (66%) of a white solid: mp=211–212° C.; $R_f$=0.16 (75% EtOAc/hexanes); IR (KBr) 1659, 1578, 1483, 1462, 1233 cm$^{-1}$; $^1$H NMR (DMSO-d$_6$) δ 3.52–3.53 (m, 2H), 4.45–4.46 (m, 2H), 7.11–7.17 (m, 2H), 7.22–7.26 (m, 1H), 7.35 (t, 1H, J=7.8 Hz), 7.45–7.50 (m, 3H), 7.58–7.66 (m, 2H), 7.85–7.91 (m, 2H), 8.43–8.47 (m, 1H). HRMS calcd for C$_{22}$H$_{16}$N$_3$O$_2$Cl 389.0931 (M$^+$), found 389.0948. Anal. (C$_{22}$H$_{16}$N$_3$O$_2$Cl.0.25 H$_2$O) C, H, N.

Example 63

1-[3-(3,4-Dichlorophenoxy)-phenyl]-8,9-dihydro-7H-2,7,9a-triaza-benzo[cd]azulen-6-one

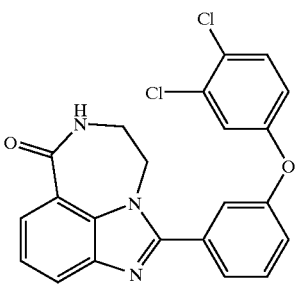

The title compound was prepared in a manner analogous to Example 55 from 3-(3,4-dichlorophenoxy)benzaldehyde to give 0.084 g (45%) of a white amorphous solid: mp=252–254° C. (dec); $R_f$=0.13 (75% EtOAc/hexanes); IR (KBr) 1657, 1578, 1468, 1263 cm$^{-1}$; $^1$H NMR (DMSO-d$_6$) δ 3.52–3.53 (m, 2H), 4.45–4.47 (m, 2H), 7.11 (dd, 1H, J=8.9, 2.8 Hz), 7.28–7.32 (m, 1H), 7.36 (t, 1H, J=7.8 Hz), 7.43 (d, 1H, J=2.8 Hz), 7.54–7.55 (m, 1H), 7.60–7.71 (m, 3H), 7.85–7.91 (m, 2H), 8.43–8.47 (m, 1H), HRMS calcd for C$_{22}$H$_{15}$N$_3$O$_2$Cl$_2$ 423.0541 (M$^+$), found 423.0538. Anal. (C$_{22}$H$_{15}$N$_3$O$_2$Cl$_2$.0.3 H$_2$O) C, H, N.

Example 64

1-[3-(4-Methoxyphenoxy)-phenyl]-8,9-dihydro-7H-2,7,9a-triaza-benzo[cd]azulen-6-one

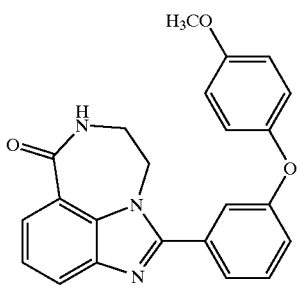

The title compound was prepared as described in Example 55 from 3-(4-methoxyphenoxy)benzaldehyde to give 0.13 g (84%) of a white solid: mp=196–198° C.; $R_f$=0.21 (90% EtOAc/hexanes); IR (KBr) 1660, 1505, 1462, 1215 cm$^{-1}$; $^1$H NMR (DMSO-d$_6$) δ 3.52–3.53 (m, 2H), 3.76 (s, 3H), 4.43–4.46 (m, 2H), 7.00 (d, 2H, J=9.2 Hz), 7.10 (d, 2H, J=9.2 Hz), 7.07–7.15 (m, 1H), 7.32–7.37 (m, 2H), 7.52–7.58 (m, 2H), 7.84–7.89 (m, 2H), 8.43–8.46 (m, 1H). HRMS calcd for $C_{23}H_{19}N_3O_3$ 385.1341 (M$^+$), found 385.1442. Anal. ($C_{23}H_{19}N_3O_3 \cdot 0.4\ H_2O$) C, H, N.

Example 65

1-[3-(3,5-Dichlorophenoxy)-phenyl]-8,9-dihydro-7H-2,7,9a-triaza-benzo[cd]azulen-6-one

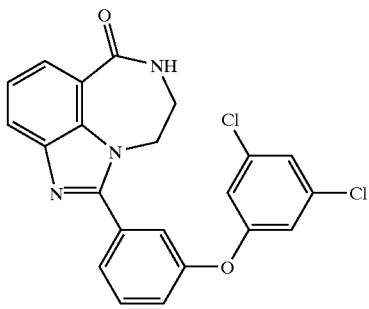

The title compound was prepared as described in Example 55 from 3-(3,5-dichlorophenoxy)benzaldehyde to give 0.14 g (86%) of a white solid: mp=258–259° C. (dec); $R_f$=0.13 (75% EtOAc/hexanes); IR (KBr) 1663, 1576, 1431, 1250 cm$^{-1}$; $^1$H NMR (DMSO-d$_6$) δ 3.53–3.54 (m, 2H), 4.47–4.49 (m, 2H), 7.18 (d, 2H, J=1.8 Hz), 7.31–7.42 (m, 3H), 7.58–7.74 (m, 3H), 7.86–7.92 (m, 2H), 8.46 (m, 1H). HRMS calcd for $C_{22}H_{15}N_3O_2Cl_2$ 423.0541 (M$^+$), found 423.0549. Anal. ($C_{22}H_{15}N_3O_2Cl_2 \cdot 0.2\ H_2O$) C, H, N.

Example 66

1-(3-Benzoylphenyl)-8,9-dihydro-7H-2,7,9a-triaza-benzo[cd]azulen-6-one

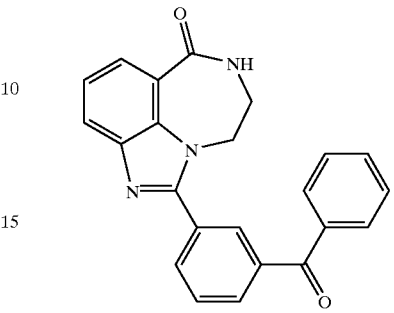

The title compound was prepared as described in Example 2 from 3-benzoylbenzoyl chloride (Ito et al., *J. Org. Chem.* (1985), 50:2893). Reaction time was 72 hours at room temperature, using CH$_2$Cl$_2$ as the workup solvent to give 0.12 g (65%) of white solid: mp=237–238° C. (dec); $R_f$=0.13 (90% EtOAc/hexanes); IR (KBr) 1659, 1464, 1312 cm$^{-1}$; $^1$H NMR (DMSO-d$_6$) δ 3.53–3.55 (m, 2H), 4.48–4.49 (m, 2H), 7.37 (t, 1H, J=7.8 Hz), 7.57–7.62 (m, 2H), 7.69–7.94 (m, 7H), 8.15–8.18 (m, 2H), 8.46 (t, 1H, J=5.6 Hz). HRMS calcd for $C_{23}H_{17}N_3O_2$ 367.1321 (M$^+$), found 367.1306. Anal. ($C_{23}H_{17}N_3O_2$) C, H, N.

Example 67

1-(3-Benzylphenyl)-8,9-dihydro-7H-2,7,9a-triaza-benzo[cd]azulen-6-one

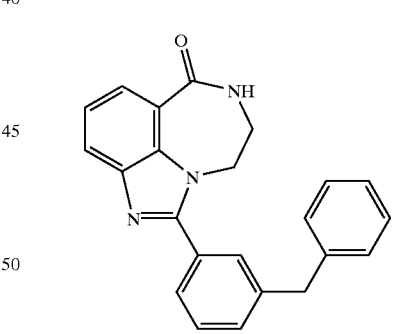

The title compound was prepared as described in Example 2 from 3-benzylbenzoyl chloride (Norris and Ware, *J. Amer. Chem. Soc.* (1939), 61:1418). Reaction time was 72 hours at room temperature, using CH$_2$Cl$_2$ as the workup solvent to give 0.13 g (68%) of white solid: mp=205–208° C.; $R_f$=0.18 (75% EtOAc/hexanes); IR (KBr) 1655, 1464, 1381, 1310 cm$^{-1}$; $^1$H NMR (DMSO-d$_6$) δ 3.50–3.51 (m, 2H), 4.06 (s, 2H), 4.43–4.44 (m, 2H), 7.16–7.22 (m, 1H), 7.26–7.37 (m, 5H), 7.43–7.52 (m, 2H), 7.66–7.68 (m, 1H), 7.74–7.75 (m, 1H), 7.84–7.90 (m, 2H), 8.44 (t, 1H, J=5.6 Hz). HRMS calcd for $C_{23}H_{19}N_3O$ 353.1528 (M$^+$), found 353.1527. Anal. ($C_{23}H_{19}N_3O \cdot 0.25\ H_2O$) C, H, N.

Example 68

1-(3-[1,3]Dioxolan-2-yl-phenyl)-4-fluoro-8,9-dihydro-7H-2,7,9a-triaza-benzo[cd]azulen-6-one

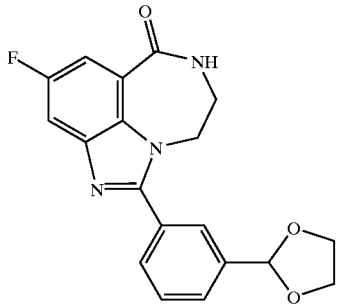

The title compound was prepared as described in Example 55 from intermediate 1 (Example 18) instead of intermediate g to give 0.60 g (54%) of a white solid: mp=262–264° C. (dec); $R_f$=0.11 (90% EtOAc/hexanes); IR (KBr) 1667, 1487, 1460, 1389 cm$^{-1}$; $^1$H NMR (DMSO-d$_6$) δ 3.54–3.55 (m, 2H), 3.96–4.12 (m, 4H), 4.45–4.46 (m, 2H), 5.85 (s, 1H), 7.58–7.66 (m, 3H), 7.75–7.79 (m, 1H), 7.85–7.88 (m, 1H), 7.92 (s, 1H), 8.59–8.63 (m, 1H). HRMS calcd for C$_{19}$H$_{16}$N$_3$O$_3$F 353.1176 (M$^+$), found 353.1183. Anal. C$_{19}$H$_{16}$N$_3$O$_3$F.0.25 H$_2$O) C, H, N.

Example 69

3-(4-Fluoro-6-oxo-6,7,8,9-tetrahydro-2,7,9a-triaza-benzo[cd]azulen-1-yl)-benzaldehyde

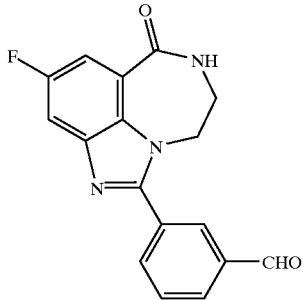

Using the deprotection procedure described in Example 31, 0.43 g (89%) of 3-(4-fluoro-6-oxo-6,7,8,9-tetrahydro-2,7,9a-triaza-benzo[cd]azulen-1-yl)-benzaldehyde was generated as a white solid: $^1$H NMR (DMSO-d$_6$) δ 3.56–3.58 (m, 2H), 4.50–4.51 (m, 2H), 7.61–7.65 (m, 1H), 7.78–7.85 (m, 2H), 8.09–8.11 (m, 1H), 8.17–8.21 (m, 1H), 8.39–8.40 (m, 1H), 8.64 (t, 1H. J=5.6 Hz), 10.14 (s, 1H).

Example 70

1-(3-Dimethylaminomethyl-phenyl)-4-fluoro-8,9-dihydro-7H-2,7,9a-triaza-benzo[cd]azulen-6-one

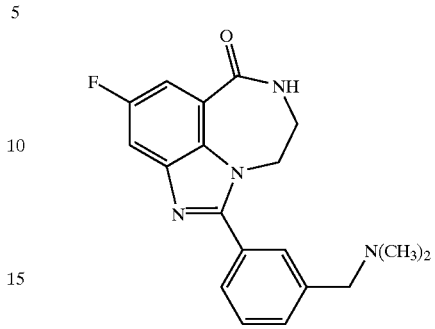

Using the reductive amination procedure described in Example 32, 0.067 g (31%) of 1-(3-dimethylaminomethyl-phenyl)-4-fluoro-8,9-dihydro-7H-2,7,9a-triaza-benzo[cd]azulen-6-one was prepared from 3-(4-fluoro-6-oxo-6,7,8,9-tetrahydro-2,7,9a-triaza-benzo[cd]azulen-1-yl)-benzaldehyde as a white solid: mp=215–217° C. (dec); $R_f$=0.11 (7% methanolic ammonia/CHCl$_3$); IR (KBr) 1663, 1485, 1383 cm$^{-1}$; $^1$H NMR (DMSO-d$_6$) δ 2.19 (s, 6H), 3.50 (s, 2H), 3.54–3.55 (m, 2H), 4.45–4.47 (m, 2H), 7.48–7.62 (m, 3H), 7.72–7.78 (m, 3H), 8.61 (t, 1H, J=5.7 Hz). HRMS calcd for C$_{19}$H$_{18}$N$_4$OF 337.1465(M–H), found 337.1464. Anal. (C$_{19}$H$_{19}$N$_4$OF.0.25 H$_2$O) C, H, N.

Example 71

1-(2-Dimethylamino-pyridin-4-yl)-8,9-dihydro-7H-2,7,9a-triaza-benzo[cd]azulen-6-one

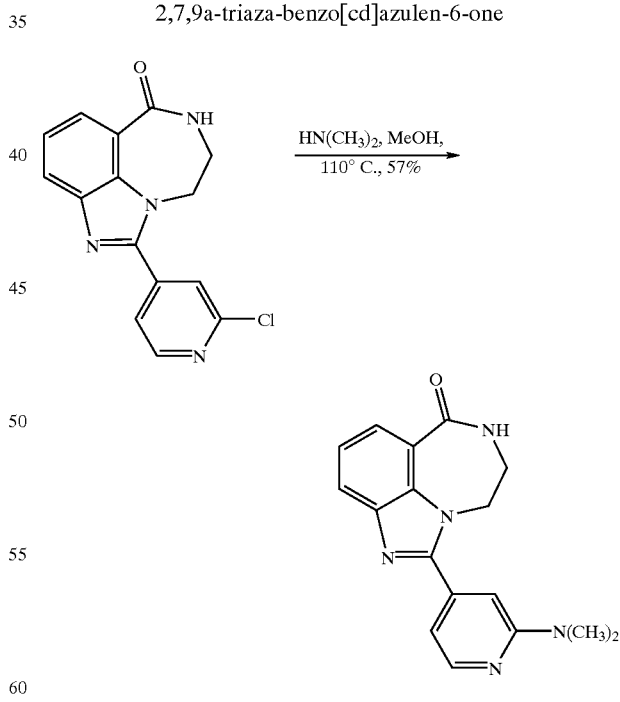

The product from Example 15 (0.087 g, 0.29 mmol) was suspended in EtOH (4 mL) in a sealed tube reaction vessel equipped with a magnetic stir bar. Dimethylamine (2M/MeOH, 4.37 mL, 8.75 mmol) was added and the vessel was sealed, stirred and heated to 110° C. for 6 h. Additional dimethylamine solution (2 mL) was added, and the reaction stirred at 110° C. overnight. The solvent was removed in vacuo, and the product was purified by column chromatography (0–5% MeOH/EtOAc) to give 0.051 g (57%) of a white solid: mp=266–268° C.; R$_f$=0.16 (5% MeOH/EtOAc); IR (KBr) 1657, 1611, 1510 cm$^{-1}$; $^1$H NMR (DMSO-d$_6$) δ 3.52–3.53 (m, 2H), 4.49–4.50 (m, 2H), 6.96–6.99 (m, 2H), 7.38 (t, 1H, J=7.8 Hz), 7.89 (dd, 1H, J=1.0, 7.7 Hz), 7.93 (dd, 1H, J=1.0, 8.0 Hz), 8.26 (d, 1H, J=5.1 Hz), 8.47 (t, 1H, J=5.6 Hz). HRMS calcd for C$_{17}$H$_{17}$N$_5$O 307.1433 (M$^+$), found 307.1431. Anal. (C$_{17}$H$_{17}$N$_5$O) C, H, N.

Example 72

1-(3-Methylaminomethyl-phenyl)-4-fluoro-8,9-dihydro-7H-2,7,9a-triaza-benzo[cd]azulen-6-one

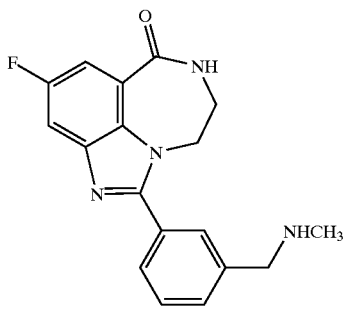

Using the reductive amination procedure described in Example 32, 0.037 g (18%) of 1-(3-methylaminomethyl-phenyl)-4-fluoro-8,9-dihydro-7H-2,7,9a-triaza-benzo[cd]azulen-6-one was prepared from methylamine (2M/MeOH) and 3-(4-fluoro-6-oxo-6,7,8,9-tetrahydro-2,7,9a-triaza-benzo[cd]azulen-1-yl)-benzaldehyde as a white solid: mp=196–198° C.; R$_f$=0.03 (7% methanolic ammonia/CHCl$_3$); IR (KBr) 1655, 1487, 1466, 1134 cm$^{-1}$; $^1$H NMR (DMSO-d$_6$) δ 2.29 (s, 3H), 3.54–3.57 (m, 2H), 3.74 (s, 2H), 4.45–4.47 (m, 2H), 7.51–7.53 (m, 2H), 7.57–7.62 (m, 1H), 7.68–7.77 (m, 2H), 7.80 (s, 1H), 8.62 (t, 1H, J=5.6 Hz). HRMS calcd for C$_{18}$H$_{17}$N$_4$OF 323.1308 (M$^+$), found 323.1305. Anal. (C$_{18}$H$_{17}$N$_4$OF.0.3 H$_2$O) C, H, N.

Example 73

3-(6-Oxo-6,7,8,9-tetrahydro-2,7,9a-triaza-benzo[cd]azulen-1-yl)-benzonitrile

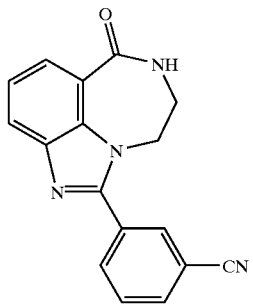

The title compound was prepared as described in Example 55 from 3-cyanobenzaldehyde to give 0.143 g (30%) of a white solid: mp=283–284° C. (dec); R$_f$=0.13 (90% EtOAc/hexanes); IR (KBr) 2233, 1659, 1462 cm$^{-1}$; $^1$H NMR (DMSO-d$_6$) δ 3.53–3.54 (m, 2H), 4.47–4.49 (m, 2H), 7.39 (t, 1H, J=7.8 Hz), 6.66–7.83 (m, 1H), 7.89–7.95 (m, 2H), 8.04–8.06 (m, 1H), 8.19–8.22 (m, 1H), 8.31–8.32 (m, 1H), 8.46–8.50 (m, 1H). HRMS calcd for C$_{17}$H$_{12}$N$_4$O 288.1011 (M$^+$), found 288.1002. Anal. (C$_{17}$H$_{12}$N$_4$O.0.5H$_2$O) C, H, N.

Example 74

6-Oxo-6,7,8,9-tetrahydro-2,7,9a-triaza-benzo[cd]azulen-1-carboxylic Acid Ethyl Ester

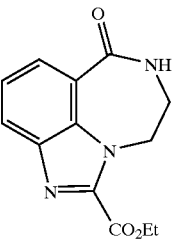

The title compound was prepared as described in Example 55 from ethyl glyoxalate (50% in toluene) to give 0.086 g (28%) of an off-white solid: mp=237–239° C. (dec); R$_f$=0.20 (5% MeOH/CHCl$_3$); IR (KBr) 1719, 1663, 1655 cm$^{-1}$; $^1$H NMR (DMSO-d$_6$) δ 1.36 (t, 3H, J=7.1 Hz), 3.35–3.36 (m, 2H), 3.58–3.60 (m, 2H), 4.39 (q, 2H, J=7.1 Hz), 7.45 (t, 1H, J=7.8 Hz), 7.99–8.04 (m, 2H), 8.47–8.50 (m, 1H). HRMS calcd for C$_{13}$H$_{13}$N$_3$O$_3$ 259.0957 (M$^+$), found 259.0965. Anal. (C$_{13}$H$_{13}$N$_3$O.0.1 H$_2$O) C, H, N.

Example 75

1-(4-Methylaminomethyl-phenyl)-8,9-dihydro-7H-2,7,9a-triaza-benzo[cd]azulen-6-one

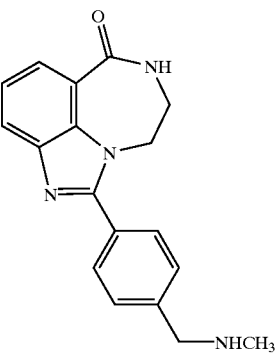

Using the reductive amination procedure described in Example 32, 0.44 g (53%) of 1-(4-methylaminomethyl-phenyl)-8,9-dihydro-7H-2,7,9a-triaza-benzo[cd]azulen-6-one was prepared from methylamine (2M/MeOH) and 4-(6-oxo-6,7,8,9-tetrahydro-2,7,9a-triaza-benzo[cd]azulen-1-yl)-benzaldehyde as a white solid: mp=169–172° C.; R$_f$=0.08 (10% methanolic ammonia/CHCl$_3$); IR (KBr) 1651, 1480, 1308 cm$^{-1}$; $^1$H NMR (DMSO-d$_6$) δ 2.30 (s, 3H), 3.52–3.53 (m, 2H), 3.75 (s, 2H), 4.45–4.46 (m, 2H), 7.35 (t, 1H, J=7.8 Hz), 7.52 (d, 2H, J=8.1 Hz), 7.81 (d, 2H, J=8.1 Hz), 7.84–7.90 (m, 2H), 8.43–8.47 (m, 1H). HRMS calcd for C$_{18}$H$_{18}$N$_4$O 306.1480 (M$^+$), found 306.1486. Anal. (C$_{18}$H$_{18}$N$_4$O.0.5 H$_2$O) C, H, N.

Example 76

1-(4-Morpholin-4-ylmethyl-phenyl)-8,9-dihydro-7H-2,7,9a-triaza-benzo[cd]azulen-6-one

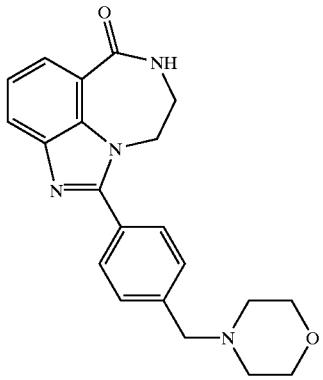

Using the reductive amination procedure described in Example 32, 0.097 g (38%) of 1-(4-morpholin-4-yl methyl-phenyl)-8,9-dihydro-7H-2,7,9a-triaza-benzo[cd]azulen-6-one was prepared from morpholine and 4-(6-oxo-6,7,8,9-tetrahydro-2,7,9a-triaza-benzo[cd]azulen-1-yl)-benzaldehyde as a white solid: mp=285–286° C. (dec); $R_f$=0.11 (5% MeOH/CHCl$_3$); IR (KBr) 1661, 1653, 1483, 1113 cm$^{-1}$; $^1$H NMR (DMSO-d$_6$) δ 2.40–2.41 (m, 4H), 3.15–3.17 (m, 2H), 3.26–3.61 (m, 6H), 4.45–4.46 (m, 2H), 7.35 (t, 1H, J=7.8 Hz), 7.51 (d, 2H, J=8.1 Hz), 7.82 (d, 2H, J=8.1 Hz), 7.84–7.90 (m, 2H), 8.43–8.47 (m, 1H). HRMS calcd for C$_{21}$H$_{22}$N$_4$O$_2$ 362.1743 (M$^+$), found 362.1737. Anal. (C$_{21}$H$_{22}$N$_4$O$_2$) C, H, N.

Example 77

1-(4-[(2-Methoxyethylamino)methyl]-phenyl)-8,9-dihydro-7H-2,7,9a-triaza-benzo[cd]azulen-6-one

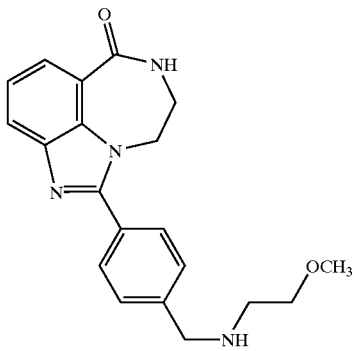

Using the reductive amination procedure described in Example 32, 0.091 g (38%) of the title compound was prepared from 2-methoxyethylamine and 4-(6-oxo-6,7,8,9-tetrahydro-2,7,9a-triaza-benzo[cd]azulen-1-yl)-benzaldehyde as a white solid: mp=154–157° C.; $R_f$=0.11 (10% MeOH/CHCl$_3$); IR (KBr) 1659, 1483, 1088 cm$^{-1}$; $^1$H NMR (DMSO-d$_6$) δ 2.67 (t, 2H, J=5.7 Hz), 3.24 (s, 3H), 3.42 (t, 2H, J=5.7 Hz), 3.52–3.53 (m, 2H), 3.81 (s, 2H), 4.45–4.46 (m, 2H), 7.35 (t, 1H, J=7.8 Hz), 7.52 (d, 2H, J=8.1 Hz), 7.80 (d, 2H, J=8.1 Hz), 7.84–7.90 (m, 2H), 8.43–8.46 (m, 1H). HRMS calcd for C$_{20}$H$_{22}$N$_4$O$_2$ 350.1743 (M$^+$), found 350.1756. Anal. (C$_{20}$H$_{22}$N$_4$O$_2$) C, H, N.

Example 78

1-(4-Phenoxyphenyl)-8,9-dihydro-7H-2,7,9a-triaza-benzo[cd]azulen-6-one

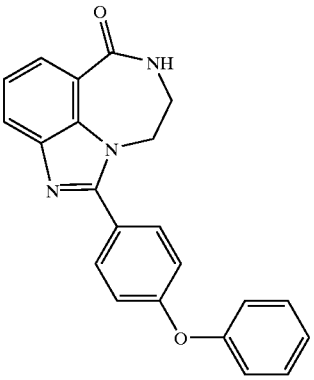

The title compound was prepared as described in Example 55 from 4-phenoxybenzaldehyde to give 0.13 g (67%) of a white solid: mp=259–264° C.; IR (KBr) 1664, 1591, 1480 1236 cm$^{-1}$; $^1$H NMR (DMSO-d$_6$) δ 3.53–3.54 (m, 2H), 4.45–4.46 (m, 2H), 7.12–7.16 (m, 4H), 7.20–7.25 (m, 11H), 7.32–7.37 (m, 1H), 7.44–2H), 7.84–7.89 (m, 4H), 8.43–8.46 (m, 1H). HRMS calcd for C$_{22}$H$_{17}$N$_3$O$_2$ 355.1321. (M$^+$), found 355.1321. Anal. (C$_{22}$H$_{17}$N$_3$O$_2$.0.5 H$_2$O) C, H, N.

Example 79

1-(4-Diethoxymethyl-phenyl)-4-fluoro-8,9-dihydro-7H-2,7,9a-triaza-benzo[cd]azulen-6-one

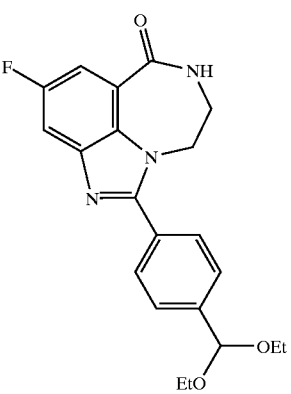

The title compound was prepared in the manner described for Example 55 from terephthalaldehyde-mono-diethyl acetal and intermediate 1 (Example 18) instead of intermediate g to give 1.61 g (79%) of a white solid: mp=219–221° C.; $R_f$=0.39 (90% EtOAc/hexanes); IR (KBr) 1667, 1611, 1464 1107 cm$^{-1}$; $^1$H NMR (DMSO-d$_6$) δ 1.17 (t, 6H, J=7.0 Hz), 3.48–3.65 (m, 6H), 4.45–4.47 (m, 2H), 5.59 (s, 1H), 7.58–7.62 (m, 3H), 7.75–7.78 (m, 1H), 7.87 (d, 2H, J=8.3 Hz), 8.61 (t, 1H, J=8.3 Hz). HRMS calcd for C$_{21}$H$_{22}$N$_3$O$_3$ 383.1645 (M$^+$), found 383.1640. Anal. (C$_{21}$H$_{22}$N$_3$O$_3$) C, H, N.

Example 80

1-(1H-Imidazol-2-yl)-8,9-dihydro-7H-2.7,9a-triaza-benzo[cd]azulen-6-one

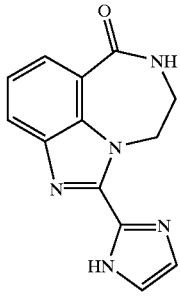

The title compound was prepared following the procedure described in Example 4 from intermediate g and imidazole-2-carboxaldehyde to give 0.047 g (33%) of a white solid: mp=227–228° C. (dec); $R_f$=0.13 (5% MeOH/EtOAc); IR (KBr) 1645, 1611, 1497, 1402 cm$^{-1}$; $^1$H NMR (DMSO-d$_6$) δ 3.36–3.38 (m, 2H), 3.46–3.50 (m, 2H), 7.21 (s, 1H), 7.35–7.40 (m, 2H), 7.87–7.92 (m, 2H), 8.42–8.45 (m, 1H), 13.34 (s, 1H). HRMS calcd for $C_{13}H_{11}N_5O$ 253.0964 (M$^+$), found 253.0957. Anal. ($C_{13}H_{11}N_5O \cdot 0.25$ MeOH) C, H, N.

Example 81

4-(1-Oxo-1,2,3,4-tetrahydro-[1,4]diazepino[6,7–1-hi]indol-6-yl)-benzaldehyde

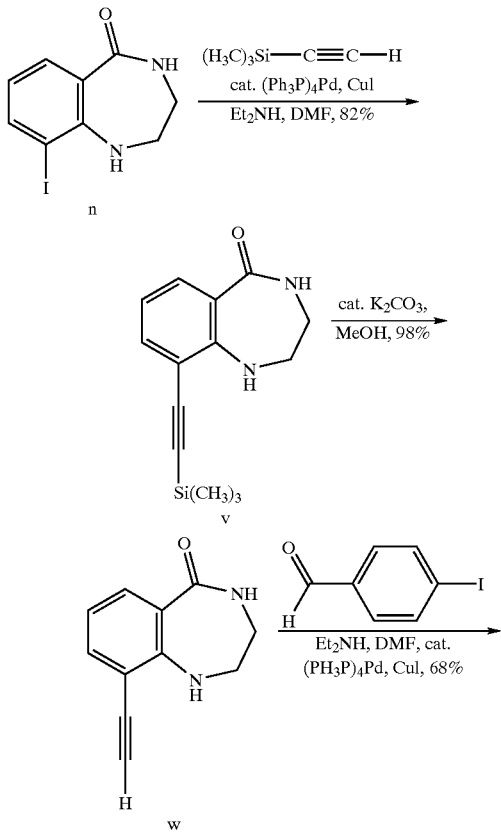

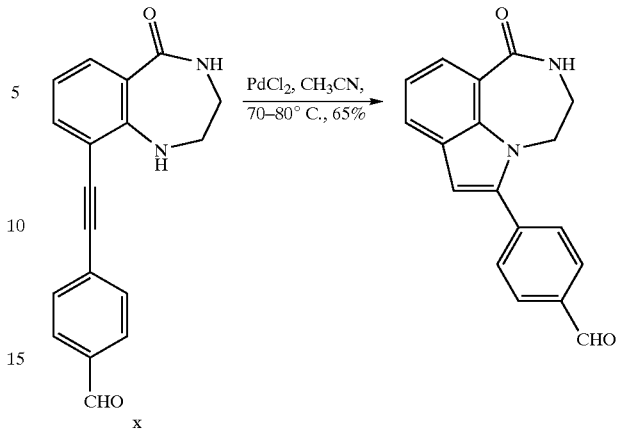

(a) Intermediate v—9(Trimethylsilanylethynyl)-1,2,3,4-tetrahydro-benzo[e][1,4]-diazepin-5-one:

A mixture of intermediate n (Example 34) (1.0 g, 3.47 mmol), (trimethylsilyl)acetylene (5.0 mL, 34.7 mmol), tetrakistriphenylphosphine palladium(0) (0.04 g, 34.7 μmol), CuI (0.013 g, 69.4 μmol) in diethylamine (10 mL), and DMF (10 mL) was stirred at rt for 5 h. The solvent was evaporated and the residue was taken up in H$_2$O, and extracted with EtOAc several times. The combined organic layers were dried over anhydrous MgSO$_4$ and concentrated. The crude mixture was purified by column chromatography eluting with a gradient of 0–5% MeOH in CHCl$_3$ to give 0.733 g (82%) of a brown solid: mp 180–182° C.; $^1$H NMR (DMSO-d$_6$) δ 0.25 (s, 9H), 3.25–3.33 (m, 2H), 3.51–3.55 (m, 2H), 5.90 (br s, 1H), 6.57 (t, 1H, J=6.0 Hz), 7.35 (d, 1H, J=6.0 Hz), 7.78 (d, 1H, J=6.0 Hz), 8.13 (t, 1H, J=6.0 Hz). LRMS 258 (M$^+$).

(b) Intermediate w—9-Ethynyl-1,2,3,4-tetrahydro-benzo[e][1,4]diazepin-5-one:

A mixture of intermediate v (0.712 g, 2.76 mmol) and K$_2$CO$_3$ (0.038 g, 0.276 mmol) in MeOH (35 mL) was stirred at rt for 2.5 h. The solvent was evaporated and the residue taken up in H$_2$O, and extracted with EtOAc several times. The combined organic extracts were dried over anhydrous MgSO$_4$ and concentrated to give 0.50 g (98%) of a brown solid, which was used in the next step without further purification: mp 146–148° C.; $^1$H NMR (DMSO-d$_6$) δ 3.15–3.23 (m, 2H), 3.48–3.52 (m, 2H), 4.50 (s, 1H), 6.13 (br s, 1H), 6.57 (t, 1H, J=9.0 Hz), 7.37 (d, 1H, J=9.0 Hz), 7.79 (d, 1H, J=9.0 Hz), 8.10 (t, 1H, J=6.0 Hz). LRMS 186 (M$^+$).

(c) Intermediate x—4(5-Oxo-2,3,4,5-tetrahydro-1H-[e][1,4]diazepin-9-ylethynyl)-benzaldehyde:

Using the procedure described for the preparation of intermediate o, intermediate w and 4-iodo-benzaldehyde were used to synthesize intermediate x in 68% yield as a bright-yellow solid: mp 178–180° C.; $^1$H NMR (DMSO-d$_6$) δ 3.30–3.33 (m, 2H), 3.54–3.57 (m, 2H), 6.39 (br s, 1H), 6.63 (t, 1H, J=6.0 Hz), 7.49 (d, 1H, 6.0 Hz), 7.48–7.51 (m, 3H), 7.95 (d, 2H, J=9.0 Hz), 8.15 (t, 1H, J=6.0 Hz). LRMS 290 (M$^+$).

(d) Title Compound:

Using the procedure described for the preparation of 6-phenyl-3,4-dihydro-2H-[1,4]diazepino[6,7,1-hi]indol-1-one (Example 33), the title compound was synthesized from intermediate x in 65% yield as a bright-yellow solid: mp 228–230° C.; $^1$H NMR (DMSO-d$_6$) δ 3.46–3.49 (m, 2H), 4.37–4.40 (m, 2H), 6.89 (s, 1H), 7.20 (t, 1H, J=6.0 Hz), 7.81–7.88 (m, 4H), 8.03 (d, 2H, J=9.0 Hz), 8.42 (t, 1H, J=6.0 Hz), 10.08 (s, 1H). LRMS 290 (M$^+$).

Example 82

6-(4-Dimethylaminomethyl-phenyl)-3,4-dihydro-2H-[1,4]diazepino[6,7,1-hi]indol-1-one

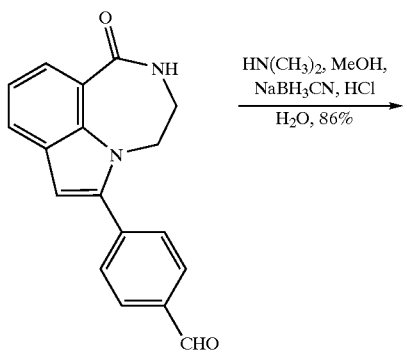

HN(CH₃)₂, MeOH,
NaBH₃CN, HCl
—————————→
H₂O, 86%

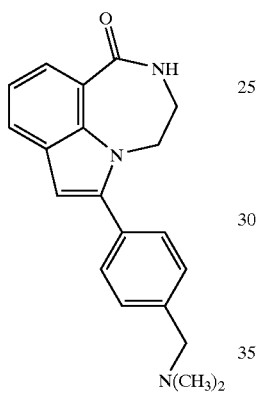

2M Dimethylamine in methanol (8.2 mL, 16.34 mmol) was added to a suspension of 4-(1-oxo-1,2,3,4-tetrahydro-[1,4]diazepino[6,7–1-hi]indol-6-yl)-benzaldehyde (0.55 g, 1.90 mmol) in MeOH (110 mL) at rt. The reaction mixture was heated to reflux until the suspension went into solution. The reaction mixture was cooled to rt, and a solution of NaCNBH₃ (0.131 g, 2.09 mmol) and ZnCl₂ (0.143 g, 1.05 mmol) in MeOH (55 mL) was slowly added. The pH of the reaction mixture was adjusted to from 3 to 4 using 2M HCl-methanol. The reaction mixture was stirred at rt for 2.5 h. Upon completion of the reaction, concentrated HCl was added (pH 1) and the solvent removed in vacuo. The residue was diluted with H₂O, made basic (pH 12–14) with 50% aqueous NaOH and extracted with EtOAc several times. The combined organic layers were dried over anhydrous MgSO₄ and concentrated. The crude mixture was purified by column chromatography eluting with a gradient of 0–7% MeOH in CHCl₃ followed by 3–8% MeOH/NH₃ in CHCl₃ to give 0.52 g (86%) of a pale-yellow solid: mp 140–142° C.; ¹H NMR (DMSO-d₆) δ 2.18 (s, 6H), 3.45 (s, 2H), 3.47–3.50 (m, 2H), 4.32 (m, 2H), 6.69 (s, 1H), 7.16 (t, 1H, J=10 Hz), 7.42 (d, 2H, J=10 Hz), 7.56 (d, 2H, J=10 Hz), 7.77 (d, 1H, J=10 Hz), 7.81 (d, 1H, J=10 Hz), 8.36 (t, 1H, J=5 Hz). HRMS calcd. for C₂₀H₂₁N₃O 319.1685 (M⁺), found 319.1678. Anal. (C₂₀H₂₁N₃O.0.3 H₂O) C, H, N.

Example 83

6-(4-Methylaminomethyl-phenyl)-3,4-dihydro-2H-[1,4]diazepino[6,7,1-hi]indol-1-one

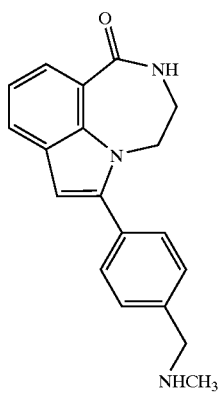

Using the reductive amination procedure described in Example 82, the title compound was synthesized from 4-(1-oxo-1,2,3,4-tetrahydro-[1,4]diazepino[6,7,1-hi]indol-6-yl)-benzaldehyde and methylamine in 71% yield as a pale-yellow solid: mp 178–180° C.; ¹H NMR (DMSO-d₆) δ 2.29 (s, 3H), 3.48 (br s, 2H), 3.70 (s, 2H), 4.30–4.33 (m, 2H), 6.68 (s, 1H), 7.16 (t, 1H, J=9.0 Hz), 7.45 (d, 2H, J=6.0 Hz), 7.55 (d, 2H, J=6.0 Hz), 7.77 (d, 1H, J=9.0 Hz), 7.80 (d, 1H, J=9.0 Hz), 8.36 (t, 1H, J=6.0 Hz). HRMS calcd. for C₁₉H₁₉N₃O 305.3828 (M⁺), found 305.1536. Anal. (C₁₉H₁₉N₃O.0.1H₂O) C, H, N.

Example 84

6-(4-Pyrrolidin-1-ylmethyl-phenyl)-3,4-dihydro-2H-[1,4]diazepino[6,7,1-hi]indol-1-one

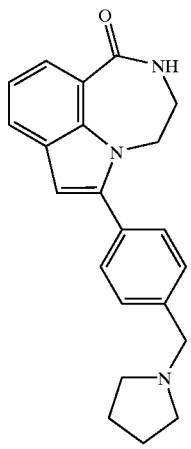

Using the reductive amination procedure described in Example 82, the title compound was synthesized from 4-(1-oxo-1,2,3,4-tetrahydro-[1,4]diazepino[6,7,1-hi]indol-6-yl)-benzaldehyde and pyrrolidine in 76% yield as a pale-yellow solid: mp 146–148° C.; ¹H NMR (DMSO-d₆) δ 1.71 (br s, 4H), 2.49 (br s, 4H), 3.48 (br s, 2H), 3.64 (br s, 2H), 4.30–4.33 (m, 2H), 6.69 (s, 1H), 7.16 (t, 1H, J=9.0 Hz), 7.43 (d, 2H, J=9.0 Hz), 7.55 (d, 2H, J=9.0 Hz), 7.77 (d, 1H, J=9.0 Hz), 7.80 (d, 1H, J=9.0 Hz), 8.38 (t, 1H, J=6.0 Hz). HRMS calcd. for 345.1841 (M⁺), found 345.1835. Anal. (C₂₂H₂₃N₃O.0.25 H₂O) C, H, N.

Example 85

3-(1-Oxo-1,2,3,4-tetrahydro-[1,4]diazepino[6,7,1-hi]indol-6-yl)-benzaldehyde

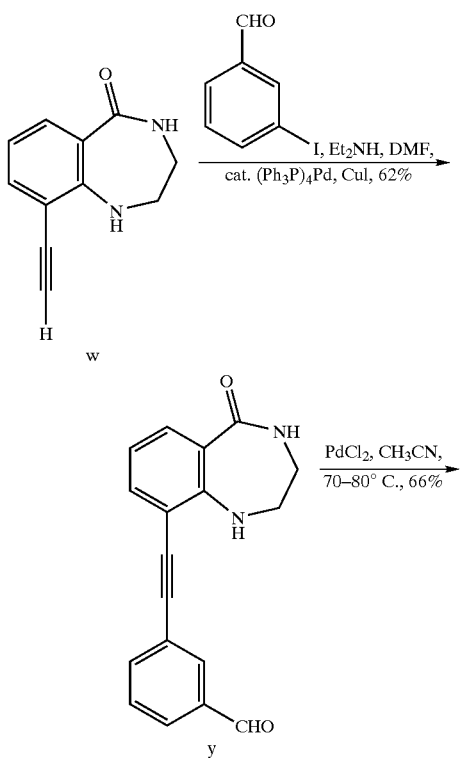

(a) Intermediate y—3-(5-Oxo-2,3,4,5-tetrahydro-1H-benzo[e][1,4]diazepin-9-ylethynyl)-benzaldehyde:

Using the procedure described for the preparation of intermediate o, intermediate w, 9-ethynyl-1,2,3,4-tetrahydro-benzo[e][1,4]diazepin-5-one, and 3-iodo-benzaldehyde were used to synthesize intermediate y in 62% yield as a yellow solid: mp 176–178° C.; $^1$H (DMSO-$d_6$) δ3.30–3.33 (m, 2H), 3.54–3.57 (m, 2H), 6.40 (br s 1H), 6.63 (t, 1H, J=6.0 Hz), 7.49 (d, 1H, J=6.0 Hz), 7.66 (t, 1H, J=9.0 Hz), 7.83 (d, 1H, J=6.0 Hz), 7.90–7.97 (m, 2H), 8.15 (br s, 1H), 8.31 (s, 1H), 10.03 (s, 1H). LRMS 291 (M$^+$+H).

(b) Title Compound:

Using the procedure described for the preparation of 6-phenyl-3,4-dihydro-2H-[1,4]diazepino[6,7,1-hi]indol-1-one (Example 33), the title compound was synthesized from intermediate y and obtain in 66% yield as a pale-yellow solid: mp 192–194° C.; $^1$H NMR (DMSO-$d_6$) δ 3.49–3.51 (m, 2H), 4.33–4.36 (m, 2H), 6.83 (s, 1H), 7.19 (t, 1H, J=6.0 Hz), 7.75 (t, 1H, J=9.0 Hz), 7.80–7.86 (m, 2H), 7.96 (d, 2H, J=6.0 Hz), 8.15 (s, 1H), 8.41 (t, 1H, J=6.0 Hz), 10.11 (s, 1H). LRMS 290 (M$^+$).

Example 86

6-(3-Dimethylaminomethyl-phenyl)-3,4-dihydro-2H-[1,4]diazepino[6,7,1-hi]indol-1-one

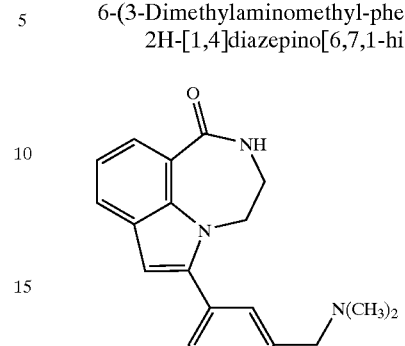

Using the reductive amination procedure described in Example 82, the title compound was synthesized from 3-(1-oxo-1,2,3,4-tetrahydro-[1,4]diazepino[6,7,1-hi]indol-6-yl)-benzaldehyde and dimethylamine in 87% yield as a white solid: mp 98–100° C.; $^1$H NMR (DMSO-$d_6$) δ 2.18 (s, 6H), 3.47 (br s, 4H), 4.30–4.32 (m, 2H), 6.70 (s, 1H), 7.17 (t, 1H, J=6.0 Hz), 7.35–7.37 (m, 1H), 7.43–7.50 (m, 3H), 7.78 (d, 1H, J=6.0 Hz), 7.81 (d, 1H, J=6.0 Hz), 8.38 (t, 1H, J=6.0 Hz). HRMS calcd. for $C_{20}H_{21}N_3O$ 319.1685 (M$^+$), found 319.1682. Anal. ($C_{20}H_{21}N_3O \cdot 0.25\ H_2O$) C, H, N.

Example 87

6-(3-Methylaminomethyl-phenyl)-3,4-dihydro-2H-[1,4]diazepino[6,7,1-hi]indol-1-one

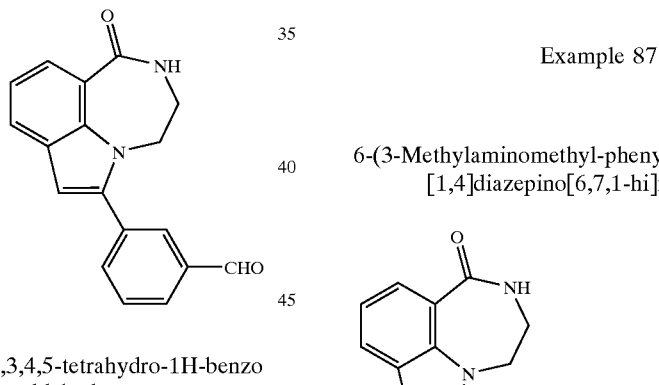

Using the reductive amination procedure described in Example 82, the title compound was synthesized from 3-(1-oxo-1,2,3,4-tetrahydro-[1,4]diazepino[6,7,1-hi]indol-6-yl)-benzaldehyde and methylamine in 94% yield as a pale-yellow solid: mp 128–130° C.; $^1$H NMR (DMSO-$d_6$) δ 2.29 (s, 3H), 3.48 (br s, 2H), 3.71 (s, 2H), 4.30–4.33 (m, 2H), 6.69 (s, 1H), 7.17 (t, 1H, J=9.0 Hz), 7.38–7.39 (m, 1H), 7.44–7.46 (m, 2H), 7.54 (s, 1H), 7.80 (t, 2H, J=9.0 Hz), 8.39 (t, 1H, J=6.0 Hz). HRMS calcd. for $C_{19}H_{19}N_3O$ 305.3828 (M$^+$), found 305.1520. Anal. ($C_{19}H_{19}N_3O \cdot 0.6\ H_2O$) C, H, N.

Example 88

6-(3-Pyrrolidin-1-ylmethyl-phenyl)-3,4-dihydro-2H-[1,4]diazepino[6,7,1-hi]indol-1-one

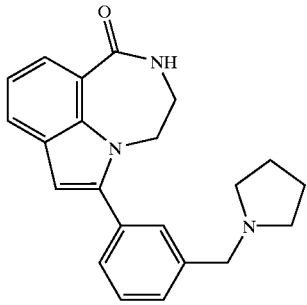

Using the reductive amination procedure described in Example 82, the title compound was synthesized from 3-(1-oxo-1,2,3,4-tetrahydro-[1,4]diazepino[6,7,1-hi]indol-6-yl)-benzaldehyde and pyrrolidine in 92% yield as a pale-yellow solid: mp 158–160° C.; $^1$H NMR (DMSO-d$_6$) δ 1.71 (br s, 4H), 2.49 (br s, 4H), 3.49 (br s, 2H), 3.68 (br s, 2H), 4.30–4.33 (m, 2H), 6.70 (s, 1H), 7.17 (t, 1H, J=9.0 Hz), 7.38–7.52 (m, 4H), 7.79 (d, 1H, J=9.0 Hz), 7.82 (d, 1H, J=9.0 Hz), 8.38 (t, 1H, J=6.0 Hz). HRMS calcd. for C$_{22}$H$_{23}$N$_3$O 345.1841 (M$^+$), found 345.1848. Anal. (C$_{22}$H$_{23}$N$_3$O.0.4 H$_2$O) C, H, N.

Example 89

6-(4-Fluoro-phenyl)-1-oxo-1,2,3,4-tetrahydro-[1,4diazepino[6,7,1-hi]indole-7-carbaldehyde

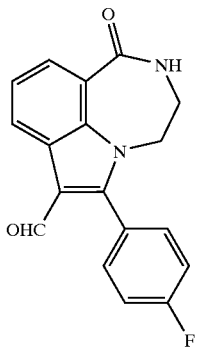

Following the procedure described in Example 38, the title compound was synthesized form 6-(4-fluorophenyl)-3,4-dihydro-2H-[1,4]diazepino[6,7,1-hi]indol-1-one as a white solid in 94% yield: mp 268–270° C.; $^1$H NMR (DMSO-d$_6$) δ 3.52–3.54 (m, 2H), 4.19–4.22 (m, 2H), 7.40–7.50 (m, 3H), 7.75 (d, 1H, J=6.0 Hz), 7.78 (d, 1H, J=6.0 Hz), 8.46 (d, 1H, J=6.0 Hz), 8.52 (t, 1H, J=6.0 Hz), 9.64 (s, 1H). LRMS 309 (M$^+$+H).

Example 90

6-(4-Fluoro-phenyl)-1-oxo-1,2,3,4-tetrahydro-[1,4]diazepino[6,7,1-hi]indole-7-carbaldehyde oxime

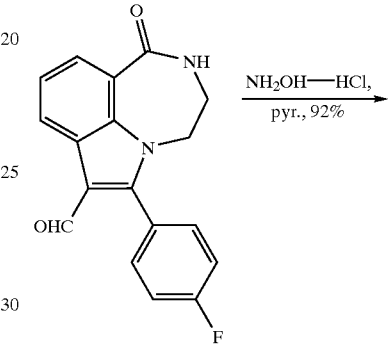

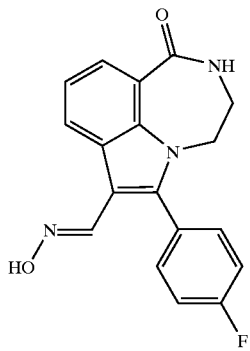

Hydroxylamine hydrochloride (0.10 g, 0.325 mmol) was added to a solution of 6-(4-fluoro-phenyl)-1-oxo-1,2,3,4-tetrahydro-[1,4]diazepino[6,7,1-hi]indole-7-carbaldehyde (56.0 mg, 0.813 mmol) in pyridine (10 mL) and stirred at rt for 20 h. Upon consumption of the aldehyde as indicated by TLC, the solvent was removed in vacuo. The residue was taken up in 2N HCl and extracted with EtOAc several times. The combined organic extracts were dried over anhydrous MgSO$_4$ and concentrated to give 97 mg (92%) of a pale-yellow solid: mp 277–279° C.; $^1$H NMR (DMSO-d$_6$) δ 3.50 (br s, 2H), 4.12–4.14 (m, 2H), 7.30 (t, 1H, J=6.0 Hz), 7.43 (t, 2H, J=9.0 Hz), 7.57–7.62 (m, 2H), 7.89 (s, 1H), 7.94 (d, 1H, J=9.0 Hz), 8.33 (d, 1H, J=6.0 Hz), 8.41 (t, 1H, J=6.0 Hz), 10.80 (s, 1H). HRMS calcd. for C$_{18}$H$_{14}$N$_3$O$_2$F 323.1070 (M$^+$), found 323.1066.

Example 91

6-(4-Fluoro-phenyl)-1-oxo-1,2,3,4-tetrahydro-[1,4]diazepino[6,7,1-hi]indole-7-carbonitrile

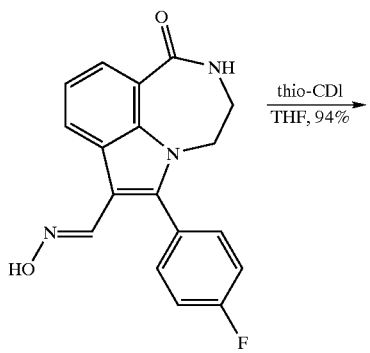

Thiocarbonyldiimidazole (0.415 g, 2.33 mmol) was added to a solution 6-(4-fluoro-phenyl)-1-oxo-1,2,3,4-tetrahydro-[1,4]diazepino[6,7,1-hi]indole-7-carbaldehyde oxime (0.301 g, 0.932 mmol) in THF (70 mL) at rt and stirred for 4 h. Upon consumption of the oxime as indicated by TLC, the solvent was removed in vacuo. The residue was dissolved in EtOAc, washed with 10% HCl and then with saturated NaHCO$_3$. The organic layer was dried over anhydrous MgSO$_4$ and concentrated to give a yellow oil, which was purified by column chromatography eluting with a gradient of 0–3% MeOH in CHCl$_3$ to give 0.268 g (94%) of a pale-yellow solid: mp 248–250° C.; $^1$H NMR (DMSO-d$_6$) δ 3.52 (br s, 2H), 4.29–4.31 (m, 2H), 7.41–7.53 (m, 3H), 7.77 (d, 1H, J=6.0 Hz), 7.80 (d, 1H, J=6.0 Hz), 7.90 (d, 1H, J=6.0 Hz), 8.01 (d, 1H, J=6.0 Hz), 8.55 (t, 1H, J=6.0 Hz). HRMS calcd. for C$_{18}$H$_{12}$N$_3$OF 305.0964 (M$^+$), found 305.0951. Anal. (C$_{18}$H$_{12}$N$_3$OF·0.1 H$_2$O) C, H, N.

Example 92

6-(4-Fluoro-phenyl)-1-oxo-1,2,3,4-tetrahydro-[1,4]diazepino[6,7,1-hi]indole-7-carboxylic Acid Amide

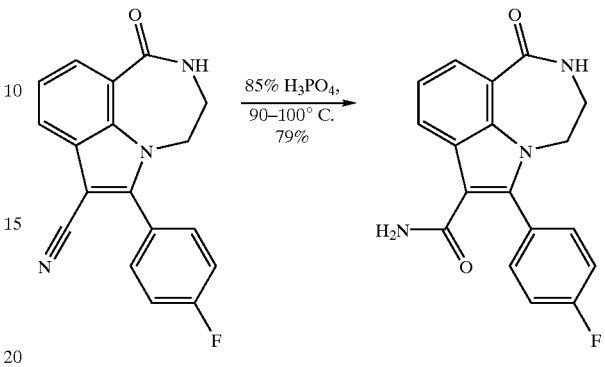

A suspension of 6-(4-fluoro-phenyl)-1-oxo-1,2,3,4-tetrahydro-[1,4]diazepino[6,7,1hi]indole-7-carbonitrile (Example 91) (0.05 g, 0.164 mmol) in 85% H$_3$PO$_4$ (7 mL) was heated at 90–100° C. for 22 h. Upon consumption of starting material (as indicated by TLC) the reaction mixture was poured into H$_2$O and extracted with EtOAc several times. The combined organic extracts were dried over anhydrous MgSO$_4$ and concentrated to give a pink oil, which was purified by column chromatography eluting with a gradient of 0–5% MeOH in CHCl$_3$ to give 0.042 g (79%) of a pale-yellow solid: mp 287–289° C.; $^1$H NMR (DMSO-d$_6$) δ 3.47 (br s, 2H), 3.98–4.06 (m, 2H), 6.46 (br s, 1H), 7.09 (br s, 1H), 7.28 (t, 1H, J=6.0 Hz), 7.38 (t, 2H, J=9.0Hz), 7.56 (d, 1H, J=6.0Hz), 7.60 (d, 1H, J=6.0Hz), 7.90 (d, 1H, J=6.0 Hz), 8.15 (d, 1H, J=6.0 Hz), 8.40 (t, 1H, J=6.0 Hz). HRMS calcd. for C$_{18}$H$_{14}$N$_3$O$_2$F 323.1070 (M$^+$), found 323.1063. Anal. (C$_{18}$H$_{14}$N$_3$O$_2$F·0.5 H$_2$O) C, H, N.

Example 93

7-Acetyl-6-(4-fluoro-phenyl)-3,4-dihydro-2H-[1,4]diazepino[6,7,1-hi]indol-1-one

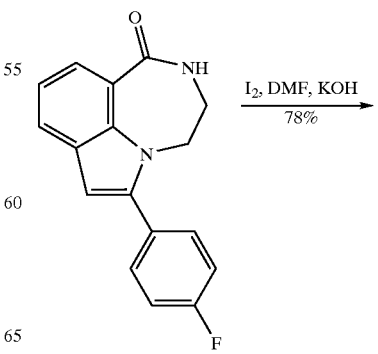

95

-continued

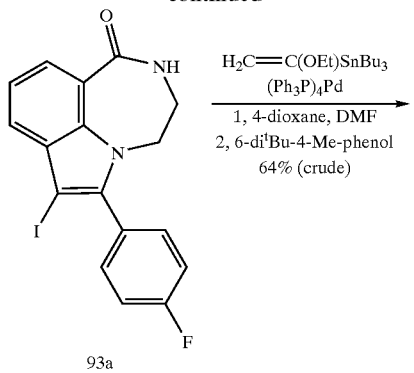

93a

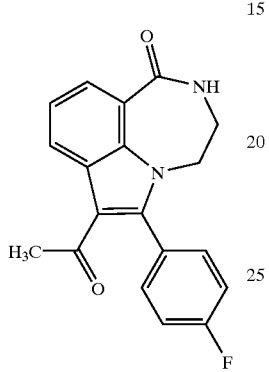

(a) 6-(4-Fluoro-phenyl)-7-iodo-1-oxo-3,4-dihydro-2H-[1,4]diazepino[6,7,1-hi]indol-1-one:

Following the procedure described in Example 43, 6-(4-fluoro-phenyl)-7-iodo-1-oxo-3,4-dihydro-2H-[1,4]diazepino[6,7,1-hi]indol-1-one was synthesized form 6-(4-fluorophenyl)-3,4-dihydro-2H-[1,4]diazepino[6,7,1-hi]indol-1-one (Example 37), yielding a pale-yellow solid in 78% yield: mp 283–285° C.; $^1$H NMR (DMSO-d$_6$) δ 3.48 (br s, 2H), 4.15–4.18 (m, 2H), 7.29 (t, 1H, J=6.0 Hz), 7.41 (t, 2H, J=9.0 Hz), 7.58–7.64 (m, 3H), 7.94 (d, 1H, J=6.0 Hz), 8.41 (t, 1H, J=6.0 Hz). LRMS 407 (M$^+$+H).

(b) Title Compound:

A solution of 6-(4-fluoro-phenyl)-7-iodo-1-oxo-3,4-dihydro-2H-[1,4]diazepino[6,7,1-hi]indol-1-one (0.10 g, 0.246 mmol), ethoxyvinyl tributyltin (0.11 mL, 0.320 mmol), tetrakistriphenyl phosphine palladium (14.0 mg, 0.0123 mmol) and a trace of 2,6-di-t-butyl-4-methyl phenol in 1,4-dioxane (20 mL) and DMF (1 mL) was heated at 90–95° C. for 20 h. Upon consumption of starting material (as indicated by TLC), the solvent was evaporated to dryness. The residue was taken up in 1N HCl and extracted with EtOAc several times. The combined organic layers were dried over anhydrous MgSO$_4$ and concentrated to give a yellow oil, which was purified by column chromatography eluting with a gradient of 0–3% MeOH in CHCl$_3$ to yield 49.0 mg (64% crude) of a yellow solid. Of this solid, 36.0 mg was further purified by preparative HPLC. A gradient mobile phase, starting with 90% H$_2$O with 0.1% TFA, 10% CH$_3$CN with 0.1% TFA up to 2 min, then reaching 35% H$_2$O with 0.1% TFA, 65% CH$_3$CN with 0.1% TFA after 22 min, was used. Rt=10.61 min. The pure fractions were collected and concentrated under vacuum to give 15 mg (26%) of the pure product: mp 275–276° C.; $^1$H NMR (DMSO-d$_6$) δ 1.86 (s, 3H), 3.45–3.52 (m, 2H), 3.96–3.98 (m, 2H), 7.37 (t, 1H, J=6.0 Hz), 7.45 (t, 2H, J=9.0 Hz), 7.64 (d, 1H, J=6.0 Hz), 7.67 (d, 1H, J=6.0 Hz), 7.96 (d, 1H, J=6.0 Hz), 8.42 (t, 1H, J=6.0 Hz), 8.55 (d, 1H, J=6.0 Hz). HRMS calcd. for C$_{19}$H$_{15}$N$_2$O$_2$F 322.1117 (M$^+$), found 322.1131. Anal HPLC R$_t$=8.61 min.

96

Example 94

1-(Thiazol-2-yl)-8,9-dihydro-7H-2,7,9a-triaza-benzo[cd]azulen-6-one

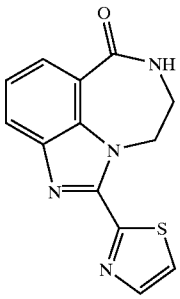

The title compound was prepared following the procedure described in Example 55 from intermediate g and 2-thiazolecarboxaldehyde to give 0.057 g (37%) of a white solid: mp=271–276° C.; R$_f$=0.31 (5% MeOH/EtOAc); IR (KBr) 1655, 1466, 1379 cm$^{-1}$; $^1$H NMR (DMSO-d$_6$) δ 3.29–3.30 (m, 2H), 3.63–3.68 (m, 2H), 7.39–7.44 (m, 1H), 7.94–7.97 (m, 2H), 8.02–8.03 (m, 1H), 8.11–8.13 (m, 1H), 8.46–8.49 (m, 1H). HRMS calcd for C$_{13}$H$_{10}$N$_4$OS 270.0575 (M$^+$), found 270.0566. Anal. (C$_{13}$H$_{10}$N$_4$OS) C, H, N.

Example 95

1-(1H-Pyrrol-2-yl)-8,9-dihydro-7H-2,7,9a-triaza-benzo[cd]azulen-6-one

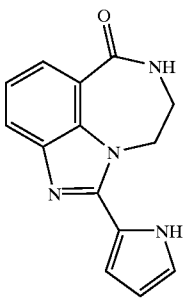

The title compound was prepared following the procedure described in Example 55 from intermediate g and pyrrole-2-carboxaldehyde to give 0.061 g (40%) of an amber solid: mp=327–332° C. (dec); R$_f$=0.25 (5% MeOH/EtOAc); IR (KBr) 1651, 1586, 1497, 1470 cm$^{-1}$; $^1$H NMR (DMSO-d$_6$) δ 3.35–3.36 (m, 2H), 4.29–4.30 (m, 2H), 6.04–6.06 (m, 1H), 6.52–6.54 (m, 1H), 6.79–6.81 (m, 1H), 7.07 (t, 1H, J=7.8 Hz), 7.53–7.57 (m, 2H), 8.20 (t, 1H, J=5.6 Hz). HRMS calcd for C$_{14}$H$_{12}$N$_4$O 252.1011 (M$^+$), found 252.1008. Anal. (C$_{14}$H$_{12}$N$_4$O.0.25 H$_2$O) C, H, N.

Example 96

1-[5-(4-Chlorophenyl)-furan-2-yl]-8,9-dihydro-7H-2,7,9a-triaza-benzo[cd]azulen-6-one

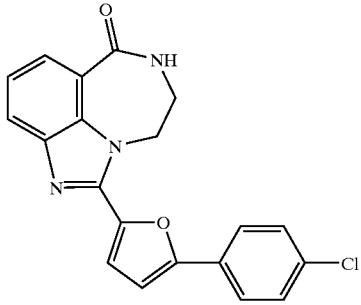

The title compound was prepared following the procedure described in Example 55 from intermediate g and 5-(4-chlorophenyl)-2-furaldehyde to give 0.038 g (22%) of a light-yellow solid: mp=341–344° C.; $R_f$=0.31 (5% MeOH/EtOAc); IR (KBr) 1651, 1487, 1381, 1090 cm$^{-1}$; $^1$H NMR (DMSO-d$_6$) δ 3.64–3.66 (m, 2H), 4.70–4.71 (m, 2H), 7.33–7.40 (m, 3H), 7.54–7.58 (m, 2H), 7.86–7.93 (m, 4H), 8.47–8.51 (m, 1H). HRMS calcd for $C_{20}H_{14}N_3O_2Cl$ 363.0775 (M$^+$), found 363.0789. Anal. ($C_{20}H_{14}N_3O_2Cl \cdot 0.25 H_2O$) C, H, N.

Example 97

4-Fluoro-1-(hydroxymethyl-phenyl)-8,9-dihydro-7H-2,7,9a-triaza-benzo[cd]azulen-6-one

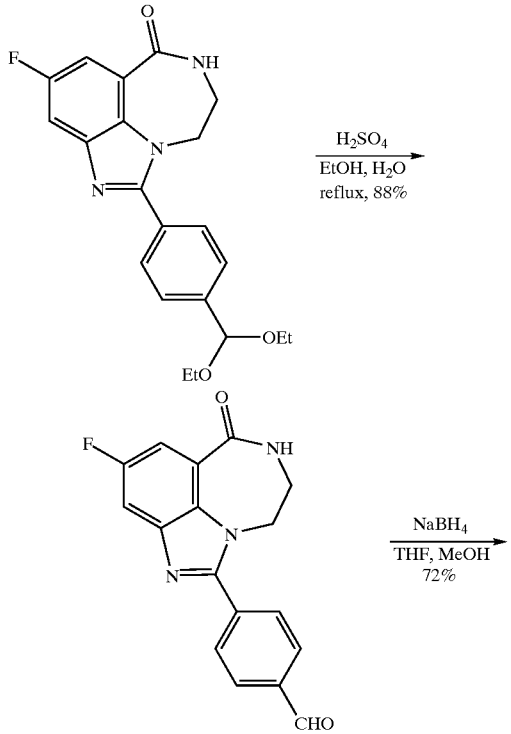

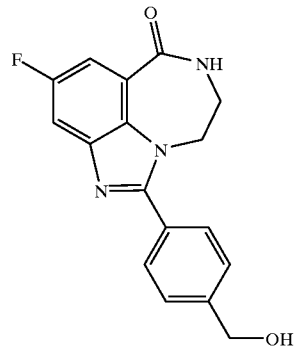

(a) 4-(4-Fluoro-6-oxo-6,7,8,9-tetrahydro-2,7,9a-triaza-benzo[cd]azulen-1-yl)-benzaldehyde (97a) was prepared following the procedure described in Example 57 from 1-(4-diethoxymethyl-phenyl)-4-fluoro-8,9-dihydro-7H-2,7,9a-triaza-benzo[cd]azulen-6-one (Example 79) to give 1.11 g (88%) of a white solid, which was used in the next step without further purification: $^1$H NMR (DMSO-d$_6$) δ 3.55–3.56 (m, 2H), 4.50–4.51 (m, 2H), 7.64 (dd, 1H, J=2.6, 10.6 Hz), 7.81 (dd, 1H, J=2.6, 8.9 Hz), 8.10 (s, 4H), 8.2–8.66 (m, 1H), 10.13 (s, 1H).

(b) Title Compound:

4-(4-Fluoro-6-oxo-6,7,8,9-tetrahydro-2,7,9a-triaza-benzo[cd]azulen-1-yl)-benzaldehyde (97a) (0.10 g, 0.33 mmol) was suspended in 1:1 THF/MeOH (2 mL). Sodium borohydride (0.014 g, 0.36 mmol) was added portionwise, and the reaction stirred at rt for 1 h. The solvents were removed in vacuo and the residue purified by column chromatography (0–2% MeOH/EtOAc) to give 0.073 g (72%) of a white solid: mp=273–275° C.; $R_f$=0.18 (5% MeOH/EtOAc); IR (KBr) 1655, 1609, 1470, 1319 cm$^{-1}$; $^1$H NMR (DMSO-d$_6$) δ 3.54–3.55 (m, 2H), 4.44–4.46 (m, 2H), 4.60 (d, 2H, J=5.7 Hz), 5.36 (t, 1H, J=5.7 Hz), 7.52 (d, 2H, J=8.2 Hz), 7.59 (dd, 1H, J=2.6, 10.6 Hz), 7.75 (dd, 1H, J=9.0 Hz), 7.81 (d, 2H, J=8.2 Hz), 8.59–8.63 (m, 1H). HRMS calcd for $C_{17}H_{14}N_3O_2F$ 311.1070 (M$^+$), found 311.1058. Anal. ($C_{17}H_{14}N_3O_2F$) C, H, N.

Example 98

4-Fluoro-1-(4-methylaminomethyl-phenyl)-8,9-dihydro-7H-2,7,9a-triaza-benzo[cd]azulen-6-one

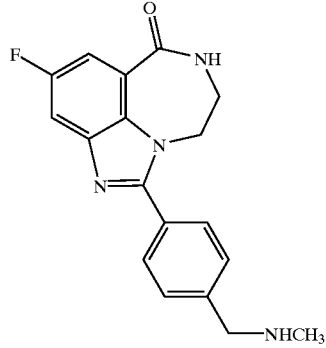

The title compound was prepared following the procedure described in Example 32 from aldehyde 97a and methylamine (2M/MeOH) to give 0.069 g (42%) of a white solid: mp=204–208° C. (dec); $R_f$=0.03 (7% methanolic ammonia/CHCl$_3$); IR (KBr) 1655, 1609, 1470, 1437 cm$^{-1}$; $^1$H NMR (DMSO-d$_6$) δ 2.30 (s, 3H), 3.54–3.55 (m, 2H), 3.75 (s, 2H), 4.45–4.46 (m, 2H), 7.52 (d, 2H, J=8.2 Hz), 7.57–7.61 (m, 1H), 7.73–7.76 (m, 1H), 7.80 (d, 2H, J=8.2 Hz), 8.59–8.63 (m, 1H). HRMS calcd for $C_{18}H_{17}N_4OF$ 324.1386 (M$^+$), found 324.1378. Anal. ($C_{18}H_{17}N_4OF\cdot0.3H_2O$) C, H, N.

Example 99

4-Fluoro-1-(4-dimethylaminomethyl-phenyl)-8,9-dihydro-7H-2,7,9a-triaza-benzo[cd]azulen-6-one

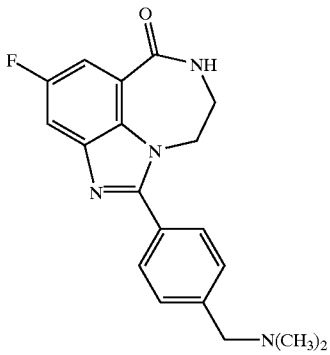

The title compound was prepared following the procedure described in Example 32 from aldehyde 97a and dimethylamine (2M/MeOH) to give 0.10 g (60%) of a white solid: mp=240° C. (dec); $R_f$=0.08 (7% methanolic ammonia/CHCl$_3$); IR (KBr) 1669, 1607, 1487, 1458 cm$^{-1}$; $^1$H NMR (DMSO-d$_6$) δ 2.20 (s, 6H), 3.51 (s, 2H), 3.54–3.55 (m, 2H), 4.45–4.47 (m, 2H), 7.50 (d, 2H, J=8.2 Hz), 7.57–7.61 (m, 1H), 7.73–7.76 (m, 1H), 7.82 (d, 2H, J=8.2 Hz), 8.59–8.63 (m, 1H). HRMS calcd for $C_{19}H_{19}N_4OF$ 338.1543 (M$^+$), found 338.1558. Anal. ($C_{19}H_{19}N_4OF\cdot0.2H_2O$) C, H, N. found 412.2124. Anal. ($C_{25}H_{25}N_5O\cdot0.5$ H$_2$O, 3.5 TFA) C, H, N.

Example 100

1-{4-[(2-Ethoxyethylamino)-methyl]-phenyl}-8,9-dihydro-7H-2,7,9a-triaza-benzo[cd]azulen-6-one

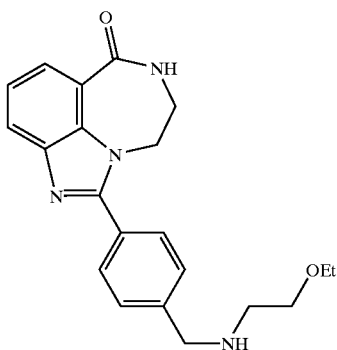

This compound was prepared from the aldehyde in Example 57 and 2-ethoxyethylamine using the procedure described in Example 32; white amorphous solid (77%): mp=138–140° C.; $R_f$=0.18 (10% MeOH/CHCl$_3$); IR (KBr) 1663, 1483, 1381, 1086 cm$^{-1}$; $^1$H NMR (DMSO-d$_6$) δ 1.10 (t, 3H, J=7.0 Hz), 2.65–2.69 (m, 2H), 3.38–3.47 (m, 4H), 3.52–3.53 (m, 2H), 3.81 (s, 2H), 4.45–4.46 (m, 2H), 7.35 (t, 1H, J=7.8 Hz), 7.52 (d, 2H, J=8.2 Hz), 7.80 (d, 2H, J=8.2 Hz), 7.84–7.90 (m, 2H), 8.47 (m, 1H). HRMS calcd for $C_{21}H_{24}N_4O_2$ 364.1899 (M$^+$), found 364.1906. Anal. ($C_{21}H_{24}N_4O_2\cdot0.2H_2O$) C, H, N.

Example 101

1-(4-Cyclopropylaminomethyl-phenyl)-8,9-dihydro-7H-2,7,9a-triaza-benzo[cd]azulen-6-one

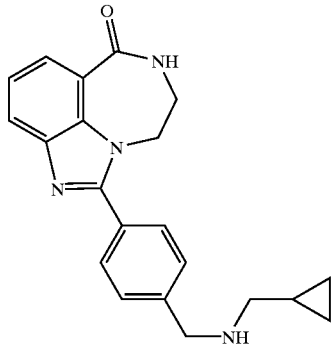

This compound was prepared from the aldehyde in Example 57 and cyclopropylamine using the procedure described in Example 32; white amorphous solid (71%): mp=84° C. (dec); $R_f$=0.18 (10% MeOH/CHCl$_3$); IR (KBr) 1655, 1481, 1381, 1308 cm$^{-1}$; $^1$H NMR (DMSO-d$_6$) δ 0.25–0.30 (m, 2H), 0.33–0.40 (m, 2H), 2.06–2.10 (m, 1H), 3.52–3.52 (m, 2H), 3.82 (s, 2H), 4.44–4.46 (m, 2H), 7.35 (t, 1H, J=7.8 Hz), 7.52 (d, 1H, J=8.2 Hz), 7.80 (d, 2H, J=8.2 Hz), 7.84–7.90 (m, 2H), 8.45 (t, 1H, J=5.6 Hz). HRMS calcd for $C_{20}H_{20}N_4O$ 332.1637 (M$^+$), found 332.1644. Anal. ($C_{20}H_{20}N_4O\cdot0.4H_2O$) C, H, N.

Example 102

[4-(6-Oxo-6,7,8,9-tetrahydro-2,7,9a-triaza-benzo[cd]azulen-1-yl)-benzylamino]-acetonitrile

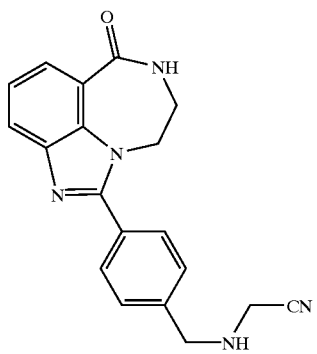

This compound was prepared from the aldehyde in Example 57 and aminoacetonitrile using the procedure described in Example 32; white solid (25%): mp=198–202° C. (dec); $R_f$=0.16 (10% MeOH/CHCl$_3$); IR (KBr) 1626, 1483, 1464, 1379 cm$^{-1}$; $^1$H NMR (DMSO-d$_6$) δ 3.37–3.39 (m, 2H), 3.64 (s, 2H), 3.86 (s, 2H), 4.45–4.46 (m, 2H), 7.35 (t, 1H, J=7.8 Hz), 7.53 (d, 2H, J=8.2 Hz), 7.81–7.91 (m, 4H), 8.43–8.47 (m, 1H). HRMS calcd for $C_{19}H_{17}N_5O$ 331.1433 (M+), found 331.1442. Anal. ($C_{19}H_{17}N_5O\cdot0.25H_2O$) C, H, N.

Example 103

1-4-[(2,2,2-Trifluoro-ethylamino)-methyl]-phenyl-8,9-dihydro-7H-2,7,9a-triaza-benzo[cd]azulen-6-one

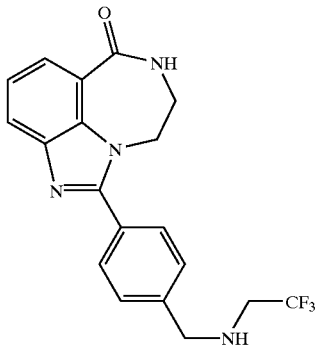

This compound was prepared from the aldehyde in Example 57 and 2,2,2-trifluoroethylamine using the procedure described in Example 32; white crystalline solid (62%): mp=221–223° C.; $R_f$=0.08 (5% MeOH/CHCl$_3$); IR (KBr) 1655, 1481, 1310, 1271 cm$^{-1}$; $^1$H NMR (DMSO-d$_6$) δ 3.04–3.08 (m, 1H), 3.17–3.28 (m, 2H), 3.52–3.53 (m, 2H), 3.89 (d, 2H, J=6.1 Hz), 4.45–4.46 (m, 2H), 7.35 (t, 1H, J=7.8 Hz), 7.53 (d, 2H, J=8.1 Hz), 7.81–7.91 (m, 4H), 8.43–8.47 (m, 1H). HRMS calcd for C$_{19}$H$_{17}$N$_4$OF$_3$ 374.1354 (M+), found 374.1342. Anal. (C$_{19}$H$_{17}$N$_4$OF$_3$) C, H, N.

Example 104

1-(4-Prop-2-ynylaminomethyl-phenyl)-8,9-dihydro-7H-2,7,9a-triaza-benzo[cd]azulen-6-one

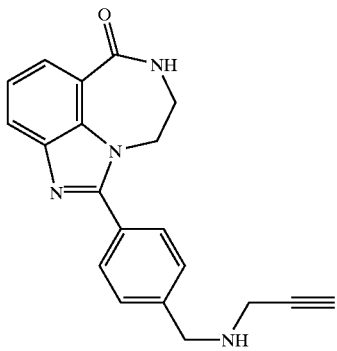

This compound was prepared from the aldehyde in Example 57 and propargylamine using the procedure described in Example 32; white amorphous solid (60%): mp=126° C. (dec); $R_f$=0.08 (5% MeOH/CHCl$_3$); IR (KBr) 1651, 1481, 1464 cm$^{-1}$; $^1$H NMR (acetone-d$_6$) δ 2.69–2.71 (m, 1H), 3.42 (d, 2H, J=2.4 Hz), 3.77–3.78 (m, 2H), 3.98 (s, 2H), 4.57–4.60 (m, 2H), 7.36 (t, 1H, J=7.8 Hz), 7.58–7.60 (m, 3H), (m, 3H), 7.98 (dd, 1H, J=7.7, 1.0 Hz). HRMS calcd for C$_{20}$H$_{18}$N$_4$O 330.1481 (M+), found 330.1472. Anal. (C$_{20}$H$_{18}$N$_4$O.0.7H$_2$O) C, H, N.

Example 105

1-(4-Thiomorpholin-4-ylmethyl-phenyl)-8,9-dihydro-7H-2,7,9a-triaza-benzo[cd]azulen-6-one

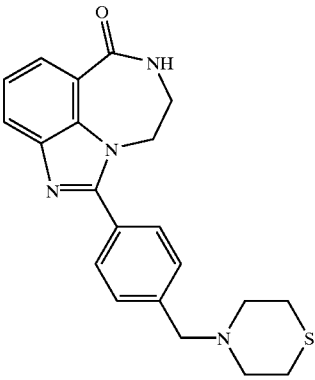

This compound was prepared from the aldehyde in Example 57 and thiomorpholine using the procedure described in Example 32; off-white solid (79%): mp=266° C. (dec); $R_f$=0.18 (5% MeOH/CHCl$_3$); IR (KBr) 1661, 1601, 1483, 1381 cm$^{-1}$; $^1$H NMR (DMSO-d$_6$) δ 2.62–2.66 (m, 8H), 3.52–3.53 (m, 2H), 3.60 (s, 2H), 4.45–4.47 (m, 2H), 7.35 (t, 1H, J=7.8 Hz), 7.49 (d, 2H, J=8.1 Hz), 7.81–7.90 (m, 4H), 8.43–8.46 (m, 1H). HRMS calcd for C$_{21}$H$_{22}$N$_4$OS 378.1514 (M+), found 378.1521. Anal. (C$_{21}$H$_{22}$N$_4$OS.0.25H$_2$O) C, H, N.

Example 106

1-(2-p-Tolyl-thiazol-4-yl)-8,9-dihydro-7H-2,7,9a-triaza-benzo[cd]azulen-6-one

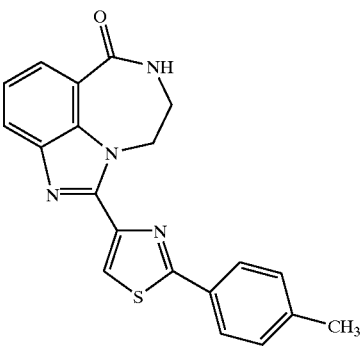

(a) 2-p-Tolyl-thiazole-4-carbonyl chloride:

This compound was prepared as generally described for 3-phenoxybenzoyl chloride in Example 6 from 2-(4-methylphenyl)-1,3-thiazole-4-carboxylic acid to give 1.0 g (quant) of a tan solid which was used without further purification: mp=92–95° C.; IR (KBr) 1765, 1470, 1007 cm$^{-1}$; H NMR (CDCl$_3$) δ 2.42 (s, 3H), 7.28 (d, 2H, J=8.2 Hz), 7.89 (d, 2H, J=8.2 Hz), 8.41 (s, 1H).

(b) Title Compound:

The compound was prepared as described in Example 4 with 2-p-tolyl-thiazole-4-carbonyl chloride and CH$_2$Cl$_2$ as the workup solvent to give 0.055 g (27%) of white solid: mp=308–313° C.; $R_f$=0.5 (5% MeOH/EtOAc); IR (KBr) 1653, 1487, 1464 cm$^{-1}$; $^1$H NMR (DMSO-d$_6$) δ 2.39 (s, 3H), 3.29–3.30 (m, 2H), 3.65–3.66 (m, 2H), 7.35–7.40 (m, 3H), 7.89–7.92 (m, 2H), 7.98 (d, 2H, J=8.1 Hz), 8.46–8.48 (m, 1H), 8.50 (s, 1H). HRMS calcd for C$_{20}$H$_{16}$N$_4$OS 360.1045 (M$^+$), found 360.1037. Anal. (C$_{20}$H$_{16}$N$_4$OS.0.5H$_2$O) C, H, N.

Example 107

1-(3-p-Tolyl-benzo[c]isoxazol-5-yl)-8,9-dihydro-7H-2,7,9a-triaza-benzo[cd]azulen-6-one

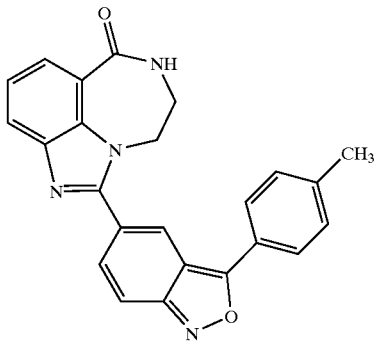

This compound was prepared from the diamine g (Example 2) and 3-(4-methylphenyl)-2,1-benzisoxazole-5-carbaldehyde using the procedure described in Example 19; yellow solid (18%): mp=297–301° C. (dec); $R_f$=0.13 (90% EtOAc/hexanes); IR (KBr) 1653, 1464, 1310 cm$^{-1}$; $^1$H NMR (DMSO-d$_6$) δ 2.43 (s, 3H), 3.54–3.55 (m, 2H), 4.59–4.61 (m, 2H), 7.39 (t, 1H, J=7.8 Hz), 7.47 (d, 2H, J=8.1 Hz), 7.82–7.95 (m, 4H), 8.11 (d, 2H, J=8.2 Hz), 8.49–8.52 (m, 2H). HRMS calcd for $C_{24}H_{18}N_4O_2$ 394.1430 (M+), found 394.1446. Anal. ($C_{24}H_{18}N_4O_2 \cdot 0.5H_2O$) C, H, N.

Example 108

1-[6-(4-Chloro-phenylsulfanyl)-pyridin-3-yl]-8,9-dihydro-7H-2,7,9a-triaza-benzo[cd]azulen-6-one

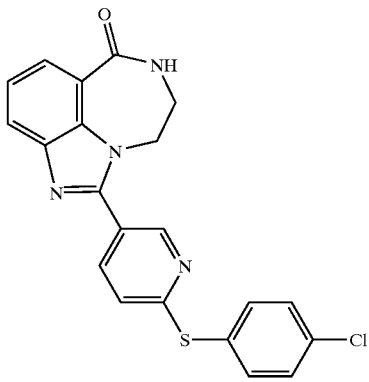

This compound was prepared from the diamine g (Example 2) and 6-[(4-chlorophenyl)sulfanyl] nicotinaldehyde using the procedure described in Example 19; yellow solid (61%): mp=280–284° C. (dec); $R_f$=0.21 (90% EtOAc/hexanes); IR (KBr) 1669, 1586, 1387, 1013 cm$^{-1}$; $^1$H NMR (DMSO-d$_6$) δ 3.50–3.51 (m, 2H), 4.43–4.45 (m, 2H), 7.21 (d, 1H, J=8.4 Hz), 7.37 (t, 1H, J=7.8 Hz), 7.60 (d, 2H, J=8.6 Hz), 7.68 (d, 2H, J=8.6 Hz), 7.86–7.93 (m, 2H), 8.12–8.16 (m, 1H), 8.45 (t, 1H, J=5.7 Hz), 8.85 (d, 1H, J=1.7 Hz). HRMS calcd for $C_{21}H_{15}N_4OSCl$ 406.0655 (M+), found 406.0651. Anal. ($C_{21}H_{15}N_4OSCl \cdot 0.2H_2O$) C, H, N.

Example 109

4-[5-(6-Oxo-6,7,8,9-tetrahydro-2,7,9a-triaza-benzo[cd]azulen-1-yl)-pyridin-2-yloxy]-benzonitrile

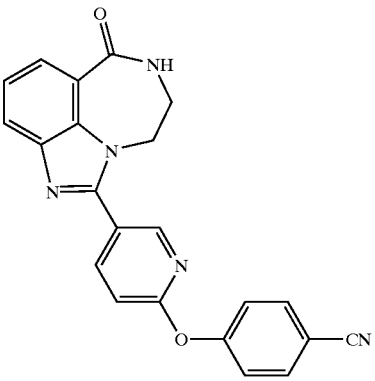

This compound was prepared from the diamine g (Example 2) and 4-[(5-formyl-2-pyridinyl)oxy] benzenecarbonitrile using the procedure described in Example 19; white solid (95%): mp=281–288° C. (dec); $R_f$=0.24 (5% MeOH/EtOAc); IR (KBr) 2228, 1669, 1603, 1258 cm$^{-1}$; $^1$H NMR (DMSO-d$_6$) δ 3.54–3.55 (m, 2H), 4.46–4.47 (m, 2H), 7.35–7.42 (m, 2H), 7.44 (d, 2H, J=8.8 Hz), 7.86–7.91 (m, 2H), 7.95 (d, 2H, J=8.8 Hz), 8.38–8.41 (m, 1H), 8.46 (t, 1H, J=5.7 Hz), 8.65 (d, 1H, J=12.0 Hz). HRMS calcd for $C_{22}H_{15}N_5O_2$ 381.1226 (M+), found 381.1211. Anal. ($C_{22}H_{15}N_5O_2 \cdot 1.2H_2O$) C, H, N.

Example 110

6-Oxo-6,7,8,9-tetrahydro-2,7,9a-triaza-benzo[cd] azulen-1-carboxylic Acid Benzylamide

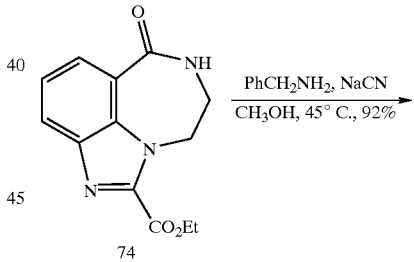

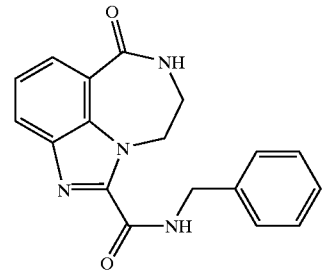

6-Oxo-6,7,8,9-tetrahydro-2,7,9a-triaza-benzo[cd]azulen-1-carboxylic acid ethyl ester (Example 74) (0.07 g, 0.27 mmol) was dissolved in 0.9 mL MeOH. Benzylamine (0.74 mL, 6.75 mmol) was added to the reaction followed by 0.0013 g (10 mol%) of sodium cyanide. The reaction was heated to 45° C. for 3 hours. The solvents were removed in vacuo, and the crude subjected to flash silica gel chromatography, (1% MeOH/EtOAc) to give 0.08 g (92%)

Example 111

3-[4-(6-Oxo-6,7,8,9-tetrahydro-2,7,9a-triaza-benzo[cd]azulen-1-yl)-benzylamino]-propionitrile

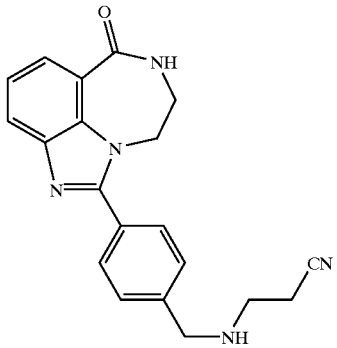

This compound was prepared from the aldehyde in Example 57 and 3-aminopropionitrile using the procedure described in Example 32; white solid (48%): mp=208–214° C.; $R_f$=0.05 (5% MeOH/EtOAc); IR (KBr) 1661, 1601, 1485, 1312 cm$^{-1}$; $^1$H NMR (DMSO-d$_6$) δ 2.61–2.65 (m, 2H), 2.73–2.78 (m, 2H), 3.52–3.52 (m, 2H), 3.82 (s, 2H), 4.45–4.47 (m, 2H), 7.35 (t, 1H, J=7.8 Hz), 7.54 (d, 2H, J=8.2 Hz), 7.82 (d, 2H, J=8.2 Hz), 7.84–7.91 (m, 2H), 8.43–8.47 (m, 1H). HRMS calcd for C$_{20}$H$_{19}$N$_5$O 345.1590 (M+), found 345.1586. Anal. (C$_{20}$H$_{19}$N$_5$O.1.6H$_2$O) C, H, N.

Example 112

1-Trifluoromethyl-8,9-dihydro-7H-2,7,9a-triaza-benzo[cd]azulen-6-one

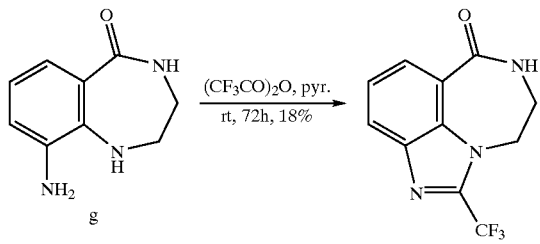

The product was prepared intermediate g and trifluoroacetic anhydride using CH$_2$Cl$_2$ as the workup solvent to give 0.26 g (18%) of a white solid: mp=277–281° C. (dec); $R_f$=0.18 (75% EtOAc/hexanes); IR (KBr) 1671, 1609, 1474, 1123 cm$^{-1}$; $^1$H NMR (DMSO-d$_6$) δ 3.66–3.71 (m, 2H), 4.50–4.51 (m, 2H), 7.50 (t, 1H, J=7.8 Hz), 8.03–8.09 (m, 2H), 8.53 (t, 1H, J=5.5 Hz). HRMS calcd for C$_{11}$H$_8$N$_3$OF$_3$ 255.0619 (M+), found 255.0610. Anal. (C$_{11}$H$_8$N$_3$OF$_3$.0.1H$_2$O) C, H, N.

of a white crystalline solid: mp=247–250° C.; $R_f$=0.32 (5% MeOH/EtOAc); IR (KBr) 1680, 1537, 1466, 758 cm$^{-1}$; $^1$H NMR (DMSO-d$_6$) δ 3.58–3.59 (m, 2H), 4.47 (d, 2H, J=6.4 Hz), 7.21–7.38 (m, 5H), 7.44 (t, 2H, J=7.8 Hz), 7.94–8.01 (m, 2H), 8.43–8.47 (m, 1H), 9.62 (t, 1H, J=6.5 Hz). HRMS calcd for C$_{18}$H$_{16}$N$_4$O$_2$ 320.1273 (M+), found 320.1276. Anal. (C$_{18}$H$_{16}$N$_4$O$_2$.0.2H$_2$O) C, H, N.

Example 113

1-(Mompholine-4-carbonyl)-8,9-dihydro-7H-2,7,9a-triaza-benzo[cd]azulen-6-one

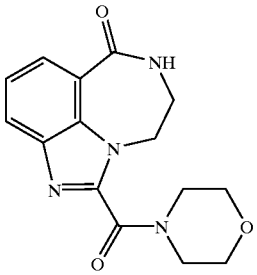

The product was prepared following the procedure in Example 110 using morpholine and EtOH as the reaction solvent to give 0.056 g (33%) of an off-white solid: mp=271–274° C. (dec); $R_f$=0.08 (5% MeOH/EtOAc); IR (KBr) 1657, 1462, 1219, 1111 cm$^{-1}$; $^1$H NMR (DMSO-d$_6$) δ 3.58–3.62 (m, 2H), 3.69–3.70 (m, 6H), 5.74–5.75 (m, 2H), 7.40 (t, 1H, J=7.8 Hz), 7.92–7.99 (m, 2H), 8.43–8.45 (m, 1H). HRMS calcd for C$_{15}$H$_{16}$N$_4$O$_3$ 300.1222 (M+), found 300.1230. Anal. (C$_{15}$H$_{16}$N$_4$O$_3$.0.4H$_2$O) C, H, N.

Example 114

1-(1-Benzyl-6-oxo-1,6-dihydro-pyridin-3-yl)-8,9-dihydro-7H-2,7,9a-triaza-benzo[cd]azulen-6-one

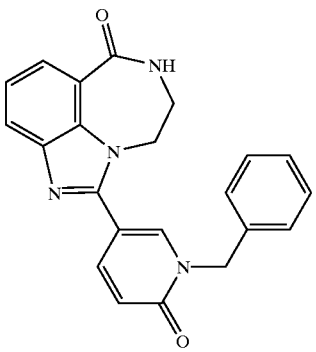

(a) 1-Benzyl-6-oxo-1,6-dihydro-pyridine-3-carbonyl chloride

This acid chloride was prepared as described in Example 106 from 1-benzyl-6-oxo-1,6-dihydro-3-pyridinecarboxylic acid in quantitative yield. The white solid was used without further purification: IR (KBr) 1750, 1671, 1223 cm$^{-1}$.

(b) Title Compound:

The compound was prepared as described in Example 4 from intermediate g and 1-Benzyl-6-oxo-1,6-dihydro-pyridine-3-carbonyl chloride (reaction time=72 h) using CH$_2$Cl$_2$ as the workup solvent; tan solid (36%): mp 265–269° C. (dec); $R_f$=0.34 (10% MeOH/CHCl$_3$); IR (KBr) 1671, 1618, 1508, 1142 cm$^{-1}$; $^1$H NMR (DMSO-d$_6$) δ 3.52–3.53 (m, 2H), 4.43–4.44 (m, 2H), 5.23 (s, 2H), 6.70 (d, 1H, J=9.5 Hz), 7.29–7.40 (m, 6H), 7.81–7.85 (m, 2H), 7.90–7.94 (m, 1H), 8.44–8.47 (m, 2H). HRMS calcd for C$_{22}$H$_{18}$N$_4$O$_2$ 370.1430 (M+), found 370.1430. Anal. (C$_{22}$H$_{18}$N$_4$O$_2$.0.4H$_2$O) C, H, N.

Example 115

1-(4-Methyl-piperazine-1-carbonyl)-8,9-dihydro-7H-2,7,9a-triaza-benzo[cd]azulen-6-one

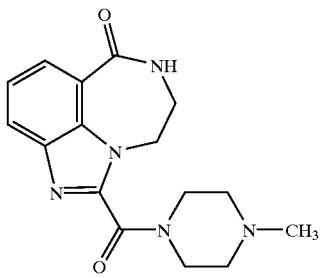

The product was prepared following the procedure in Example 110 using 1-methyl-piperazine and EtOH as the reaction solvent to give 0.09 g (47%) of a white solid: mp=311–316° C. (dec); $R_f$=0.08 (10% MeOH/CHCl$_3$); IR (KBr) 1682, 1638, 1508, 1225 cm$^{-1}$; $^1$H NMR (DMSO-d$_6$) δ 2.21 (s, 3H), 2.33–2.36 (m, 2H), 2.39–2.42 (m, 2H), 3.59–3.71 (m, 6H), 4.35–4.45 (m, 2H), 7.40 (t, 1H, J=7.8 Hz), 7.91–7.98 (m, 2H), 8.41–8.45 (m, 1H). HRMS calcd for $C_{16}H_{19}N_5O_2$ 313.1539 (M+), found 313.1522. Anal. ($C_{16}H_{19}N_5O_2$·0.3H$_2$O) C, H, N.

Example 116

4-[5-(6-Oxo-6,7,8,9-tetrahydro-2,7,9a-triaza-benzo[cd]azulen-1-yl)-pyridin-2-yloxy]-benzamide

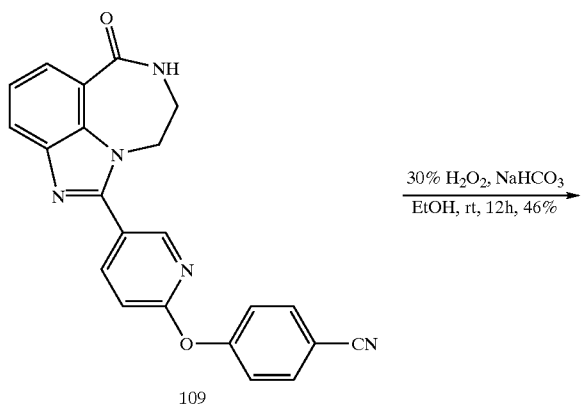

4-[5-(6-Oxo-6,7,8,9-tetrahydro-2,7,9a-triaza-benzo[cd]azulen-1-yl)-pyridin-2-yloxy]-benzonitrile (Example 109) (0.10 g, 0.26 mmol) was dissolved in EtOH (0.26 mL). 30% H$_2$O$_2$ (0.16 mL) was added followed by 3N NaHCO$_3$ (0.52 mL). The reaction was stirred at room temperature overnight. The solvents were then removed under reduced pressure, and the residual solids washed with water to give 0.042 g (46%) of a white solid: mp=244–248° C. (dec); $R_f$=0.39 (10% MeOH/EtOAc); IR (KBr) 1684, 1593, 1462, 1260 cm$^{-1}$; $^1$H NMR (DMSO-d$_6$) δ 3.55–3.56 (m, 2H), 4.46–4.47 (m, 2H), 7.27–7.40 (m, 5H), 7.86–7.99 (m, 5H), 8.34–8.38 (m, 1H), 8.45–8.47 (m, 1H), 8.63–8.64 (m, 1H). HRMS calcd for $C_{22}H_{17}N_5O_3$ 399.1331 (M+), found 399.1312. Anal. ($C_{22}H_{17}N_5O_3$·1.0H$_2$O) C, H, N.

Example 117

1-Tricyclo[3.3.1.1]dec-1-yl-8,9-dihydro-7H-2,7,9a-triaza-benzo[cd]azulene-6-one

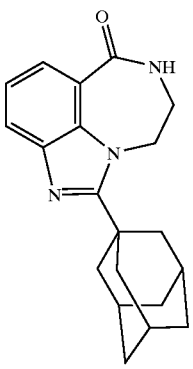

The product was prepared following the procedure from diamine g and 1-adamantane-carbaldehyde, heating the reaction mixture to 135° C. overnight to give 0.12 g (62%) of a white solid: mp=304–306° C.; $R_f$=0.21 (90% EtOAc/hexanes); IR (KBr) 2906, 1656, 1491, 1462, 1308 cm$^{-1}$; $^1$H NMR (DMSO-d$_6$) δ 1.72–1.95 (m, 6H), 2.07–2.14 (m, 3H), 2.26–2.27 (m, 6H), 3.58–3.66 (m, 2H), 4.80–4.87 (m, 2H), 7.24 (t, 1H, J=7.8 Hz), 7.75–7.83 (m, 2H), 8.34–8.38 (m, 1H). HRMS calcd for $C_{20}H_{23}N_3O$ 321.1841 (M+), found 321.1842. Anal. ($C_{20}H_{23}N_3O$) C, H, N.

Example 118

1-(6-Chloro-pyridin-3-yl)-8,9-dihydro-7H-2,7,9a-triaza-benzo[cd]azulen-6-one

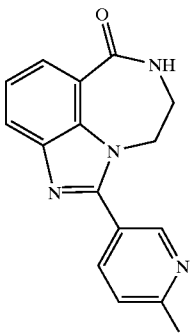

The desired was prepared from intermediate g and 6-chloro-nicotinoyl chloride hydrochloride as described in Example 6 to give 0.31 g (32%) of an off-white solid: mp >280° C. (dec); $R_f$=0.24 (5% MeOH/EtOAc); IR (KBr) 1650, 1466, 1399 cm$^{-1}$; $^1$H NMR (DMSO-d$_6$) δ 3.53–3.54

(m, 2H), 4.47–4.49 (m, 2H), 7.39 (t, 1H, J=7.8 Hz), 7.77 (d, 1H, J=8.3 Hz), 7.90 (dd, 1H, J=8.0, 1.0 Hz), 7.95 (dd, 1H, J=8.0, 1.0 Hz), 8.34 (dd, 1H, J=8.3, 2.5 Hz), 8.46–8.50 (m, 1H), 8.89 (d, 1H, J=2.2 Hz). HRMS calcd for $C_{15}H_{11}N_4OCl$ 298.0621 (M+), found 298.0609. Anal. ($C_{15}H_{11}N_4OCl.0.1H_2O$) C, H, N.

Example 119

1-(4-Imidazol-1-yl-phenyl)-8,9-dihydro-7H-2,7,9a-triaza-benzo[cd]azulen-6-one

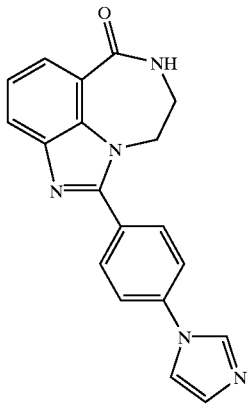

This compound was prepared from the diamine g (Example 2) and 4-(1H-imidazol-1-yl)benzaldehyde using the procedure described in Example 19; off-white solid (85%): mp >300° C. (dec); $R_f$=0.11 (7% MeOH/CHCl$_3$); IR (KBr) 1640, 1487, 1382, 1271 1061 cm$^{-1}$; $^1$H NMR (DMSO-d$_6$) δ 3.54–3.55 (m, 2H), 4.50–4.51 (m, 2H), 7.16 (s, 1H), 7.35–7.40 (m, 1H), 7.87–7.93 (m, 5H), 8.01 (d, 2H, J=8.5 Hz), 8.43 (s, 1H), 8.47 t, 1H, J=5.6 Hz). HRMS calcd for $C_{19}H_{15}N_5O$ 329.1277 (M+), found 329.1265. Anal. ($C_{19}H_{15}N_5O.0.3H_2O$) C, H, N.

Example 120

1-[4-(2-Hydroxy-ethoxy)-phenyl]-8,9-dihydro-7H-2,7,9a-triaza-benzo[cd]azulen-6-one

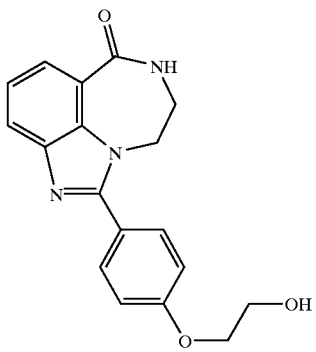

The compound was prepared from diamine g and 4-(2-hydroxyethoxy)benzaldehyde as described in Example 19 except upon removal of the solvent during workup, the residue was dissolved in $CH_2Cl_2/H_2O$. The aqueous layer was separated, and the product crystallized out upon standing. The solids were filtered and washed with water and dried to give 0.89 g (60%) of a yellow fibrous solid: mp=253–254° C. (dec); $R_f$=0.01 (5% MeOH/EtOAc); IR (KBr) 1666, 1481, 1310, 1256 cm$^{-1}$; $^1$H NMR (DMSO-d$_6$) δ 3.52–3.53 (m, 2H), 3.75–3.76 (m, 2H), 4.07–4.11 (m, 2H), 4.43–4.45 (m, 2H), 4.85–4.95 (m, 1H), 7.13 (d, 2H, J=8.8 Hz), 7.33 (t, 1H, J=7.8 Hz), 7.78–7.87 (m, 4H), 8.40 (t, 1H, J=5.7 Hz). HRMS calcd for $C_{18}H_{17}N_3O_3$ 323.1270 (M+), found 323.1268. Anal. ($C_{18}H_{17}N_3O_3.2.0H_2O$) C, H, N.

Example 121

1-[4-(3-Dimethylamino-propoxy)-phenyl]-8,9-dihydro-7H-2,7,9a-triaza-benzo[cd]azulen-6-one

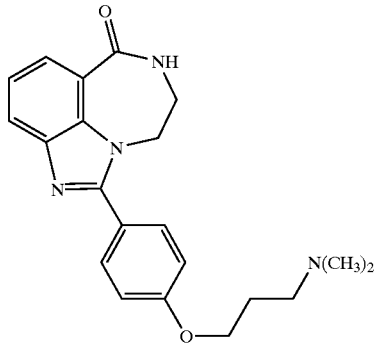

The compound was prepared from diamine g and 4-[3-dimethylamino)propoxy]benzaldehyde as described in Example 19 using CHCl$_3$ as the workup solvent. White amorphous solid (49%): mp=177,178° C.; $R_f$=0.13 (7% methanolic ammonia/CHCl$_3$); IR (KBr) 1650, 1483, 1380, 1254 cm$^{-1}$; $^1$H NMR (DMSO-d$_6$) δ 1.84–1.93 (m, 2H), 2.18 (s, 6H), 2.38–2.43 (m, 2H), 3.52–3.53 (m, 2H), 4.10 (t, 2H, J=6.4 Hz), 4.42–4.45 (m, 2H), 7.11 (d, 2H, J=8.8 Hz), 7.33 (t, 1H, J=7.8 Hz), 7.79 (d, 2H, J=8.8 Hz), 7.82–7.87 (m, 2H), 8.38–8.42 (m, 1H). HRMS calcd for $C_{21}H_{24}N_4O_2$ 364.1899 (M+), found 364.1890. Anal. ($C_{21}H_{24}N_4O_2.0.1H_2O$) C, H, N.

Example 122

1-[4-(Oxo-1λ$^4$-thiomorpholin-4-ylmethyl)-phenyl]-8,9-dihydro-7H-2,7,9a-triaza-benzo[cd]azulen-6-one

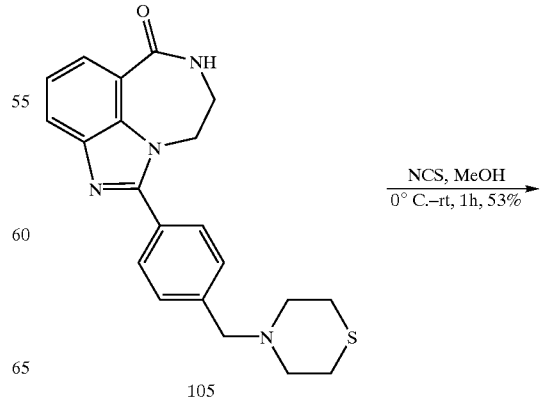

105

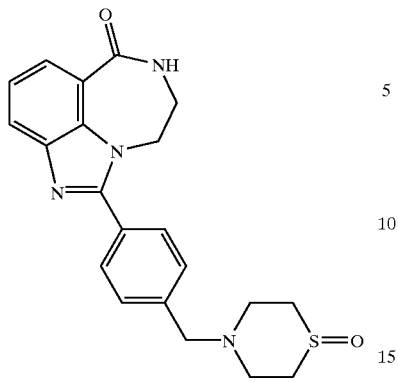

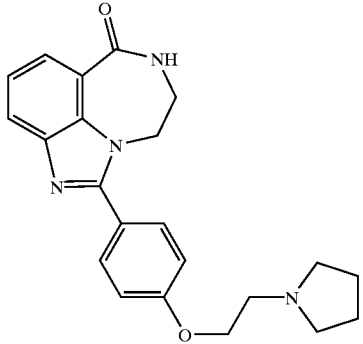

1-[4-(2-Hydroxy-ethoxy)-phenyl]-8,9-dihydro-7H-2,7,9a-triaza-benzo[cd]azulen-6-one (Example 120) (0.51 g, 1.59 mmol) was dissolved in pyridine (16 mL) and cooled to 0° C. Methanesulfonyl chloride (0.15 mL, 1.91 mmol) was added dropwise followed by 0.01 g of 4-dimethylaminopyridine. The reaction mixture was warmed to rt and stirred 5 h. The solvent was removed in vacuo. The residue was dissolved in $CHCl_3$/water, and the organic layer was separated, washed with brine, dried ($MgSO_4$) and concentrated to give 0.25 g of the crude mesylate. A portion of the mesylate (0.11 g, 0.28 mmol) was dissolved in dimethylacetamide (3 mL). Pyrrolidine (0.07 mL, 0.83 mmol) was added, and the reaction heated to 100° C. overnight. The solvent was removed in vacuo, and the residue subjected to flash silica gel chromatography eluting with 0–5% MeOH/$CHCl_3$, then 5% methanolic ammonia/$CHCl_3$ to obtain 0.073 g (24% from 1-[4-(2-Hydroxy-ethoxy)-phenyl]-8,9-dihydro-7H-2,7,9a-triaza-benzo[cd]azulen-6-one; Example 120) as an amorphous tan solid: mp=172–175° C.; $R_f$=0.18 (7% methanolic ammonia/$CHCl_3$); IR (KBr) 1627, 1600, 1480, 1252 $cm^{-1}$; $^1H$ NMR (DMSO-$d_6$) δ 1.75–1.71 (m, 4H), 2.53–2.54 (m, 4H), 2.83 (t, 2H, J=5.8 Hz), 3.52–3.53 (m, 2H), 4.17 (t, 2H, J=5.8 Hz), 4.43–4.45 (m, 2H), 7.13 (d, 2H, J=8.8 Hz), 7.33 (t, 1H, J=7.8 Hz), 7.78–7.87 (m, 4H), 8.41 (t, 1H, J=5.6 Hz). HRMS calcd for $C_{22}H_{24}N_4O_2$ 376.1899 (M+), found 376.1913. Anal. ($C_{22}H_{24}N_4O_2$) C, H, N.

1-(4-Thiomorpholin-4-ylmethyl-phenyl)-8,9-dihydro-7H-2,7,9a-triaza-benzo[cd]azulen-6-one (Example 105) (0.058 g, 0.15 mmol) was suspended in MeOH (3 mL) and cooled to 0° C. N-Chlorosuccinimide (0.021 g, 0.15 mmol) was added, and the reaction stirred 1 hour at 0° C. before being slowly warmed to room temperature. The solvent was removed in vacuo, and the crude product purified by flash silica gel chromatography eluting with 3–10% MeOH/$CHCl_3$ to afford 0.031 g (53%) of an off-white solid: mp=247° C. (dec); $R_f$=0.18 (10% MeOH/$CHCl_3$); IR (KBr) 1658, 1481, 1380, 1022 $cm^{-1}$; $^1H$ NMR (DMSO-$d_6$) δ 2.66–2.80 (m, 4H), 2.86–2.93 (m, 4H), 3.53–3.54 (m, 2H), 3.67 (s, 2H), 4.45–4.48 (m, 2H), 7.35 (t, 1H, J=7.8 Hz), 7.53 (d, 2H, J=7.8 Hz), 7.82–7.90 (m, 4H), 8.40 (m, 1H). HRMS calcd for $C_{21}H_{22}N_4O_2S$ 394.1463 (M+), found 394.1463. Anal. ($C_{21}H_{22}N_4O_2S\cdot1.25H_2O$) C, H, N.

Example 123

1-[4-(2-Pyrrolidin-1-yl-ethoxy)-phenyl]-8,9-dihydro-7H-2,7,9a-triaza-benzo[cd]azulen-6-one

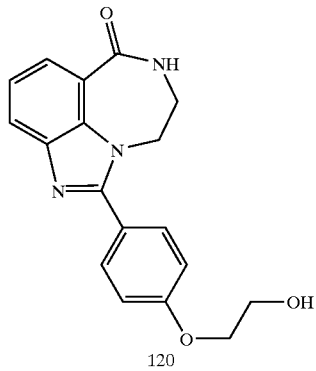

1. $CH_3SO_2Cl$, pyr., cat. DMAP, 0° C.–rt, 5h
2. pyrrolidine, DMA, 100° C., 12h, 23% (2 steps)

Example 124

1-[4-(2-Dimethylamino-ethoxy)-phenyl]-8,9-dihydro-7H-2,7,9a-triaza-benzo[cd]azulen-6-one

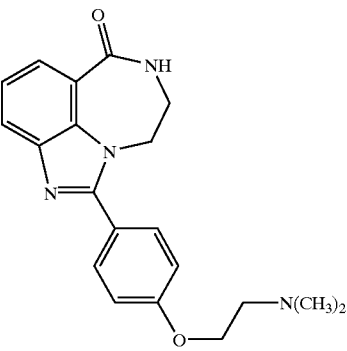

Using the procedure to prepare 1-[4-(2-Pyrrolidin-1-yl-ethoxy)-phenyl]-8,9-dihydro-7H-2,7,9a-triaza-benzo[cd]

azulen-6-one (Example 123) the mesylate (0.103 g, 0.26 mmol) was treated with dimethylamine (2M solution in MeOH, 1.03 mL, 2.05 mmol) in dimethylacetamide (3 mL) and heated to 100° C. overnight. The solvent was removed in vacuo, and the residue subjected to flash silica gel chromatography eluting with 0–5% MeOH/CHCl$_3$, then 5% methanolic ammonia/CHCl$_3$ to obtain 0.051 g (18% from 1-[4-(2-Hydroxy-ethoxy)-phenyl]-8,9-dihydro-7H-2,7,9a-triaza-benzo[cd]azulen-6-one; Example 120) as an amorphous white solid: mp=184–186° C.; R$_f$=0.26 (7% methanolic ammonia/CHCl$_3$); IR (KBr) 1627, 1479, 1251, 1180 cm$^{-1}$; $^1$H NMR (DMSO-d$_6$) δ 2.23 (s, 6H), 2.67 (t, 2H, J=5.8 Hz), 3.52–3.53 (m, 2H), 4.15 (t, 2H, J=5.8 Hz), 4.43–4.44 (m, 2H), 7.13 (d, 2H, J=8.7 Hz), 7.33 (t, 1H, J=7.8 Hz), 7.87–7.87 (m, 4H), 8.40 (t, 1H, J=5.6 Hz). HRMS calcd for C$_{20}$H$_{22}$N$_4$O$_2$ 350.1743 (M+), found 350.1756. Anal. (C$_{20}$H$_{22}$N$_4$O$_2$) C, H, N.

Example 125

1-{4-[2-(Tetrahydro-pyran-2-yloxy)-ethyl]-phenyl}-8,9-dihydro-7H-2,7,9a-triaza-benzo[cd]azulen-6-one

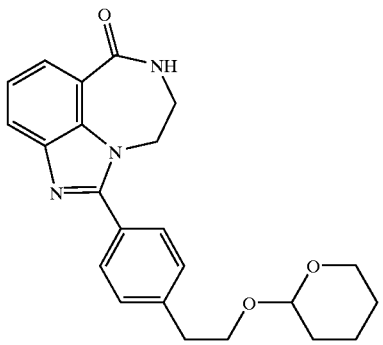

The product was prepared from diamine g and 4-[2-(tetrahydro-pyran-2-yloxy)-ethyl]-benzaldehyde [Ackerley, et al., *J. Med. Chem.* 38, 1608 (1995)] as described in Example 19 to give 0.95 g (76%) of a white solid: mp=189–190° C.; R$_f$=0.11 (90% EtOAc/hexanes); IR (KBr) 1627, 1482, 1379, 1028 cm$^{-1}$; $^1$H NMR (DMSO-d$_6$) δ 1.42–1.52 (m, 4H), 1.57–1.71 (m, 2H), 2.94 (t, 2H, J=6.7 Hz), 3.36–3.43 (m, 1H), 3.50–3.53 (m, 2H), 3.60–3.69 (m, 2H), 3.84–3.92 (m, 1H), 4.43–4.46 (m, 2H), 4.60–4.61 (m, 1H), 7.35 (t, 1H, J=7.8 Hz), 7.46 (d, 2H, J=8.1 Hz), 7.78 (d, 2H, J=8.1 Hz), 7.85–7.90 (m, 2H), 8.39–8.43 (m, 1H). HRMS calcd for C$_{23}$H$_{25}$N$_3$O$_3$ 391.1896 (M+), found 391.1902. Anal. (C$_{23}$H$_{25}$N$_3$O$_3$) C, H, N.

Example 126

1-(4-Pyridin-2-yl-phenyl)-8,9-dihydro-7H-2,7,9a-triaza-benzo[cd]azulen-6-one

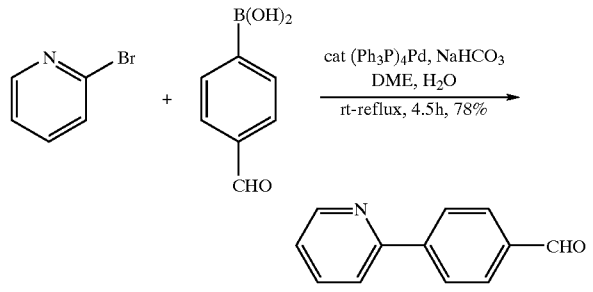

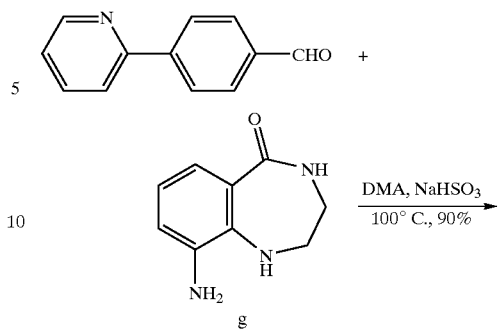

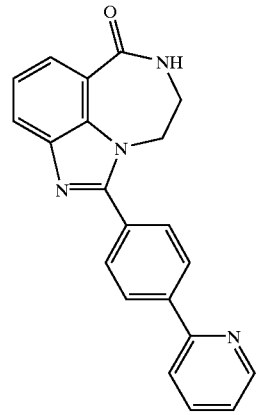

(a) 4-Pyridin-2-yl-benzaldehyde [Bold, et al., *J. Med. Chem.* 41, 3387(1998)]: 2-Bromopyridine (0.50 g, 3.16 mmol) was dissolved in DME (26 mL). Tetrakis (triphenylphospine)palladium(0) (0.11 g, 0.09 mmol) was added, and the reaction stirred at room temperature for 10 minutes. 4-Formylboronic acid (0.55 g, 3.54 mmol) was added to the reaction followed by a solution of 0.80 g of NaHCO$_3$ in 13 mL of water. The reaction was refluxed for 4.5 hours. The solvent was removed in vacuo, and the residue dissolved in EtOAc/H$_2$O. The organic layer was separated and washed with water and brine, then dried (MgSO$_4$). The product was purified by flash silica gel chromatography eluting with 5–10% EtOAc/hexanes to give 0.45 g (78%) of a white solid whose NMR data matched the literature: mp=50–52° C.

(b) Title Compound:

The product was prepared following the procedure from diamine g and 4-pyridin-2-yl-benzaldehyde as described in Example 19 to give 0.61 g (90%) of an off-white solid: mp=277–279° C.; R$_f$=0.32 (10% MeOH/EtOAc); IR (KBr) 1647, 1466, 1431, 1302 cm$^{-1}$; $^1$H NMR (DMSO-d$_6$) δ 3.56–3.57 (m, 2H), 4.52–4.54 (m, 2H), 7.35–7.43 (m, 2H), 7.87–7.97 (m, 3H), 8.00 (d, 2H, J=8.4 Hz), 8.09 (d, 1H, J=8.0 Hz), 8.30 (d, 2H, J=8.4 Hz), 8.44 (t, 1H, J=5.8 Hz), 8.72 (d, 1H, J=3.9 Hz). HRMS calcd for C$_{21}$H$_{16}$N$_4$O 340.1324 (M+), found 340.1323. Anal. (C$_{21}$H$_{16}$N$_4$O·0.5H$_2$O) C, H, N.

Example 127

1-[4-(2-Hydroxy-ethyl)-phenyl]-8,9-dihydro-7H-2,7,9a-triaza-benzo[cd]azulen-6-one

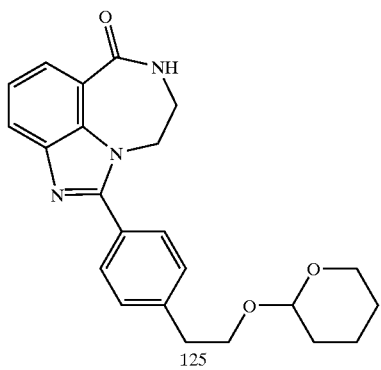

125

HCl, 1,4-dioxane
―――――――――→
MeOH, rt, 3h, 93%

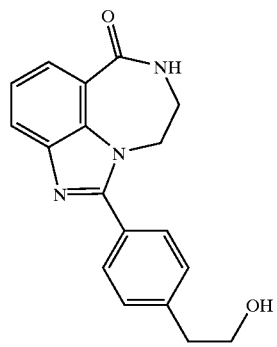

1-{4-[2-(Tetrahydro-pyran-2-yloxy)-ethyl]-phenyl}-8,9-dihydro-7H-2,7,9a-triaza-benzo[cd]azulen-6-one (Example 125) (0.81 g, 2.07 mmol) was dissolved in MeOH (21 mL). 4M HCl/dioxane (0.57 mL, 2.27 mmol) was added, and the reaction stirred at rt for 3 h. The solvent was removed in vacuo, and the residue subjected to silica gel chromatography eluting with 3% methanolic ammonia/CHCl₃ to give 0.59 g (93%) of a white solid: mp=263–265° C.; R$_f$=0.08 (5% MeOH/EtOAc); IR (KBr) 1655, 1602, 1482, 1382 cm$^{-1}$; $^1$H NMR (DMSO-d$_6$) δ 2.82 (t, 2H, J=6.8 Hz), 3.53–3.55 (m, 2H), 3.64–3.71 (m, 2H), 4.44–4.46 (m, 2H), 4.67 (t, 1H, J=5.2 Hz), 7.34 (t, 1H, J=7.8 Hz), 7.43 (d, 2H, J=8.2 Hz), 7.77 (d, 2H, J=8.2 Hz), 7.84–7.90 (m, 2H), 8.39–8.43 (m, 1H). HRMS calcd for C$_{18}$H$_{17}$N$_3$O$_2$ 307.1321 (M+), found 307.1331. Anal. (C$_{18}$H$_{17}$N$_3$O$_2$·0.4H$_2$O) C, H, N.

Example 128

1-[4-(2-Pyrrolidin-1-yl-ethyl)-phenyl]-8,9-dihydro-7H-2,7,9a-triaza-benzo[cd]azulen-6-one

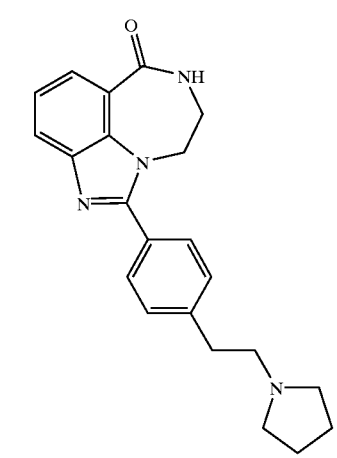

The product was prepared following the procedure used for 1-[4-(2-Pyrrolidin-1-yl-ethoxy)-phenyl]-8,9-dihydro-7H-2,7,9a-triaza-benzo[cd]azulen-6-one (Example 123) from 1-[4-(2-hydroxy-ethyl)-phenyl]-8,9-dihydro-7H-2,7,9a-triaza-benzo[cd]azulen-6-one (Example 127) and pyrrolidine, heating to 85° C. overnight to give 0.13 g (49%) of a yellow solid: mp >201° C. (dec); R$_f$=0.08 (7% methanolic ammonia/CHCl₃); IR (KBr) 1655, 1627, 1481, 1461, 1379 cm$^{-1}$; $^1$H NMR (DMSO-d$_6$) δ 1.70–1.75 (m, 4H), 2.49–2.55 (m, 4H), 2.73–2.75 (m, 2H), 2.83–2.88 (m, 2H), 3.50–3.53 (m, 2H), 4.44–4.46 (m, 2H), 7.34 (t, 1H, J=7.8 Hz), 7.44 (d, 2H, J=8.1 Hz), 7.77 (d, 2H, J=8.1 Hz), 7.84–7.90 (m, 2H), 8.41 (t, 1H, J=5.6 Hz). HRMS calcd for C$_{22}$H$_{25}$N$_4$O 361.2028 (M+H), found 361.2037. Anal. (C$_{22}$H$_{24}$N$_4$O) C, H, N.

Example 129

1-[4-(2-Dimethylamino-ethyl)-phenyl]-8,9-dihydro-7H-2,7,9a-triaza-benzo[cd]azulen-6-one

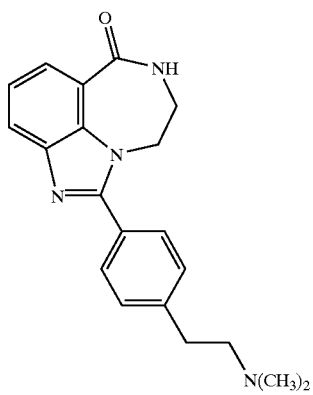

The product was prepared following the procedure used for 1-[4-(2-Pyrrolidin-1-yl-ethoxy)-phenyl]-8,9-dihydro-7H-2,7,9a-triaza-benzo[cd]azulen-6-one (Example 123) from 1-[4-(2-hydroxy-ethyl)-phenyl]-8,9-dihydro-7H-2,7,9a-triaza-benzo[cd]azulen-6-one (Example 127) and methanolic dimethylamine heating to 85° C. overnight to give a 26% yield (2 steps) of a yellow solid: mp >98° C. (dec); $R_f$=0.08 (7% methanolic ammonia/CHCl$_3$); IR (KBr) 1653, 1479, 1381, 1307 cm$^{-1}$; $^1$H NMR (DMSO-d$_6$) δ 2.21 (s, 6H), 2.50–2.56 (m, 2H), 2.79–2.84 (m, 2H), 3.52–3.53 (m, 2H), 4.44–4.46 (m, 2H), 7.34 (t, 1H, J=7.8 Hz), 7.43 (d, 2H, J=8.2 Hz), 7.77 (d, 2H, J=8.2 Hz), 7.84–7.90 (m, 2H), 8.39–8.43 (m, 1H). HRMS calcd for $C_{20}H_{23}N_4O$ 335.1872 (M+H), found 335.1865. Anal. ($C_{20}H_{22}N_4O$) C, H, N.

Example 130

1-(4-Piperidin-2-yl-phenyl)-8,9-dihydro-7H-2,7,9a-triaza-benzo[cd]azulen-6-one

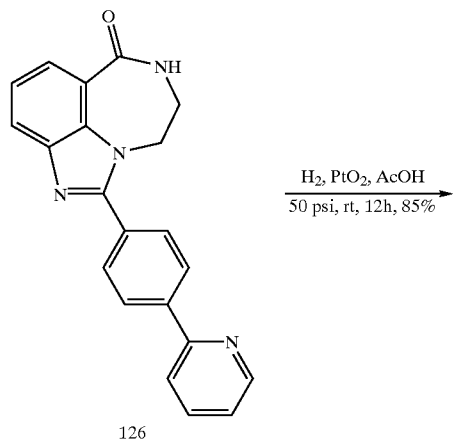

1-(4-Pyridin-2-yl-phenyl)-8,9-dihydro-7H-2,7,9a-triaza-benzo[cd]azulen-6-one (Example 126) (1.26 g, 3.72 mmol) was dissolved in acetic acid (60 mL). Platinum oxide (0.065 g) was added. The flask was evacuated, placed under a hydrogen atmosphere at 50 psi and shaken on a Parr apparatus overnight. The catalyst was filtered off, and the solvent removed. The crude product was purified by flash silica gel chromatography eluting with 1–9% methanolic ammonia/CHCl$_3$ to give 1.45 g (85%) of a white solid: mp=263–265° C.; $R_f$=0.08 (7% methanolic ammonia/CHCl$_3$); IR (KBr) 1662, 1472, 1381, 840 cm$^{-1}$; $^1$H NMR (DMSO-d$_6$) δ 1.34–1.60 (m, 4H), 1.74–1.81 (m, 2H), 2.66–2.73 (m, 1H), 3.07–3.11 (m, 1H), 3.52–3.53 (m, 2H), 3.66–3.69 (m, 1H), 4.44–4.46 (m, 2H), 7.35 (t, 1H, J=7.8 Hz), 7.56 (d, 2H, J=8.3 Hz), 7.80 (d, 2H, J=8.3 Hz), 7.84–7.90 (m, 2H), 8.39–8.43 (m, 1H). HRMS calcd for $C_{21}H_{21}N_4O$ 345.1715 (M–H), found 345.1719. Anal. ($C_{21}H_{22}N_4O$) C, H, N.

Example 131

1-[4-(Dimethylamino-N-oxide)methyl-phenyl-8,9-dihydro-7H-2,7,9a-triaza-benzo[cd]azulen-6-one

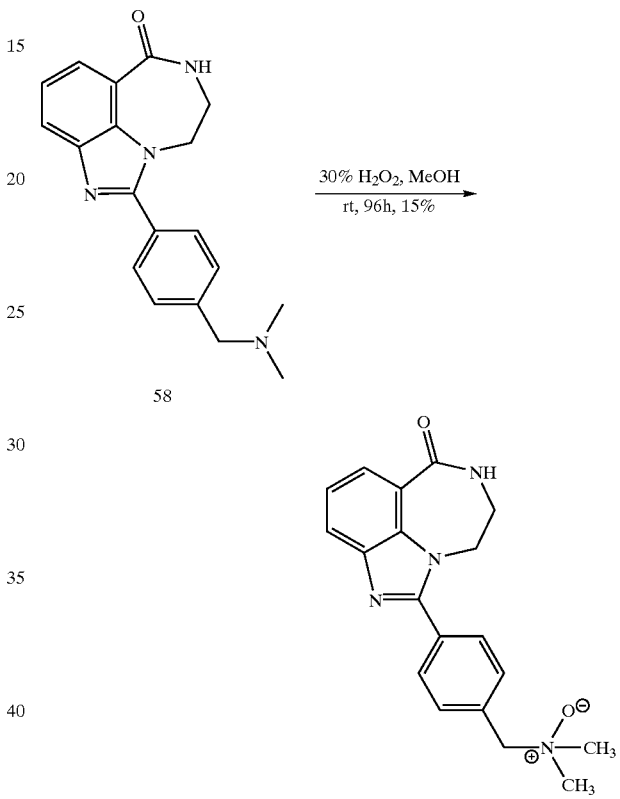

1-(4-Dimethylaminomethyl-phenyl)-8,9-dihydro-7H-2,7,9a-triaza-benzo[cd]azulen-6-one (Example 58) (0.19 g, 0.60 mmol) was dissolved in MeOH (10 mL). Hydrogen peroxide (30% solution in water) was added, and the reaction stirred at rt for 4 days. The solvents were removed in vacuo to give 0.2 g of crude. Of the crude product, 0.05 g was purified by preparative HPLC using a MetaSil AQ column (10μ C18 120A 250×21.2 mm), eluting with a gradient mobile phase starting with 95% water/acetonitrile for 4 minutes, then reaching 40% water/acetonitrile after 12 minutes, and finally 5% water/acetonitrile after 15 minutes to the length of the 20 minute run time ($R_f$=12.27 minutes, flow rate=15 mL/min.) to give 0.03 g (15%) of a hygroscopic solid: IR (KBr) 1645, 1463, 1382, 1308 cm$^{-1}$; $^1$H NMR (DMSO-d$_6$) δ 3.03 (s, 6H), 3.53–3.54 (m, 2H), 4.41 (s, 2H), 4.47–4.49 (m, 2H), 7.36 (t, 1H, J=7.8 Hz), 7.78 (d, 2H, J=8.2 Hz), 7.86–7.92 (m, 4H), 8.42–8.46 (m, 1H). HRMS calcd for $C_{19}H_{21}N_4O_2$ 337.1664 (M+H), found 337.1661. Anal. ($C_{19}H_{21}N_4O_2$·2.0H$_2$O) C, H, N.

Example 132

1-[4-(1-Methyl-piperidin-2-yl)-phenyl]-8,9-dihydro-7H-2,7,9a-triaza-benzo[cd]azulen-6-one

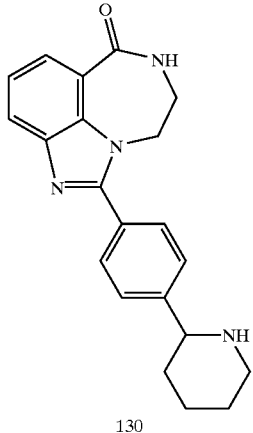

NaCNBH₃, MeOH, AcOH
CH₂O, H₂O, rt, 1.5h, 83%
→

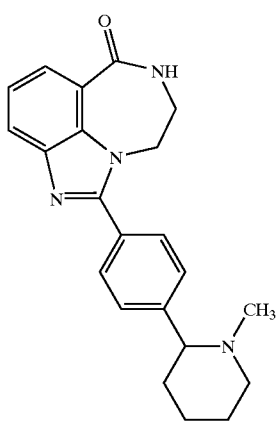

130

1-(4-Piperidin-2-yl-phenyl)-8,9-dihydro-7H-2,7,9a-triaza-benzo[cd]azulen-6-one (Example 130) (0.31 g, 0.89 mmol) was dissolved in MeOH (13 mL) and acetic acid (0.21 mL, 3.57 mmol). NaCNBH₃ (0.056 g, 0.89 mmol) was added, followed by a solution of 37% formaldehyde in water (0.09 mL) in 5 mL of MeOH. The reaction was stirred at room temperature for 1.5 hours. The solvents were removed in vacuo, and the residue was dissolved in CH₂Cl₂/saturated NaHCO₃. The organic phase was separated, washed with brine, and dried (MgSO₄). The solvent was removed to give 0.25 g (83%) of a white solid: mp >180° C. (dec); R$_f$=0.21 (10% methanolic ammonia/CHCl₃); IR (KBr) 1662, 1601, 1479, 1309 cm⁻¹; ¹H NMR (DMSO-d₆) δ 1.23–1.78 (m, 6H), 1.94 (s, 3H), 2.02–2.11 (m, 1H), 2.86–2.89 (m, 1H), 2.95–2.99 (m, 1H), 3.53–3.54 (m, 2H), 4.45–4.48 (m, 2H), 7.35 (t, 1H, J=7.8 Hz), 7.49 (d, 2H, J=8.2 Hz), 7.81 (d, 2H, J=8.2 Hz), 7.84–7.90 (m, 2H), 8.39–8.43 (m, 1H). HRMS calcd for C₂₂H₂₄N₄O 360.1950 (M+), found 360.1942. Anal. (C₂₂H₂₄N₄O.0.75H₂O) C, H, N.

Example 133

1-[4-(2-Methyl-2H-tetrazol-5-yl)-phenyl]-8,9-dihydro-7H-2,7,9a-triaza-benzo[cd]azulen-6-one

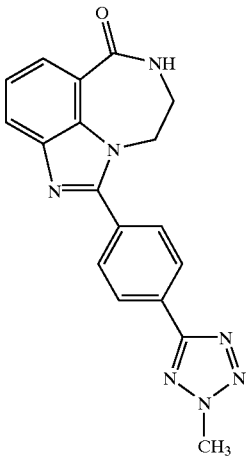

The product was prepared from diamine g and 4-(2-methyl-2H-tetrazol-5-yl)-benzaldehyde [Bold, et al., *J. Med. Chem.* 41, 3387(1998)] using the procedure described in Example 19 to give a tan solid (50%): mp=280° C. (dec); R$_f$=0.29 (5% MeOH/EtOAc); IR (KBr) 1667, 1455, 1306 cm⁻¹; ¹H NMR (DMSO-d₆) δ 3.55–3.58 (m, 2H), 4.46 (s, 3H), 4.51–4.53 (m, 2H), 7.38 (t, 1H, J=7.8 Hz), 7.88–7.94 (m, 2H), 8.07 (d, 2H, J=8.5 Hz), 8.24 (d, 2H, J=8.5 Hz), 8.42–8.46 (m, 1H). HRMS calcd for C₁₈H₁₅N₇O 345.1338 (M+), found 345.1340. Anal. (C₁₈H₁₅N₇O.0.25H₂O) C, H, N.

Example 134

1-(4-Pyridin-3-yl-phenyl)-8,9-dihydro-7H-2,7,9a-triaza-benzo[cd]azulen-6-one

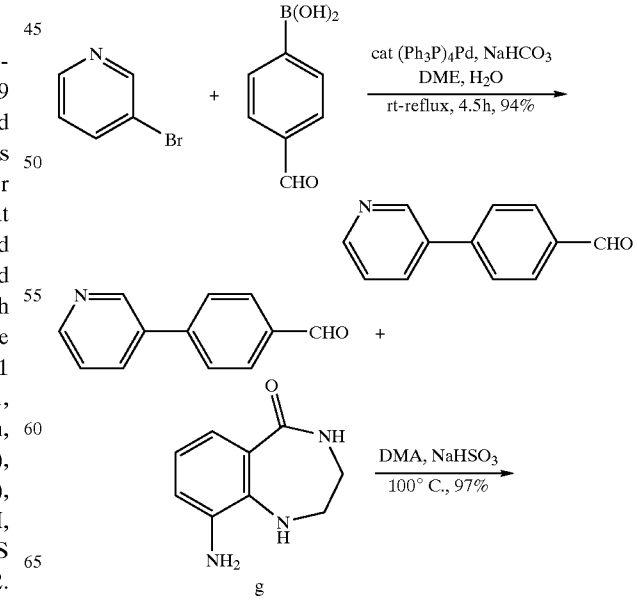

121
-continued

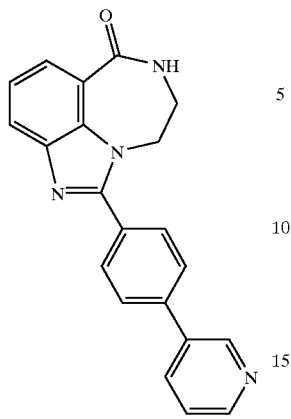

(a) 4-Pyridin-3-yl-benzaldehyde

This aldehyde was prepared using the procedure for 4-pyridin-2-yl-benzaldehyde in Example 126 from 3-bromopyridine and 4-formylboronic acid to give a white crystalline solid (94%): mp=53–55° C.; $R_f$=0.08 (30% EtOAc/hexanes); IR (KBr) 1700, 1605, 1219 cm$^{-1}$; $^1$H NMR (CDCl$_3$) δ 7.55–7.60 (m, 1H), 7.76–7.79 (m, 2H), 8.01–8.05 (m, 2H), 8.08–8.12 (m, 1H), 8.69–8.71 (m, 1H), 8.94–8.95 (m, 1H), 10.10 (s, 1H). LRMS 184 (M+H).

(b) Title Compound:

The product was prepared according to the procedure described in Example 19 from diamine g and 4-pyridin-3-yl-benzaldehyde to give a cream-colored solid (97%): mp=284–286° C.; $R_f$=0.16 (10% MeOH/EtOAc); IR (KBr) 1656, 1468, 1399, 1306 cm$^{-1}$; $^1$H NMR (DMSO-d$_6$) δ 3.55–3.58 (m, 2H), 4.51–4.54 (m, 2H), 7.37 (t, 1H, J=7.8 Hz), 7.51–7.56 (m, 1H), 7.87–8.02 (m, 6H), 8.17–8.21 (m, 1H), 8.42–8.46 (m, 1H), 8.62 (dd, 1H, J=1.5, 4.8 Hz), 9.00 (d, 1H, J=1.8 Hz). HRMS calcd for C$_{21}$H$_{16}$N$_4$O 340.1324 (M+), found 340.1313. Anal. (C$_{21}$H$_{16}$N$_4$O) C, H, N.

Example 135

1-(4-Pyridin-4-yl-phenyl)-8,9-dihydro-7H-2,7,9a-triaza-benzo[cd]azulen-6-one

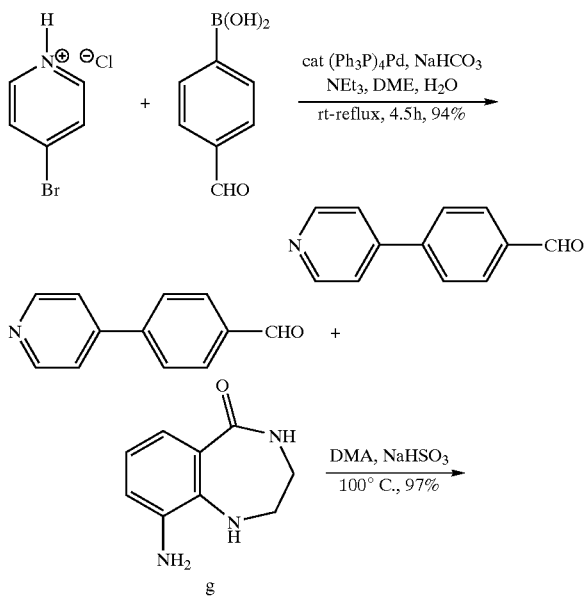

122
-continued

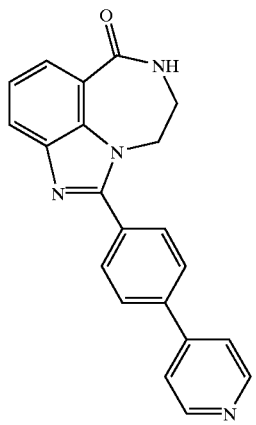

(a) 4-Pyridin-4-yl-benzaldehyde (Patent WO 9919300)

This aldehyde was prepared using the procedure for 4-pyridin-2-yl-benzaldehyde in Example 126 from 4-bromopyridine hydrochloride, triethylamine and 4-formylboronic acid to give a yellow crystalline solid (51%): mp=90–91° C.; $R_f$=0.08 (30% EtOAc/hexanes); IR (KBr) 1697, 1595, 1214, 1169, 801 cm$^{-1}$; $^1$H NMR (CDCl$_3$) δ 7.74 (d, 2H, J=5.8 Hz), 7.84 (d, 2H, J=8.3 Hz), 8.05 (d, 2H, J=8.1 Hz), 8.77–8.78 (m, 2H), 10.11 (s, 1H). LRMS 184 (M+H).

(b) Title Compound:

The product was prepared according to the procedure in Example 19 from diamine g and 4-pyridin-4-yl-benzaldehyde to give a yellow solid (55%): mp=370–372° C. (dec); $R_f$=0.13 (10% MeOH/EtOAc); IR (KBr) 1648, 1596, 1477, 1304 cm$^{-1}$; $^1$H NMR (DMSO-d$_6$) δ 3.55–3.56 (m, 2H), 4.52–4.53 (m, 2H), 7.38 (t, 1H, J=7.8 Hz), 7.81–7.83 (m, 2H), 7.88–7.94 (m, 2H), 8.02 (s, 4H), 8.42–8.46 (m, 1H), 8.69 (d, 2H, J=5.9 Hz). HRMS calcd for C$_{21}$H$_{16}$N$_4$O 340.1324 (M+), found 340.1330. Anal. (C$_{21}$H$_{16}$N$_4$O) C, H, N.

Example 136

1-[4-(2H-Tetrazol-5-yl)-phenyl]-8,9-dihydro-7H-2,7,9a-triaza-benzo[cd]azulen-6-one

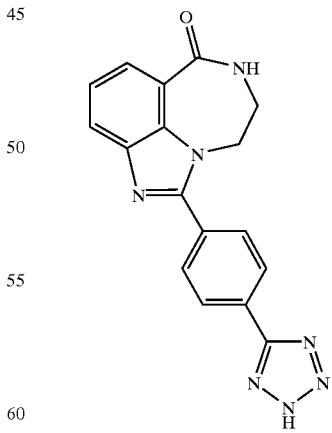

Using the procedure described in Example 19 the product was prepared from using diamine g and 4-(2H-tetrazol-5-yl)-benzaldehyde [Bold, et al., *J. Med. Chem.* 41, 3387 (1998)] to yield a yellow solid (46%). The material was further purified by dissolving in 10% NaOH and adjusting the pH to 2 with 10% HCl. The resulting precipitate was collected to give a white solid (19%): mp >290° C. (dec); $R_f$=0.13 (10% MeOH/0.5% HOAc/CHCl$_3$); IR (KBr) 1656, 1482, 1311, 1076 cm$^{-1}$; $^1$H NMR (DMSO-d$_6$) δ 3.55–3.56 (m, 2H), 4.52–4.53 (m, 2H), 7.39 (t, 1H, J=7.8 Hz), 7.88–7.96 (m, 2H), 8.12 (d, 2H, J=8.5 Hz), 8.24 (d, 2H, J=8.5 Hz), 8.47–8.51 (m, 1H), HRMS calcd for C$_{17}$H$_{14}$N$_7$O 332.1260 (M+H), found 332.1257. Anal. (C$_{17}$H$_{13}$N$_7$O.0.75H$_2$O) C, H, N.

Example 137

1-(4-Piperidin-4-yl-phenyl)-8,9-dihydro-7H-2,7,9a-triaza-benzo[cd]azulen-6-one

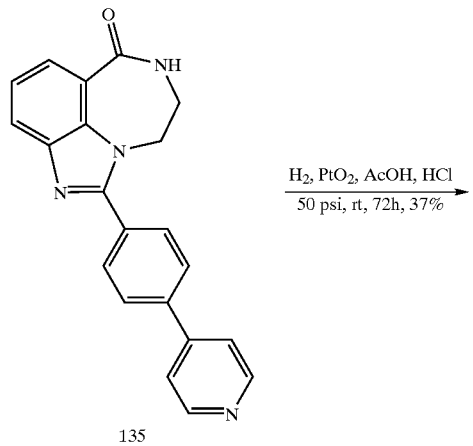

1-(4-Pyridin-4-yl-phenyl)-8,9-dihydro-7H-2,7,9a-triaza-benzo[cd]azulen-6-one (Example 135) (0.24 g, 0.71 mmol) was dissolved in acetic acid (15 mL). Platinum oxide (0.015 g) was added followed by 1 drop of conc. HCl. The flask was evacuated and refilled under a hydrogen atmosphere at 50 psi on a Parr apparatus overnight. An additional 0.02 g of catalyst and 2 more drops of HCl were added, and the reaction returned to the Parr apparatus overnight. This process was repeated for a total reaction time of 3 days. The catalyst was filtered and the solvent removed. The crude was purified by flash silica gel chromatography eluting with 10 MeOH/CHCl$_3$. Then 10% methanolic ammonia/CHCl$_3$ to give 0.091 g (37%) of a white solid: mp >192° C. (dec); $R_f$=0.08 (10% methanolic ammonia/CHCl$_3$); IR (KBr) 1653, 1601, 1479, 1382 cm$^{-1}$; $^1$H NMR (DMSO-d$_6$) δ 1.54–1.66 (m, 2H), 1.74–1.78 (m, 2H), 2.53–2.75 (m, 2H), 3.06–3.17 (m, 2H), 3.51–3.52 (m, 2H), 4.45–4.46 (m, 2H), 7.34 (t, 1H, J=7.8 Hz), 7.43 (d, 2H, J=7.7 Hz), 7.77 (d, 2H, J=7.7 Hz), 7.81–7.90 (m, 2H), 8.42–8.46 (m, 1H), HRMS calcd for C$_{21}$H$_{22}$N$_4$O 346.1794 (M+), found 346.1778. Anal. (C$_{21}$H$_{22}$N$_4$O.0.5H$_2$O) C, H, N.

Example 138

1-Methylsulfanyl-8,9-dihydro-7H-2,7,9a-triaza-benzo[cd]azulen-6-one

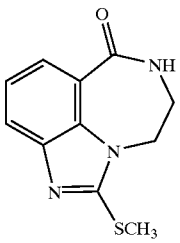

The product was prepared following the procedure for 1-benzylsulfanyl-8,9-dihydro-7H-2,7,9a-triaza-benzo[cd]azulen-6-one (Example 29) using iodomethane in place of benzyl bromide to give a white solid (65%): mp=223–225° C.; $R_f$=0.29 (3% MeOH/CHCl$_3$); IR (KBr) 1659, 1468, 1355 cm$^{-1}$; $^1$H NMR (DMSO-d$_6$) δ 2.73 (s, 3H), 3.56–3.61 (m, 2H), 4.17–4.18 (m, 2H), 7.25 (t, 1H, J=7.8 Hz), 7.72–7.77 (m, 2H), 8.35–8.38 (m, 1H). HRMS calcd for C$_{11}$H$_{11}$N$_3$OS 233.0623 (M+), found 233.0613. Anal. (C$_{11}$H$_{11}$N$_3$OS.0.2H$_2$O) C, H, N.

Example 139

1-Methanesulfinyl-8,9-dihydro-7H-2,7,9a-triaza-benzo[cd]azulen-6-one

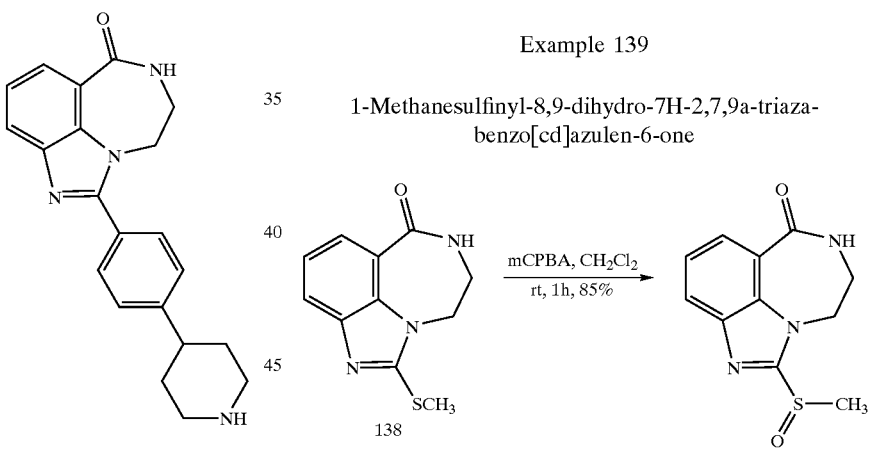

1-Methylsulfanyl-8,9-dihydro-7H-2,7,9a-triaza-benzo[cd]azulen-6-one (Example 138) (0.29 g, 1.25 mmol) was dissolved in CH$_2$Cl$_2$ (25 mL). m-CPBA (57–86%, 0.25 g, 1 eq.assuming 86%) was added, and the reaction stirred at rt for 1 h. An additional 0.02 g of m-CPBA was added with an additional fifteen minutes of stirring. The solvent was removed in vacuo, and the residue subjected to flash silica gel chromatography eluting with 1–3% methanolic ammonia/CHCl$_3$ to give 0.26 g (85%) of a white solid: mp=241–242° C. (dec); $R_f$=0.24 (7% methanolic ammonia/CHCl$_3$); IR (KBr) 1645, 1596, 1467, 1358, 1081 cm$^{-1}$; $^1$H NMR (DMSO-d$_6$) δ 3.17 (s, 3H), 3.65–3.66 (m, 2H), 4.55–4.85 (br, 2H), 7.42–7.48 (m, 1H), 7.99–8.02 (m, 2H), 8.50 (t, 1H, J=5.5 Hz). HRMS calcd for C$_{11}$H$_{11}$N$_3$O$_2$S 249.0572 (M+), found 249.0583. Anal. (C$_{11}$H$_{11}$N$_3$O$_2$S) C, H, N.

Example 140

1-Methanesulfonyl-8,9-dihydro-7H-2,7,9a-triaza-benzo[cd]azulen-6-one

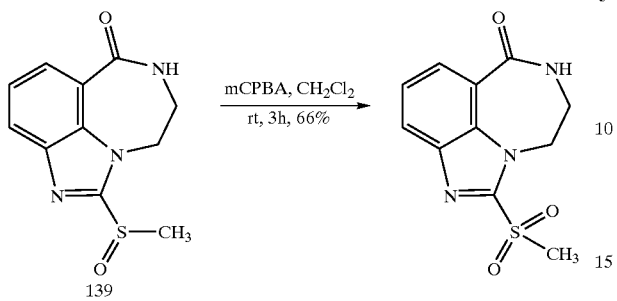

1-Methanesulfinyl-8,9-dihydro-7H-2,7,9a-triaza-benzo[cd]azulen-6-one (Example 139) (0.05 g, 0.20 mmol) was partially dissolved in $CH_2Cl_2$ (4 mL). m-CPBA (57–86%, 0.05 g) was added, and the reaction was stirred at rt for 3 h. An additional 0.015 g of mCPBA was added, and the reaction stirred an additional hour. The solvent was removed in vacuo, and the product purified by flash silica gel chromatography eluting with 2% MeOH/$CHCl_3$ to give 0.036 g (66%) of a white solid: mp >190° C. (dec); $R_f$=0.34 (7% methanolic ammonia/$CHCl_3$); IR (KBr) 1658, 1474, 1372, 1317 $cm^{-1}$; $^1H$ NMR (DMSO-$d_6$) δ 3.61 (s, 3H), 3.66–3.71 (m, 2H), 4.60–4.90 (br, 2H), 7.52 (t, 1H, J=7.8 Hz), 8.04–8.11 (m, 2H), 8.52–8.56 (m, 1H). HRMS calcd for $C_{11}H_{11}N_3O_3S$ 265.0521 (M+), found 265.0529. Anal. ($C_{11}H_{11}N_3O_3S$) C, H, N.

Example 141

1-[4-(1-Methyl-piperidin-4-yl)-phenyl]-8,9-dihydro-7H-2,7,9a-triaza-benzo[cd]azulen-6-one

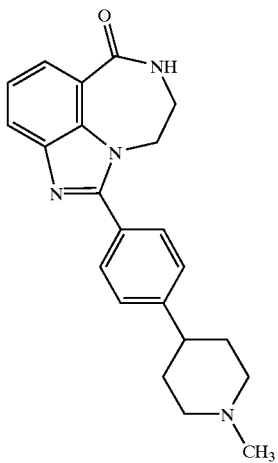

The product was prepared from 1-(4-piperidin-4-yl-phenyl)-8,9-dihydro-7H-2,7,9a-triaza-benzo[cd]azulen-6-one (Example 137) following the procedure for Example 132 a white solid (77%): mp >240° C. (dec); $R_f$=0.21 (10% methanolic ammonia/$CHCl_3$); IR (KBr) 1662, 1473, 1379, 1304 $cm^{-1}$; $^1H$ NMR (DMSO-$d_6$) δ 1.69–1.81 (m, 4H), 2.00–2.07 (m, 2H), 2.23 (s, 3H), 2.53–2.58 (m, 1H), 2.89–2.93 (m, 2H), 3.51–3.52 (m, 2H), 4.45–4.47 (m, 2H), 7.34 (t, 1H, J=7.8 Hz), 7.45 (d, 2H, J=8.2 Hz), 7.79 (d, 2H, J=8.3 Hz), 7.84–7.90 (m, 2H), 8.44 (t, 1H, J=5.6 Hz). HRMS calcd for $C_{22}H_{24}N_4O$ 360.1950 (M+), found 360.1944. Anal. ($C_{22}H_{24}N_4O.0.25H_2O$) C, H, N.

Example 142

1-(4-Piperidin-3-yl-phenyl)-8,9-dihydro-7H-2,7,9a-triaza-benzo[cd]azulen-6-one

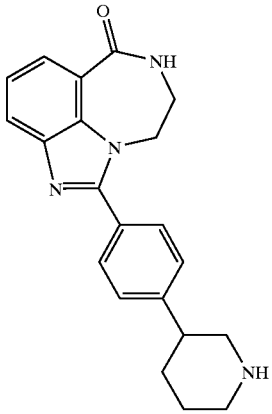

The compound was prepared from Example 134 using the procedure to prepare Example 137 to give a white solid (71%): mp >230° C. (dec); $R_f$=0.05 (10% methanolic ammonia/$CHCl_3$); IR (KBr) 1655, 1478, 1381, 1307 $cm^{-1}$; $^1H$ NMR (DMSO-$d_6$) δ 1.48–1.70 (m, 4H), 1.90–1.93 (m, 1H), 2.54–2.61 (m, 1H), 2.68–2.75 (m, 1H), 2.93–3.04 (m, 2H), 3.50–3.51 (m, 2H), 4.45–4.46 (m, 2H), 7.34 (t, 1H, J=7.8 Hz), 7.44 (d, 2H, J=8.2 Hz), 7.78 (d, 2H, J=8.2 Hz), 7.84–7.90 (m, 2H), 8.42–8.46 (m, 1H). HRMS calcd for $C_{21}H_{22}N_4O$ 346.1794 (M+), found 346.1788. Anal. ($C_{21}H_{22}N_4O.1.0H_2O$) C, H, N.

Example 143

3-[4-(6-oxo-6,7,8,9-Tetrahydro-2,7,9a-triaza-benzo[cd]azulen-1-yl)-phenyl]-piperidine-1-carboxylic Acid t-Butyl Ester

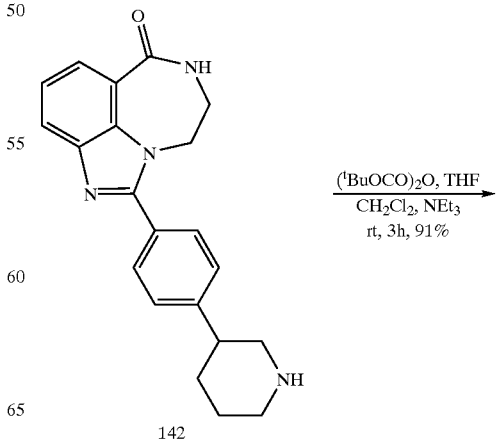

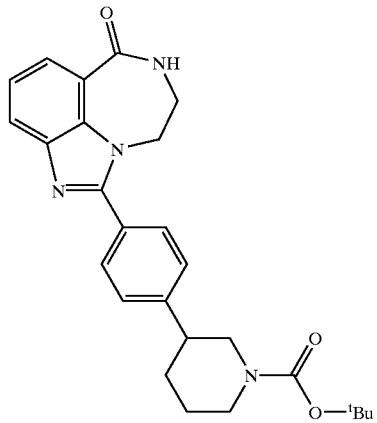

Example 142 (0.13 g, 0.37 mmol) was suspended in THF (4 mL) and CH$_2$Cl$_2$ (3 mL). Triethylamine (0.062 mL, 0.45 mmol) was added followed by di-tert-butyl-dicarbonate (0.10 mL, 0.45 mmol). The reaction stirred at rt for 3 h, and the solvent was removed in vacuo. The residue was purified by flash silica gel chromatography eluting with 1–3% MeOH/CHCl$_3$ to give 0.15 g (91%) of a white solid: mp=202–203° C.; R$_f$=0.21 (7% MeOH/CHCl$_3$); IR (KBr) 1660, 1418, 1308, 1173 cm$^{-1}$; $^1$H NMR (DMSO-d$_6$) δ 1.41 (s, 9H), 1.46–1.48 (m, 1H), 1.69–1.76 (m, 2H), 1.92–1.95 (m, 1H), 2.68–2.82 (m, 3H), 3.51–3.52 (m, 2H), 3.96–4.01 (m, 2H), 4.46–4.47 (m, 2H), 7.35 (t, 1H, J=7.8 Hz), 7.48 (d, 2H, J=8.2 Hz), 7.80–7.91 (m, 4H), 8.42–8.46 (m, 1H). HRMS calcd for C$_{26}$H$_{30}$N$_4$O$_3$ 446.2318 (M+), found 446.2311. Anal. (C$_{26}$H$_{30}$N$_4$O$_3$) C, H, N.

Example 144

1-[4-(Methyl-piperidin-3-yl)-phenyl]-8,9-dihydro-7H-2,7,9a-triaza-benzo[cd]azulen-6-one

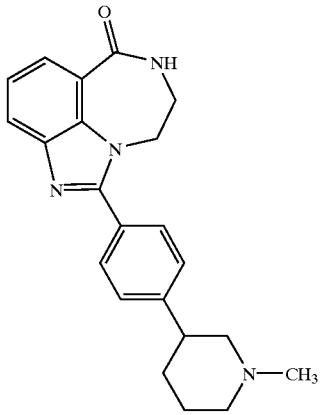

The product was prepared from Example 142 following the procedure for Example 132 to give a white solid (58%): mp=240–242° C.; R$_f$=0.32 (10% methanolic ammonia/CHCl$_3$); IR (KBr) 1628, 1480, 1462, 1380 cm$^{-1}$; $^1$H NMR (DMSO-d$_6$) δ 1.45–2.18 (m, 6H), 2.24 (s, 3H), 2.87–2.90 (m, 3H), 3.45–3.52 (m, 2H), 4.45–4.46 (m, 2H), 7.35 (t, 1H, J=7.8 Hz), 7.47 (d, 2H, J=8.3 Hz), 7.79 (d, 2H, J=8.3 Hz), 7.84–7.90 (m, 2H), 8.42–8.46 (m, 1H). HRMS calcd for C$_{22}$H$_{24}$N$_4$O 360.1950 (M+), found 360.1963. Anal. (C$_{22}$H$_{24}$N$_4$O·0.5H$_2$O) C, H, N.

Example 145

1-Benzylamino-8,9-dihydro-7H-2,7,9a-triaza-benzo[cd]azulen-6-one

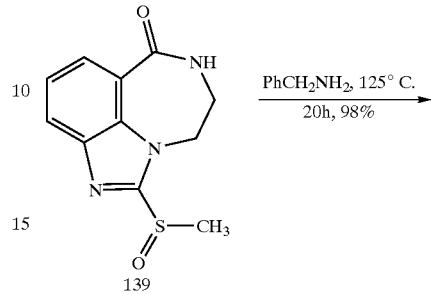

Sulfoxide 139 (0.10 g, 0.40 mmol) was dissolved in benzylamine (4 mL) and heated to 125° C. for 20 h. The solvent was removed in vacuo, and the product purified by flash silica gel chromatography eluting with 1–5% MeOH/CHCl$_3$ to give 0.12 g (98%) of a white solid: mp=186° C. (dec); R$_f$=0.11 (7% MeOH/CHCl$_3$); IR (KBr) 1644, 1572, 1466, 1368 cm$^{-1}$; $^1$H NMR (DMSO-d$_6$) δ 3.53–3.56 (m, 2H), 4.04–4.05 (m, 2H), 4.59 (d, 2H, J=5.8 Hz), 7.02 (t, 1H, J=7.8 Hz), 7.20–7.41 (m, 7H), 7.44–7.47 (m, 1H), 8.18–8.22 (m, 1H). HRMS calcd for C$_{17}$H$_{16}$N$_4$O 292.1324 (M+), found 292.1315. Anal. (C$_{17}$H$_{16}$N$_4$O) C, H, N.

Example 146

1-Amino-8,9-dihydro-7H-2,7,9a-triaza-benzo[cd]azulen-6-one Hydrochloride

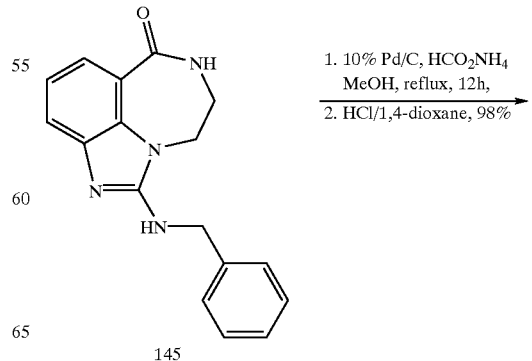

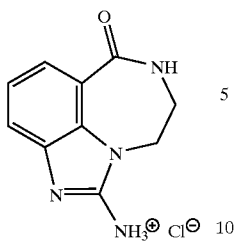

Example 145 (0.08 g, 0.27 mmol) was dissolved in MeOH. 10% Palladium on carbon (0.08 g) was added followed by ammonium formate (0.09 g, 1.36 mmol). The reaction was refluxed overnight. The catalyst was filtered off and the solvent removed in vacuo. The residue was dissolved in dioxane (2 mL) and MeOH (2 mL) and treated with 4M HCl/dioxane (1 mL). The solvents were removed in vacuo and the resulting solids triturated and washed with $Et_2O$ to give 0.06 g (98%) of a yellow solid: mp >260° C. (dec); IR (KBr) 1670, 1459, 1379, 754 $cm^{-1}$; $^1H$ NMR (DMSO-$d_6$) δ 3.58–3.61 (m, 2H), 4.10–4.11 (m, 2H), 7.35 (t, 1H, J=7.8 Hz), 7.58 (dd, 1H, J=7.9, 1.0 Hz), 7.77 (dd, 1H, J=7.9, 1.0 Hz), 8.50–8.54 (m, 1H), 8.87 (s, 2H), 13.05 (br, 1H). HRMS calcd for $C_{10}H_{10}N_4O$ 202.0854 (M+), found 202.0853. Anal. ($C_{10}H_{10}N_4O \cdot HCl \cdot 1.5H_2O$) C, H, N.

Example 147

1-[4-(1H-Imidazol-4-yl)-phenyl]-8,9-dihydro-7H-2,7,9a-triaza-benzo[cd]azulen-6-one

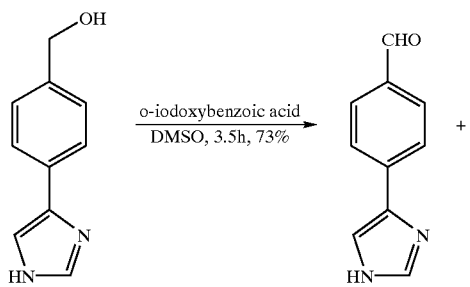

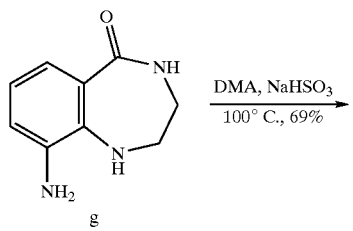

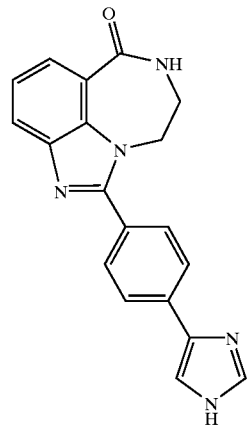

(a) 4-(1H-Imidazol-4-yl)-benzaldehyde:
[4-(1H-Imidazol-4-yl)-phenyl]-methanol (0.21 g, 1.23 mmol) was dissolved in DMSO (12 mL). o-Iodoxybenzoic acid (Frigerio, et al., *J. Org. Chem.* 1995, 60, 7272) (1.03 g, 3.70 mmol) was added, and the reaction stirred at room temperature for 3.5 hours. The solvent was removed in vacuo, and the residue dissolved in 4:1 $CHCl_3$/iPrOH. The resultant solids were filtered off, and the filtrate washed in turn with 5% $Na_2SO_3$/5% $NaHCO_3$ solution, water, and brine, dried ($MgSO_4$) and the solvent removed to give 0.15 g (73%) of 4-(1H-imidazol-4-yl)-benzaldehyde as a yellow solid which was used without further purification: (DMSO-$d_6$) δ 7.84–7.79 (m, 2H), 7.87 (d, 2H, J=8.4 Hz), 7.98 (d, 2H, J=8.2 Hz), 9.94 (s, 1H), 12.30–12.50 (br, 1H).
(b) Title Compound:
According to the procedure used in Example 19, 4-(1H-imidazol-4-yl)-benzaldehyde and diamine g was used to prepare the desired compound as a light tan solid (69%): mp >198° C. (dec); $R_f$=0.08 (10% MeOH/$CHCl_3$); IR (KBr) 1647, 1473, 1381, 1309 $cm^{-1}$; $^1H$ NMR (DMSO-$d_6$) δ 3.54–3.55 (m, 2H), 4.49–4.50 (m, 2H), 7.35 (t, 1H, J=7.8 Hz), 7.77–7.98 (m, 8H), 8.44–8.47 (m, 1H), 12.25–12.40 (br, 1H). HRMS calcd for $C_{19}H_{15}N_5O$ 329.1277 (M+), found 329.1280. Anal. ($C_{19}H_{15}N_5O \cdot 0.25H_2O$) C, H, N.

Example 148

1-(4-Pyrrolidin-2-yl-phenyl)-8,9-dihydro-7H-2,7,9a-triaza-benzo[cd]azulen-6-one

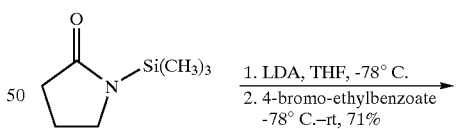

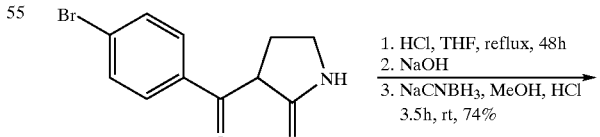

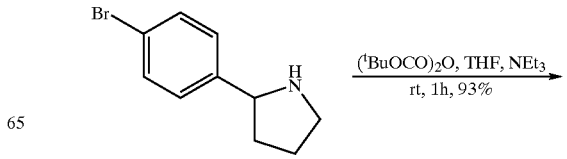

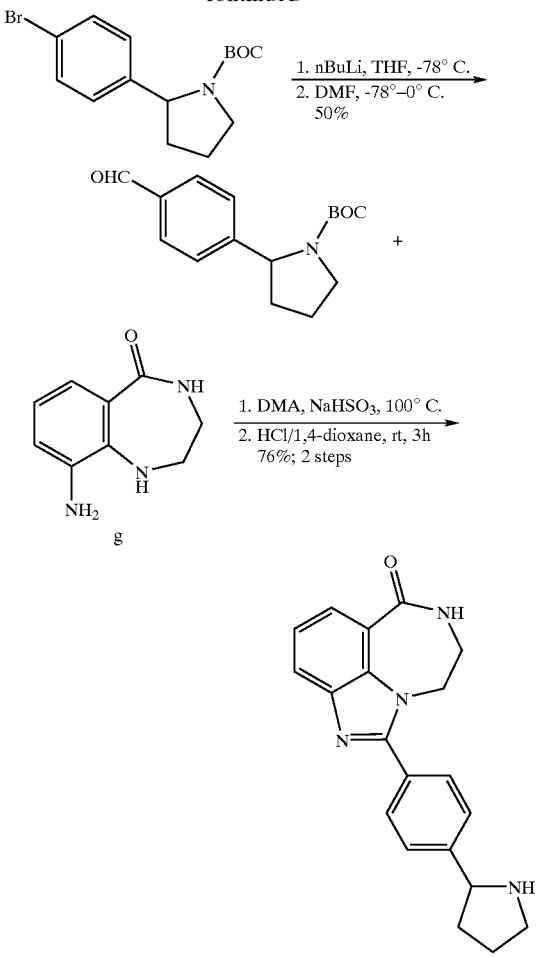

(a) 3-[1-(4-Bromo-phenyl)-methanoyl]pyrrolidin-2-one:

Diisopropylamine (3.75 mL, 26.73 mmol) was dissolved in THF (70 mL) and cooled to −78° C. n-Butyllithium (2.5M/hexanes, 10.69 mL, 26.73 mmol) was added dropwise, and the reaction stirred for 15 minutes at that temperature. 1-(Trimethylsilyl)-2-pyrrolidinone (Aldrich Chemical Co.) (4.28 mL, 25.67 mmol) was added dropwise and again stirred for 15 minutes at −78° C. Ethyl-4-bromobenzoate (5.00 g, 3.56 mL, 21.39 mmol) was added dropwise. The reaction was allowed to warm to rt and stirred overnight. The THF was removed in vacuo. The solids were redissolved in THF (70 mL) and 10% HOAc (40 mL). The THF was again removed and replaced with water. The product was extracted in EtOAc (3x). The organic phases were combined, washed with sat. NaHCO$_3$, water, and brine, then dried (MgSO$_4$). The product was purified by flash silica gel chromatography eluting with 0–2% MeOH/CHCl$_3$ to give 4.08 g (71%) of a white solid: mp=167–169° C.; R$_f$=0.16 (2% MeOH/CHCl$_3$); IR (KBr) 1699, 1587, 1397, 1273 cm$^{-1}$; $^1$H NMR (DMSO-d$_6$) δ 2.18–2.28 (m, 1H), 2.40–2.51 (m, 1H), 3.24–3.30 (m, 2H), 4.55–4.60 (m, 1H), 7.76 (d, 2H, J=8.7 Hz), 7.95–7.99 (m, 3H). LRMS 270 (M+H).

(b) 2-(4-Bromo-phenyl)-pyrrolidine

3-[1-(4-Bromo-phenyl)-methanoyl]pyrrolidin-2-one (4.08 g, 15.21 mmol) was dissolved in 6N HCl and THF (60 mL). The reaction was refluxed 2 days. The THF was removed in vacuo, and the aqueous layer extracted with EtOAc and separated. The water was removed to form a syrup, then basified with 10% NaOH. The product was extracted into Et$_2$O, dried (MgSO$_4$) and concentrated to give the crude pyrroline. This was dissolved in MeOH (50 mL). A trace amount of bromocresol green indicator was added followed by NaCNBH$_3$ (1.01 g, 15.37 mmol). 2M HCl/MeOH, prepared from conc. HCl and MeOH, was added as needed to maintain a yellow color (approx. 10 mL) and the reaction stirred at rt for 3.5 h. 5 mL of conc. HCl was added dropwise. When gas evolution had ceased, the solvent was removed in vacuo, and the residue dissolved in water. The water was washed with Et$_2$O and basified to pH=11 with 50% NaOH. The product was extracted into Et$_2$O which was subsequently washed with water and brine, dried (MgSO$_4$), and concentrated to give 2.54 g (74%) of an oil: R$_f$=0.16 (5% methanolic ammonia/CHCl$_3$); IR (KBr) 1485, 1404, 1103, 1070, 1011 cm$^{-1}$; $^1$H NMR (Benzene-d$_6$) δ 1.23–1.49 (m, 2H), 1.55–1.60 (m, 1H), 1.70–1.81 (m, 1H), 2.55–2.64 (m, 1H), 2.84–2.91 (m, 1H), 3.59–3.64 (m, 1H), 7.03 (d, 2H, J=8.3 Hz), 7.32 (d, 2H, J=8.3 Hz). LRMS 226,228 (M+H).

(c) 2-(4-Bromo-phenyl)-pyrrolidine-1-carboxylic Acid tert-Butyl Ester 2-(4-Bromo-phenyl)-pyrrolidine (0.49 g, 1.77 mmol) was dissolved in THF (9 mL). Triethylamine (0.30 mL, 2.12 mmol) was added followed by di-tert-butyl-dicarbonate (0.49 mL, 2.12 mmol). The reaction stirred at rt for 1 h, and the solvent was removed in vacuo. The product was purified by flash silica gel chromatography eluting with 3–5% EtOAc/hexanes to give 0.53 g (93%) of a clear oil: R$_f$=0.18 (10% EtOAc/hexanes); IR (KBr) 1703, 1487, 1400, 1167, 1117 cm$^{-1}$; $^1$H NMR (CDCl$_3$) major rotamer δ 1.58 (s, 9H), 1.72–1.92 (m, 3H), 2.28–2.34 (m, 1H), 3.58–3.60 (m, 2H), 4.72 (m, 1H), 7.04 (d, 2H, J=8.3 Hz), 7.42 (d, 2H, J=8.3 Hz). LRMS 350 (M+Na).

(d) 2-(4-Formyl-phenyl)-pyrrolidine-1-carboxylic Acid tert-Butyl Ester 2-(4-Bromo-phenyl)-pyrrolidine-1-carboxylic acid tert-butyl ester (0.43 g, 1.34 mmol) was dissolved in THF (4 mL) and cooled to −78° C. n-Butyllithium (2.5M/hexanes, 0.62 mL, 1.6 mmol) was added dropwise. The reaction stirred at −78° C. for 1 h, then DMF (0.13 mL, 1.6 mmol) was added dropwise. The reaction stirred at −78° C. for an additional hour. Sat. NaHCO$_3$ (5 mL) was added, and the reaction warmed to 0° C. The reaction was poured into EtOAc/water. The organic phase was separated and washed with brine, dried (MgSO$_4$) and concentrated. The product was purified by flash silica gel chromatography eluting with 5–15% EtOAc/hexanes to give 0.18 g (50%) of a clear oil: R$_f$=0.13 (20% EtOAc/hexanes); IR (KBr) 1696, 1607, 1393, 1165, 1113 cm$^{-1}$; $^1$H NMR (CDCl$_3$) δ major rotamer 1.58 (s, 9H), 1.78–1.92 (m, 3H), 2.35–2.37 (m, 1H), 3.60–3.66 (m, 2H), 4.82–4.84 (m, 1H), 7.34 (d, 2H, J=8.2 Hz), 7.83 (d, 2H, J=8.3 Hz), 9.99 (s, 1H). LRMS 220 (M−C$_4$H$_9$+H).

(e) Title Compound

Using the method described in Example 19, 2-(4-Formyl-phenyl)-pyrrolidine-1-carboxylic acid tert-butyl ester (0.16 g, 0.59 mmol) and diamine g (0.11 g, 0.61 mmol) were condensed. The crude product was then dissolved in dioxane (8 mL) and treated with 4M HCl/dioxane (4 mL). The reaction was stirred at rt for 3 h upon which a gummy solid appeared which was manually broken up to form white solids. The solvent was removed, and the residual solids treated with methanolic ammonia. The product was then purified by flash silica gel chromatography eluting with 3–5% MeOH/CHCl$_3$, then 5% methanolic ammonia/CHCl$_3$ to give 0.14 g (76%) of a white solid: mp=220–223° C. (dec); R$_f$=0.11 (7% methanolic ammonia/CHCl$_3$); IR (KBr) 1662, 1472, 1304, 741 cm$^{-1}$; $^1$H NMR (DMSO-d$_6$) δ 1.48–1.57 (m, 1H), 1.72–1.83 (m, 2H), 2.12–2.23 (m, 2H), 2.88–2.96 (m, 1H), 3.00–3.07 (m, 1H), 3.51–3.52 (m, 2H), 4.11–4.16 (m, 1H), 4.45–4.46 (m, 2H), 7.34 (t, 1H, J=7.8 Hz), 7.56 (d, 2H, J=8.2 Hz), 7.79 (d, 2H, J=8.2 Hz), 7.84–7.90 (m, 2H), 8.42–8.46 (m, 1H). HRMS calcd for $C_{20}H_{18}N_4O$ 330.1481 (M−2H), found 330.1480. Anal. ($C_{20}H_{20}N_4O$) C, H, N.

Example 149

1-[4-(1-Methyl-pyrrolidin-2-yl)-phenyl-8,9-dihydro-7H-2,7,9a-triaza-benzo[cd]azulen-6-one

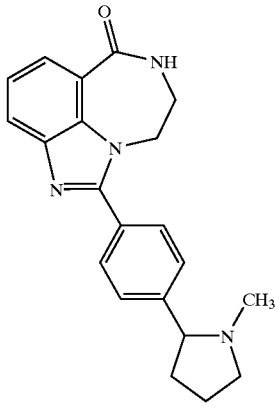

The product was prepared from 1-(4-Pyrrolidin-2-yl-phenyl)-8,9-dihydro-7H-2,7,9a-triaza-benzo[cd]azulen-6-one (Example 148) following the procedure used in Example 132 to give a white solid (78%): mp=235–238° C. (dec); IR (KBr) 2780, 1472, 1278 cm$^{-1}$; $^1$H NMR (DMSO-$d_6$) δ 1.61–1.70 (m, 1H), 1.76–1.98 (m, 2H), 2.13 (s, 3H), 2.17–2.29 (m, 2H), 3.18–3.29 (m, 2H), 3.52–3.53 (m, 2H), 4.45–4.46 (m, 2H), 7.35 (t, 1H, J=7.8 Hz), 7.52 (d, 2H, J=7.8 Hz), 7.81–7.90 (m, 4H), 8.42–8.46 (m, 1H). HRMS calcd for $C_{21}H_{22}N_4O$ 346.1794 (M+), found 346.1796. Anal. ($C_{21}H_{22}N_4O \cdot 0.3H_2O$) C, H, N.

Example 150

1-[4-(1-Cyclopropylmethyl-piperidin-2-yl)-phenyl]-8,9-dihydro-7H-2,7,9a-triaza-benzo[cd]azulen-6-one

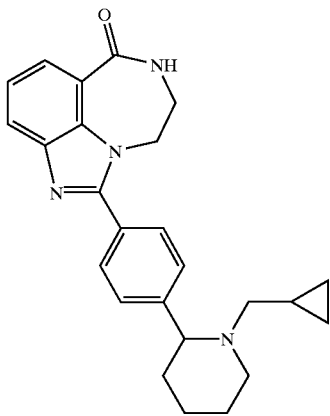

The product was prepared following the procedure for Example 132 using 1-(4-Piperidin-2-yl-phenyl)-8,9-dihydro-7H-2,7,9a-triaza-benzo[cd]azulen-6-one (Example 130) (0.06 g, 0.19 mmol) and cyclopropanecarboxaldehyde (0.11 mL, 1.53 mmol) in place of formaldehyde to give 0.054 g (71%) after silica gel chromatography (0–1.5% MeOH/CHCl$_3$, followed by 3% methanolic ammonia/CHCl$_3$) of a white solid: >150° C. (dec); $R_f$=0.26 (5% methanolic ammonia/CHCl$_3$); IR (KBr) 1656, 1479, 1380, 1308 cm$^{-1}$; $^1$H NMR (DMSO-$d_6$) δ (−0.15)–(−0.10) (m, 2H), 0.31–0.42 (m, 2H), 0.78–0.85 (m, 1H), 1.32–1.80 (m, 7H), 2.11–2.19 (m, 1H), 2.26–2.33 (m, 1H), 3.15–3.17 (m, 1H), 3.36–3.37 (m, 1H), 3.52–3.52 (m, 2H), 4.46–4.48 (m, 2H), 7.35 (t, 1H, J=7.8 Hz), 7.50 (d, 2H, J=8.2 Hz), 7.81 (d, 2H, J=8.2 Hz), 7.84–7.89 (m, 2H), 8.44 (t, 1H, J=5.6 Hz). HRMS calcd for $C_{25}H_{28}N_4O$ 400.2263 (M+), found 400.2256. Anal. ($C_{25}H_{28}N_4O \cdot 0.25H_2O$) C, H, N.

Example 151

1-(4-Isopropyl-piperidin-2-yl)-phenyl-8,9-dihydro-7H-2,7,9a-triaza-benzo[cd]azulen-6-one

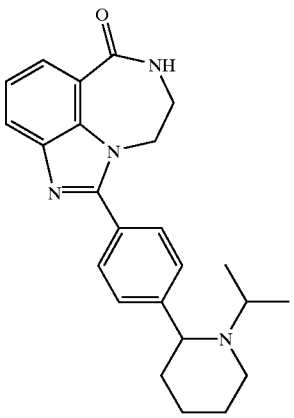

Similar to conditions used to prepare Example 132, 1-(4-Piperidin-2-yl-phenyl)-8,9-dihydro-7H-2,7,9a-triaza-benzo[cd]azulen-6-one (Example 130) 0.077 g, 0.22 mmol) was dissolved in MeOH (4 mL), acetic acid (0.05 mL), and acetone (1 mL). Sodium cyanoborohydride (0.044 g) was added, and the reaction stirred at room temperature overnight. The solvent was removed in vacuo, and the residue dissolved in CH$_2$Cl$_2$/sat. NaHCO$_3$. The organic layer was separated, washed with water and brine, dried (MgSO$_4$) and concentrated. The product was purified by flash silica gel chromatography eluting with 1% methanolic ammonia/CHCl$_3$ to give 0.26 g (30%) of a white solid: mp >260° C. (dec); $R_f$=0.34 (7% methanolic ammonia/CHCl$_3$); IR (KBr) 1661, 1478, 1382, 1308 cm$^{-1}$; $^1$H NMR (DMSO-$d_6$) δ 0.77 (d, 3H, J=6.3 Hz), 0.96 (d, 3H, J=6.7 Hz), 1.29–1.52 (m, 3H), 1.64–1.72 (m, 3H), 2.13–2.20 (m, 1H), 2.69–2.76 (m, 1H), 2.92–2.96 (m, 1H), 3.35–3.45 (m, 1H), 3.52–3.53 (m, 2H), 4.46–4.47 (m, 2H), 7.35 (t, 1H, J=7.8 Hz), 7.51 (d, 2H, J=8.0 Hz), 7.80–7.89 (m, 4H), 8.42–8.46 (m, 1H). HRMS calcd for $C_{24}H_{28}N_4O$ 388.2263 (M+), found 388.2253. Anal. ($C_{24}H_{28}N_4O \cdot 0.7H_2O$) C, H, N.

Example 152

1-[4-(1H-Imidazol-2-yl)-phenyl]-8,9-dihydro-7H-2,7,9a-triaza-benzo[cd]azulen-6-one

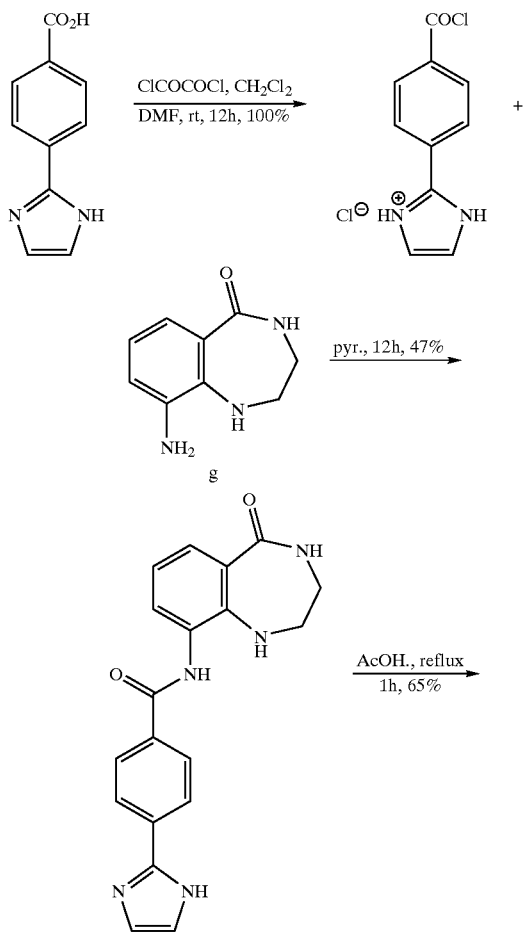

(a) 4-(1H-Imidazol-2-yl)-benzoyl Chloride Hydrochloride:

4-(1H-Imidazol-2-yl)-benzoic acid [*J. Med. Chem.* 30, 1342 (1987)] (0.69 g, 3.70 mmol) was suspended in $CH_2Cl_2$ (20 mL). Oxalyl chloride (0.39 mL, 4.44 mmol) was added followed by a drop of DMF. The reaction was stirred overnight at rt. The solvent was removed to give 0.94 g (quant) of the acid chloride which was used without purification.

(b) 4-(1H-Imidazol-2-yl)-N-(5-oxo-2,3,4,5-tetrahydro-1H-benzo[e][1,4]diazepin-9-yl)-benzamide The solvent was removed to give 0.94 g (quant) of the acid chloride. Diamine g (0.60 g, 3.40 mmol) was dissolved in pyridine (35 mL). The acid chloride (0.91 g, 3.74 mmol) was added, and the reaction stirred overnight upon which solids precipitated out of solution. The pyridine was removed in vacuo. The solids were taken up in 4:1 $CHCl_3$/iPrOH and water but did not dissolve in either. They were then filtered and washed with water to give 0.56 g (47%) of 4-(1H-imidazol-2-yl)-N-(5-oxo-2,3,4,5-tetrahydro-1H-benzo[e][1,4]diazepin-9-yl)-benzamide: $^1$H NMR (DMSO-$d_6$) δ 2.48–2.50 (m, 2H), 3.41–3.42 (m, 2H), 5.57–5.59 (m, 1H), 6.63 (t, 1H, J=7.7 Hz), 7.18–7.20 (m, 1H), 7.22 (s, 2H), 7.69 (dd, 1H, J=8.1, 1.6 Hz), 8.03–8.10 (m, 5H), 9.65 (s, 1H), 12.70–13.00 (br, 1H). LRMS 348 (M+H).

(c) Title Compound:

4-(1H-imidazol-2-yl)-N-(5-oxo-2,3,4,5-tetrahydro-1H-benzo[e][1,4]diazepin-9-yl)-benzamide (0.53 g, 1.52 mmol) was refluxed in acetic acid (15 mL) for 1 h. The solvent was removed in vacuo, and the residue dissolved in 4:1 $CHCl_3$/iPrOH and sat. $NaHCO_3$. The pH was adjusted to 6.5, and the organic phase separated. This was washed with water and brine, dried ($MgSO_4$), and concentrated. The product was purified by flash silica gel chromatography eluting with 3–15% MeOH/$CHCl_3$ to give 0.32 g (65%) of a gold-orange crystalline solid: mp >325° C.; $R_f$=0.16 (10% MeOH/$CHCl_3$); IR (KBr) 1664, 1479, 1108 $cm^{-1}$; $^1$H NMR (DMSO-$d_6$) δ 3.54–3.55 (m, 2H), 4.51–4.52 (m, 2H), 7.09 (s, 1H), 7.33 (s, 1H), 7.36 (t, 1H, J=7.8 Hz), 7.87 (dd, 1H, J=7.8, 1.1 Hz), 7.91 (dd, 1H, J=7.8, 1.1 Hz), 7.95 (d, 2H, J=8.5 Hz), 8.12 (d, 2H, J=8.5 Hz), 8.45–8.49 (m, 1H), 12.71 (s, 1H). HRMS calcd for $C_{19}H_{15}N_5O$ 329.1277 (M+), found 329.1291. Anal. ($C_{19}H_{15}N_5O \cdot 0.6H_2O \cdot 0.2MeOH$) C, H, N.

Example 153

6-(4-Fluoro-phenyl)-1-oxo-1,2,3,4-tetrahydro-[1,4]diazepino[6,7,1-hi]indole-7-carbothioic Acid Amide

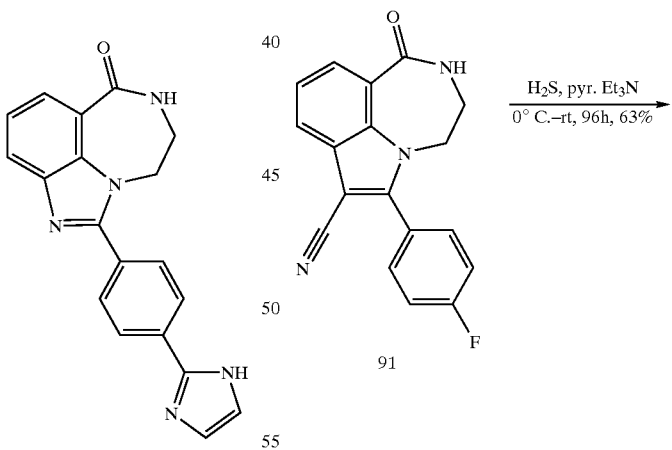

91

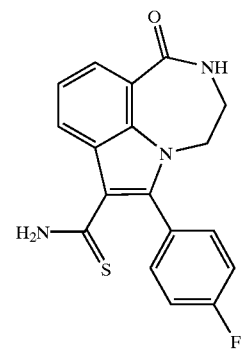

$H_2S$ gas was bubbled through a solution of the Example 91 (0.5 mmol, 0.153 g) in $Et_3N$ (1 ml) and pyridine (2.4 ml) at 0° C. for 1 h in a seal tube. The tube was then sealed, allowed to warm to rt and stirred for 4 days. Argon gas was bubbled through the dark green solution to remove $H_2S$. The reaction mixture was diluted with EtOAc and washed with 2N HCl and then with $H_2O$. The organic layer was dried over anhydrous $MgSO_4$ and concentrated to give a yellow solid which was purified by flash silica gel chromatography eluting with a gradient of 0–3% MeOH in $CHCl_3$ to give 0.107 g (63%) of a yelow solid: $^1H$ NMR (DMSO-$d_6$) δ 3.47 (br s, 2H), 4.01–4.11 (m, 2H), 7.27 (t, 1H, J=9.0 Hz), 7.37 (t, 2H, J=9.0 Hz), 7.54–7.58 (m, 2H), 7.88 (d, 1H, J=9.0 Hz), 8.19 (d, 1H, J=9.0 Hz), 8.42 (t, 1H, J=6.0 Hz), 8.63 (br s, 1H), 9.50 (br s, 1H); HRMS calcd. for $C_{18}H_{14}N_3OSF$ ($M^+$) 339.084162, found ($M^+$) 339.0833; mp 238–240° C.; Anal. ($C_{18}H_{14}N_3OSF \cdot 0.3H_2O \cdot 0.3MeOH$) C, H, N.

Example 154

6-(4-Fluoro-phenyl)-1-oxo-1,2,3,4-tetrahydro-[1,4]diazepino[6,7,1-hi]indole-7-carboximidothioic Acid Methyl Ester

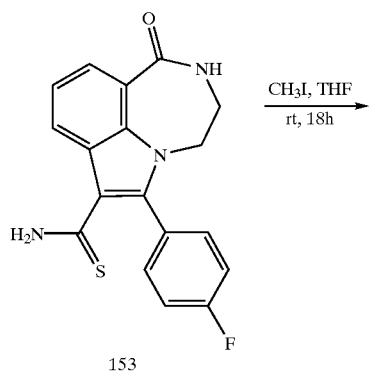

153

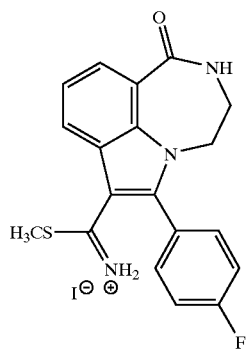

Iodomethane (3.218 mmol, 0.2 ml) was added to a solution of the 152 (0.354 mmol, 0.120 g) in 50 mL THF at rt. The reaction mixture was stirred for 18 h at rt. The solvent was removed to give a yellow solid (0.130 g) which was used without further purification: $^1H$ NMR (DMSO-$d_6$) δ 2.63 (s, 3H), 3.51 (br s, 2H), 4.01–4.05 (m, 2H), 7.42–7.53 (m, 3H), 7.62 (d, 1H, J=6.0 Hz), 7.65 (d, 1H, J=6.0 Hz), 8.02 (d, 1H, J=3.0 Hz), 8.05 (d, 1H, J=3.0 Hz), 8.57 (t, 1H, J=6.0 Hz).

Example 155

6-(4-Fluoro-phenyl)-N-hydroxy-1-oxo-1,2,3,4-tetrahydro-[1,4]diazepino[6,7,1-hi]indole-7-carboxmidine

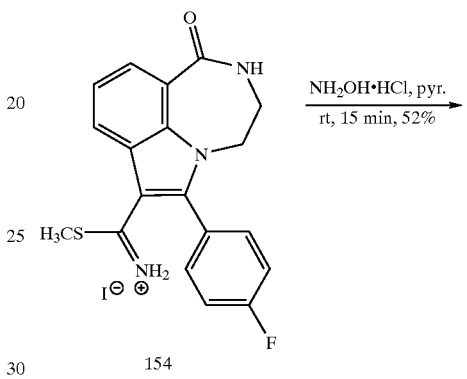

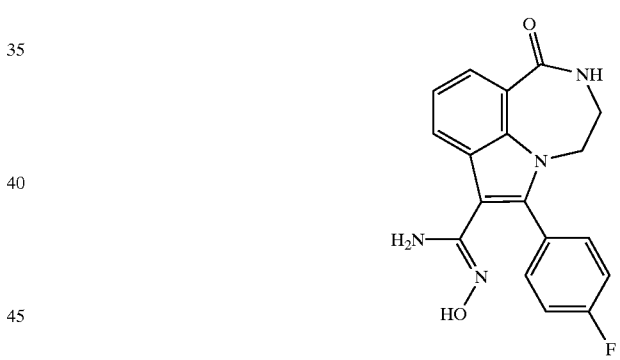

Hydroxylamine hydrochloride (0.852 mmol, 0.059 g) was added to a solution of the 154 (0.142 mmol, 0.05 g) in 5 mL pyridine at rt. The reaction mixture was stirred at rt for 15 min. Upon completion of the reaction (as indicated by TLC) the solvent was removed to give an oil which was purified by flash silica gel chromatography eluting with a gradient of 0–5% MeOH in $CHCl_3$ initially, followed by 2–10% MeOH/ $NH_3$ in $CHCl_3$ to give 0.025 g (52%) of a pale yellow solid: mp=257–259° C.; $^1H$ NMR (DMSO-$d_6$) δ 3.45–3.47 (m, 2H), 4.10–4.12 (m, 2H), 5.41 (br s, 2H), 7.23 (t, 1H, J=6.0 Hz), 7.34 (t, 2H, J=9.0 Hz), 7.57 (d, 1H, J=6.0 Hz), 7.59 (d, 1H, J=6.0 Hz), 7.88 (d, 1H, J=9.0 Hz), 7.93 (d, 1H, J=9.0 Hz), 8.39 (br s, 1H), 9.33 (br s, 1H); HRMS calcd. for $C_{18}H_{15}N_4O_2F$ ($M^+$) 338.1179, found ($M^+$) 338.1182; Anal. ($C_{18}H_{15}N_4O_2F \cdot 0.5H_2O$) C, H, N.

Example 156

7-Formyl-6-(4-fluorophenyl)-1-oxo-3,4-dihydro-[1,4]diazepino[6,7,1-hi]indole Amidrazone Hydrochloride

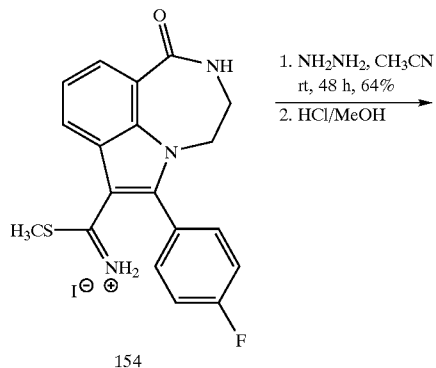

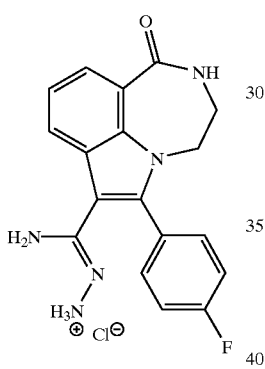

Anhydrous hydrazine (2.92 mmol, 0.092 ml) was added to a solution of 154 (0.139 mmol, 0.049 g) in 25 ml acetonitrile at rt. The reaction mixture was stirred at rt for 48 h. Upon completion of the reaction (as indicated by TLC) the solvent was removed to give an oil which was purified by flash silica gel chromatography eluting with a gradient of 0–10% MeOH in CHCl$_3$ initially, followed by 2–10% MeOH/NH$_3$ in CHCl$_3$ to give 0.028 g (64%) of a white crystalline solid. This solid was dissolved in MeOH saturated with HCl gas and stirred at rt for 30 min. Diethyl ether was added to the solution and the solvent was then evaporated to give an orange solid (9 mg): mp=272–274° C.; $^1$H NMR (DMSO-d$_6$) δ 3.58 (br s, 2H), 4.22–4.23 (m, 2H), 5.18 (br s, 2H), 7.37–7.46 (m, 3H), 7.54–7.58 (m, 2H), 7.82 (d, 1H, J=6.0 Hz), 8.00 (d, 1H, J=6.0 Hz), 8.55 (t, 1H, J=6.0 Hz), 8.79 (br s, 1H), 9.08 (br s, 1H), 10.60 (br s, 1H); HRMS calcd. for C$_{18}$H$_{16}$N$_5$OF (M$^+$) 337.1339, found (M$^+$) 337.1326.

Example 157

6-(4-Fluoro-phenyl)-7-(1-hydroxy-ethyl)-3,4-dihydro-2H-[1,4]diazepino[6,7,1-hi]indol-1-one

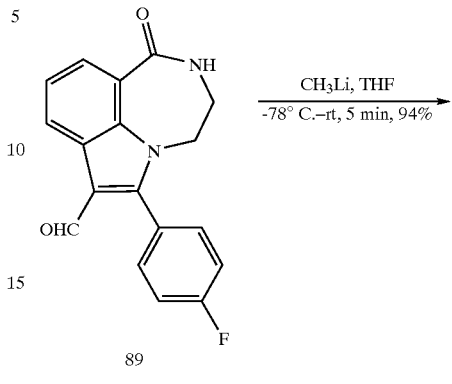

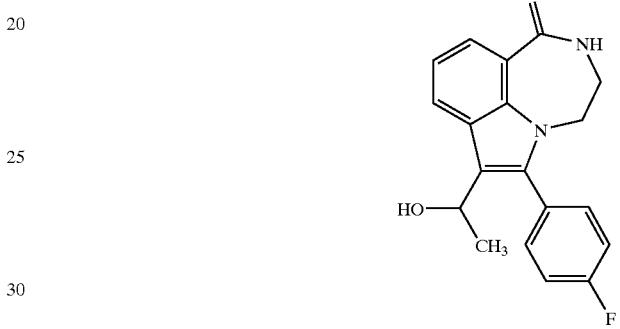

1.5M methyl lithium (4.87 mmol, 3.25 ml) was added to a solution of Example 89 (0.487 mmol, 0.150 g) in 100 mL THF at −78° C. The reaction was warm rt and stirred for 5 min. The reaction mixture was poured into H$_2$O and extracted with EtOAc several times. The combined organic extracts was dried over anhydrous MgSO$_4$ and concentrated to give a pale yellow solid (0.149 g. 94%) which was used without further purification: mp=220–222° C.; $^1$H NMR (DMSO-d$_6$) δ 1.47 (d, 3H, J=6.0 Hz), 3.45 (br s, 2H), 4.03 (br s, 2H), 4.74–4.77 (m, 1H), 4.96 (d, 1H, J=3.0 Hz), 7.16 (t, 1H, J=6.0 Hz), 7.38 (t, 2H, J=9.0 Hz), 7.51–7.55 (m, 2H), 7.84 (d, 1H, J=6.0 Hz), 8.09 (d, 1H, J=6.0 Hz), 8.31 (t, 1H, J=6.0 Hz); HRMS calcd. for C$_{19}$H$_{17}$N$_2$O$_2$F (M$^+$) 324.1274, found (M$^+$) 324.1260; Anal. for (C$_{19}$H$_{17}$N$_2$O$_2$F.0.1H$_2$O) C, H, N.

Example 158

6-(4-Fluoro-phenyl)-7-(1-hydroxyimino-ethyl)-3,4-dihydro-2H-[1,4]diazepino[6,7,1-hi]indol-1-one

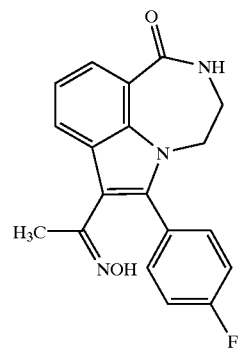

The product was prepared from Example 93 using the procedure to prepare Example 90 in 60% yield as a white solid: mp=248–250° C.; $^1$H NMR (DMSO-$d_6$) δ 1.70 (s, 3H), 3.49 (br s, 2H), 4.07–4.09 (m, 2H), 7.21 (t, 1H, J=6.0 Hz), 7.37 (t, 2H, J=9.0 Hz), 7.51 (d, 1H, J=6.0 Hz), 7.55 (d, 1H, J=6.0 Hz), 7.89 (d, 1H, J=6.0 Hz), 8.09 (d, 1H, J=6.0 Hz), 8.37 (t, 1H, J=6.0 Hz), 10 93 (s, 1H); HRMS calcd. for $C_{19}H_{16}N_3O_2F$ (M$^+$) 337.1226, found (M$^+$) 337.1230; Anal. for ($C_{19}H_{16}N_3O_2F$·0.1H$_2$O) C, H, N.

Example 159

7-[(E)-3-Dimethylamino-allanoyl]-6-(4-fluoro-phenyl)-3,4-dihydro-2H-[1,4]diazepino[6,7,1-hi]indol-1-one

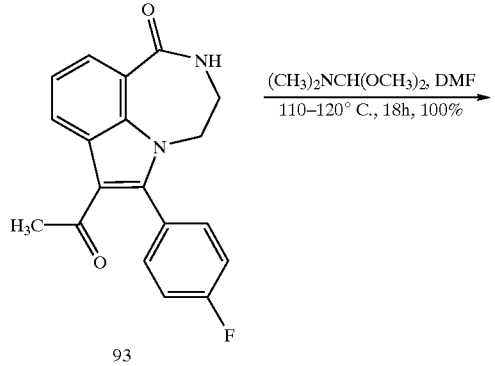

N,N'-dimethylformamide dimethyl acetal (13.88 mmol, 2 mL) was added to a solution of the methyl ketone (0.217 mmol, 0.070 g) in DMF (1 mL) at rt. The reaction mixture was stirred at 110–120° C. for 18 h. Upon completion of reaction as indicated by TLC, the solvent was removed in vacuo to give 0.101 g (quantitative yield) of an orange solid which was used without further purification: $^1$H NMR (DMSO-$d_6$) δ 3.30 (s, 6H), 3.50 (br s, 2H), 3.98–4.05 (m, 2H), 4.61 (d, 1H, J=12 Hz), 7.26 (t, 1H, J=6.0 Hz), 7.35–7.43 (m, 3H), 7.54–7.58 (m, 2H), 7.89 (d, 1H, J=6.0 Hz), 8.37–8.43 (m, 2H); LC/MS (M$^+$+H) 378.

Example 160
6-(4-Fluoro-phenyl)-7-(2H-pyrazol-3-yl)-3,4-dihydro-2H-[1,4]diazepino[6,7,1-hi]indol-1-one

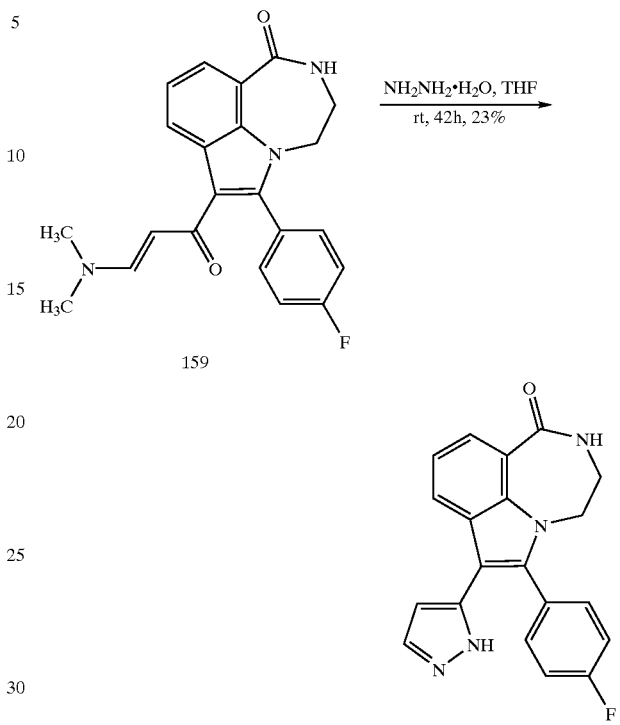

Hydrazine monohydrate (5.14 mmol, 0.26 mL) was added to a solution of 7-[(E)-3-Dimethylamino-allanoyl]-6-(4-fluoro-phenyl)-3,4-dihydro-2H-[1,4]diazepino[6,7,1-hi]indol-1-one (Example 159) (0.257 mmol, 0.097 g) in 10 mL THF at rt. The reaction mixture was stirred for 42 h. The reaction mixture was evaporated to dryness. The residue was taken up in 2N HCl and extracted with EtOAc several times. The combined organic layers was dried over anhydrous MgSO$_4$ and concentrated to give a yellow oil which was purified by flash silica gel chromatography eluting with a gradient of 0–3% MeOH in CHCl$_3$ to give 0.020 g (23%) of a yellow solid: mp=173–175° C.; $^1$H NMR (DMSO-$d_6$) δ 3.45–3.52 (m, 2H), 4.03–4.08 (m, 2H), 5.64 (br s, 1H), 7.23 (t, 1H, J=6.0 Hz), 7.32 (t, 2H, J=9.0 Hz), 7.38–7.55 (m, 3), 7.88 (d, 1H, J=6.0 Hz), 8.36–8.43 (m, 2H), 12.67 (br s, 1H); HRMS calcd. for $C_{20}H_{15}N_4OF$ (M$^+$) 346.1221, found (M$^+$) 346.1225; Anal. for ($C_{20}H_{15}N_4OF$·1.0MeOH) C, H, N.

Example 161
(E)-5-Methyl-6-(5-oxo-2,3,4,5-tetrahydro-1H-benzo[e][1,4]diazepin-9-yl)-hex-5-enoic Acid Methyl Ester

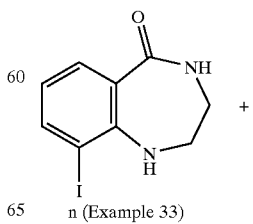

n (Example 33)

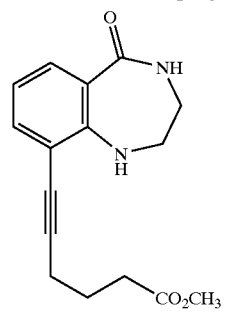

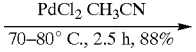

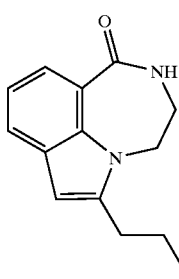

Example 162

(E)-5-Methyl-6-(5-oxo-2,3,4,5-tetrahydro-1H-benzo[e][1,4]diazepin-9-yl)-hex-5-enoic Acid

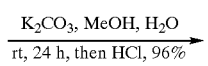

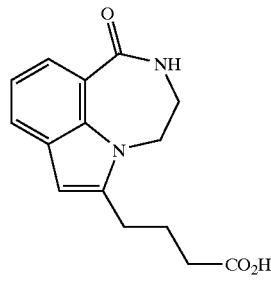

(a) 6-(5-oxo-2,3,4,5-Tetrahydro-1H-benzo[e][1,4]diazepin-9-yl)-hex-5-ynoic Acid Methyl Ester:

To a solution of the intermediate n (Example 33) (9.72 mmol, 2.80 g) in 30 mL DMF and 30 mL diethylamine was added tetrakistriphenylphosphine palladium(0) (0.194 mmol, 0.224 g) triphenyl phosphine (0.0972 mmol, 0.025 g), methyl-5-hexynoate (Footnote) (36.94 mmol, 4.66 g) and CuI (0.194 mmol, 0.037 g) at rt. The reaction mixture was stirred at ambient temperature for 19 h. Upon completion of reaction as indicated by TLC, the solvent was removed in vacuo. The residue was taken up in $H_2O$ and extracted with EtOAc several times. The combined organic extracts was dried over anhydrous $MgSO_4$ and concentrated to give a reddish brown oil which was purified by flash silica gel chromatography eluting with a gradient of 0–5% MeOH in EtOAc to give 2.51 g (90%) of a yellow solid: mp=74–76° C.; $^1$H NMR (DMSO-$d_6$) δ 1.78–1.87 (m, 2H), 2.43–2.54 (m, 4H), 3.24–3.28 (m, 2H), 3.48–3.52 (m, 2H), 3.59 (s, 3H), 6.01 (br s, 1H), 6.54 (t, 1H, J=9.0 Hz), 7.29 (d, 1H, J=9.0 Hz), 7.73 (d, 1H, J=9.0 Hz), 8.04 (t, 1H, J=6.0 Hz); HRMS calcd. for $C_{16}H_{18}N_2O_3$ (M$^+$) 286.1317, found (M$^+$) 286.1318.

(b) Title Compound

Palladium chloride (0.418 mmol, 0.074 g) was added to a solution of 6-(5-Oxo-2,3,4,5-tetrahydro-1H-benzo[e][1,4]diazepin-9-yl)-hex-5-ynoic acid methyl ester (8.36 mmol, 2.39 g) in 50 mL $CH_3CN$. The reaction mixture was heated at 70–80° C. for 2.5 h. The solvent was removed and the residue was purified by flash silica gel chromatography eluting with a gradient of 0–5% MeOH in EtOAc to give 2.11 g (88%) of a yellow solid: mp=175–176° C.; $^1$H NMR (DMSO-$d_6$) δ 1.86–1.98 (m, 2H), 2.43 (t, 2H, J=6.0 Hz), 2.75 (t, 2H, J=6.0 Hz), 3.52–3.54 (m, 2H), 3.57 (s, 3H), 4.21 (br s, 2H), 6.34 (s, 1H), 7.07 (t, 1H, J=6.0 Hz), 7.65 (d, 1H, J=6.0 Hz), 7.75 (d, 1H, J=6.0 Hz), 8.23 (t, 1H, J=6.0 Hz); HRMS calcd. for $C_{16}H_{18}N_2O_3$ (M$^+$) 286.1317, found (M$^+$) 286.1310; Anal. $C_{16}H_{18}N_2O_3 \cdot 0.25H_2O$ C, H, N.

Potassium carbonate (43.32 mmol, 5.987 g) was added to a solution of Example 161 (7.22 mmol, 2.066 g) in 200 mL MeOH (gently heated with a heat gun to get it in solution) and 100 mL $H_2O$. The reaction mixture was stirred at rt for 24 h. The MeOH was removed in vacuo and the residue was taken up in $H_2O$ and extracted with EtOAc. The aqueous layer was made acidic (pH 0–1) using 2N HCl when the product precipitates out of solution as a white solid. The solid was filtered, washed with $H_2O$ and dried (1.878 g; 96%). The product was used without further purification: mp=257–259° C.; $^1$H NMR (DMSO-$d_6$) δ 1.83–1.93 (m, 2H), 2.33 (t, 2H, J=6.0 Hz), 2.75 (t, 2H, J=6.0 Hz), 3.52–3.56 (m, 2H), 4.22 (br s, 2H), 6.34 (s, 1H), 7.07 (t, 1H, J=6.0 Hz), 7.65 (d, 1H, J=6.0 Hz), 7.75 (d, 1H, J=6.0 Hz), 8.23 (t, 1H, J=6.0 Hz), 11.98 (br s, 1H); HRMS calcd. for $C_{15}H_{16}N_2O_3$ (M$^+$) 272.1161, found (M$^+$) 272.1151.

Example 163

7-(1-Hydroxy-ethyl)-3,4-dihydro-2H-[1,4]diazepino[6,7,1-hi]indol-1-one

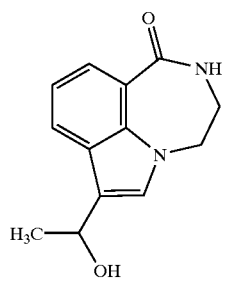

Following the procedure to prepare Example 157, the product was synthesized from 1-oxo-1,2,3,4-tetrahydro-[1,4]diazepino[6,7,1-hi]indole-7-carbaldehyde oxime (Example 45) in 69% yield. Yellow solid: mp=295–297° C.; $^1$H NMR (DMSO-d$_6$) δ 1.47 (d, 3H, J=6.0 Hz), 3.50–3.55 (m, 2H), 4.29–4.31 (m, 2H), 4.95 (d, 1H, J=6.0 Hz), 4.97–5.03 (m, 1H), 7.10 (t, 1H, J=6.0 Hz), 7.25 (s, 1H), 7.81 (d, 1H, J=6.0 Hz), 7.86 (d, 1H, J=6.0 Hz), 8.25 (t, 1H, J=6.0 Hz); HRMS calcd. for $C_{13}H_{14}N_2O_2$ (M$^+$) 231.1134, found (M$^+$) 231.1143; Anal. ($C_{13}H_{14}N_2O_2$) C, H, N.

Example 164

7-Acetyl-3,4-dihydro-2H-[1,4]diazepino[6,7,1-hi]indol-1-one

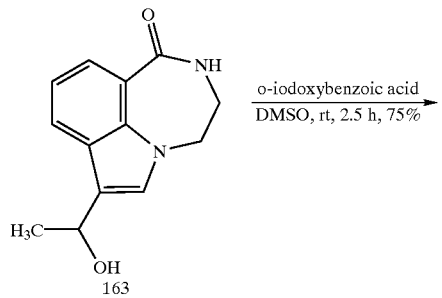

163

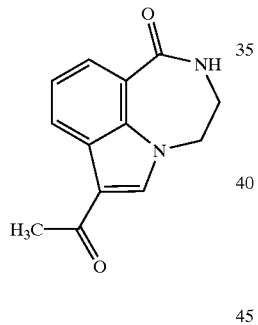

o-Iodoxybenzoic acid (Frigerio, et al., *J. Org. Chem.* 1995, 60, 7272) (2.217 mmol, 0.621 g) was added to a solution of 7-(1-Hydroxy-ethyl)-3,4-dihydro-2H-[1,4]diazepino[6,7,1-hi]indol-1-one (Example 163) (0.739 mmol, 0.170 g) in DMSO (8 mL) at rt. The reaction mixture was stirred at rt for 2.5 h. The solvent was removed in vacuo and the residue was taken up in EtOAc and washed with 5% Na$_2$S$_2$O$_3$/5% NaHCO$_3$, H$_2$O and brine. The organic layer was dried over anhydrous MgSO$_4$ and concentrated to give an orange solid. The solid was purified by flash silica gel chromatography eluting with a gradient of 0–5% MeOH in CHCl$_3$ to give 0.094 g (75%) of a pale pink solid: mp=285–287° C.; $^1$H NMR (DMSO-d$_6$) δ 2.42 (s, 3H), 3.56–3.61 (m, 2H), 4.44 (br s, 2H), 7.32 (t, 1H, J=6.0 Hz), 7.92 (d, 1H, J=6.0 Hz), 8.40–8.44 (m, 3H); HRMS calcd. for $C_{13}H_{12}N_2O_2$ (M$^+$) 228.0899, found (M$^+$) 228.0890; Anal. ($C_{13}H_{12}N_2O_2$) C, H, N.

Example 165

7-(1-Hydroxyimino-ethyl)-3,4-dihydro-2H-[1,4]diazepino[6,7,1-hi]indol-1-one

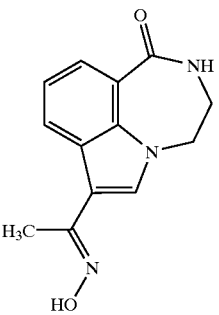

The product was prepared from Example 164 using the procedure to prepare Example 90 in 68% yield as a pale yellow solid: mp=238–240° C.; $^1$H NMR (DMSO-d$_6$) δ 2.16 (s, 3H), 3.56 (br s, 2H), 4.36 (br s, 2H), 7.19 (t, 1H, J=6.0 Hz), 7.77 (s, 1H), 7.87 (d, 1H, J=6.0 Hz), 8.33 (t, 1H, J=6.0 Hz), 8.38 (d, 1H, J=6.0 Hz), 10.67 (s, 1H); HRMS calcd. for $C_{13}H_{13}N_3O_2$ (M$^+$) 243.1008, found (M$^+$) 243.0997; Anal. ($C_{13}H_{13}N_3O_2$) C, H, N.

Example 166

7-(1-Hydroxy-1-phenyl-methyl)-3,4-dihydro-2H-[1,4]diazepino[6,7,1-hi]indol-1-one

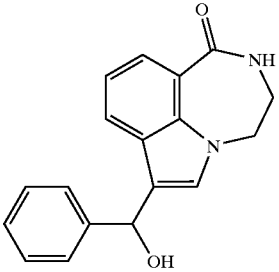

Following the procedure to prepare Example 157, replacing methyllithium with phenyllithium, the product was synthesized from 1-oxo-1,2,3,4-tetrahydro-[1,4]diazepino[6,7,1-hi]indole-7-carbaldehyde oxime (Example 45) in 74% yield as a yellow solid. mp=178–180° C.; $^1$H NMR (DMSO-d$_6$) δ 3.51–3.52 (m, 2H), 4.28–4.29 (m, 2H), 5.70 (d, 1H, J=6.0 Hz), 5.96 (d, 1H, J=6.0 Hz), 7.05 (t, 1H, J=6.0 Hz), 7.14 (s, 1H), 7.17–7.22 (m, 1H), 7.30 (t, 2H, J=6.0 Hz), 7.45 (d, 2H, J=6.0 Hz), 7.72 (d, 1H, J=6.0 Hz), 7.79 (d, 1H, J=6.0 Hz), 8.24 (t, 1H, J=6.0 Hz); HRMS calcd. for $C_{18}H_{16}N_2O_2$ (M$^+$) 292.1212, found (M$^+$) 292.1202; Anal. ($C_{18}H_{16}N_2O_2 \cdot 0.25H_2O$) C, H, N.

Example 167

7-(1-Benzoyl)-3,4-dihydro-2H-[1,4]diazepino[6,7,1-hi]indol-1-one

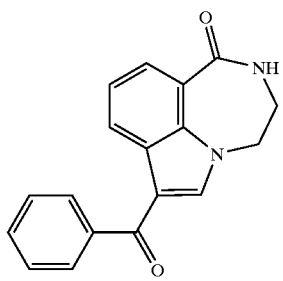

Following the procedure to prepare Example 164, the product was synthesized from Example 166 in 80% yield as a pale yellow solid. mp=229–230° C.; $^1$H NMR (DMSO-$d_6$) δ 3.58–3.61 (m, 2H), 4.47 (br s, 2H), 7.40 (t, 1H, J=6.0 Hz), 7.52–7.65 (m, 3H), 7.79–7.82 (m, 2H), 7.98 (d, 1H, J=6.0 Hz), 8.08 (s, 1H), 8.44 (t, 1H, J=6.0 Hz), 8.51 (d, 1H, J=6.0 Hz); HRMS calcd. for $C_{18}H_{14}N_2O_2$ (M$^+$) 290.1055, found (M$^+$) 290.1042; Anal. ($C_{18}H_{14}N_2O_2$) C, H, N.

Example 168

7-(1-Hydroxyimino-1-phenyl-methyl)-3,4-dihydro-2H-[1,4]diazepino[6,7,1-hi]indol-1-one

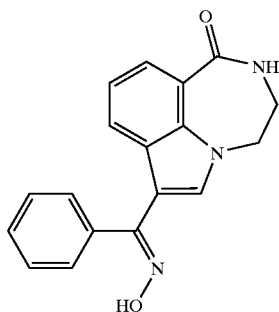

The product was prepared from Example 167 using the procedure to prepare Example 90 in 76% yield as a pale yellow solid: mp=263–265° C.; $^1$H NMR (DMSO-$d_6$) δ 3.51 (br s, 2H), 3.60 (br s, 2H), 4.29 (br s, 2H), 4.45 (br s, 2H), 6.97–7.04 (m, 3H), 7.24 (t, 1H, J=6.0 Hz), 7.34–7.46 (m, 10H), 7.82 (d, 1H, J=6.0 Hz), 7.89–7.93 (m, 2H), 8.31–8.36 (m, 3H), 10.74 (s, 1H), 11.37 (s, 1H); HRMS calcd. for $C_{18}H_{15}N_3O_2$ (M$^+$) 305.1164, found (M$^+$) 305.1177; Anal. ($C_{18}H_{15}N_3O_2 \cdot 0.1H_2O$) C, H, N.

Example 169

4-(9-Fluoro-1-oxo-1,2,3,4-tetrahydro-[1,4]diazepino[6,7,1-hi]indol-6-yl)-benzaldehyde

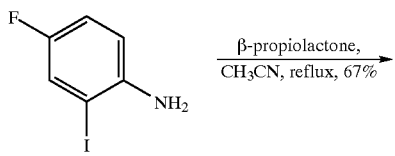

-continued

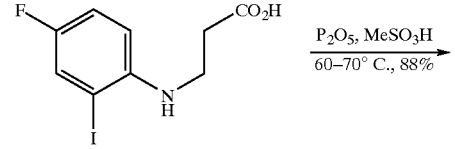

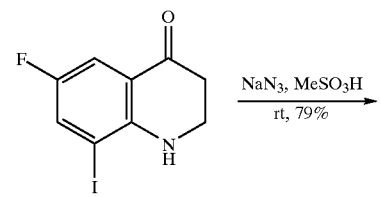

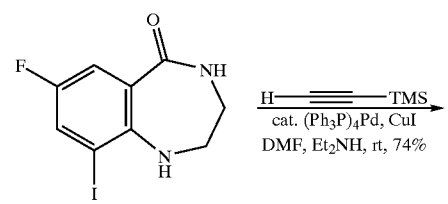

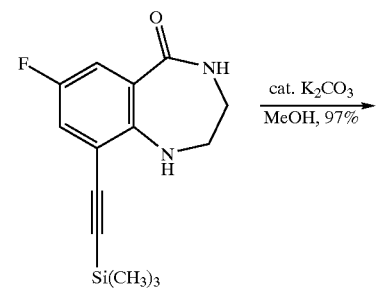

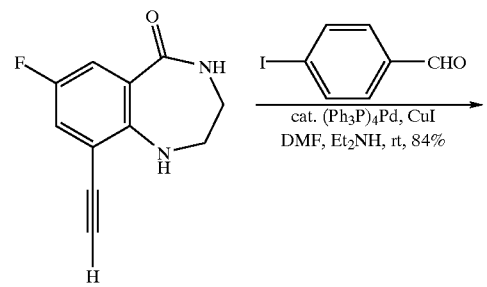

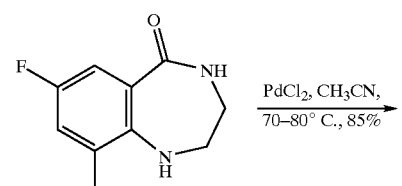

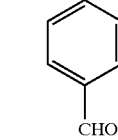

149

-continued

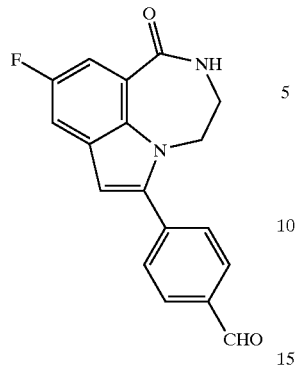

This compound was prepared using the procedures described in Example 33 and 81, starting from 4-Fluoro-2-iodoaniline (Beugelmans, et al., *Bull. Soc. Chim. Fr.*, 1995, 132, 306).

(a) 3-(4-Fluoro-2-iodo-phenylamino)-propionic Acid:

pale purple solid (67%); mp=163–165° C.; $^1$H NMR (DMSO-$d_6$) δ 2.50–2.54 (m, 2H), 3.27–3.33 (m, 2H), 4.72 (t, 1H, J=6.0 Hz), 6.61 (dd, 1H, J=9.0 Hz, 3.0 Hz), 7.06–7.12 (m, 1H), 7.52 (dd, 1H, J=9.0 Hz, 3.0 Hz), 12.27 (br s, 1H); LCMS (M$^+$+H) 310.

(b) 6-Fluoro-8-iodo-2,3-dihydro-1H-quinolin-4-one:

yellow solid (88%); mp=110–112° C.; $^1$H NMR (DMSO-$d_6$) δ 2.52–2.57 (m, 2H), 3.45–3.51 (m, 2H), 6.04 (br s, 1H), 7.36 (dd, 1H, J=9.0, 3.0 Hz), 7.82 (dd, 1H, J=9.0 Hz, 3.0 Hz); LCMS (M$^+$+H) 292.

(c) 7-Fluoro-9-iodo-1,2,3,4-tetrahydro-benzo[e][1,4]diazepin-5-one:

pale yellow solid (79%): mp=138–140° C.; $^1$H NMR (DMSO-$d_6$) δ 3.22–3.29 (m, 2H), 3.43–3.47 (m, 2H), 5.29 (br s, 1H), 7.50 (dd, 1H, J=9.0 Hz, 3.0 Hz), 7.75 (dd, 1H, J=9.0, 3.0 Hz) 8.29 (br s, 1H); LCMS (M$^+$+H) 307.

(d) 7-Fluoro-9-trimethylsilanylethynyl-1,2,3,4-tetrahydro-benzo[e][1,4]diazepin-5-one:

yellow solid (74%); mp=150–152° C.; $^1$H NMR (DMSO-$d_6$) δ 0.24 (s, 9H), 3.25–3.31 (m, 2H), 3.49–3.53 (m, 2H), 5.83 (t, 1H, J=6.0 Hz), 7.28 (dd, 1H, J=9.0, J=3.0 Hz), 7.54 (dd, 1H, J=9.0, 3.0 Hz) 8.27 (t, 1H, J=6.0 Hz); LCMS (M$^+$+H) 277.

(e) 9-Ethynyl-7-fluoro-1,2,3,4-tetrahydro-benzo[e][1,4]diazepin-5-one:

yellow solid (97%); mp=142–144° C.; $^1$H NMR (DMSO-$d_6$) δ 3.24–3.28 (m, 2H), 3.45–3.50 (m, 2H), 4.63 (s, 1H), 6.07 (t, 1H, J=6.0 Hz), 7.32 (dd, 1H, J=9.0, 3.0 Hz), 7.54 (dd, 1H, J=9.0, J=3.0 Hz), 8.25 (t, 1H, J=6.0 Hz); LCMS (M$^+$+H) 205.

(f) 4-(7-Fluoro-5-oxo-2,3,4,5-tetrahydro-1H-benzo[e][1,4]diazepin-9-ylethynyl)-benzaldehyde:

bright yellow solid (84%); mp 228–230° C.; $^1$H NMR (DMSO-$d_6$) δ 3.29–3.32 (m, 2H), 3.52–3.54 (m, 2H), 6.31 (t, 1H, J=6.0 Hz), 7.45 (dd, 1H, J=9.0 Hz, J=3.0 Hz), 7.60 (dd, 1H, J=9.0 Hz, 3.0 Hz), 7.88 (d, 2H, J=9.0 Hz), 7.96 (d, 2H, J=9.0 Hz), 8.31 (t, 1H, J=6.0 Hz), 10.03 (s, 1H); LCMS (M$^+$+H) 309.

(g) Title Compound:

pale yellow solid (85%); mp=212–214° C.; $^1$H NMR (DMSO-$d_6$) δ 3.48–3.53 (m, 2H), 4.36–4.39 (m, 2H), 6.87 (s, 1H), 7.58 (dd, 1H, J=9.0, 3.0 Hz), 7.65 (dd, 1H, J=9.0, 3.0 Hz), 7.86 (d, 2H, J=9.0 Hz), 8.03 (d, 2H, J=9.0 Hz), 8.58 (t, 1H, J=6.0 Hz), 10.09 (s, 1H); LCMS (M$^+$+H) 309.

150

Example 170

6-(4-Dimethylaminomethyl-phenyl)-9-fluoro-3,4-dihydro-2H-[1,4]diazepino[6,7,1-hi]indol-1-one

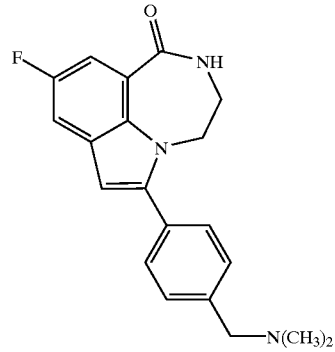

This compound was prepared from 4-(9-Fluoro-1-oxo-1,2,3,4-tetrahydro-[1,4]diazepino[6,7,1-hi]indol-6-yl)-benzaldehyde (Example 169) as described in Example 82 in 91% yield as a pale yellow solid. mp=172–174° C.; $^1$H NMR (DMSO-$d_6$) δ 2.18 (s, 6H), 3.45 (s, 2H), 3.47–3.52 (m, 2H), 4.30–4.33 (m, 2H), 6.69 (s, 1H), 7.43 (d, 2H, J=9.0 Hz), 7.51–7.61 (m, 4H), 8.54 (t, 1H, J=6.0 Hz); HRMS calcd. for $C_{20}H_{20}N_3OF$ (M$^+$) 337.1590, found (M$^+$) 337.1580; Anal. ($C_{20}H_{20}N_3OF$) C, H, N.

Example 171

1-[4-(2,5-Dihydro-pyrrol-1-ylmethyl)-phenyl]-8,9-dihydro-7H-2,7,9a-triaza-benzo[cd]azulen-6-one

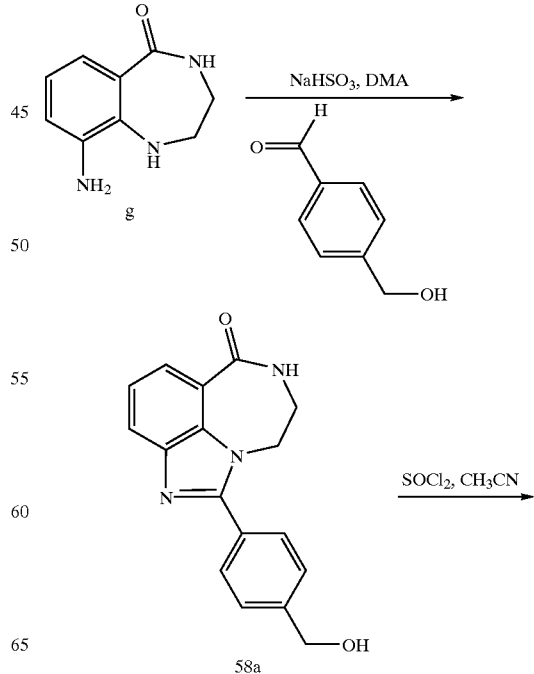

-continued

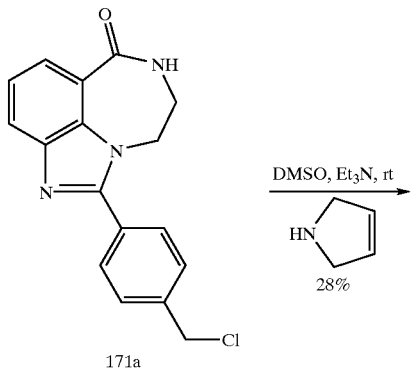

171a

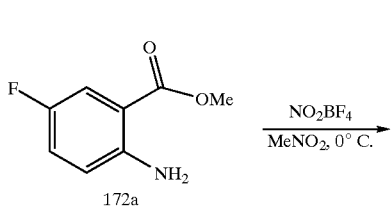

171

(58a) 1-(4-Hydroxymethyl-phenyl)-8,9-dihydro-7H-2,7,9a-triaza-benzo[cd]azulen-6-one, An alternative method for the preparation of Example 58a is to react diamine intermediate g (from Example 2) with 4-hydroxymethyl-benzaldehyde [prepared from sodium borohydride and terephthalaldehyde-mono-diethyl acetal] according to the procedure used in Example 19.

(171a) 1-(4-Chloromethyl-phenyl)-8,9-dihydro-7H-2,7,9a-triaza-benzo[cd]azulen-6-one This compound was prepared by reacting 500 mg (1.7 mmol) of alcohol 58a, suspended in 25 mL of acetonitrile with 4 equivalents of thionyl chloride. After complete conversion as determined by HPLC analysis the reaction was concentrated in vacuo and the crude benzylchloride was without further purification. HPLC Rt=3.060 min.

(171) Title Compound

GENERAL PROCEDURE FOR BENZYLCHLORIDE DISPLACEMENT

A solution containing 0.34 mmol of crude benzylchloride 171a, 2.05 mmol (6 equivalents) of 3-pyrroline and 2.05 mmol (6 equivalents) of triethylamine in 2 mL of DMSO was stirred at rt. for 5 hours. The crude reaction mixture was purified directly by semi-preparative RP HPLC. The appropriate fractions was combined and neutralized with 50% NaOH solution. The product was extracted with EtOAc (×5) to give 36.2 mg (28%) of an off white solid. Subsequently, most compounds were concentrated directly from the HPLC fractions and will contain some fractional percent of TFA.

$^1$H NMR (DMSO-d$_6$) δ 3.45–3.58 (m, 6H), 3.88 (s, 2H), 4.43–4.49 (m, 2H), 5.83 (m, 2H), 7.35 (t, 1H, J=7.8 Hz), 7.53 (d, 2H, J=8.1 Hz), 7.81–7.90 (m, 4H), 8.41 (br s, 1H). HPLC Rt=2.448 min. HRMS calcd for $C_{21}H_{21}N_4O$ 345.1715 (M+H)$^+$, found 345.1699. Anal. ($C_{21}H_{20}N_4O$·0.25EtOAc) C, H, N.

Example 172

4-Fluoro-1-[4-(3-hydroxy-pyrrolidin-1-ylmethyl)-phenyl]-8,9-dihydro-7H-2,7,9a-triaza-benzo[cd]azulen-6-one

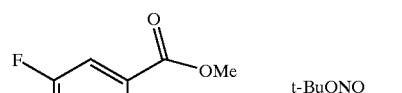

172a

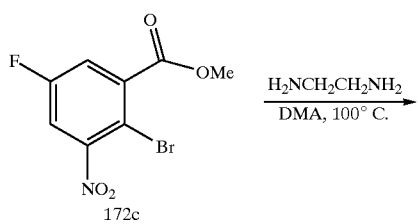

172b

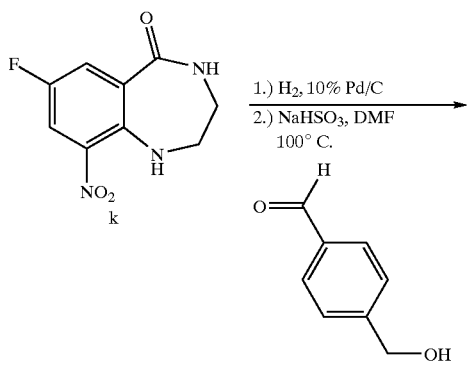

172c

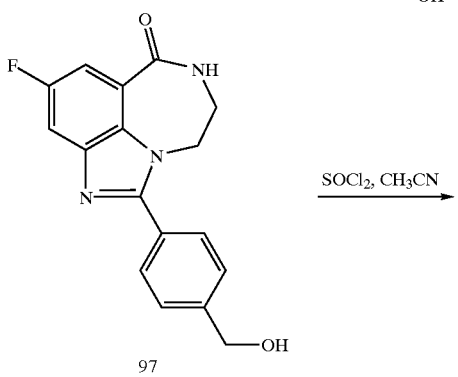

97

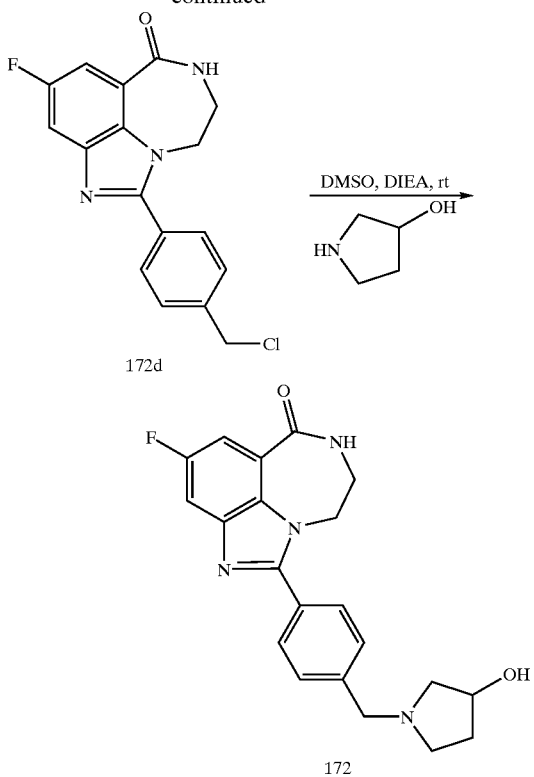

See Example 97 for compound characterization.

Preparation of Example 172.

(172d) 1-(4-Chloromethyl-phenyl)-4-fluoro-8,9-dihydro-7H-2,7,9a-triaza-benzo[cd]azulen-6-one This compound was prepared from intermediate 97 and thionyl chloride using the procedure described in Example 171 for 171a. HPLC Rt=3.260 min.

(172) Title Compound

This compound was prepared from benzylchloride 172d and the appropriate amine as described in Example 171, with exception of substituting DIEA for Et$_3$N. Received 73.3 mg (43%).

$^1$H NMR (DMSO-d$_6$) δ 1.48–1.62 (m, 1H), 1.98–2.05 (m, 1H), 2.37–2.39 (m, 1H), 2.48–2.53 (m, 2H), 2.63–2.75 (m, 2H), 3.54–3.74 (m, 4H), 4.16–4.28 (m, 1H), 4.36–4.51 (m, 2H), 4.63–4.72 (m, 1H), 7.51 (d, 2H, J=8.0 Hz), 7.59 (dd, 1H, J=10.6, 2.6 Hz), 7.72 (dd, 1H, J=10.6, 2.6 Hz), 7.81 (d, 2H, J=8.0 Hz), 8.54–8.58 (m, 1H). HPLC Rt=2.532 min. HRMS calcd for C$_{21}$H$_{22}$FN$_4$O$_2$ 381.1727 (M+H)$^+$, found 381.1717. Anal. (C$_{21}$H$_{21}$FN$_4$O$_2$.0.25H$_2$O) C, H, N.

Example 173

1-[4-((2R)-2-Hydroxymethyl-pyrrolidin-1-ylmethyl)-phenyl]-8,9-dihydro-7H-2,7,9a-triaza-benzo[cd]azulen-6-one

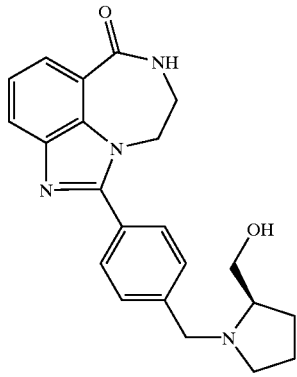

This compound was prepared from intermediate 171a and the appropriate amine using the procedure described in Example 171. Received 54.3 mg (41%).

$^1$H NMR (DMSO-d$_6$) δ 1.53–1.95 (m, 4H), 2.07–2.33 (m, 1H), 2.55–2.93 (m, 2H), 3.35–3.59 (m, 5H), 4.10–4.31 (m, 1H), 4.42–4.53 (m, 3H), 7.35 (t, 1H, J=7.8 Hz), 7.56–7.71 (m, 2H), 7.80–7.90 (m, 4H), 8.40–8.43 (m, 1H). HPLC Rt=2.401 min. HRMS calcd for C$_{22}$H$_{25}$N$_4$O$_2$ 377.1977 (M+H)$^+$, found 377.1989. Anal. (C$_{22}$H$_{24}$N$_4$O$_2$.0.25H$_2$O, 0.40TFA) C, H, N.

Alternate method for formation of intermediate k (from Example 18) and Example 97.

(172b) 2-Amino-5-fluoro-3-nitro-benzoic Acid Methyl Ester

To a solution of nitroso tetrafluoroborate (4.75 g, 35.8 mmol) in 250 mL of nitromethane at 0° C., was added methyl 2-amino-4-fluorobenzoate (Rodriguez, U.S. Pat. No. 3,949,081) (5.50 g, 32.5 mmol). The reaction was stirred at reduced temperature until complete by TLC. The reaction was then concentrated and purified by silica gel chromatography (10–25% EtOAc/Hex) to give 5.05 g of product (72%).

$^1$H NMR (CDCl$_3$) δ 3.95 (s, 3H), 8.04 (dd, 1H, J=8.4, 3.2 Hz), 8.15 (dd, 1H, J=8.4, 3.2 Hz), 8.32 (br s, 2H). LRMS (m/z) 199 (M–CH$_3$).

(172c) 2-Bromo-5-fluoro-3-nitro-benzoic Acid Methyl Ester

This compound was prepared from 2-amino-5-fluoro-3-nitro-benzoic acid methyl ester according to the procedure described in Example 2 for the intermediate b'. Obtained 4.02 g (100%).

$^1$H NMR (DMSO-d$_6$) δ 3.90 (s, 3H), 7.99 (dd, 1H, J=8.3, 3.0 Hz), 8.30 (dd, 1H, J=7.7, 3.0 Hz). HPLC Rt=4.384 min.

(k) 7-Fluoro-9-nitro-1,2,3,4-tetrahydro-benzo[e][1,4]diazepin-5-one

This compound was prepared from 2-bromo-5-fluoro-3-nitro-benzoic acid methyl ester according to the procedure described in Example 2 for the intermediate f. Obtained 2.20 g (68%).

See Example 18 for compound characterization.

(97) 4-Fluoro-1-(4-hydroxymethyl-phenyl)-8,9-dihydro-7H-2,7,9a-triaza-benzo[cd]azulen-6-one This compound was prepared from 7-fluoro-9-nitro-1,2,3,4-tetrahydro-benzo[e][1,4]diazepin-5-one, via reduction to intermediate 1 (Example 18), and 4-hydroxymethyl-benzaldehyde using the procedure described in Example 171.

Example 174

1-[4-(2-Hydroxy-pyrrolidin-1-ylmethyl)-phenyl]-8,9-dihydro-7H-2,7,9a-triaza-benzo[cd]azulen-6-one

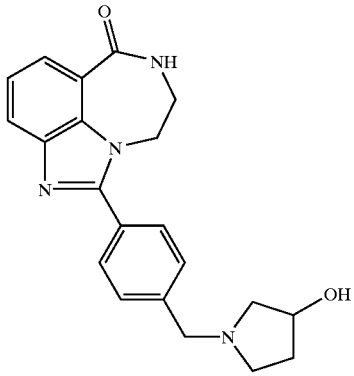

This compound was prepared from intermediate 171a and the appropriate amine using the procedure described in Example 171. Received 26.1 mg (21%).

$^1$H NMR (DMSO-$d_6$) δ 1.55–1.59 (m, 1H), 1.98–2.05 (m, 1H), 2.35–2.39 (m, 1H), 2.59–2.75 (m, 3H), 3.47–3.59 (m, 2H), 3.61–3.72 (m, 2H), 4.19–4.26 (m, 1H), 4.45 (s, 2H), 4.69 (s, 1H), 7.35 (t, 1H, J=7.8 Hz), 7.50 (d, 2H, J=7.8 Hz), 7.80–7.90 (m, 4H), 8.39–8.43 (m, 1H). HPLC Rt=2.281 min. HRMS calcd for $C_{21}H_{23}N_4O_2$ 363.1821 (M+H)$^+$, found 363.1831. Anal. ($C_{21}H_{22}N_4O_2 \cdot 0.25H_2O$) C, H, N.

Example 175

1-[4-(3-Hydroxymethyl-piperidin-1-ylmethyl)-phenyl]-8,9-dihydro-7H-2,7,9a-triaza-benzo[cd]azulen-6-one

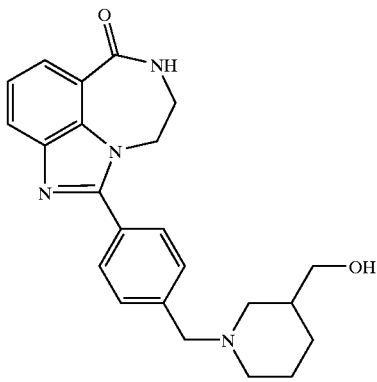

This compound was prepared from intermediate 171a and the appropriate amine using the procedure described in Example 171. Received 57.3 mg (43%).

$^1$H NMR (DMSO-$d_6$) δ 0.82–0.98 (m, 2H), 1.46–1.65 (m, 5H), 1.82–2.12 (m, 1H), 2.73–2.97 (m, 2H), 3.16–3.32 (m, 2H), 3.48–3.69 (m, 3H), 4.33–4.57 (m, 3H), 7.35 (t, 1H, J=7.8 Hz), 7.46–7.67 (m, 2H), 7.78–7.96 (m, 4H), 8.37–8.41 (m, 1H). HPLC Rt=2.496 min. HRMS calcd for $C_{23}H_{27}N_4O_2$ 391.2134 (M+H)$^+$, found 391.2140. Anal. ($C_{23}H_{26}N_4O_2 \cdot 0.25H_2O$) C, H, N.

Example 176

1-(4-{[(2,3-Dihydroxy-propyl)-methyl-amino]-methyl}-phenyl)-8,9-dihydro-7H-2,7,9a-triaza-benzo[cd]azulen-6-one

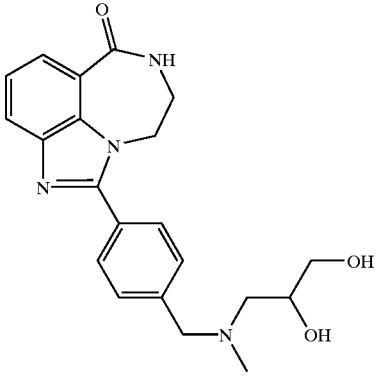

This compound was prepared from intermediate 171a and the appropriate amine using the procedure described in Example 171. Received 36.2 mg (28%).

$^1$H NMR (DMSO-$d_6$) δ 2.2 (s, 3H), 2.33–2.46 (m, 1H), 3.42–3.42 (m, 3H), 3.52–3.78 (m, 5H), 4.33–4.57 (m, 4H), 7.35 (t, 1H, J=7.8 Hz), 7.49–7.62 (m, 2H), 7.78–7.90 (m, 4H), 8.39–8.43 (m, 1H). HPLC Rt=2.247 min. HRMS calcd for $C_{21}H_{25}N_4O_3$ 381.1927 (M+H)$^+$, found 381.1916. Anal. ($C_{21}H_{24}N_4O_3 \cdot 0.25H_2O$, 0.10TFA) C, H, N.

Example 177

1-[4-(2,5-Dihydro-pyrrol-1-ylmethyl)-phenyl]-4-fluoro-8,9-dihydro-7H-2,7,9a-triaza-benzo[cd]azulen-6-one

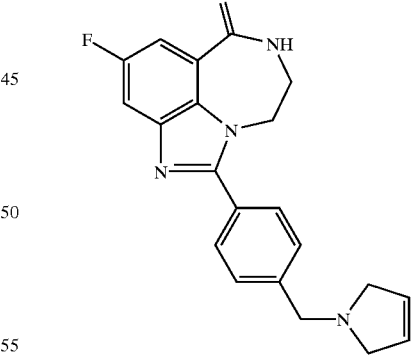

This compound was prepared from intermediate 172d and the appropriate amine using the procedure described in Example 172. Received 50.7 mg (31%).

$^1$H NMR (DMSO-$d_6$) δ 3.46–3.64 (m, 6H), (3.81–3.97 (m, 2H), 4.41–1.62 (m, 2H), 5.82 (s, 2H), 7.52–7.62 (m, 3H), 7.74 (dd, 1H, J=8.2, 2.6 Hz), 7.81 (d, 2H, J=8.1 Hz), 8.55–8.58 (m, 1H). HPLC Rt=3.182 min. HRMS calcd for $C_{21}H_{20}FN_4O$ 363.1621 (M+H)$^+$, found 363.1624. Anal. ($C_{21}H_{19}FN_4O \cdot 0.25H_2O$) C, H, N.

Example 178

1-[4-(4-Allyl-piperazin-1-ylmethyl)-phenyl]-2,7,8,9-tetrahydro-2,7,9a-triaza-benzo[cd]azulen-6-one

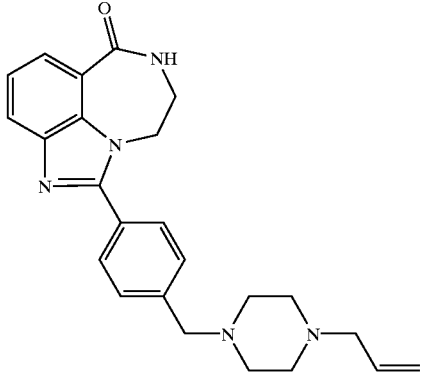

This compound was prepared from intermediate 171a and the appropriate amine using the procedure described in Example 171. Received 65.8 mg (48%).

$^1$H NMR (DMSO-d$_6$) δ 2.27–2.53 (m, 4H), 2.72–3.05 (m, 4H), 3.22–3.35 (m, 2H), 3.48–3.58 (m, 2H), 3.62–3.71 (m, 2H), 4.42–4.59 (m, 2H), 5.36–5.52 (m, 2H), 5.78–5.92 (m, 1H), 7.36 (t, 1H, J=7.8 Hz), 7.48–7.58 (m, 2H), 7.83–7.90 (m, 4H), 8.41–8.45 (m, 1H). HPLC Rt=2.506 min. HRMS calcd for C$_{24}$H$_{28}$N$_4$O 402.2294 (M+H)$^+$, found 402.2288. Anal. (C$_{24}$H$_{27}$N$_4$O.0.80TFA) C, H, N.

Example 179

1-{4-[(Methyl-phenethyl-amino)-methyl]-phenyl}-2,7,8,9-tetrahydro-2,7,9a-triaza-benzo[cd]azulen-6-one

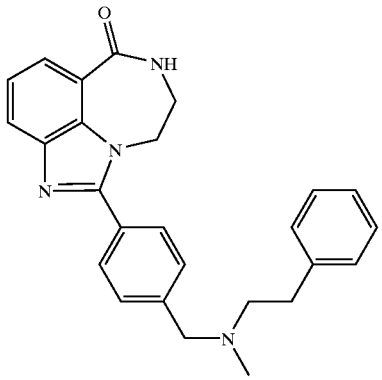

This compound was prepared from intermediate 171a and the appropriate amine using the procedure described in Example 171. Received 47.0 mg (34%).

$^1$H NMR (DMSO-d$_6$) δ 2.65–3.15 (m, 4H), 3.27–3.38 (m, 5H), 3.55–3.64 (m, 2H), 3.62–3.71 (m, 2H), 4.42–4.59 (m, 2H), 7.23–7.47 (m, 6H), 7.89–8.06 (m, 4H), 8.45–8.53 (m, 1H). HPLC Rt=3.075 min. HRMS calcd for C$_{26}$H$_{27}$N$_4$O 411.2185 (M+H)$^+$, found 411.2188. Anal. (C$_{26}$H$_{26}$N$_4$O.0.60TFA) C, H, N.

Example 180

1-(4-{[Butyl-(2-hydroxy-ethyl)-amino]-methyl}-phenyl)-2,7,8,9-tetrahydro-2,7,9a-triaza-benzo[cd]azulen-6-one

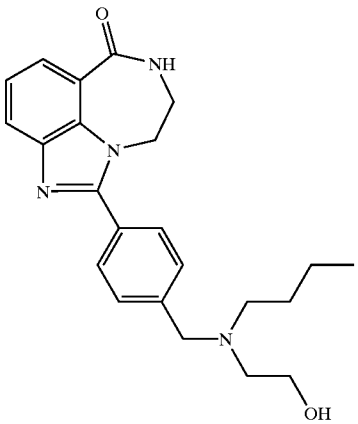

This compound was prepared from intermediate 171a and the appropriate amine using the procedure described in Example 171. Received 32.3 mg (24%).

$^1$H NMR (DMSO-d$_6$) δ 0.81–0.94 (m, 3H), 1.16–1.79 (m, 5H), 2.97–3.37 (m, 4H), 3.46–3.83 (m, 4H), 4.24–4.58 (m, 4H), 7.31–7.40 (m, 1H), 7.46–7.66 (m, 2H), 7.77–7.99 (m, 4H), 8.37–8.46 (m, 1H). HPLC Rt=2.646 min. HRMS calcd for C$_{23}$H$_{29}$N$_4$O 393.2290 (M+H)$^+$, found 393.2288. Anal. (C$_{23}$H$_{28}$N$_4$O.0.60TFA) C, H, N.

Example 181

1-[4-((2S)-2-Hydroxymethyl-pyrrolidin-1-ylmethyl)-phenyl]-2,7,8,9-tetrahydro-2,7,9a-triaza-benzo[cd]azulen-6-one

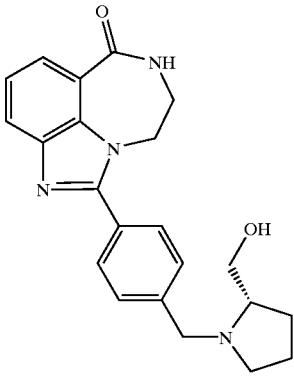

This compound was prepared from intermediate 171a and the appropriate amine using the procedure described in Example 171. Received 31.9 mg (25%).

$^1$H NMR (DMSO-d$_6$) δ 1.71–2.20 (m, 4H), 3.13–3.29 (m, 2H), 3.51–3.66 (m, 5H), 4.32–4.51 (m, 3H), 4.58–4.71 (m, 1H), 5.49–5.58 (m, 1H), 7.37 (t, 1H, J=7.8 Hz), 7.68–7.78 (m, 2H), 7.86–7.99 (m, 4H), 8.42–8.48 (m, 1H). HPLC Rt=2.443 min. HRMS calcd for C$_{22}$H$_{25}$N$_4$O$_2$ 377.1977 (M+H)$^+$, found 377.1993. Anal. (C$_{22}$H$_{24}$N$_4$O$_2$.1.0TFA) C, H, N.

Example 182

1-[4-(3,6-Dihydro-2H-pyridin-1-ylmethyl)-phenyl]-2,7,8,9-tetrahydro-2,7,9a-triaza-benzo[cd]azulen-6-one

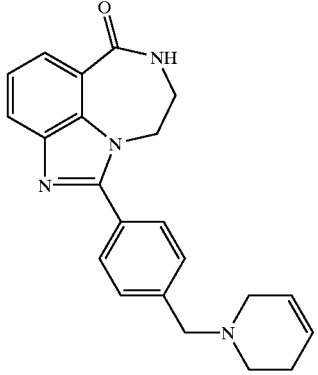

This compound was prepared from intermediate 171a and the appropriate amine using the procedure described in Example 171. Received 48 mg (39%).

$^1$H NMR (DMSO-d$_6$) δ 2.14–2.45 (m, 2H), 2.95–3.21 (m, 2H), 3.43–3.82 (m, 4H), 4.17–4.63 (m, 4H), 5.61–5.78 (m, 1H), 5.81–6.06 (m, 1H), 7.37 (t, 1H, J=7.8 Hz), 7.62–7.76 (m, 2H), 7.86–7.99 (m, 4H), 8.41–8.48 (m, 1H). HPLC Rt=2.610 min. HRMS calcd for C$_{22}$H$_{23}$N$_4$O 359.1872 (M+H)$^+$, found 359.1886. Anal. (C$_{22}$H$_{22}$N$_4$O.0.85TFA) C, H, N.

Example 183

1-[4-(Phenethylamino-methyl)-phenyl]-2,7,8,9-tetrahydro-2,7a-triaza-benzo[cd]azulen-6-one

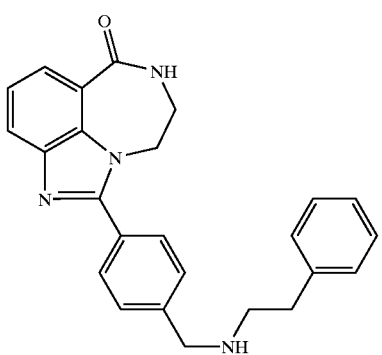

This compound was prepared from intermediate 171a and the appropriate amine using the procedure described in Example 171. Received 188 mg (59%).

$^1$H NMR (DMSO-d$_6$) δ 2.83–2.96 (m, 2H), 3.09–3.20 (m, 2H), 3.41–3.49 (m, 2H), 4.28–4.37 (m, 2H), 4.41–4.52 (m, 3H), 7.12–7.33 (m, 6H), 7.60–7.76 (m, 2H), 7.79–7.89 (m, 4H), 8.33–8.41 (m, 1H). HPLC Rt=2.907 min. HRMS calcd for C$_{25}$H$_{25}$N$_4$O 397.2028 (M+H)$^+$, found 397.2018. Anal. (C$_{25}$H$_{24}$N$_4$O.2.0TFA) C, H, N.

Example 184

1-(4-{[2-(3-Methoxy-phenyl)-ethylamino]-methyl}-phenyl)-2,7,8,9-tetrahydro-2,7,9a-triaza-benzo[cd]azulen-6-one

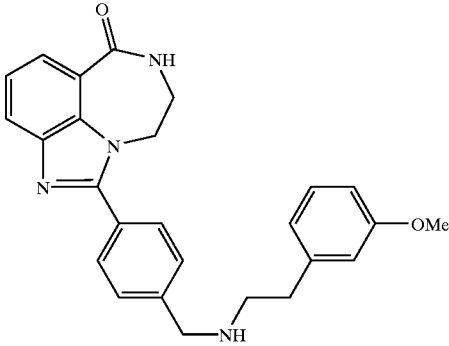

This compound was prepared from intermediate 171a and the appropriate amine using the procedure described in Example 171. Received 148.7 mg (45%).

$^1$H NMR (DMSO-d$_6$) δ 1.91–1.98 (m, 2H), 2.91–2.28 (m, 2H), 3.52–3.61 (m, 2H), 3.73 (s, 3H), 4.30–4.38 (m, 2H), 4.43–4.50 (m, 2H), 6.80–6.89 (m, 4H), 7.25 (t, 1H, J=7.7 Hz), 7.36 (t, 1H, J=7.8 Hz), 7.67 (d, 2H, J=7.8 Hz), 8.84–8.98 (m, 4H), 8.48 (br s, 1H). HPLC Rt=2.970 min. HRMS calcd for C$_{26}$H$_{27}$N$_4$O$_2$ 427.2134 (M+H)$^+$, found 427.2117. Anal. (C$_{26}$H$_{26}$N$_4$O$_2$.2.0TFA) C, H, N.

Example 185

1-(4-{[2-(4-Fluoro-phenyl)-ethylamino]-methyl}-phenyl)-2,7,8,9-tetrahydro-2,7,9a-triaza-benzo[cd]azulen-6-one

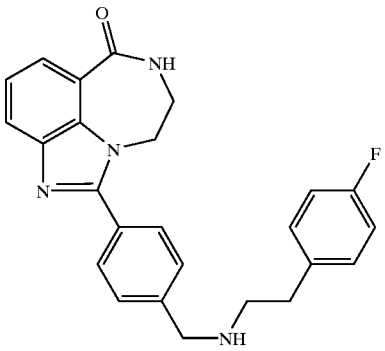

This compound was prepared from intermediate 171a and the appropriate amine using the procedure described in Example 171. Received 132 mg (45%).

$^1$H NMR (DMSO-d$_6$) δ 3.02–3.08 (m, 2H), 3.23–3.33 (m, 2H), 3.58–3.66 (m, 2H), 4.34–4.45 (m, 3H), 4.51–4.59 (m, 2H), 7.22 (t, 1H, J=7.7 Hz), 7.33–7.48 (m, 4H), 7.74 (d, 2H, J=7.7 Hz), 8.93–8.07 (m, 4H), 8.53 (br s, 1H). HPLC Rt=3.000 min. HRMS calcd for C$_{25}$H$_{24}$FN$_4$O 415.1934 (M+H)$^+$, found 415.1914. Anal. (C$_{25}$H$_{23}$FN$_4$O.1.6TFA) C, H, N.

Example 186

1-(4-{[2-(4-Methoxy-phenyl)-ethylamino]-methyl}-phenyl)-2,7,8,9-tetrahydro-2,7,9a-triaza-benzo[cd]azulen-6-one

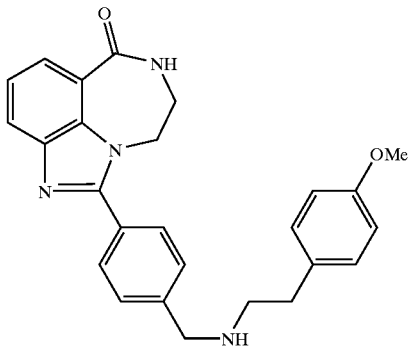

This compound was prepared from intermediate 171a and the appropriate amine using the procedure described in Example 171. Received 163.7 mg (49%).

$^1$H NMR (DMSO-d$_6$) δ 3.04–3.13 (m, 2H), 3.28–3.42 (m, 2H), 3.61–3.77 (m, 2H), 3.88 (s, 3H), 4.45–4.52 (m, 3H), 4.61–4.72 (m, 2H), 7.11 (d, 2H, J=7.7 Hz), 7.35 (d, 2H, J=7.7 Hz), 7.54 (t, 1H, J=7.7 Hz), 7.87 (d, 2H, J=7.7 Hz), 8.06–8.17 (m, 4H), 8.63 (br s, 1H). HPLC Rt=2.970 min. HRMS calcd for C$_{26}$H$_{27}$N$_4$O$_2$ 427.2134 (M+H)$^+$, found 427.2117. Anal. (C$_{26}$H$_{26}$N$_4$O$_2$·2.0TFA) C, H, N.

Example 187

1-{4-[(Isobutyl-methyl-amino)-methyl]-phenyl}-8,9-dihydro-7H-2,7,9a-triaza-benzo[cd]azulen-6-one

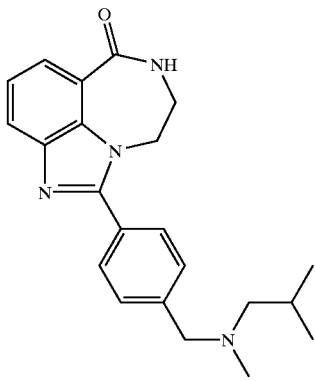

This compound was prepared from intermediate 171a and the appropriate amine using the procedure described in Example 171. Received 64.9 mg (26%).

$^1$H NMR (DMSO-d$_6$) δ 0.88–1.01 (m, 6H), 1.81–1.98 (m, 1H), 2.73–2.84 (m, 3H), 2.85–3.02 (m, 2H), 3.51–3.63 (m, 2H), 4.32–4.55 (m, 4H), 7.37 (t, 1H, J=7.7 Hz), 7.73 (d, 2H, J=7.7 Hz), 7.96–8.14 (m, 4H), 8.43 (br s, 1H). HPLC Rt=2.167 min. HRMS calcd for C$_{22}$H$_{27}$N$_4$O 363.2185 (M+H)$^+$, found 363.2180. Anal. (C$_{22}$H$_{26}$N$_4$O·0.75H$_2$O, 1.0TFA) C, H, N.

Example 188

1-(4-Cyclobutylaminomethyl-phenyl)-8,9-dihydro-7H-2,7,9a-triaza-benzo[cd]azulen-6-one

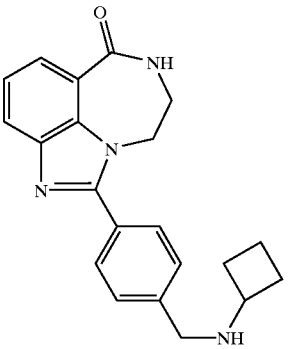

This compound was prepared from intermediate 171a and the appropriate amine using the procedure described in Example 171. Received 58 mg (21%).

$^1$H NMR (DMSO-d$_6$) δ 1.71–1.89 (m, 2H), 2.08–2.24 (m, 4H), 3.51–3.62 (m, 2H), 3.67–3.79 (m, 1H), 4.12–4.18 (m, 2H), 4.39–4.50 (m, 2H), 7.37 (t, 1H, J=7.7 Hz), 7.68 (d, 2H, J=7.7 Hz), 7.87–7.96 (m, 4H), 8.43 (br s, 1H). HPLC Rt=2.531 min. HRMS calcd for C$_{22}$H$_{27}$N$_4$O 363.2185 (M+H)$^+$, found 363.2180. Anal. (C$_{22}$H$_{26}$N$_4$O·0.75H$_2$O, 1.0TFA) C, H, N.

Example 189

1-(4-{[(Thiophen-2-ylmethyl)-amino]-methyl}-phenyl)-8,9-dihydro-7H-2,7,9a-triaza-benzo[cd]azulen-6-one

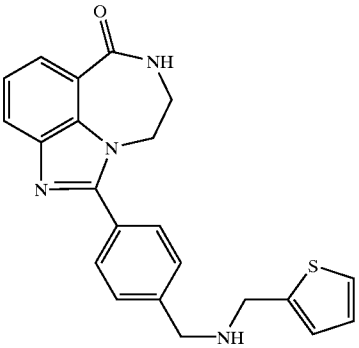

This compound was prepared from intermediate 171a and the appropriate amine using the procedure described in Example 171. Received 63.2 mg (20%).

$^1$H NMR (DMSO-d$_6$) δ 3.51–3.59 (m, 2H), 4.24–4.32 (m, 3H), 4.42–4.51 (m, 4H), 7.11–7.13 (m, 1H), 7.28–7.44 (m, 2H), 7.66–7.70 (m, 3H), 7.78–7.96 (m, 4H), 8.46 (br s, 1H). HPLC Rt=2.686 min. LRMS (m/z) 389 (M+H). Anal. (C$_{22}$H$_{20}$N$_4$OS·2.0TFA) C, H, N.

Example 190

1-(4-Dipropylaminomethyl-phenyl)-8,9-dihydro-7H-2,7,9a-triaza-benzo[cd]azulen-6-one

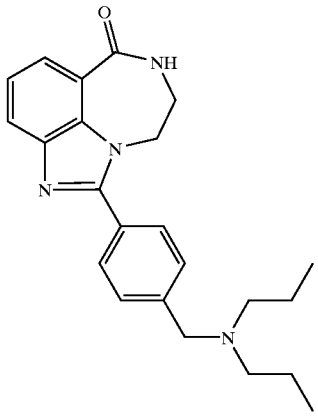

This compound was prepared from intermediate 171a and the appropriate amine using the procedure described in Example 171. Received 56.3 mg (17%).

$^1$H NMR (DMSO-d$_6$) δ 0.90 (t, 6H, J=7.5 Hz), 1.67–1.77 (m, 4H), 2.95–3.07 (m, 4H), 3.52–3.62 (m, 2H), 4.41–4.51 (m, 4H), 7.39 (t, 1H, J=7.8 Hz), 7.73 (d, 2H, J=8.1 Hz), 7.89–7.92 (m, 2H), 7.98 (d, 2H, J=8.1 Hz ), 8.46 (br s, 1H). HPLC Rt=2.844 min. HRMS calcd for C$_{23}$H$_{29}$N$_4$O 377.2341 (M+H)$^+$, found 377.2336. Anal. (C$_{23}$H$_{28}$N$_4$O.0.58H$_2$O, 2.0TFA) C, H, N.

Example 191

1-(4-{[(Benzo[1,3]dioxol-5-ylmethyl)-amino]-methyl}-phenyl)-8,9-dihydro-7H-2,7,9a-triaza-benzo[cd]azulen-6-one

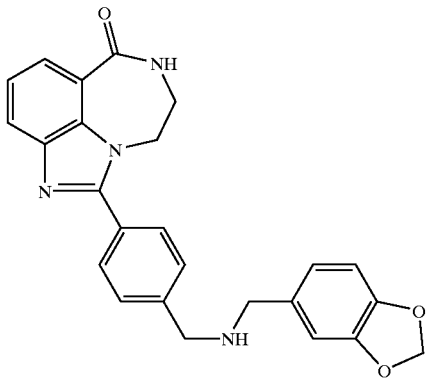

This compound was prepared from intermediate 171a and the appropriate amine using the procedure described in Example 171. Received 154.8 mg (15%).

$^1$H NMR (DMSO-d$_6$) δ 3.51–3.59 (m, 2H), 4.11–4.18 (m, 2H), 4.22–4.31 (m, 3H), 4.43–4.50 (m, 2H), 6.06 (s, 2H), 6.99 (s, 2H), 7.09 (s, 1H), 7.39 (t, 1H, J=7.8 Hz), 7.67 (d, 2H, J=8.2 Hz), 7.89–7.96 (m, 4H), 8.47 (br s, 1H). HPLC Rt=2.839 min. HRMS calcd for C$_{25}$H$_{23}$N$_4$O$_3$ 477.1770 (M+H)$^+$, found 477.1770. Anal. (C$_{25}$H$_{22}$N$_4$O$_3$.2.25TFA) C, H, N.

Example 192

1-[4-(Indan-1-ylaminomethyl)-phenyl]-8,9-dihydro-7H-2,7,9a-triaza-benzo[cd]azulen-6-one

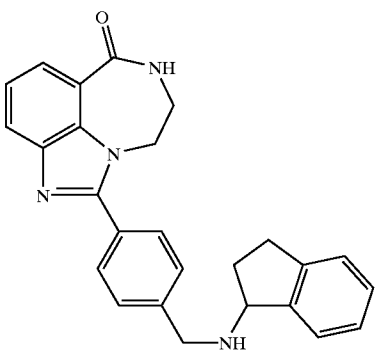

This compound was prepared from intermediate 171a and the appropriate amine using the procedure described in Example 171. Received 75 mg (24%).

$^1$H NMR (DMSO-d$_6$) δ 2.14–2.24 (m, 1H), 2.34–2.42 (m, 1H), 2.74–2.84 (m, 1H), 2.97–3.07 (m, 1H), 3.36–3.46 (m, 2H), 4.19–4.36 (m, 5H), 4.69–4.81 (m, 1H), 7.16–7.27 (m, 4H), 7.53–7.60 (m, 3H), 7.74–7.83 (m, 4H), 8.33 (br s, 1H). HPLC Rt=2.927 min. HRMS calcd for C$_{26}$H$_{25}$N$_4$O 409.2028 (M+H)$^+$, found 409.2030. Anal. (C$_{26}$H$_{24}$N$_4$O.1.9TFA) C, H, N.

Example 193

3-{[4-(6-oxo-6,7,8,9-Tetrahydro-2,7,9a-triaza-benzo[cd]azulen-1-yl)-benzyl]-furan-2-ylmethyl-amino}-propionic Acid Ethyl Ester

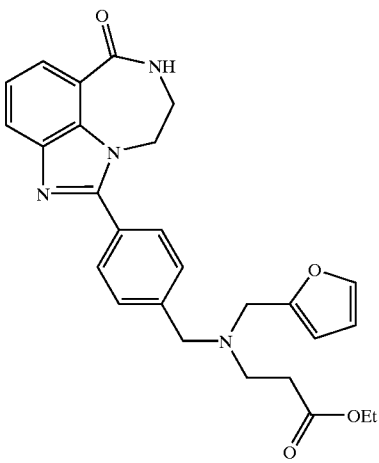

This compound was prepared from intermediate 171a and the appropriate amine using the procedure described in Example 171. Received 55.6 mg (16%).

$^1$H NMR (DMSO-d$_6$) δ 1.17 (t, 3H, J=6.9 Hz), 2.53–2.77 (m, 2H), 2.93–3.13 (m, 2H), 3.51–3.59 (m, 2H), 4.06 (q, 2H, J=8.1 Hz), 4.15–4.47 (m, 6H), 6.53–6.66 (m, 2H), 7.37–7.42 (m, 1H), 7.67–7.92 (m, 7H) 8.45 (br s, 1H). HPLC Rt=3.008 min. HRMS calcd for C$_{27}$H$_{29}$N$_4$O$_4$ 473.2189 (M+H)$^+$, found 473.2208. Anal. (C$_{27}$H$_{28}$N$_4$O$_4$.1.75TFA) C, H, N.

Example 194

1-(4-{[2-(1-Methyl-pyrrolidin-2-yl)-ethylamino]-methyl}-phenyl)-8,9-dihydro-7H-2,7,9a-triaza-benzo[cd]azulen-6-one

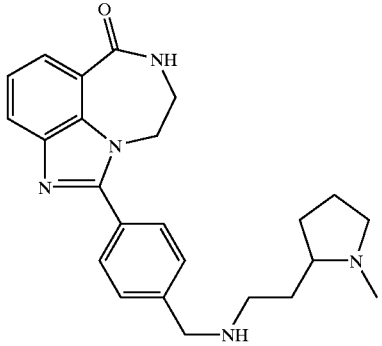

This compound was prepared from intermediate 171a and the appropriate amine using the procedure described in Example 171. Received 57.9 mg (15%).

$^1$H NMR (DMSO-d$_6$) δ 1.53–1.69 (m, 2H), 1.80–2.07 (m, 4H), 2.18–2.34 (m, 2H), 2.82 (s, 3H), 2.97–3.13 (m, 2H), 3.24–3.38 (m, 1H), 3.50–3.64 (m, 3H), 4.23–4.34 (m, 2H), 4.41–4.58 (m, 2H), 7.39 (t, 1H, J=7.8 Hz), 7.81 (d, 2H, J=8.2 Hz), 7.89–8.02 (m, 4H), 8.47 (br s, 1H). HPLC Rt=2.351 min. HRMS calcd for C$_{24}$H$_{30}$N$_5$O 404.2450 (M+H)$^+$, found 404.2456. Anal. (C$_{24}$H$_{29}$N$_5$O.3.25TFA) C, H, N.

Example 195

1-(4-{[(5-Methyl-furan-2-ylmethyl)-amino]-methyl}-phenyl)-8,9-dihydro-7H-2,7,9a-triaza-benzo[cd]azulen-6-one

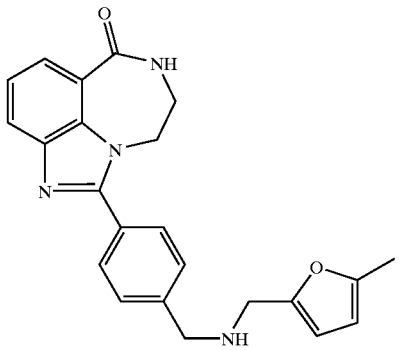

This compound was prepared from intermediate 171a and the appropriate amine using the procedure described in Example 171. Received 64.7 mg (24%).

$^1$H NMR (DMSO-d$_6$) δ 2.30 (s, 3H), 3.49–3.59 (m, 3H), 4.19–4.33 (m, 4H), 4.41–4.51 (m, 2H), 6.15 (m, 1H), 6.51 (m, 1H), 7.37 (t, 1H, J=7.8 Hz), 7.68 (d, 2H, J=8.1 Hz), 7.88–7.95 (m, 4H), 8.46 (br s, 1H). HPLC Rt=2.713 min. HRMS calcd for C$_{23}$H$_{23}$N$_4$O$_2$ 387.1821 (M+H)$^+$, found 387.1817. Anal. (C$_{23}$H$_{22}$N$_4$O$_2$.1.25TFA) C, H, N.

Example 196

1-[4-(Benzylamino-methyl)-phenyl]-8,9-dihydro-7H-2,7,9a-triaza-benzo[cd]azulen-6-one

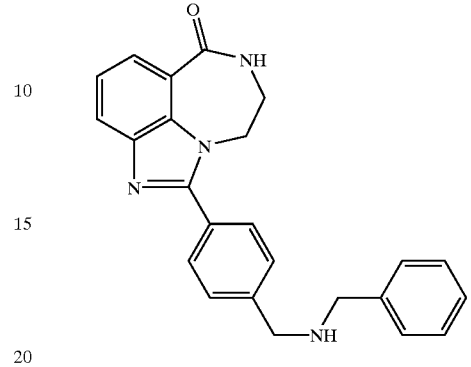

This compound was prepared from intermediate 171a and the appropriate amine using the procedure described in Example 171. Received 73.9 mg (26%).

$^1$H NMR (DMSO-d$_6$) δ 3.51–3.59 (m, 2H), 4.20–4.27 (m, 3H), 4.28–4.35 (m, 2H), 4.47–4.50 (m, 2H), 7.38 (t, 1H, J=7.8 Hz), 7.43–7.53 (m, 5H), 7.70 (d, 2H, J=8.3 Hz), 7.89–7.96 (m, 4H), 8.46 (br s, 1H). HPLC Rt=2.470 min. HRMS calcd for C$_{24}$H$_{23}$N$_4$O 383.1866 (M+H)$^+$, found 383.1883. Anal. (C$_{24}$H$_{22}$N$_4$O.0.5H$_2$O, 1.5TFA) C, H, N.

Example 197

1-[4-(Indan-2-ylaminomethyl)-phenyl]-8,9-dihydro-7H-2,7,9a-triaza-benzo[cd]azulen-6-one

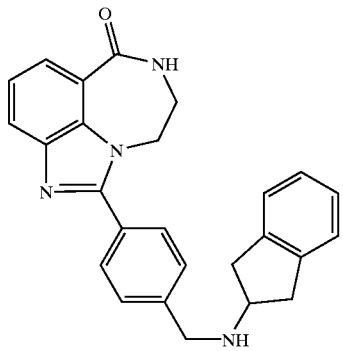

This compound was prepared from intermediate 171a and the appropriate amine using the procedure described in Example 171. Received 138.9 mg (43%).

$^1$H NMR (DMSO-d$_6$) δ 3.13–3.21 (m, 2H), 3.33–3.42 (m, 2H), 3.52–3.59 (m, 2H), 4.05–4.17 (m, 2H), 4.34–4.41 (m, 2H), 4.43–4.50 (m, 2H), 7.20–7.31 (m, 4H), 7.38 (t, 1H, J=7.8 Hz), 7.74 (d, 2H, J=8.3 Hz), 7.88–7.93 (m, 2H), 7.97 (d, 2H, J=8.3 Hz), 8.47 (br s, 1H). HPLC Rt=2.554 min. HRMS calcd for C$_{26}$H$_{25}$N$_4$O 409.2023 (M+H)$^+$, found 409.2034. Anal. (C$_{26}$H$_{24}$N$_4$O.2.0TFA) C, H, N.

Example 198

1-[4-(3,4-Dihydro-1H-isoquinolin-2-ylmethyl)-phenyl]-8,9-dihydro-7H-2,7,9a-triaza-benzo[cd]azulen-6-one

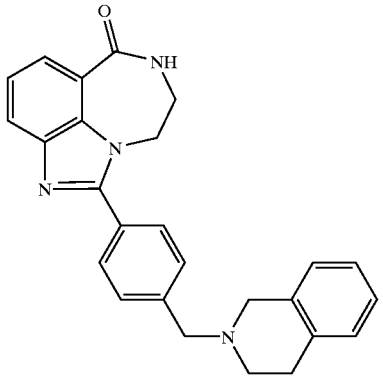

This compound was prepared from intermediate 171a and the appropriate amine using the procedure described in Example 171. Received 142.4 mg (44%).

$^{1}$H NMR (DMSO-d$_{6}$) δ 3.09–3.17 (m, 2H), 3.33–3.46 (m, 1H), 3.51–3.60 (m, 2H), 3.67–3.79 (m, 1H), 4.37–4.44 (m, 2H), 4.47–4.54 (m, 2H), 4.55–4.63 (m, 2H), 7.21–7.31 (m, 4H), 7.39 (t, 1H, J=7.8 Hz), 7.77 (d, 2H, J=8.2 Hz), 7.89–7.94 (m, 2H), 7.99 (d, 2H, J=8.2 Hz), 8.47 (br s, 1H). HPLC Rt=2.336 min. HRMS calcd for C$_{26}$H$_{25}$N$_{4}$O 409.2023 (M+H)$^{+}$, found 409.2015. Anal. (C$_{26}$H$_{24}$N$_{4}$O.2.0TFA) C, H, N.

Example 199

1-[4-(Benzyl-methyl-amino-methyl)-phenyl]-8,9-dihydro-7H-2,7,9a-triaza-benzo[cd]azulen-6-one

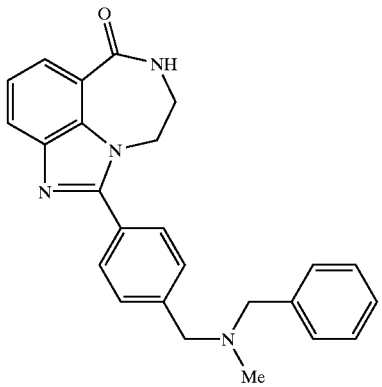

This compound was prepared from intermediate 171a and the appropriate amine using the procedure described in Example 171. Received 197.6 mg (62%).

$^{1}$H NMR (DMSO-d$_{6}$) δ 2.61 (s, 3H), 3.52–3.59 (m, 2H), 4.22–4.40 (m, 2H), 4.45–4.62 (m, 4H), 7.39 (t, 1H, J=7.8 Hz), 7.43–7.56 (m, 5H), 7.73 (d, 2H, J=8.2 Hz) 7.89–7.93 (m, 2H), 7.97 (d, 2H, J=8.2 Hz), 8.47 (br s, 1H). HPLC Rt=2.333 min. HRMS calcd for C$_{25}$H$_{25}$N$_{4}$O 397.2023 (M+H)$^{+}$, found 397.2035. Anal. (C$_{25}$H$_{24}$N$_{4}$O.0.25H$_{2}$O, 2.0TFA) C, H, N.

Example 200

1-{4-[(2-Phenyl-propylamino)-methyl]-phenyl}-8,9-dihydro-7H-2,7,9a-triaza-benzo[cd]azulen-6-one

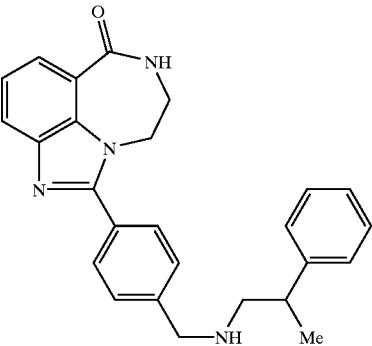

This compound was prepared from intermediate 171a and the appropriate amine using the procedure described in Example 171. Received 108.2 mg (33%).

$^{1}$H NMR (DMSO-d$_{6}$) δ 1.28 (s, 3H), 3.14–3.24 (m, 3H), 3.51–3.59 (m, 2H), 4.22–4.30 (m, 2H), 4.42–4.50 (m, 3H), 7.25–7.41 (m, 6H), 7.68 (d, 2H, J=8.3 Hz), 7.88–7.96 (m, 4H), 8.47 (br s, 1H). HPLC Rt=2.248 min. HRMS calcd for C$_{26}$H$_{27}$N$_{4}$O 411.2179 (M+H)$^{+}$, found 411.2193. Anal. (C$_{26}$H$_{26}$N$_{4}$O.2.0TFA) C, H, N.

Example 201

1-{4-[(3-Phenyl-propylamino)-methyl]-phenyl}-8,9-dihydro-7H-2,7,9a-triaza-benzo[cd]azulen-6-one

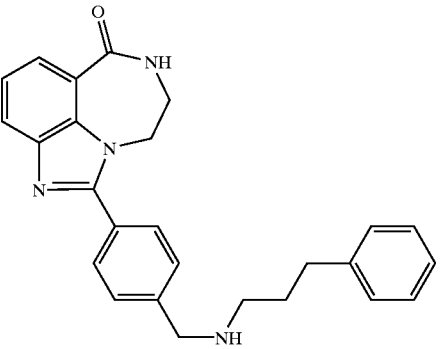

This compound was prepared from intermediate 171a and the appropriate amine using the procedure described in Example 171. Received 73.2 mg (22%).

$^{1}$H NMR (DMSO-d$_{6}$) δ 1.90–2.00 (m, 2H), 2.64–2.69 (m, 2H), 2.93–3.05 (m, 2H), 3.50–3.60 (m, 2H), 4.25–4.31 (m, 2H), 4.40–4.51 (m, 3H), 7.18–7.36 (m, 5H), 7.39 (t, 1H, J=7.9 Hz), 7.68 (d, 2H, J=8.2 Hz), 7.88–7.96 (m, 4H), 8.47 (br s, 1H). HPLC Rt=3.092 min. HRMS calcd for C$_{26}$H$_{27}$N$_{4}$O 411.2179 (M+H)$^{+}$, found 411.2186. Anal. (C$_{26}$H$_{26}$N$_{4}$O.2.0TFA) C, H, N.

Example 202

1-(4-{[Methyl-(2-pyridin-2-yl-ethyl)-amino]-methyl}-phenyl)-8,9-dihydro-7H-2,7,9a-triaza-benzo[cd]azulen-6-one

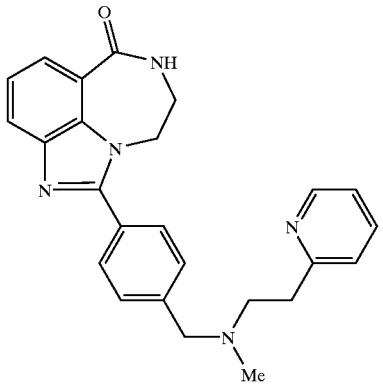

This compound was prepared from intermediate 171a and the appropriate amine using the procedure described in Example 171. Received 16.2 mg (6%).

$^1$H NMR (DMSO-d$_6$) δ 2.51 (s, 3H), 3.27–3.46 (m, 4H), 3.55–3.67 (m, 2H), 4.01–4.13 (m, 2H), 4.48–4.59 (m, 2H), 7.37–7.49 (m, 2H), 7.54–7.75 (m, 3H), 7.84–8.11 (m, 6H), 8.50 (br s, 1H). HPLC Rt=2.174 min. HRMS calcd for C$_{25}$H$_{26}$N$_5$O 412.2132 (M+H)$^+$, found 412.2139. Anal. (C$_{25}$H$_{25}$N$_5$O.1.0H$_2$O, 3.0TFA) C, H, N.

Example 203

1-(4-{[Ethyl-(2-pyridin-2-yl-ethyl)-amino]-methyl}-phenyl)-8,9-dihydro-7H-2,7,9a-triaza-benzo[cd]azulen-6-one

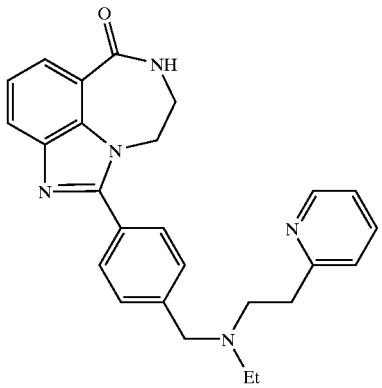

This compound was prepared from intermediate 171a and the appropriate amine using the procedure described in Example 171. Received 14 mg (4%).

$^1$H NMR (DMSO-d$_6$) δ 1.06–1.23 (m, 3H), 2.62–2.79 (m, 4H), 3.53–3.67 (m, 4H), 3.87–3.98 (m, 2H), 4.46–4.58 (m, 2H), 7.35–7.46 (m, 2H), 7.55–7.67 (m, 3H), 7.82–8.00 (m, 6H), 8.48 (br s, 1H). HPLC Rt=2.214 min. HRMS calcd for C$_{26}$H$_{28}$N$_5$O 426.2288 (M+H)$^+$, found 426.2285. Anal. (C$_{26}$H$_{27}$N$_5$O.0.5H$_2$O, 3.0TFA) C, H, N.

Example 204

1-{4-[(2-Pyridin-2-yl-ethylamino)-methyl]-phenyl}-8,9-dihydro-7H-2,7,9a-triaza-benzo[cd]azulen-6-one

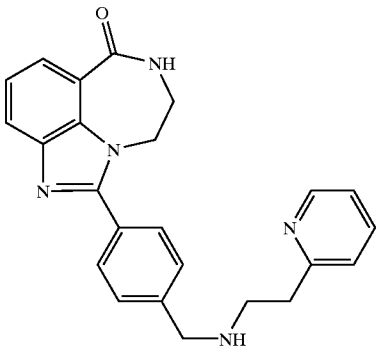

This compound was prepared from intermediate 171a and the appropriate amine using the procedure described in Example 171. Received 15.8 mg (5%).

$^1$H NMR (DMSO-d$_6$) δ 3.13–3.21 (m, 2H), 3.34–3.44 (m, 2H), 3.51–3.59 (m, 2H), 4.32–4.39 (m, 3H), 4.44–4.49 (m, 2H), 7.30–7.42 (m, 3H), 7.59 (d, 2H, J=8.2 Hz), 7.67–7.83 (m, 1H), 7.89–7.98 (m, 4H), 8.47 (br s, 1H), 8.54 (s, 1H). HPLC Rt=2.506 min.

HRMS calcd for C$_{24}$H$_{24}$N$_5$O 398.1975 (M+H)$^+$, found 398.1969. Anal. (C$_{24}$H$_{23}$N$_5$O.0.5H$_2$O, 2.25TFA) C, H, N.

Example 205

1-(4-{[Methyl-(2-pyridin-4-yl-ethyl)-amino]-methyl}-phenyl)-8,9-dihydro-7H-2,7,9a-triaza-benzo[cd]azulen-6-one

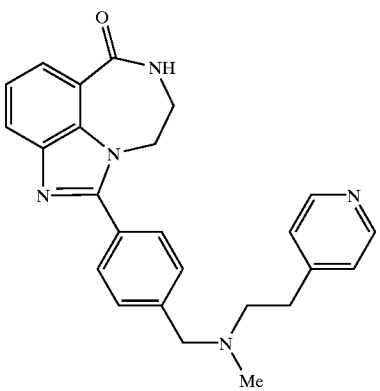

This compound was prepared from intermediate 171a and the appropriate amine using the procedure described in Example 171. Received 5.4 mg (5%).

$^1$H NMR (DMSO-d$_6$) δ 2.93–3.23 (m, 3H), 3.24–3.87 (m, 8H), 3.88–4.15 (m, 2H), 4.44–4.49 (m, 2H), 7.06–8.01 (m, 9H), 8.54 (br s, 1H). HPLC Rt=2.275 min. HRMS calcd for C$_{25}$H$_{26}$N$_5$O 412.2132 (M+H)$^+$, found 412.2124. Anal. (C$_{25}$H$_{25}$N$_5$O.0.5H$_2$O, 3.5TFA) C, H, N.

Example 206

1-{4-[(2-Pyridin-4-yl-ethylamino)-methyl]-phenyl}-8,9-dihydro-7H-2,7,9a-triaza-benzo[cd]azulen-6-one

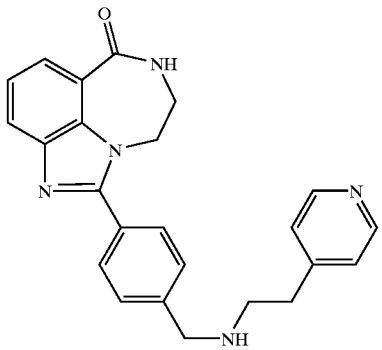

This compound was prepared from intermediate 171a and the appropriate amine using the procedure described in Example 171. Received 11.6 mg (3%).

$^1$H NMR (DMSO-d$_6$) δ 2.75–2.89 (m, 4H), 3.48–3.57 (m, 3H), 3.84–3.89 (m, 2H), 4.41–4.50 (m, 2H), 7.24–7.27 (m, 2H), 7.35 (t, 1H, J=7.8 Hz), 7.52 (d, 2H, J=8.1 Hz), 7.81 (d, 2H, J=8.1 Hz), 7.87 (t, 2H, J=7.6 Hz), 8.38–8.48 (m, 3H). HPLC Rt=2.346 min. HRMS calcd for C$_{24}$H$_{24}$N$_5$O 398.1975 found 398.1969. Anal. (C$_{24}$H$_{23}$N$_5$O.0.75H$_2$O, 3.25TFA) C, H, N.

Example 207

1-[4-({[2-(1H-Indol-2-yl)-ethyl]-methyl-amino}-methyl)-phenyl]-8,9-dihydro-7H-2,7,9a-triaza-benzo[cd]azulen-6-one

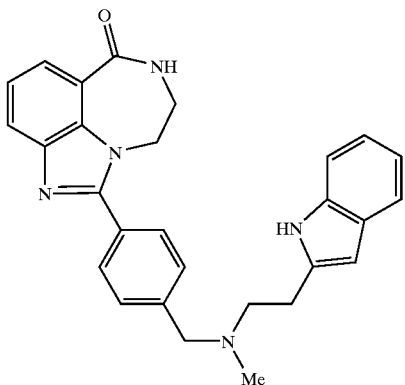

This compound was prepared from intermediate 171a and the appropriate amine using the procedure described in Example 171. Received 18.8 mg (5%).

$^1$H NMR (DMSO-d$_6$) δ 2.32 (s, 3H), 2.64–2.78 (m, 2H), 2.88–2.97 (m, 2H), 3.49–3.57 (m, 2H), 3.63–3.75 (m, 2H), 4.42–4.49 (m, 2H), 6.93 (t, 1H, J=6.9 Hz), 7.04 (t, 1H, J=7.1 Hz), 7.14 (s, 1H), 7.31 (d, 1H, J=7.2 Hz), 7.31 (d, 1H, J=7.2 Hz), 7.36 (d, 1H, J=7.8 Hz), 7.45 (d, 1H, J=7.8 Hz), 7.49–7.55 (m, 2H), 7.78–7.83 (m, 2H), 7.88 (t, 2H, J=8.6 Hz), 8.41 (br s, 1H). HPLC Rt=3.170 min. HRMS calcd for C$_{28}$H$_{28}$N$_5$O 450.2288 (M+H)$^+$, found 450.2279. Anal. (C$_{28}$H$_{27}$N$_5$O.1.0H$_2$O, 2.5TFA) C, H, N.

Example 208–209

1-(4-Aminomethyl-phenyl)-8,9-dihydro-7H-2,7,9a-triaza-benzo[cd]azulen-6-one

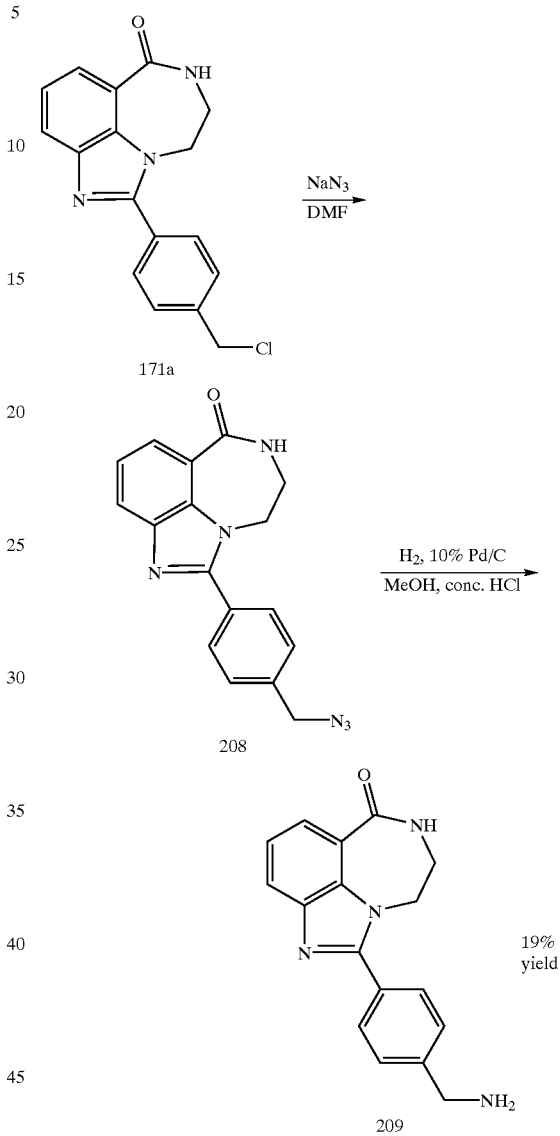

(208) 1-(4-Azidomethyl-phenyl)-8,9-dihydro-7H-2,7,9a-triaza-benzo[cd]azulen-6-one 1-(4-Chloromethyl-phenyl)-8,9-dihydro-7H-2,7,9a-triaza-benzo[cd]azulen-6-one (0.24 g, 0.77 mmol) was stirred in DMF (8 mL) with sodium azide (0.050 g, 0.77 mmol) for three hours. The solvent was removed by evaporation and the product was used without further purification.

IR (KBr) 3204, 3096, 2229, 1654, 1600, 1603, 1319, 1139 cm$^{-1}$, $^1$H NMR (DMSO-d$_6$) δ 3.50–3.58 (m, 2H), 4.43–4.50 (m, 2H), 4.59 (s, 2H), 7.36 (t, 1H, J=7.9 Hz), 7.58 (d, 2H, J=8.2 Hz), 7.86–7.94 (m, 4H), 8.44 (br s, 1H). HPLC Rt=3.059 min.

(209) Title Compound

The crude 1-(4-azidomethyl-phenyl)-8,9-dihydro-7H-2,7,9a-triaza-benzo[cd]azulen-6-one from above was dissolved in 10 mL of 9:1 CH$_3$OH/HCl(conc.) and placed in a Parr shaker under H$_2$ atmosphere (60 psi) with 200 mg 10% Pd/C. After 2 hours, the reaction mixture was filtered through Celite®, the solvent reduced and the residue purified by prep RP-HPLC. Received 49.0 mg (19%).

¹H NMR (DMSO-d₆) δ 3.46–3.54 (m, 2H), 4.06–4.15 (m, 2H), 4.36–4.43 (m, 2H), 7.32 (t, 1H, J=7.5 Hz), 7.60 (d, 2H, J=8.2 Hz), 7.81–7.90 (m, 4H), 8.17 (br s, 2H), 8.40 (br s, 1H). HPLC Rt=2.109 min. HRMS calcd for C₁₇H₁₇N₄O 293.1406 (M+H)⁺, found 293.1397. Anal. (C₁₇H₁₆N₄O.0.5H₂O, 1.75 TFA) C, H, N.

Example 210

1-(4-Pyrrolidin-1-ylmethyl-phenyl)-8,9-dihydro-7H-2,7,9a-triaza-benzo[cd]azulen-6-one

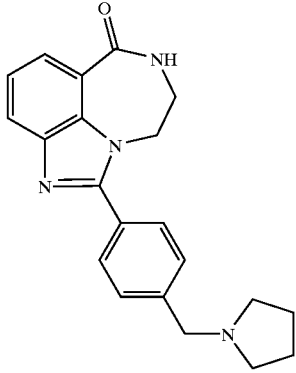

This compound was prepared from intermediate 171a and the appropriate amine using the procedure described in Example 171. Received 145.0 mg (41%)

¹H NMR (DMSO-d₆) δ 1.69–1.76 (m, 4H), 2.50–2.55 (m, 4H), 3.50–3.56 (m, 2H), 3.67–3.72 (m, 2H), 4.43–4.48 (m, 2H), 7.35 (t, 1H, J=7.8 Hz), 7.51 (d, 2H, J=8.1 Hz), 7.81 (d, 2H, J=8.1 Hz), 7.85–7.91 (m, 2H), 8.41 (br s, 1H). HPLC Rt=2.501 min. HRMS calcd for C₂₁H₂₃N₄O 347.1866 (M+H)⁺, found 347.1877. Anal. (C₂₁H₂₂N₄O.0.25EtOAc) C, H, N.

Example 211

4-Fluoro-1-(4-pyrrolidin-1-ylmethyl-phenyl)-8,9-dihydro-7H-2,7,9a-triaza-benzo[cd]azulen-6-one

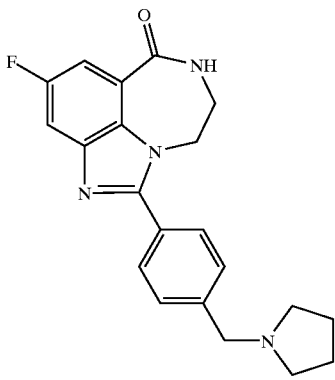

This compound was prepared from intermediate 172d and the appropriate amine using the procedure described in Example 172. Received 180.0 mg (47%)

¹H NMR (DMSO-d₆) δ 1.69–1.75 (m, 4H), 2.44–2.48 (m, 4H), 3.51–3.58 (m, 2H), 3.66–3.69 (m, 2H), 4.43–4.48 (m, 2H), 7.51 (d, 2H, J=8.2 Hz), 7.59 (dd, 1H, J=10.7, 2.6 Hz), 7.74 (dd, 1H, J=9.0, 2.6 Hz), 7.80 (d, 2H, J=8.2 Hz), 8.57 (br s, 1H). HPLC Rt=2.560 min. HRMS calcd for C₂₁H₂₂FN₄O 365.1772 (M+H)⁺, found 365.1759. Anal. (C₂₁H₂₁FN₄O.0.1EtOAc) C, H, N.

Example 212

1-[4-(2-Methyl-pyrrolidin-1-ylmethyl)-phenyl]-8,9-dihydro-7H-2,7,9a-triaza-benzo[cd]azulen-6-one

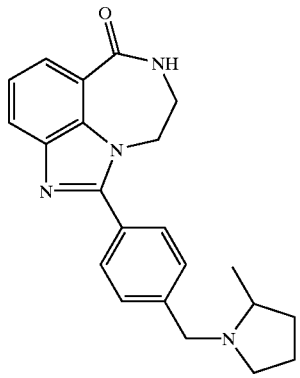

This compound was prepared from intermediate 171a and the appropriate amine using the procedure described in Example 171. Received 155.7 mg (67%)

¹H NMR (DMSO-d₆) δ 1.12 (d, 3H, J=6 Hz), 1.33–1.39 (m, 1H), 1.58–1.65 (m, 1H), 1.90–1.96 (m, 2H), 2.06–2.11 (m, 1H), 2.41–2.53 (m, 1H), 2.80–2.86 (m, 1H), 3.24 (d, 1H, J=13.5 Hz), 3.50–3.57 (m, 2H), 4.05 (d, 1H, J=13.5 Hz), 4.43–4.49 (m, 2H), 7.35 (t, 1H, J=7.8 Hz), 7.49 (d, 2H, J=8.1 Hz), 7.80 (d, 2H, J=8.1 Hz), 7.85–7.90 (m, 2H), 8.41 (br s, 1H). HPLC Rt=2.622 min. LRMS (m/z) 361 (M+H). Anal. (C₂₂H₂₄N₄O) C, H, N.

Example 213

1-(4-Imidazol-1-ylmethyl-phenyl)-8,9-dihydro-7H-2,7,9a-triaza-benzo[cd]azulen-6-one

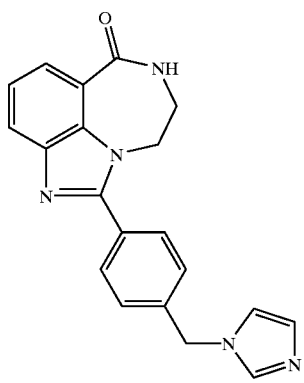

This compound was prepared from intermediate 171a and the appropriate amine using the procedure described in Example 171. Received 141 mg (26%)

¹H NMR (DMSO-d₆) δ 3.48–3.57 (m, 2H), 3.40–4.48 (m, 2H), 5.55 (s, 2H), 7.38 (t, 1H, J=7.8 Hz), 7.61 (d, 2H, J=8.1 Hz), 7.72 (m, 1H), 7.85 (m, 1H), 7.88–7.93 (m, 4H), 8.45 (t, 1H, J=5.5 Hz), 9.29 (s, 1H). HPLC Rt=2.410 min. HRMS calcd for C₂₀H₁₈N₅O 344.1506 (M+H)⁺, found 344.1517. Anal. (C₂₀H₁₇N₅O.2.0TFA) C, H, N.

Example 214

1-[4-(2,5-Dimethyl-pyrrolidin-1-ylmethyl)-phenyl]-8,9-dihydro-7H-2,7,9a-triaza-benzo[cd]azulen-6-one

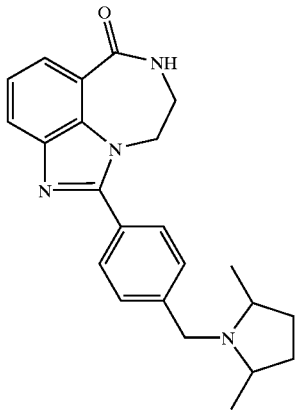

This compound was prepared from intermediate 171a and the appropriate amine using the procedure described in Example 171. Received 153.7 mg (43%)

$^1$H NMR (DMSO-d$_6$) δ 0.98 (s, 3H), 1.00 (s, 3H), 1.28–1.37 (m, 2H), 1.77–1.85 (m, 2H), 2.54–2.73 (m, 2H), 3.49–3.56 (m, 2H), 3.76 (s, 2H), 4.42–4.48 (m, 2H), 7.35 (t, 1H, J=7.8 Hz), 7.51 (d, 2H, J=8.1 Hz), 7.79 (d, 2H, J=8.1 Hz), 7.84–7.89 (m, 2H), 8.41 (br s, 1H). HPLC Rt=2.646 min. LRMS (m/z) 375 (M+H). Anal. (C$_{23}$H$_{26}$N$_4$O) C, H, N.

Example 215

1-[4-(1,3,3-Trimethyl-6-aza-bicyclo[3.2.1]oct-6-ylmethyl)-phenyl]-8,9-dihydro-7H-2,7,9a-triaza-benzo[cd]azulen-6-one

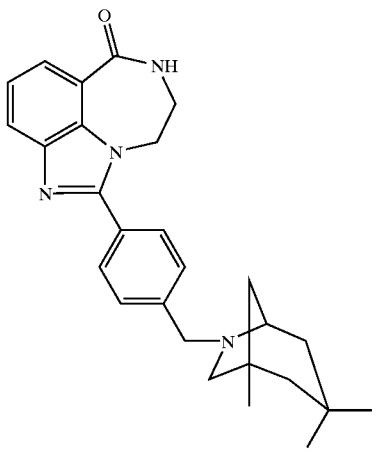

This compound was prepared from intermediate 171a and the appropriate amine using the procedure described in Example 171. Received 155.3 mg (36%)

$^1$H NMR (DMSO-d$_6$) δ 0.88 (s, 3H), 1.01 (s, 3H), 1.31 (t, 2H, J=10.3 Hz), 1.30–1.43 (m, 5H), 1.48–1.59 (m, 1H), 1.61–1.72 (m, 1H), 2.12 (d, 1H, J=9.4 Hz), 2.91 (d, 1H, J=9.4 Hz), 3.04 (m, 1H), 3.48–3.57 (m, 2H), 3.75 (d, 1H, J=14.2 Hz), 3.89 (d, 1H, J=14.2 Hz), 4.42–4.49 (m, 2H), 7.34 (t, 1H, J=7.8 Hz), 7.53 (d, 2H, J=8.2 Hz), 7.80 (d, 2H, J=8.2 Hz), 7.84–7.90 (m, 2H), 8.41 (br s, 1H). HPLC Rt=3.256 min. LRMS (m/z) 429 (M+H). Anal. (C$_{27}$H$_{32}$N$_4$O·0.5CH$_3$OH) C, H, N.

Example 216

1-[4-((2S,5S)-2,5-bis-Methoxymethyl-pyrrolidin-1-ylmethyl)-phenyl]-8,9-dihydro-7H-2,7,9a-triaza-benzo[cd]azulen-6-one

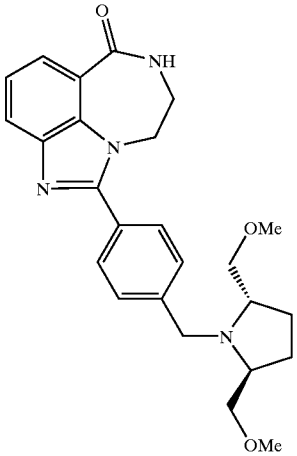

This compound was prepared from intermediate 171a and the appropriate amine using the procedure described in Example 171. Received 123 mg (29%)

$^1$H NMR (DMSO-d$_6$) δ 1.50–1.63 (m, 2H), 1.82–1.95 (m, 2H), 3.05–3.17 (m, 2H), 3.23–3.37 (m, 10H), 3.49–3.57 (m, 2H), 3.93 (d, 1H, J=14.9 Hz), 4.05 (d, 1H, J=14.9 Hz), 4.43–4.49 (m, 2H), 7.35 (t, 1H, J=7.8 Hz), 7.53 (d, 2H, J=8.1 Hz), 7.79 (d, 2H, J=8.1 Hz), 7.84–7.90 (m, 2H), 8.41 (br s, 1H). HPLC Rt=2.819 min. LRMS (m/z) 435 (M+H). Anal. (C$_{25}$H$_{30}$N$_4$O) C, H, N.

Example 217

(R)-1-[4-(6-oxo-6,7,8,9-Tetrahydro-2,7,9a-triaza-benzo[cd]azulen-1-yl)-benzyl]-pyrrolidine-2-carboxylic Acid Benzyl Ester

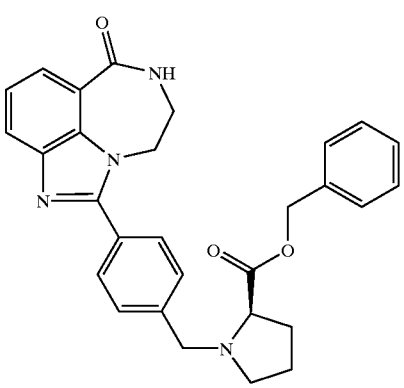

This compound was prepared from intermediate 171a and the appropriate amine using the procedure described in Example 171. Received 192.3 mg (41%)

$^1$H NMR (DMSO-d$_6$) δ 1.74–1.91 (m, 3H), 2.08–2.15 (m, 1H), 2.42–2.53 (m, 1H), 2.86–2.93 (m, 1H), 3.36–3.43 (m, 1H), 3.47–3.55 (m, 2H), 3.61 (d, 1H, J=13.5 Hz), 3.98 (d, 1H, J=13.5 Hz), 4.40–4.48 (m, 2H), 5.11 (s, 2H), 7.29–7.38 (m, 6H), 7.45 (d, 2H, J=8.1 Hz), 7.78 (d, 2H, J=8.1 Hz), 7.85–7.91 (m, 2H), 8.41 (br s, 1H). HPLC Rt=3.214 min. LRMS (m/z) 481 (M+H). Anal. (C$_{29}$H$_{28}$N$_4$O$_3$) C, H, N.

Example 218

(R)-1-[4-(6-oxo-6,7,8,9-Tetrahydro-2,7,9a-triaza-benzo[cd]azulen-1-yl)-benzyl]-pyrrolidine-2-carboxylic Acid tert-Butyl Ester

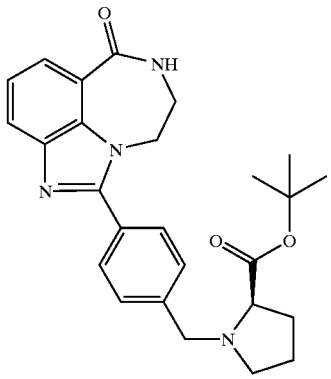

This compound was prepared from intermediate 171a and the appropriate amine using the procedure described in Example 171. Received 24.7 mg (5%)

¹H NMR (DMSO-d₆) δ 1.41 (s, 9H), 1.72–1.85 (m, 3H), 1.99–2.10 (m, 1H), 2.36–2.46 (m, 1H), 2.83–2.93 (m, 1H), 3.16–3.26 (m, 1H), 3.48–3.57 (m, 2H), 3.61 (d, 1H, J=13.6 Hz), 3.98 (d, 1H, J=13.6 Hz), 4.42–4.50 (m, 2H), 7.35 (t, 1H, J=7.8 Hz), 7.50 (d, 2H, J=8.1 Hz), 7.81 (d, 2H, J=8.1 Hz), 7.84–7.90 (m, 2H), 8.41 (br s, 1H). HPLC Rt=2.958 min. HRMS calcd for $C_{26}H_{31}N_4O_3$ 447.2391 (M+H)⁺, found 447.2377. Anal. ($C_{26}H_{30}N_4O_3$·0.5H₂O, 0.75 TFA) C, H, N.

Example 219

{1-[4-(6-oxo-6,7,8,9-Tetrahydro-2,7,9a-triaza-benzo[cd]azulen-1-yl)-benzyl]-pyrrolidin-3-yl}-carbamic Acid tert-Butyl Ester

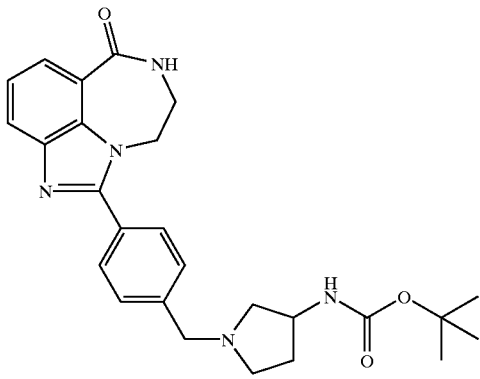

This compound was prepared from intermediate 171a and the appropriate amine using the procedure described in Example 171. Received 39.8 mg (9%)

¹H NMR (DMSO-d₆) δ 1.36 (s, 9H), 1.54–1.66 (m, 1H), 1.97–2.11 (m, 1H), 2.24–2.33 (m, 1H), 2.52–2.59 (m, 1H), 2.71–2.81 (m, 1H), 3.49–3.57 (m, 2H), 3.65 (s, 2H), 3.86–3.97 (m, 2H), 4.42–4.49 (m, 2H), 6.93 (br s, 1H), 7.35 (t, 1H, J=7.8 Hz), 7.50 (d, 2H, J=8.2 Hz), 7.81 (d, 2H, J=8.2 Hz), 7.84–7.91 (m, 2H), 8.41 (br s, 1H). HPLC Rt=2.968 min. HRMS calcd for $C_{26}H_{32}N_5O_3$ 461.2519 (M+H)⁺, found 461.2500. Anal. ($C_{26}H_{31}N_5O_3$·0.5 Acetone) C, H, N.

Example 220

1-(4-Pyrrol-1-ylmethyl-phenyl)-8,9-dihydro-7H-2,7,9a-triaza-benzo[cd]azulen-6-one

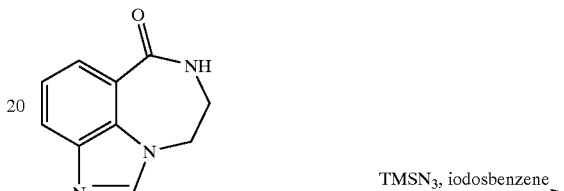

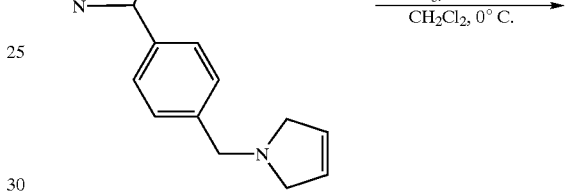

171

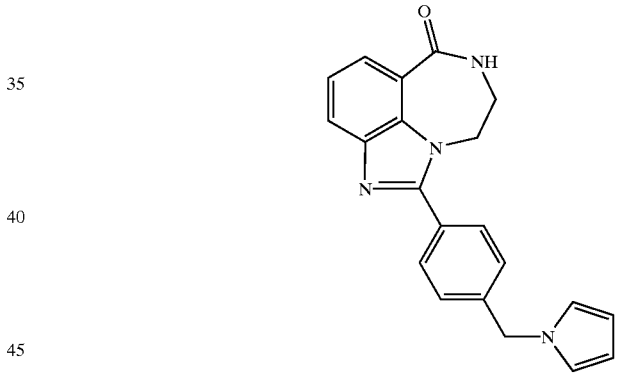

220

To a solution of 1-[4-(2,5-dihydro-pyrrol-1-ylmethyl)-phenyl]-8,9-dihydro-7H-2,7,9a-triaza-benzo[cd]azulen-6-one (32.4 mg, 0.09 mmol, Example 171) in 2 mL of CH₂Cl₂ at 0° C., was added iodosobenzene (41.4 mg, 0.19 mmol) and azidotrimethylsilane (25 μL, 0.19 mmol). This mixture then stirred at room temperature for 1 hour. The solvent was stripped and the residue was purified by prep HPLC. Received 20.1 mg (55%).

¹H NMR (DMSO-d₆) δ 3.46–3.54 (m, 2H), 4.40–4.46 (m, 2H), 5.22 (s, 2H), 6.05 (t, 2H, J=2.1 Hz), 6.87 (t, 2H, J=2.1 Hz), 7.32–7.37 (m, 3H), 7.81–7.90 (m, 4H), 8.41 (br s, 1H). HPLC Rt=3.349 min. HRMS calcd for $C_{21}H_{19}N_4O$ 443.1553 (M+H)⁺, found 443.1558. Anal. ($C_{21}H_{18}N_4O$·0.5 Acetone, 0.45 TFA) C, H, N.

Example 221

(S)-1-(4-Dimethylaminomethyl-phenyl)-8-methyl-8,9-dihydro-7H-2,7,9a-triaza-benzo[cd]azulen-6-one

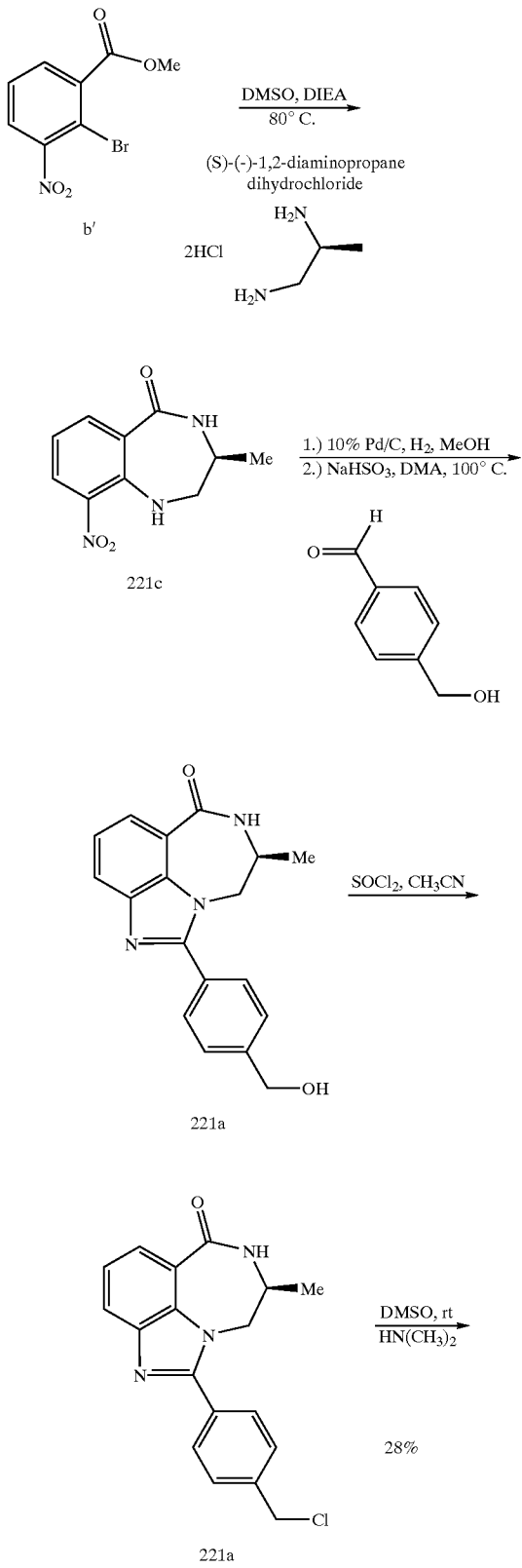

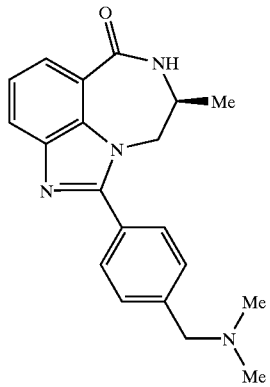

(221c) (S)-3-Methyl-9-nitro-1,2,3,4-tetrahydro-benzo[e][1,4]diazepin-5-one

A suspension of 10.1 g of intermediate b' (38.4 mmol, Example 2), (S)-(−)-1,2-diaminopropane dihydrochloride (5.65 g, 38.4 mmol) and DIEA (22 mL, 126 mmol) in 130 mL of DMSO was heated to 80° C. for 16 hours. The reaction was then concentrated in vacuo. To the resulting crude oil was added 200 mL of 1.0 M $NaHSO_4$. The aqueous layer was extracted with $CH_2Cl_2$ (2×200 mL). The combined organic layers were washed with water, dried ($MgSO_4$), filtered and concentrated. The product was then purified by silica gel chromatography eluting with 2–5% $MeOH/CH_2Cl_2$ to give 3.60 g (42%) of a yellow/orange solid.

mp=215–216° C.; IR (KBr) 3360, 3179, 3040, 2922, 1654, 1599, 1510, 1451, 1438, 1387, 1263, 1193, 1113, 1092, 891 740, 647 $cm^{-1}$; $^1H$ NMR ($CDCl_3$) δ 1.35 (d, 3H, J=6.7 Hz), 3.50–3.90 (m, 3H), 6.38 (br s, 1H), 6.77 (t, 1H, J=8.1 Hz), 8.34–8.46 (m, 2H), 9.04 (br s, 1H). HPLC Rt=3.351 min. LRMS (m/z) 222 (M+H). Anal. ($C_{10}H_{11}N_3O_3$) C,H,N.

(221a) (S)-1-(4-Hydroxymethyl-phenyl)-8-methyl-8,9-dihydro-7H-2,7,9a-triaza-benzo[cd]azulen-6-one A sample of (S)-3-methyl-9-nitro-1,2,3,4-tetrahydro-benzo[e][1,4]diazepin-5-one (2.00 g, 9.04 mmol) was reduced as in Example 2, except using MeOH as solvent. The resulting diamine was cyclized to benzylic alcohol 221a as described in Example 19. Received 2.30 g (82% overall).

mp=268–270° C.; IR (KBr) 3199, 1654, 1482, 1438, 1389, 1332, 750 $cm^{-1}$; $^1H$ NMR ($CDCl_3$) δ 1.19 (d, 3H, J=6.1 Hz), 3.80–3.94 (m, 1H), 4.28 (d, 1H, J=13.0 Hz), 4.45 (dd, 1H, J=13.0, 7.8 Hz), 4.61 (d, 2H, J=5.4 Hz), 5.33 (t, 1H, J=5.4 Hz), 7.36 (t, 1H, J=7.7 Hz), 7.52 (d, 2H, J=7.9 Hz), 7.81 (d, 2H, J=7.9 Hz), 7.85–7.93 (m, 2H), 8.29 (d, 1H, J=3.3 Hz). HPLC Rt=2.543 min. LRMS (m/z) 308 (M+H). Anal. ($C_{18}H_{17}N_3O_2$) C, H, N.

(221b) (S)-1-(4-Chloromethyl-phenyl)-8-methyl-8,9-dihydro-7H-2,7,9a-triaza-benzo[cd]azulen-6-one Benzyl alcohol 221a was converted to a crude benzyl chloride 221b as described in Example 171.

HPLC Rt=3.233 min.

(221) Title Compound

This compound was synthesis from chloride 221b and the appropriate amine as described in Example 171. Received 61.7 mg (20%)

$^1H$ NMR (DMSO-$d_6$) δ 1.16–1.24 (m, 3H), 2.22 (s, 6H), 3.52 (s, 2H), 3.83–3.89 (m, 1H), 4.27–4.49 (m, 2H), 7.35 (t, 1H, J=7.8 Hz), 7.49 (d, 2H, J=8.1 Hz), 7.81 (d, 2H, J=8.1 Hz), 7.85–7.89 (m, 2H), 8.28 (br s, 1H). HPLC Rt=2.471 min. LRMS (m/z) 335 (M+H). Anal. ($C_{20}H_{22}N_4O \cdot 0.6H_2O$) C, H, N.

Example 222

(S)-8-Methyl-1-(4-methylaminomethyl-phenyl)-8,9-dihydro-7H-2,7,9a-triaza-benzo[cd]azulen-6-one

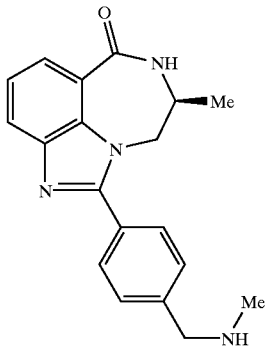

This compound was prepared from intermediate 221b and the appropriate amine using the procedure described in Example 171. Received 87.9 mg (35%)

$^1$H NMR (DMSO-$d_6$) δ 1.16–1.23 (m, 3H), 2.60–2.65 (m, 3H), 3.81–3.94 (m, 1H), 4.21–4.31 (m, 3H), 4.44–4.51 (m, 2H), 7.38 (t, 1H, J=7.8 Hz), 7.67 (d, 2H, J=8.2 Hz), 7.88–7.95 (m, 4H), 8.33 (br s, 1H). HPLC Rt=2.315 min. LRMS (m/z) 321 (M+H). Anal. ($C_{19}H_{20}N_4O \cdot 2.0TFA$) C, H, N.

Example 223

(S)-1-[4-(2,5-Dihydro-pyrrol-1-ylmethyl)-phenyl]-8-methyl-8,9-dihydro-7H-2,7,9a-triaza-benzo[cd]azulen-6-one

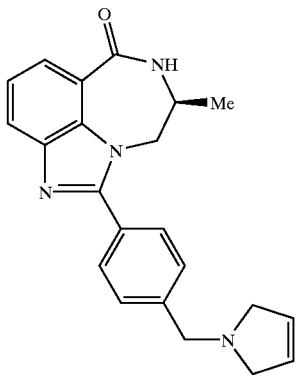

This compound was prepared from intermediate 221b and the appropriate amine using the procedure described in Example 171. Received 173 mg (63%)

$^1$H NMR (DMSO-$d_6$) δ 1.17–1.24 (m, 3H), 3.84–3.93 (m, 1H), 4.01–4.19 (m, 4H), 4.24–4.53 (m, 2H), 4.57–4.63 (m, 2H), 5.97 (m, 2H), 7.39 (t, 1H, J=7.8 Hz), 7.76 (d, 2H, J=8.3 Hz), 7.89–7.93 (m, 2H), 7.95 (d, 2H, J=8.3 Hz), 8.34 (br s, 1H). HPLC Rt=2.554 min. LRMS (m/z) 359 (M+H). Anal. ($C_{22}H_{22}N_4O$, 0.5$H_2O$, 2 TFA) C, H, N.

Example 224

1-[4-(2,5-Dihydro-pyrrol-1-ylmethyl)-phenyl]-8,9-dihydro-7H-2,7,9a-triaza-benzo[cd]azulen-6-one, Hydrochloride Salt

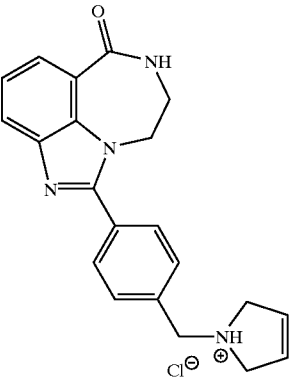

GENERAL METHOD FOR AMINE SALT FORMATION

To a solution of 1-[4-(2,5-dihydro-pyrrol-1-ylmethyl)-phenyl]-8,9-dihydro-7H-2,7,9a-triaza-benzo[cd]azulen-6-one (Example 171) (40 mg, 0.12 mmol) in 5 mL MeOH, was added (1.13 mL, 0.12 mmol) 0.10 N HCl. The solvent was stripped and the residue lyophilized from acetonitrile and water. Received 39.4 mg (84%)

$^1$H NMR (DMSO-$d_6$) δ 3.50–3.59 (m, 2H), 3.88–4.12 (m, 4H), 4.42–4.57 (m, 4H), 5.93 (s, 2H), 7.37 (t, 1H, J=7.7 Hz), 7.75–7.84 (m, 2H), 7.86–7.98 (m, 4H), 8.45 (br s, 1H), 11.41 br s, 1H). HPLC Rt=2.527 min. LRMS (m/z) 345 (M+H). Anal. ($C_{21}H_{20}N_4O \cdot 1.0HCl$, 1.25 $H_2O$) C, H, N.

Example 225

1-[4-(2,5-Dihydro-pyrrol-1-ylmethyl)-phenyl]-8,9-dihydro-7H-2,7,9a-triaza-benzo[cd]azulen-6-one, Maleate Salt

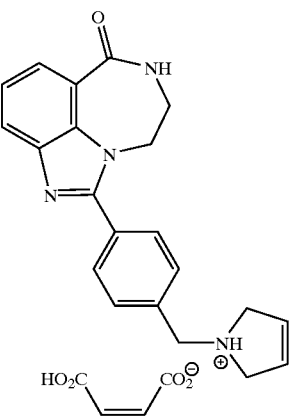

The compound was prepared from 1-[4-(2,5-dihydro-pyrrol-1-ylmethyl)-phenyl]-8,9-dihydro-7H-2,7,9a-triaza-benzo[cd]azulen-6-one [Example 171] and maleic acid using the procedure described in Example 224. Received 42.3 mg (75%)

$^1$H NMR (DMSO-$d_6$) δ 3.51–3.59 (m, 2H), 3.90–4.07 (m, 4H), 4.43–4.55 (m, 4H), 5.94 (s, 2H), 6.02 (s, 2H), 7.37 (t,

1H, J=7.8 Hz), 7.68–7.75 (m, 2H), 7.86–7.98 (m, 4H), 8.45 (br s, 1H), 10.65 (br s, 2H). HPLC Rt=2.521 min. LRMS (m/z) 345 (M+H). Anal. ($C_{21}H_{20}N_4O\cdot1.0C_4H_4O_4$, 1.5 $H_2O$) C, H, N.

Example 226

1-[4-(2,5-Dihydro-pyrrol-1-ylmethyl)-phenyl]-8,9-dihydro-7H-2,7,9a-triaza-benzo[cd]azulen-6-one, Methanesulfonic Acid Salt

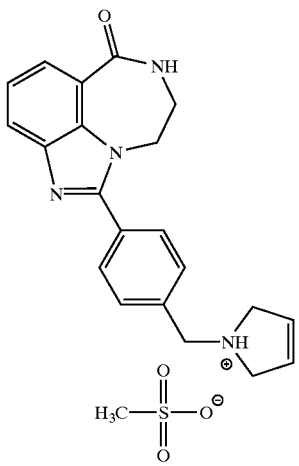

The compound was prepared from 1-[4-(2,5-dihydro-pyrrol-1-ylmethyl)-phenyl]-8,9-dihydro-7H-2,7,9a-triaza-benzo[cd]azulen-6-one [Example 171] and methanesulfonic acid using the procedure described in Example 224. Received 42.3 mg (75%)

$^1$H NMR (DMSO-$d_6$) δ 2.29 (s, 3H), 3.52–3.58 (m, 2H), 3.90.4.14 (m, 4H), 4.43–4.60 (m, 4H), 5.96 (s, 2H), 7.38 (t, 1H, J=7.8 Hz), 7.74 (d, 2H, J=8.2 Hz), 7.86–7.92 (m, 2H), 7.96 (d, 2H, J=8.2 Hz), 8.45 (br s, 1H), 10.52 (br s, 1H). HPLC Rt=2.525 min. LRMS (m/z) 345 (M+H). Anal. ($C_{21}H_{20}N_4O\cdot1.0CH_4O_3S$, 1.25 $H_2O$) C,H, N.

Example 227

4-(6-oxo-6,7,8,9-Tetrahydro-2,7,9a-triaza-benzo[cd]azulen-1-y)-benzonitrile

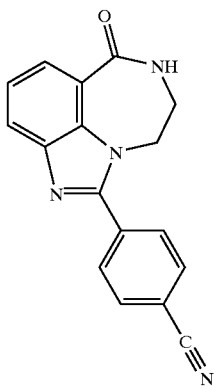

This compound was prepared from diamine intermediate g (from Example 2) and 4-cyanobenzaldehyde according to the procedure used in Example 19. Received 316.7 mg (57%)

$^1$H NMR (DMSO-$d_6$) δ 3.49–3.58 (m, 2H), 4.44–4.52 (m, 2H), 7.39 (t, 1H, J=7.9 Hz), 7.89–7.96 (m, 2H), 8.06 (m, 4H), 8.45 (br s, 1H). HPLC Rt=2.842 min. LRMS (m/z) 289 (M+H). Anal. ($C_{17}H_{12}N_4O\cdot0.25H_2O$) C, H, N.

Examples 228–229

1-{4-[1-(2,5-Dihydro-pyrrol-1-yl)-3-methyl-butyl]-phenyl}-8,9-dihydro-7H-2,7,9a-triaza-benzo[cd]azulen-6-one

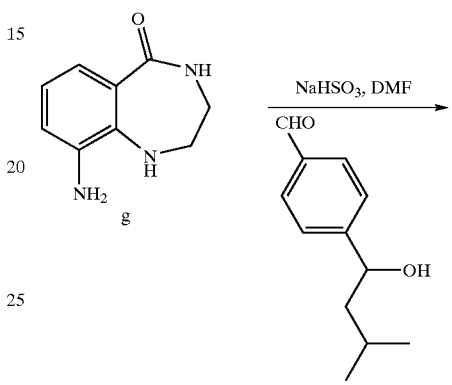

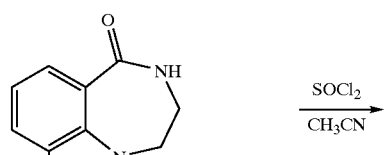

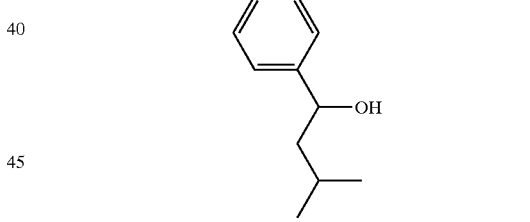

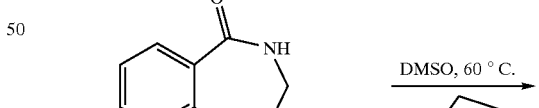

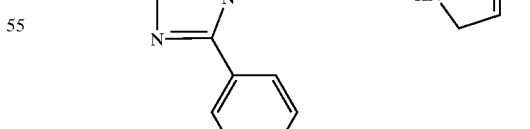

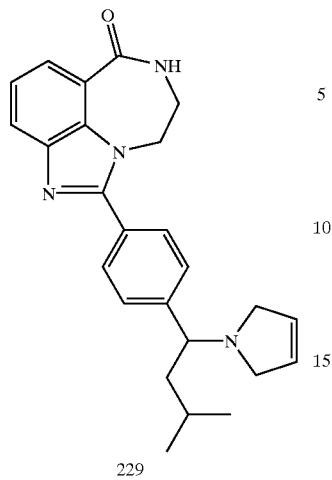

229

(228) 1-[4-(1-Hydroxy-3-methyl-butyl)-phenyl]-8,9-dihydro-7H-2,7,9a-triaza-benzo[cd]azulen-6-one This compound was prepared from diamine intermediate g (from Example 2) and 4-(1-hydroxy-3-methyl-butyl)-benzaldehyde [prepared from isobutylmagnesium bromide and terephthalaldehyde-mono-diethyl acetal following the procedure Hulin et al., *J. Med. Chem.* 35, 1853 (1992)] according to the procedure used in Example 19. Received 8.36 g (91%)

$^1$H NMR (DMSO-d$_6$) δ 0.89–0.95 (s, 6H), 1.34–1.44 (m, 1H), 1.53–1.64 (m, 1H), 1.66–1.79 (m, 1H), 3.48–3.57 (m, 2H), 4.42–4.49 (m, 2H), 4.64–4.70 (m, 1H), 5.21 (d, 1H, J=4.9 Hz), 7.35 (t, 1H, J=7.8 Hz), 7.51 (d, 2H, J=8.2 Hz), 7.81 (d, 2H, J=8.2 Hz), 7.84–7.90 (m, 2H), 8.41 (br s, 1H), 10.52 (br s, 1H). HPLC Rt=3.171 min. LRMS (m/z) 350 (M+H). Anal. (C$_{21}$H$_{23}$N$_3$O$_2$) C, H, N.

(229a) 1-[4-(1-Chloro-3-methyl-butyl)-phenyl]-8,9-dihydro-7H-2,7,9a-triaza-benzo[cd]azulen-6-one This compound was prepared from intermediate 228 and thionyl chloride according to the procedure used in Example 171. Received 8.36 g (91%)

LRMS (m/z) 368 (M+H).

(229) Title Compound

This compound was prepared from intermediate 229a and 6 equivalents of 3-pyrroline according to the procedure described in Example 171, with the exception of heating to 60° C. Received 83.3 mg (30%)

$^1$H NMR (DMSO-d$_6$) δ 0.90 (d, 3H, J=6.6 Hz), 0.91 (d, 3H, J=6.6 Hz), 1.11–1.25 (m, 1H), 1.59–1.76 (m, 2H), 3.35–3.68 (m, 7H), 4.424.52 (m, 2H), 5.77 (s, 2H), 7.35 (t, 1H, J=7.8 Hz), 7.50 (d, 2H, J=8.1 Hz), 7.79–7.89 (m, 4H), 8.42 (br s, 1H). HPLC Rt=3.034 min. LRMS (m/z) 401 (M+H). Anal. (C$_{25}$H$_{28}$N$_4$O.0.3H$_2$O) C, H, N.

Example 230

1-[4-(3-Methyl-1-pyrrolidin-1-yl-butyl)-phenyl]-8,9-dihydro-7H-2,7,9a-triaza-benzo[cd]azulen-6-one

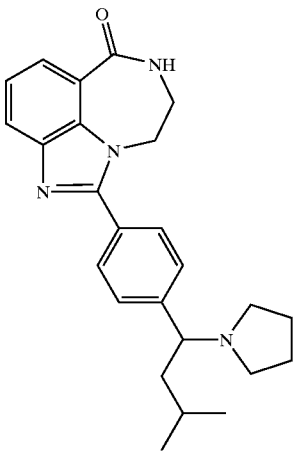

This compound was prepared from intermediate 229a and the appropriate amine using the procedure described in Example 229. Received 118 mg (43%)

$^1$H NMR (DMSO-d$_6$) δ 0.80 (d, 3H, J=6.6 Hz), 0.88 (d, 3H, J=6.6 Hz), 1.10–1.25 (m, 1H), 1.57–1.79 (m, 6H), 2.21–2.33 (m, 2H), 2.52–2.57 (m, 2H), 3.32–3.38 (m, 1H), 3.49–3.58 (m, 2H), 4.43–4.51 (m, 2H), 7.35 (t, 1H, J=7.8 Hz), 7.47 (d, 2H, J=8.2 Hz), 7.82 (d, 2H, J=8.2 Hz), 7.85–7.89 (m, 2H), 8.42 (br s, 1H). HPLC Rt=3.029 min. LRMS (m/z) 403 (M+H). Anal. (C$_{25}$H$_{30}$N$_4$O.0.25H$_2$O) C, H, N.

Example 231

1-[4-(Dimethylamino-methyl-butyl)-phenyl]-8,9-dihydro-7H-2,7,9a-triaza-benzo[cd]azulen-6-one

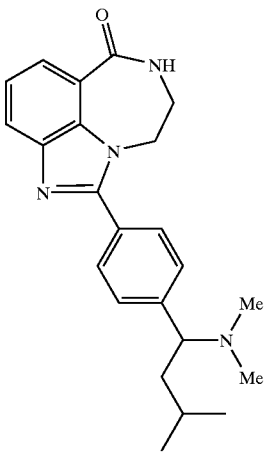

This compound was prepared from intermediate 229a and the appropriate amine using the procedure described in Example 229. Received 85.1 mg (33%)

$^1$H NMR (DMSO-d$_6$) δ 0.85 (d, 3H, J=6.6 Hz), 0.88 (d, 3H, J=6.6 Hz), 1.28–1.39 (m, 1H), 1.56–1.67 (m, 1H), 1.69–7.80 (m, 1H), 2.09 (s, 6H), 3.40–3.49 (m, 1H), 3.50–3.58 (m, 2H), 4.44–4.51 (m, 2H), 7.35 (t, 1H, J=7.8 Hz), 7.43 (d, 2H, J=8.2 Hz), 7.83 (d, 2H, J=8.2 Hz), 7.84–7.90 (m, 2H), 8.42 (br s, 1H). HPLC Rt=2.869 min. LRMS (m/z) 377 (M+H). Anal. (C$_{23}$H$_{28}$N$_4$O.0.25H$_2$O) C, H, N.

Example 232

1-[4-(2,5-Dihydro-pyrrol-1-ylmethyl)-phenyl]-4-fluoro-8,9-dihydro-7H-2,7,9a-triaza-benzo[cd]azulen-6-one, Methanesulfonic Acid Salt

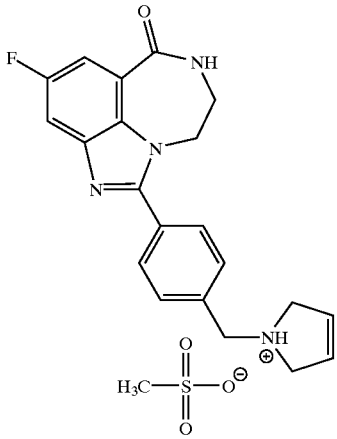

The compound was prepared from 1-[4-(2,5-dihydro-pyrrol-1-ylmethyl)-phenyl]-4-fluoro-8,9-dihydro-7H-2,7,9a-triaza-benzo[cd]azulen-6-one [Example 177] and methanesulfonic acid using the procedure described in Example 224. Received 577.9 mg (90%)

$^1$H NMR (DMSO-d$_6$) δ 2.31 (s, 3H), 3.54–3.60 (m, 2H), 4.03–4.15 (m, 4H), 4.44–4.50 (m, 4H), 5.98 (s, 2H), 7.64 (dd, 1H, J=10.6, 2.6 Hz), 7.75–7.81 (m, 3H), 7.98 (d, 2H, J=8.3 Hz), 8.63 (br s, 1H), 10.57 (br s, 1H). HPLC Rt=2.813 min. LRMS (m/z) 363 (M+H). Anal. (C$_{21}$H$_{19}$FN$_4$O.1.0CH$_4$O$_3$S, 0.25 H$_2$O) C, H, N.

Example 233

(S)-8-Methyl-1-(4-pyrrolidin-1-ylmethyl-phenyl)-8,9-dihydro-7H-2,7,9a-triaza-benzo[cd]azulen-6-one

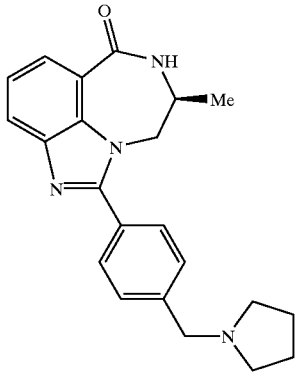

This compound was prepared from intermediate 221b and the appropriate amine using the procedure described in Example 171, with the exception of using acetonitrile as solvent. Received 50 mg (11%).

$^1$H NMR (DMSO-d$_6$) δ 1.20 (d, 3H, J=6.3 Hz), 1.68–1.87 (m, 4H), 2.43–2.57 (m, 4H), 3.69 (s, 2H), 3.81–3.93 (m, 1H), 4.30 (d, 1H, J=13.2 Hz), 4.46 (dd, 1H, J=13.2, 7.8 Hz), 7.35 (t, 1H, J=7.8 Hz), 7.51 (d, 2H, J=8.2 Hz), 7.81 (d, 2H, J=8.2 Hz), 7.85–7.95 (m, 2H), 8.29 (d, 1H, J=4.2 Hz). LRMS (m/z) 361 (M+H). Anal. (C$_{22}$H$_{24}$N$_4$O.0.2H$_2$O) C, H, N.

Example 234

(S)-8-Methyl-1-(4-pyrrol-1-ylmethyl-phenyl)-8,9-dihydro-7H -2,7,9a-triaza-benzo[cd]azulen-6-one

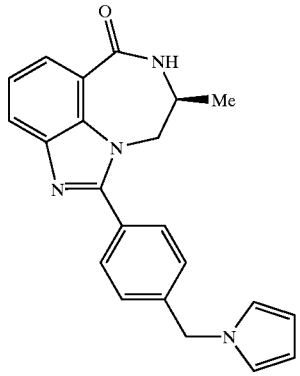

This compound was isolated as a side product during formation of Example 223. Received 50 mg (3%).

$^1$H NMR (DMSO-d$_6$) δ 1.18 (d, 3H, J=6.3 Hz), 3.78–3.90 (m 1H), 4.27 (d, 2H, J=13.2 Hz), 4.44 (dd, 1H, J=13.2, 7.8 Hz), 5.22 (s, 2H), 6.06 (t, 1H, J=2.1 Hz), 6.88 (t, 1H, J=2.1 Hz), 7.30–7.39 (m, 3H), 7.79–7.92 (m, 4H), 8.29 (d, 1H, J=4.31 Hz). HRMS calcd for C$_{22}$H$_{21}$N$_4$O 357.1710 (M+H)$^+$, found 357.1711.

Example 235

(S)-1-(4-Chloro-phenyl)-8-methyl-8,9-dihydro-7H-2,7,9a-triaza-benzo[cd]azulen-6-one

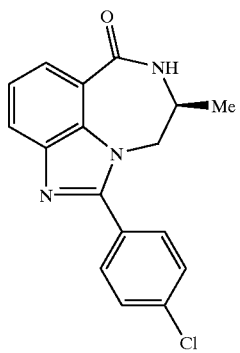

This compound was prepared from (S)-3-methyl-9-nitro-1,2,3,4-tetrahydro-benzo[e][1,4]diazepin-5-one and 4-chlorobenzyldehyde, via reduction and cyclization, as described in Example 221. Received 35 mg (7%).

mp=244–246° C.; $^1$H NMR (DMSO-d$_6$) δ 1.20 (d, 3H, J=4.8 Hz), 3.77–3.93 (m, 1H), 4.29 (d, 1H, J=12.6 Hz), 4.45 (dd, 1H, J=13.0, 7.9 Hz), 7.37 (t, 1H, J=7.8 Hz), 7.66 (d, 2H, J=8.4 Hz), 7.82–7.96 (m, 4H), 8.33 (br s, 1H). HPLC Rt=3.217 min. LRMS (m/z) 312 (M+H). Anal. (C$_{17}$H$_{14}$ClN$_3$O) C, H, Cl, N.

Example 236

(R)-1-(4-Chloro-phenyl)-8-methyl-8,9-dihydro-7H-2,7,9a-triaza-benzo[cd]azulen-6-one

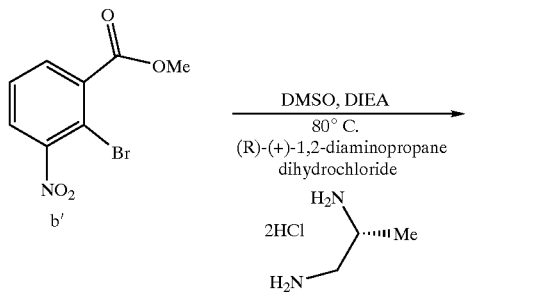

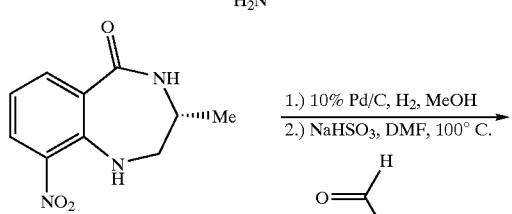

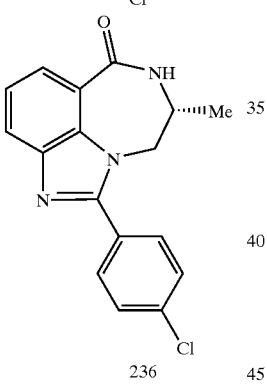

(236a) (R)-3-Methyl-9-nitro-1,2,3,4-tetrahydro-benzo[e][1,4]diazepin-5-one

This compound is the enantiomer of intermediate 221c from Example 221, prepared in the same manner. Received 2.14 g (29%).

HPLC Rt=3.379 min.

(236) Title Compound

This compound, the enantiomer of Example 235, was prepared from (R)-3-methyl-9-nitro-1,2,3,4-tetrahydro-benzo[e][1,4]diazepin-5-one and 4-chlorobenzyaldehyde as described in Example 235. Received 210 mg (37%).

LRMS (m/z) 312 (M+H). Anal. ($C_{17}H_{14}ClN_3O \cdot 0.10 CH_2Cl_2$, 0.05 Hexanes) C, H, Cl, N.

Example 237

(R)-1-(4-Chloro-phenyl)-8-hydroxymethyl-8,9-dihydro-7H-2,7,9a-triaza-benzo[cd]azulen-6-one

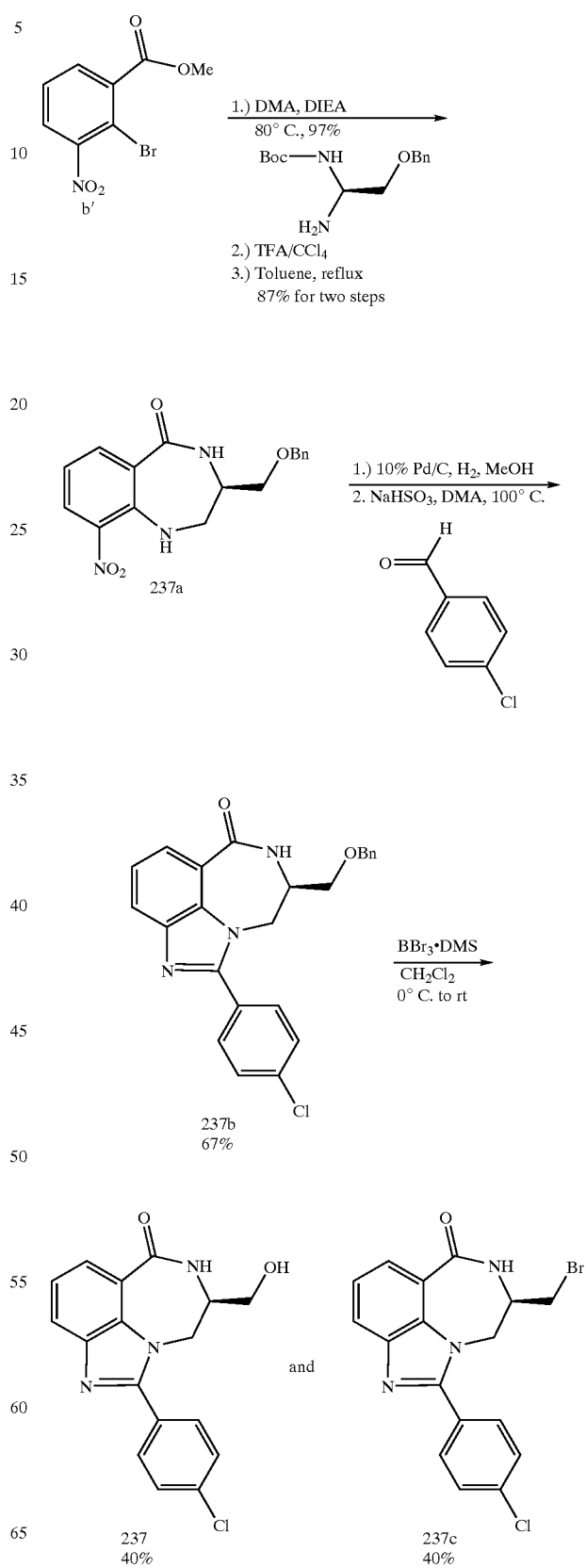

191

(237a) (R)-3-Benzyloxymethyl-9-nitro-1,2,3,4-tetrahydro-benzo[e][1,4]diazepin-5-one A suspension of 2.23 g of intermediate b' (8.57 mmol, Example 2), ((R)-2-amino-1-benzyloxymethyl-ethyl)-carbamic acid tert-butyl ester (2.40 g, 8.56 mmol) and DIEA (2.5 mL, 14.4 mmol) in 50 mL of DMA was heated to 80° C. overnight. The crude reaction was added to 500 mL of 1.0 M $NaH_2PO_4$ and the aqueous layer was extracted with 1:1 $Et_2O$/Hexanes (3×250 mL). The combined organic layers were dried ($MgSO_4$), filtered and concentrated. The product was then purified by silica gel chromatography eluting with 5% t-BuOMe/(1:1$CH_2Cl_2$/Hexanes) to give 3.81 g (97%) of 2-((R)-3-benzyloxy-2-tert-butoxycarbonylamino-propylamino)-3-nitro-benzoic acid methyl ester as a yellow oil. [First intermediate]

IR (KBr) 3314, 2977, 1715, 1694, 1606, 1531, 1505, 1366, 1348, 1260, 1165, 1120, 741 cm$^{-1}$; $^1$H NMR (CDCl$_3$) δ 1.41 (s, 9H), 3.08–3.21 (m, 2H), 3.47–3.58 (m, 2H), 3.87 (s, 3H), 3.98 (br s, 1H), 4.43–4.54 (m, 2H), 4.92 (br d, 1H, J=8.6 Hz), 6.69 (t, 1H, J=7.9 Hz), 7.24–7.36 (m, 5H), 7.96–8.05 (m, 2H), 8.57 (br s, 1H). HPLC Rt=5.030 min. HRMS calcd for $C_{23}H_{29}N_3NaO_7$ 482.1903 (M+Na)$^+$, found 482.1901. Anal. ($C_{10}H_{11}N_3O_3$) C, H, N.

The Boc protecting group was removed by treating the ester derived about with 75 mL of 1:1 TFA/CCl$_4$ for 2 hours at room temperature. The reaction was then concentrated, suspended in 250 mL of pH 7 phosphate buffer and the amine extracted out by CHCl$_3$ (4×100 mL). ). The combined organic layers were dried (MgSO$_4$), filtered and concentrated to give 3.25 g of crude amine as a light yellow solid. [HRMS calcd for $C_{18}H_{22}N_3O_5$ 360.1559 (M+H)$^+$, found 360.1557.] This compound was cyclized to the final product by refluxing in 150 mL of toluene overnight. Concentration gave 2.33 g of 237a as a red/orange solid.

$^1$H NMR (DMSO-d$_6$) δ 3.48 (d, 2H, J=6.2 Hz), 3.60–3.75 (m, 3H), 4.464.56 (m, 2H), 6.76 (t, 1H, J=8.0 Hz), 7.20–7.36 (m, 5H), 8.21–8.34 (m, 3H), 8.79 (br s,1H). HPLC Rt=4.441 min. LRMS (m/z) 328 (M+H). Anal. ($C_{17}H_{17}N_3O_4.0.60H_2O$) C, H, N.

(237b) (R)-8-Benzyloxymethyl-1-(4-chloro-phenyl)-8,9-dihydro-7H-2,7,9a-triaza-benzo[cd]azulen-6-one AG-14523

This compound was prepared from (R)-3-benzyloxymethyl-9-nitro-1,2,3,4-tetrahydro-benzo[e][1,4]diazepin-5-one and 4-chlorobenzyaldehyde, via reduction and cyclization, as described in Example 221.

$^1$H NMR (CDCl$_3$) δ 3.62 (d, 2H, J=5.6 Hz), 3.96–4.05 (m, 1H), 4.38 (d, 1H, J=12.5 Hz), 4.46–4.60 (m, 3H), 6.61 (d, 1H, J=4.3 Hz), 7.18–7.39 (m, 5), 7.42 (t, 1H, J=7.9 Hz), 7.49 (d, 2H, J=8.5 Hz), 7.70 (d, 2H, J=8.5 Hz), 7.99 (dd, 1H, J=8.0, 0.8 Hz), 8.13 (dd, 1H, J=7.7, 0.8 Hz). HPLC Rt=4.228 min. HRMS calcd for $C_{24}H_{21}ClN_3O_2$ 418.1322 (M+H)$^+$, found 418.1334. Anal. ($C_{24}H_{20}ClN_3O_2$) C, H, Cl, N.

(237) Title Compound

To a solution of intermediate 237b (0.21 g, 0.50 mmol) in 7.5 mL of CH$_2$Cl$_2$ at 0° C., was added a solution of boron tribromide dimethylsulfide complex (1.0M in CH$_2$Cl$_2$, 2.5 mL, 2.5 mmol) dropwise via syringe. The reaction was stirred overnight, with warming to room temperature. The reaction was concentrated and excess reagent was quenched by addition of 10 mL of 1.0M LiOH, 15 mL Et$_2$O and 2 mL MeOH. After 3 hours, the mixture was poured into 75 mL of 1.0M KH$_2$PO$_4$ and extracted with EtOAc (3×50 mL). The combined organic layers were dried (MgSO$_4$), filtered and concentrated. The product was then purified by silica gel chromatography eluting with 2.5–5% MeOH/CH$_2$Cl$_2$ to give 70 mg (40%) of an off white solid.

$^1$H NMR (DMSO-d$_6$) δ 3.30–3.78 (m, 3H), 4.40–4.57 (m, 2H), 5.02 (br s, 1H), 7.38 (t, 1H, J=7.8 Hz), 1.67 (d, 2H, J=8.3 Hz), 7.85–7.97 (m, 4H), 8.16 (br d, 1H, J=3.9 Hz). HPLC Rt=2.822 min. HRMS calcd for $C_{17}H_{15}ClN_3O_2$ 328.0853 (M+H)$^+$, found 328.0825. Anal. ($C_{17}H_{14}ClN_3O_2.0.15CH_2Cl_2$) C, H, Cl, N.

192

(237c) (R)-8-Bromomethyl-1-(4-chloro-phenyl)-8,9-dihydro-7H-2,7,9a-triaza-benzo[cd]azulen-6-one Was isolated as side product in the formation of Example 237. Obtained 80 mg (40%) as an off white solid.

$^1$H NMR (CDCl$_3$) δ 3.38–3.57 (m, 2H), 4.06–4.17 (m, 1H), 4.50 (dd, 1H, J=13.3, 1.2 Hz), 4.74 (dd, 1H, J=13.3, 6.7 Hz), 6.65 (br s, 1H), 7.45 (t, 1H, J=7.9 Hz), 7.52–7.74 (m, 4H), 8.02 (dd, 1H, J=8.0, 1.1 Hz), 8.15 (dd, 1H, J=7.7, 1.1 Hz). HPLC Rt=3.506 min. LRMS (m/z) 390 (M+H).

Example 238

(R)-1-(4-Dimethylaminomethyl-phenyl)-8-hydroxymethyl-8,9-dihydro-7H-2,7,9a-triaza-benzo[cd]azulen-6-one

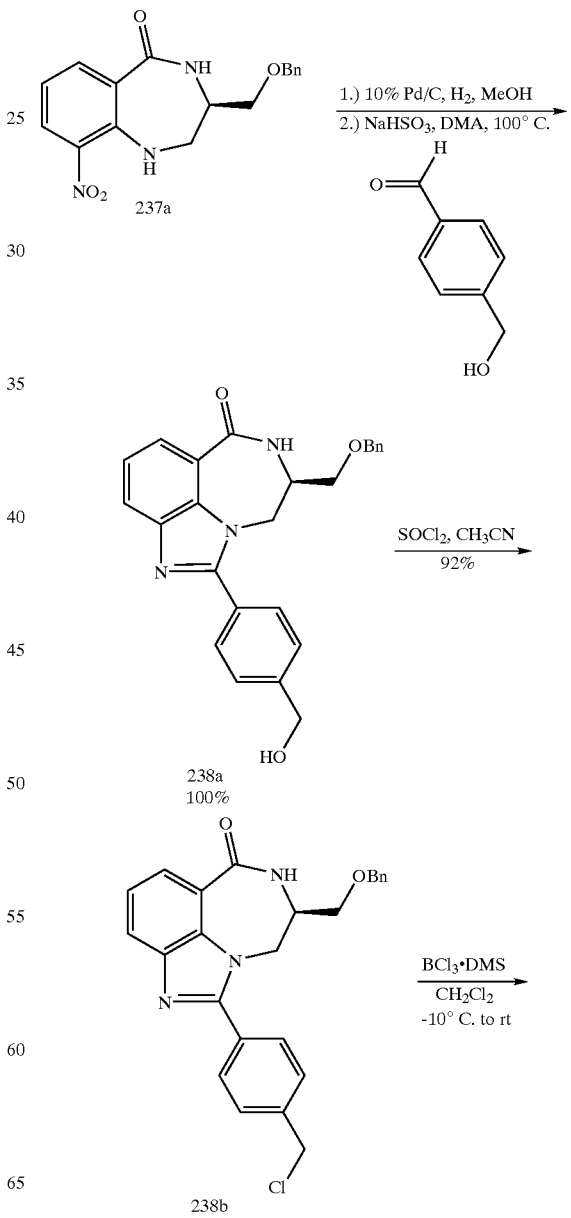

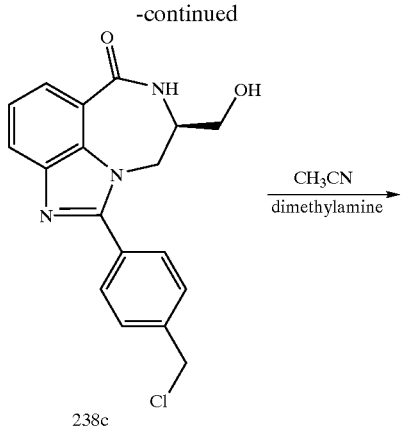

238c (238a) (R)-8-Benzyloxymethyl-1-(4-hydroxymethyl-phenyl)-8,9-dihydro-7H-2,7,9a-triaza-benzo[cd]azulen-6-one AG-14563

This compound was prepared from (R)-3-benzyloxymethyl-9-nitro-1,2,3,4-tetrahydro-benzo[e][1,4]diazepin-5-one and 4-hydroxymethyl-benzaldehyde, via reduction and cyclization, as described in Example 237.

IR (KBr) 3293, 2925, 1654, 1602, 1482, 1115, 750 cm$^{-1}$; $^1$H NMR (CDCl$_3$) δ 2.09 (br s, 1H), 3.56–3.66 (m, 2H), 3.95–4.04 (m, 1H), 4.37–4.60 (m, 4H), 4.82 (s, 2H), 6.51 (d, 1H, J=4.4 Hz), 7.20–7.38 (m, 5H), 7.42 (t, 1H, J=7.9 Hz), 7.51 (d, 2H, J=8.2 Hz), 7.73 (d, 2H, J=8.2 Hz), 8.00 (dd, 1H, J=8.0, 1.0 Hz), 8.12 (dd, 1H, J=7.7, 1.0 Hz). HPLC Rt=3.330 min. HRMS calcd for C$_{25}$H$_{24}$N$_3$O$_3$ 414.1818 (M+H)$^+$, found 414.1822.

(238b) (R)-8-Benzyloxymethyl-1-(4-chloromethyl-phenyl)-8,9-dihydro-7H-2,7,9a-triaza-benzo[cd]azulen-6-one This compound was prepared from benzyl alcoholol 238a and thionyl chloride as described in Example 171.

$^1$H NMR (CDCl$_3$) δ 3.60–3.68 (m, 2H), 3.97–4.06 (m, 1H), 4.38–4.60 (m, 2H), 4.52 (s, 2H), 4.67 (s, 2H), 6.52 (d, 1H, J=4.4 Hz), 7.20–7.40 (m, 5H), 7.42 (t, 1H, J=7.9 Hz), 7.55 (d, 2H, J=8.2 Hz), 7.76 (d, 2H, J=8.2 Hz), 8.00 (dd, 1H, J=8.0, 1.0 Hz), 8.13 (dd, 1H, J=7.7, 1.0 Hz). HPLC Rt=3.953 min. HRMS calcd for C$_{25}$H$_{22}$ClN$_3$O$_2$ 432.1473 (M+H)$^+$, found 432.1457. Anal. (C$_{25}$H$_{22}$ClN$_3$O$_2$·0.50H$_2$O) C, H, N.

(238c) (R)-1-(4-Chloromethyl-phenyl)-8-hydroxymethyl-8,9-dihydro-7H-2,7,9a-triaza-benzo[cd]azulen-6-one To a solution of intermediate 238b (1.35 g, 3.12 mmol) in 75 mL of CH$_2$Cl$_2$ at 0° C., was added solid boron trichloride dimethylsulfide complex (2.75 g, 15.3 mmol) all at once. The reaction was stirred overnight, allowing to warm to room temperature. The reaction was quenched by addition to 400 mL of pH 7 phosphate buffer and 200 mL Et$_2$O. After stirring overnight, the aqueous layer was extracted with EtOAc. The combined organic layers were dried (MgSO$_4$), filtered and concentrated. The product was used without further purification. Obtained 680 mg (64%) of an off white solid.

HPLC Rt=2.904 min. LRMS (m/z) 342 (M+H).

(238) Title Compound

This compound was prepared from intermediate 238c and dimethylamine using the procedure described in Example 171, except with acetonitrile as solvent. Received 85.1 mg (33%).

$^1$H NMR (CDCl$_3$) δ 2.30 (s, 6H), 3.52 (s, 2H), 3.86–3.95 (m, 2H), 3.97–4.08 (m, 1H), 4.48–4.62 (m, 2H), 7.41 (t, 1H, J=7.9 Hz), 7.50 (d, 2H, J=8.2 Hz), 7.73 (d, 2H, J=8.2 Hz), 8.01 (dd, 1H, J=8.0, 1.0 Hz), 8.07 (dd, 1H, J=7.7, 1.0 Hz), 8.60 (br s, 1H). HPLC Rt=2.254 min. HRMS calcd for C$_{20}$H$_{23}$N$_4$O$_2$ 351.1821 (M+H)$^+$, found 351.1821.

Example 239

(R)-8-Hydroxymethyl-1-{4-[(methyl-phenethyl-amino)-methyl]-phenyl}-8,9-dihydro-7H-2,7,9a-triaza-benzo[cd]azulen-6-one

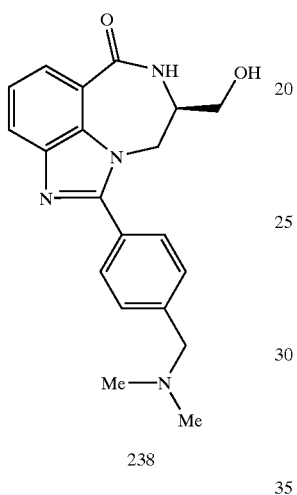

This compound was prepared from intermediate 238c and the appropriate amine using the procedure described in Example 238. Received 15.0 mg (15%).

$^1$H NMR (CDCl$_3$) δ 2.33 (s, 3H), 2.66–2.90 (m, 4H), 3.60 (br s, 1H), 3.64 (s, 2H), 3.84–4.07 (m, 3H), 4.49–4.61 (m, 2H), 7.16–7.33 (m, 5H), ), 7.42 (t, 1H, J=7.9 Hz), 7.46 (d, 2H, J=8.2 Hz), 7.70 (d, 2H, J=8.2 Hz), 8.01 (dd, 1H, J=8.0, 1.0 Hz), 8.08 (dd, 1H, J=7.7, 1.0 Hz), 8.52 (br s, 1H). HPLC Rt=2.917 min. HRMS calcd for C$_{27}$H$_{29}$N$_4$O$_2$ 441.2285 (M+H)$^+$, found 441.2286.

Example 240

(R)-8-Hydroxymethyl-1-(4-methylaminomethyl-phenyl)-8,9-dihydro-7H-2,7,9a-triaza-benzo[cd]azulen-6-one

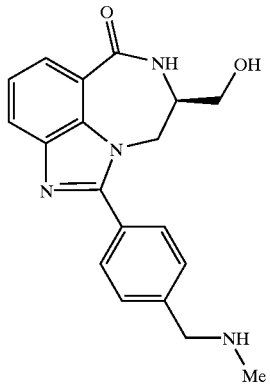

This compound was prepared from intermediate 238c and the appropriate amine using the procedure described in Example 238. Received 31.5 mg (32%).

$^1$H NMR (DMSO-d$_6$) δ 2.33 (s, 3H), 3.32–3.77 (m, 3H), 3.77 (s, 2H), 4.45–4.56 (m, 2H), 5.05 (br s, 1H), 7.36 (t, 1H, J=7.8 Hz), 7.53 (d, 2H, J=8.0 Hz), 7.82 (d, 2H, J=8.0 Hz), 7.86–7.95 (m, 2H), 8.16 (d, 1H, J=3.5 Hz). HPLC Rt=2.119 min. LRMS (m/z) 328 (M+H). Anal. (C$_{19}$H$_{20}$N$_4$O$_2$.0.30CH$_2$Cl$_2$) C, H, N.

Example 241

(R)-8-Hydroxymethyl-1-(4-pyrrolidin-1-ylmethyl-phenyl)-8,9-dihydro-7H-2,7,9a-triaza-benzo[cd]azulen-6-one

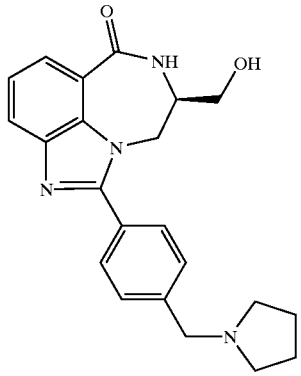

This compound was prepared from intermediate 238c and the appropriate amine using the procedure described in Example 238. Received 78 mg (72%).

$^1$H NMR (DMSO-d$_6$) δ 1.73 (s, 4H), 2.50 (s, 4H), 3.30–3.78 (m, 5H), 4.42–4.58 (m, 2H), 5.04 (br s, 1H), 7.36 (t, 1H, J=7.8 Hz), 7.51 (d, 2H, J=7.8 Hz), 7.81 (d, 2H, J=7.8 Hz), 7.89 (d, 2H, J=7.8 Hz), 8.15 (br s, 1H). HPLC Rt=2.375 min. LRMS (m/z) 377 (M+H). Anal. (C$_{22}$H$_{24}$N$_4$O$_2$.0.20H$_2$O) C, H, N.

Example 242

[4-(6-oxo-6,7,8,9-Tetrahydro-2,7,9a-triaza-benzo[cd]azulen-1-yl)-phenyl]-acetonitrile

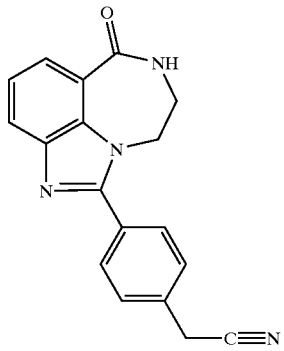

This compound was prepared from intermediate 171a, KCN and catalytic KI using the procedure described in Example 171. Received 78 mg (72%).

IR (KBr) 3197, 3071, 2932, 2253, 1661, 1600, 1485, 1460, 1390, 1310, 1218, 1088, 824, 760 cm$^{-1}$; $^1$H NMR (DMSO-d$_6$) δ 3.48–3.58 (m, 2H), 4.18 (s, 2H), 4.43–4.52 (m, 2H), 7.37 (t, 1H, J=7.8 Hz), 7.57 (d, 2H, J=8.2 Hz), 7.86–7.95 (m, 4H), 8.43 (t, 1H, J=5.6 Hz). HPLC Rt=2.689 min. HRMS calcd for C$_{18}$H$_{15}$N$_4$O 303.1240 (M+H)$^+$, found 303.1248. Anal. (C$_{18}$H$_{14}$N$_4$O.0.50H$_2$O) C, H, N.

Example 243

1-[4-(2,5-Dimethyl-2,5-dihydro-pyrrol-1-ylmethyl)-phenyl]-8,9-dihydro-7H-2,7,9a-triaza-benzo[cd]azulen-6-one

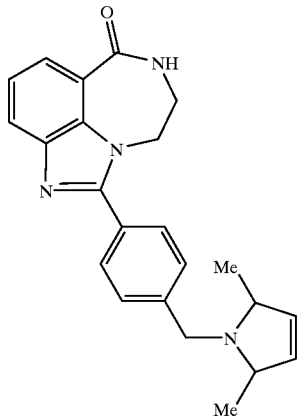

This compound was prepared from intermediate 171a and the appropriate amine using the procedure described in Example 171. Received 80 mg (17%).

$^1$H NMR (DMSO-d$_6$, racemic mixture of cis and trans isomers) δ 1.01 (d, 6H, J=6.2 Hz), 3.50–4.03 (m, 4H), 3.92 (s, 2H), 5.62–5.77 (m, 2H), 7.36 (t, 1H, J=7.8 Hz), 7.50–7.60 (m, 2H), 7.77–7.93 (m, 4H), 8.42 (t, 1H, J=5.7 Hz). HPLC Rt=2.611 min. LRMS (m/z) 373 (M+H). Anal. (C$_{23}$H$_{24}$N$_4$O.0.10H$_2$O) C, H, N.

Example 244

1-[4-(2,5-Dimethyl-pyrrol-1-ylmethyl)-phenyl]-8,9-dihydro-7H-2,7,9a-triaza-benzo[cd]azulen-6-one

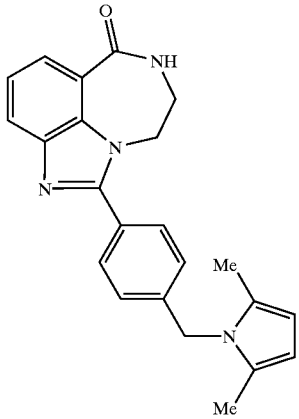

This compound was recovered as a side product from formation of Example 243. Received 15 mg (3%).

$^1$H NMR (DMSO-d$_6$) δ 2.11 (s, 6H), 3.47–3.58 (m, 2H), 4.39–4.48 (m, 2H), 5.16 (s, 2H), 5.75 (s, 2H), 7.06 (d, 2H, J=8.2 Hz), 7.35 (t, 1H, J=7.8 Hz), 7.78–7.93 (m, 4H), 8.41 (t, 1H, J=5.7 Hz). HPLC Rt=3.613 min. HRMS calcd for C$_{23}$H$_{23}$N$_4$O 371.1866 (M+H)$^+$, found 371.1863.

Example 245

1-[4-(1-Dimethylamino-ethyl)-phenyl]-8,9-dihydro-7H-2,7,9a-triaza-benzo[cd]azulen-6-one

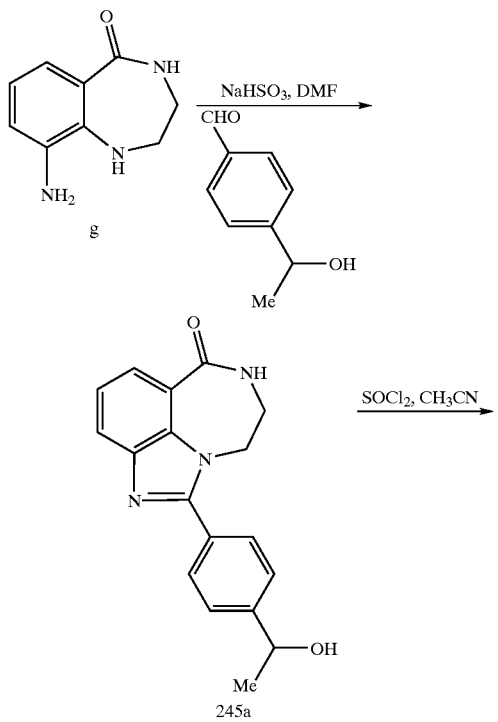

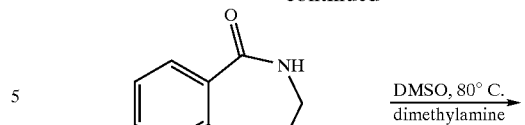

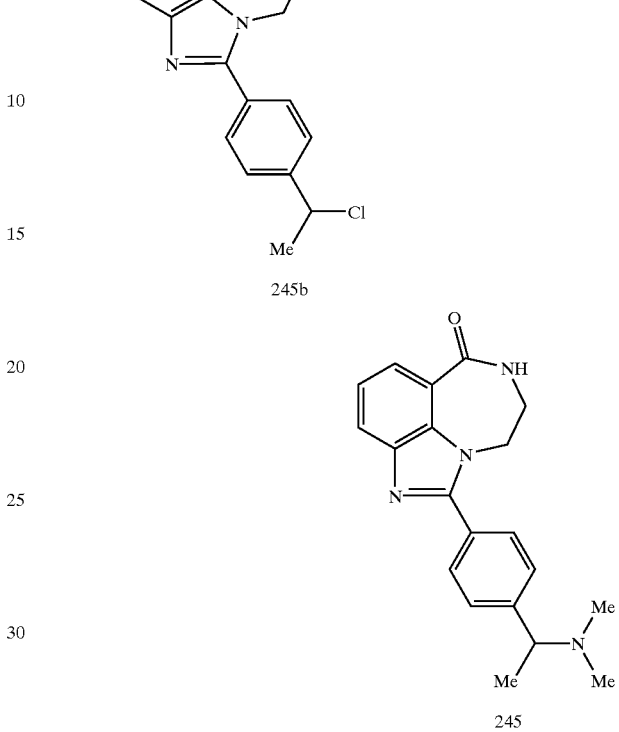

(245a) 1-[4-(1-Hydroxy-ethyl)-phenyl]-8,9-dihydro-7H-2,7,9a-triaza-benzo[cd]azulen-6-one AG-14657

This compound was prepared from diamine intermediate g (from Example 2) and 4-(1-hydroxy-ethyl)-benzaldehyde [prepared from methylmagnesium bromide and terephthalaldehyde-mono-diethyl acetal following the procedure Hulin et al., *J. Med. Chem.* 35, 1853 (1992)] according to the procedure used in Example 19. Received 1.60 g (42%).

$^1$H NMR (DMSO-d$_6$) δ 1.86 (d, 3H, J=6.7 Hz), 3.48–3.60 (m, 2H), 4.43–4.52 (m, 2H), 4.78–4.89 (m, 1H), 5.30 (d, 1H, J=4.3 Hz), 7.36 (t, 1H, J=7.8 Hz), 7.55 (d, 2H, J=8.2 Hz), 7.82 (d, 2H, J=8.2 Hz), 7.85–7.93 (m, 2H), 8.43 (t, 1H, J=5.7 Hz). LRMS (m/z) 308 (M+H). Anal. (C$_{18}$H$_{17}$N$_3$O$_2$) C, H, N.

(245b) 1-[4-(1-Chloro-ethyl)-phenyl]-8,9-dihydro-7H-2,7,9a-triaza-benzo[cd]azulen-6-one This compound was prepared from intermediate 245a and thionyl chloride according to the procedure used in Example 171. Received 0.85 g (70%).

$^1$H NMR (DMSO-d$_6$) δ 1.38 (d, 3H, J=6.5 Hz), 3.48–3.60 (m, 2H), 4.42–4.525 (m, 2H), 5.47 (q, 1H, J=6.7 Hz), 7.40 (t, 1H, J=7.8 Hz), 7.71 (d, 2H, J=8.2 Hz), 7.85–7.97 (m, 4H), 8.46 (t, 1H, J=5.7 Hz). HPLC Rt=3.280 min. Anal. (C$_{18}$H$_{16}$ClN$_3$O) C, H, Cl, N.

(245) Title Compound

This compound was prepared from intermediate 245b and dimethylamine according to the procedure described in Example 171, with the exception of heating to 80° C. Received 69 mg (77%)

$^1$H NMR (DMSO-$d_6$) δ 1.32 (d, 3H, J=6.7 Hz), 2.15 (s, 6H), 3.34–3.44 (m, 1H), 3.47–3.60 (m, 2H), 4.43–4.52 (m, 2H), 7.36 (t, 1H, J=7.8 Hz), 7.50 (d, 2H, J=8.2 Hz), 7.82 (d, 2H, J=8.2 Hz), 7.85–7.93 (m, 2H), 8.42 (t, 1H, J=5.7 Hz). HPLC Rt=2.461 min. LRMS (m/z) 335 (M+H). Anal. ($C_{20}H_{22}N_4O$) C, H, N.

Example 246

1-[4-(1-Pyrrolidin-1-yl-ethyl)-phenyl]-8,9-dihydro-7H-2,7,9a-triaza-benzo[cd]azulen-6-one

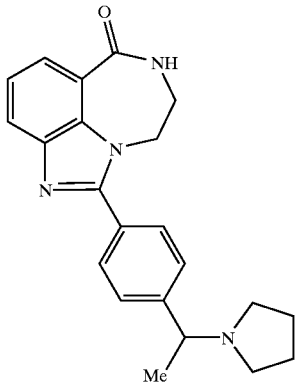

This compound was prepared from intermediate 245b and the appropriate amine using the procedure described in Example 245. Received 118 mg (66%).

$^1$H NMR (DMSO-$d_6$) δ 1.35 (d, 3H, J=6.5 Hz), 1.63–1.75 (m, 4H), 2.28–2.55 (m, 4H), 3.23–3.38 (m, 3H), 3.47–3.60 (m, 2H), 4.43–4.52 (m, 2H), 7.35 (t, 1H, J=5.7 (d, 2H, J=8.2 Hz), 7.81 (d, 2H, J=8.2 Hz), 7.85–7.93 (m, 2H), 8.42 (t, 1H, J=5.7 Hz). HPLC Rt=2.683 min. LRMS (m/z) 361 (M+H). Anal. ($C_{22}H_{24}N_4O$) C, H, N.

Example 247

1-[4-(2-Phenyl-1-pyrrolidin-1-yl-ethyl)-phenyl]-8,9-dihydro-7H-2,7,9a-triaza-benzo[cd]azulen-6-one

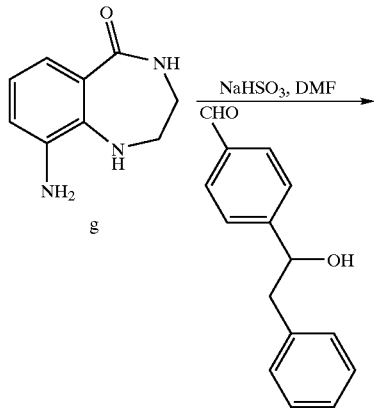

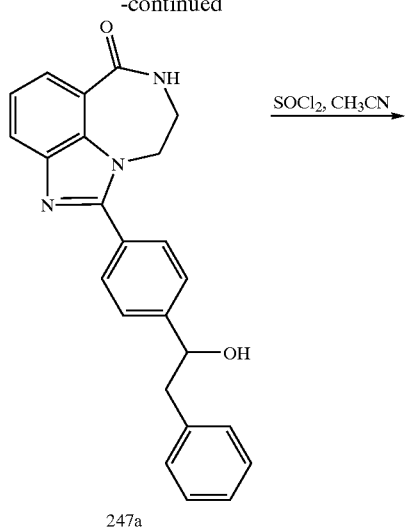

247a

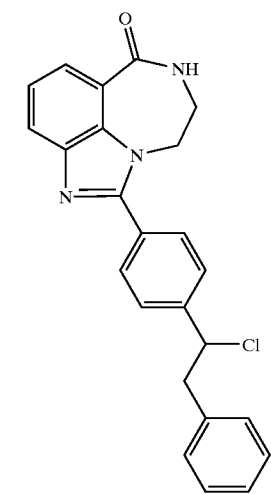

247b

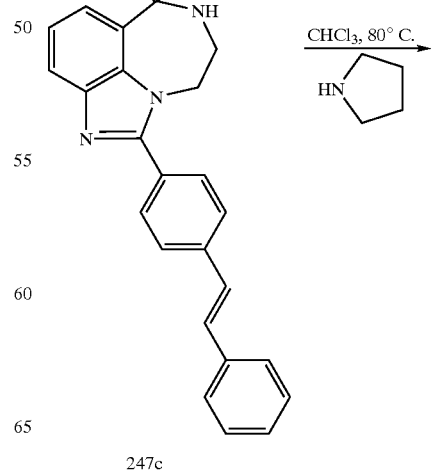

247c

-continued

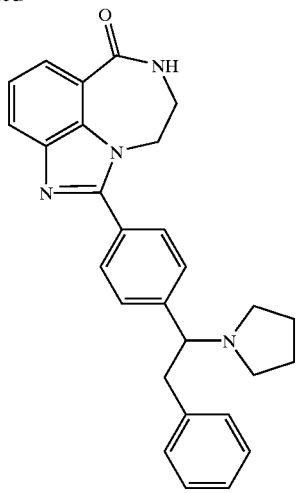

247

(247a) 1-[4-(1-Hydroxy-2-phenyl-ethyl)-phenyl]-8,9-dihydro-7H-2,7,9a-triaza-benzo[cd]azulen-6-one This compound was prepared from diamine intermediate g (from Example 2) and 4-(1-hydroxy-2-phenyl-ethyl)-benzaldehyde [Hulin et al., *J. Med. Chem.* 35, 1853 (1992)] according to the procedure used in Example 19. Received 9.30 g (96%).

$^1$H NMR (DMSO-d$_6$) δ 2.95 (d, 2H, J=6.5 Hz), 3.50–3.60 (m, 2H), 4.40–4.52 (m, 2H), 4.88 (t, 1H, J=6.5 Hz), 5.43 (br s, 1H), 7.13–7.30 (m, 5H), 7.38 (t, 1H, J=7.8 Hz), 7.52 (d, 2H, J=8.2 Hz), 7.80 (d, 2H, J=8.2 Hz), 7.86–7.94 (m, 2H), 8.45 (t, 1H, J=5.7 Hz). HPLC Rt=3.263 min. LRMS (m/z) 384 (M+H). Anal. (C$_{24}$H$_{21}$N$_3$O$_2$.0.50H$_2$O) C, H, N.

(247b) 1-[4-(1-Chloro-2-phenyl-ethyl)-phenyl]-8,9-dihydro-7H-2,7,9a-triaza-benzo[cd]azulen-6-one This compound was prepared from intermediate 247a and thionyl chloride according to the procedure used in Example 171. Received 3.53 g (75%).

HPLC Rt=3.871 min. LRMS (n/z) 402 (M+H).

(247c) 1-[4-((E)-Styryl)-phenyl]-8,9-dihydro-7H-2,7,9a-triaza-benzo[cd]azulen-6-one AG-14660

This compound was formed as a byproduct during preparation of Example 247b.

$^1$H NMR (DMSO-d$_6$) δ 3.50–3.60 (m, 2H), 4.46–4.57 (m, 2H), 7.28–7.47 (m, 6H), 7.63–7.95 (m, 8H), 8.45 (t, 1H, J=5.7 Hz). HPLC Rt=3.929 min. LRMS (m/z) 366 (M+H). Anal. (C$_{24}$H$_{19}$N$_3$O.0.10H$_2$O) C, H, N.

(247) Title Compound

This compound was prepared from intermediate 247b and pyrrolidine according to the procedure described in Example 245, with the exception of chloroform as solvent. Received 40 mg (11%).

$^1$H NMR (DMSO-d$_6$) δ 1.63–1.76 (m, 4H), 2.34–2.68 (m, 4H), 2.92 (dd, 1H, J=12.9, 10.0 Hz), 3.30–3.40 (m, 1H), 3.48–3.62 (m, 3H), 4.354.46 (m, 2H), 6.93–7.39 (m, 8H), 7.66–7.90 (m, 4H), 8.41 (t, 21H, J=5.7 Hz). HPLC Rt=3.120 min. LRMS (m/z) 437 (M+H). Anal. (C$_{28}$H$_{28}$N$_4$O) C, H, N.

PARP Enzyme Inhibition Assay:

The PARP enzyme-inhibiting activities of the compounds were assayed as described by Simonin et al. (*J. Biol. Chem.* (1993), 268:8529–8535) and Marsischky et al. (*J. Biol. Chem.* (1995), 270:3247–3254) with minor modifications as follows. Samples (50 μL) containing 20 nM purified PARP protein, 10 μg/mL DNAse I-activated calf thymus DNA (sigma), 500 μM NAD$^+$, 0.5 μCi [$^{32}$P]NAD$^+$, 2% DMSO, and various concentrations of test compounds were incubated in sample buffer (50 mM Tris pH 8.0, 10 mM MgCl$_2$, 1 mM tris(carboxyethyl)phosphine HCl) at 25° C. for 5 minutes. Under these conditions, the reaction rate was linear for times up to 10 minutes. The reaction was stopped by the addition of an equal volume of ice-cold 40% trichloroacetic acid to the samples, which were then incubated on ice for 15 minutes. The samples were then transferred to a Bio-Dot microfiltration apparatus (BioRad), filtered through Whatman GF/C glass-fiber filter paper, washed 3 times with 150 μL of wash buffer (5% trichloroacetic acid, 1% inorganic pyrophosphate), and dried. [$^{32}$P]ADP-Ribose incorporation into the acid-insoluble material was quantitated using a PhosphorImager (Molecular Dynamics) and ImageQuant software. Inhibition constants (K$_i$) were calculated by non-linear regression analyses using the velocity equation for competitive inhibition (Segel, *Enzyme Kinetics: Behavior and Analysis of Rapid Equilibrium and Steady-State Enzyme Systems*, John Wiley & Sons, Inc., New York (1975), 100–125). In the case of tight-binding inhibitors, 5 nM enzyme was used and the reaction was incubated at 25° C. for 25 minutes. K$_i$ values for tight-binding inhibitors were calculated using the equation described Sculley et al. (*Biochim. Biophys. Acta* (1986), 874:44–53).

Cytotoxicity Potentiation Assay:

A549 cells (ATCC, Rockville, Md.) were seeded into 96-well cell culture plates (Falcon brand, Fisher Scientific, Pittsburgh, Pa.) 16 to 24 hours before experimental manipulation. Cells were then treated with a test compound (or a combination of test compounds where indicated) each at a concentration of 0.4 μM for either 3 days or 5 days. At the end of treatments, relative cell number was determined either by MTT assay or SRB assay. For the MTT assay, 0.2 μg/μl of MTT (3-(4,5-dimethylthiazol-2-yl)-2,5-diphenyltetrazolium bromide) (Sigma Chemical Co., St. Louis, Mo.) was added to each well of a plate, and the plate was incubated in a cell-culture incubator for 4 hours. Metabolized MTT in each well was solubilized in 150 μl of DMSO (Sigma Chemical Co.) with shaking and quantified with a Wallac 1420 Victor plate reader (EG&G Wallac, Gaithersburg, Md.) at 540 nm. For the SRB assay, cells were fixed with 10% trichloroacetic acid (Sigma Chemical Co) for an hour at 4° C. After extensively washing, fixed cells were stained for 30 minutes with 0.4% sulforhodamine B (SRB, Sigma Chemical Co.) in 1% acetic acid (Sigma Chemical Co). Unbound SRB was washed away with 1% acetic acid. Then the cultures were air-dried, and dye was solubilized with 10 mM unbuffered Tris base (Sigma Chemical Co) with shaking. The bound dye was measured photometrically with the Wallac Victor plate reader at 515 nm. The ratio of the OD (optical density) value of a compound-treated culture to the OD value of a mock-treated culture, expressed in percentage, was used to quantify the cytotoxicity of a compound. The concentration at which a compound causes 50% cytotoxicity is referred to as IC$_{50}$. To quantify the potentiation of the cytotoxicity of topotecan or temozolomide by test compounds, a dimensionless parameter PF$_{50}$ is used and is defined as the ratio of the IC$_{50}$ of topotecan or temozolomide alone to the IC$_{50}$ of topotecan or temozolomide in combination with a test compound. For the compounds of the invention, PF$_{50}$ values were determined by testing with topotecan.

Inhibitor constants (K$_i$ values) and cytotoxicity potentiation parameters (PF$_{50}$ values) as determined for the exemplary compounds are presented in Table 1 below.

TABLE 1

PARP Enzyme Inhibition and Cytotoxicity Potentiation

| Compound/Example No. | Inhibition Constant $K_i$ (nM) | Cytotoxicity Potentiation $PF_{50}$ |
|---|---|---|
| 1 | 4.1, 6.2 | 1.5 |
| 2 | 8.0, 6.0 | 1.6 |
| 3 | 10.9, 12 | 1.4 |
| 4 | 6.5 | 1.5 |
| 5 | 7.7 | 1.3 |
| 6 | 4.3 | 2 |
| 7 | 5.1 | 1.4 |
| 8 | 6.2 | 1.9 |
| 9 | 49 | 1.4 |
| 10 | 11.2 | 1.7 |
| 11 | 5.6 | 2.1 |
| 12 | 21, 17 | 1.3 |
| 13 | 10.1 | ND |
| 14 | 5.7, 7.6 | 1.8 |
| 15 | 12.1 | ND |
| 16 | 7.2 | ND |
| 17 | 4.8, 5.3 | 1.7 |
| 18 | 3.4 | 2 |
| 19 | 13 | ND |
| 20 | 11.9 | ND |
| 21 | 13.7, 13.0 | ND |
| 22 | 13, 14, 15 | ND |
| 23 | 17.3 | ND |
| 24 | 29 | ND |
| 25 | 176 | 1.4 |
| 26 | 102 | 1.1 |
| 27 | >5000 | ND |
| 28 | 10 | ND |
| 29 | 24 | ND |
| 30 | ND | ND |
| 31 | ND | ND |
| 31a | 22 | ND |
| 32 | 6.3 | 1.8 |
| 32a | 8.8 | ND |
| 33 | 14.3 | ND |
| 34 | 11 | 1.8 |
| 35 | 8.2 | ND |
| 36 | 27 | ND |
| 37 | 11 | 1.8 |
| 38 | 43 | ND |
| 39 | 7.5 | 1 |
| 40 | 68 | ND |
| 41 | 54, 60 | ND |
| 42 | 103, 105, 107 | ND |
| 43 | 317, 290 | ND |
| 44 | 900 | ND |
| 45 | 167, 185 | ND |
| 46 | 9, 9.8 | 1.3 |
| 47a | 121 | ND |
| 47b | 809 | ND |
| 48 | 79 | ND |
| 49 | 122 | ND |
| 50 | 22 | 1.1 |
| 51 | 41 | ND |
| 52 | 79 | ND |
| 53 | 1800 | ND |
| 54 | 600 | ND |
| 55 | 10 | ND |
| 56 | 32 | ND |
| 57 | ND | ND |
| 58 | 5.8 | 2.0 |
| 58a | 4.2 | ND |
| 59 | 4.2 | 1.8 |
| 60 | 6.2 | ND |
| 61 | 6.2 | ND |
| 62 | 6.1 | ND |
| 63 | 13 | ND |
| 64 | 6.2 | ND |
| 65 | 11 | ND |
| 66 | 8.9 | ND |
| 67 | 9.3 | ND |
| 68 | 5.8 | ND |
| 69 | ND | ND |
| 70 | 4.4 | ND |
| 71 | 13 | ND |
| 72 | 3.5 | ND |
| 73 | 10 | ND |
| 74 | 33 | ND |
| 75 | 1.9 | 1.8 |
| 76 | 5.1 | 1.6 |
| 77 | 6.9 | 1.7 |
| 78 | 5.2 | ND |
| 79 | 11 | ND |
| 80 | 9 | ND |
| 81 | ND | ND |
| 82 | 6.2, 6.6 | 1.9 |
| 83 | 3.5, 4 | ND |
| 84 | 6.5, 7.1 | ND |
| 85 | 12, 13 | ND |
| 86 | 9.1 | 1.6 |
| 87 | 6.7, 7 | ND |
| 88 | 12, 13 | ND |
| 89 | ND | ND |
| 90 | 6 | 1.2 |
| 91 | 54 | ND |
| 92 | 200 | ND |
| 93 | 306 | ND |
| 93a | ND | ND |
| 94 | 4.3 | ND |
| 95 | 6.2 | ND |
| 96 | 10 | ND |
| 97 | 1.6 | ND |
| 97a | ND | ND |
| 98 | 3.3 | 2.1 |
| 99 | 1.7 | 2.0 |
| 100 | 2.7 | ND |
| 101 | 2.3 | 2.1 |
| 102 | 5.6 | ND |
| 103 | 6.2 | ND |
| 104 | 4.5 | ND |
| 105 | 6.2 | ND |
| 106 | 8.0 | ND |
| 107 | 25 | ND |
| 108 | 6.0 | ND |
| 109 | 5.5 | ND |
| 110 | 18 | ND |
| 111 | 5.1 | ND |
| 112 | 18 | ND |
| 113 | 24 | ND |
| 114 | 9.9 | ND |
| 115 | 116 | ND |
| 116 | 5.2 | ND |
| 117 | 9.5 | ND |
| 118 | 4.4 | ND |
| 119 | 3.2, 4.2 | 2.2 |
| 120 | 7.3 | ND |
| 121 | 4.0 | ND |
| 122 | 7.0 | ND |
| 123 | 9.0 | ND |
| 124 | 8.0 | ND |
| 125 | 11 | ND |
| 126 | 4.1 | 2.2 |
| 127 | 3.5, 3.6 | ND |
| 128 | 4.0, 5.4 | 1.8 |
| 129 | 5.0 | 1.9 |
| 130 | 4.4, 5.6 | 3.4 |
| 131 | 22 | ND |
| 132 | 6.8 | 2.4 |
| 133 | 6.9 | ND |
| 134 | 2.8 | 2.5 |
| 135 | 3.8 | ND |
| 136 | 96 | ND |
| 137 | 5.4 | 2.2 |
| 138 | 11 | ND |
| 139 | 12 | ND |
| 140 | 6.8 | ND |

TABLE 1-continued

PARP Enzyme Inhibition and Cytotoxicity Potentiation

| Compound/Example No. | Inhibition Constant $K_i$ (nM) | Cytotoxicity Potentiation $PF_{50}$ |
|---|---|---|
| 141 | 5.5 | 2.3 |
| 142 | 3.8 | 2.2 |
| 143 | 22 | ND |
| 144 | 7.4 | ND |
| 145 | 20 | ND |
| 146 | 35 | ND |
| 147 | 4.0 | ND |
| 148 | 2.8 | 2.5 |
| 149 | 4.2 | 2.6 |
| 150 | 5.0 | ND |
| 151 | 6.9 | ND |
| 152 | 3.2 | ND |
| 153 | 219 | ND |
| 154 | ND | ND |
| 155 | 87 | ND |
| 156 | 57 | ND |
| 157 | 540 | ND |
| 158 | 9.1 | ND |
| 159 | ND | ND |
| 160 | 249 | ND |
| 161 | 116 | ND |
| 162 | ND | ND |
| 163 | 692 | ND |
| 164 | 606 | ND |
| 165 | 39 | ND |
| 166 | 380 | ND |
| 167 | 337 | ND |
| 168 | 38 | ND |
| 169 | ND | ND |
| 170 | 3.1 | 1.9 |
| 171 | 4.5 | 2.5 |
| 171a | ND | ND |
| 172 | 4.6 | ND |
| 172d | ND | ND |
| 173 | 6.3 | ND |
| 174 | 6.2 | ND |
| 175 | 6.6 | ND |
| 176 | 9.0 | ND |
| 177 | 4.1 | 2.5 |
| 178 | 12 | ND |
| 179 | 5.6 | ND |
| 180 | 7.4 | ND |
| 181 | 3.9 | ND |
| 182 | 4.7 | ND |
| 183 | 8.0 | ND |
| 184 | 6.0 | 2.2 |
| 185 | 5.6 | ND |
| 186 | 5.5 | 2.2 |
| 187 | 7.0 | ND |
| 188 | 4.8 | ND |
| 189 | 5.1 | ND |
| 190 | 8.1 | ND |
| 191 | 4.3 | ND |
| 192 | 4.5 | ND |
| 193 | 11 | ND |
| 194 | 6.2 | ND |
| 195 | 4.7, 5.9 | ND |
| 196 | 3.9 | ND |
| 197 | 2.8, 5.2 | 2.5 |
| 198 | 7.9 | ND |
| 199 | 6.8 | ND |
| 200 | 6.0 | ND |
| 201 | 5.8 | ND |
| 202 | 3.2 | ND |
| 203 | 4.6 | 2.0 |
| 204 | 7.9 | ND |
| 205 | 4.7 | ND |
| 206 | 6.4 | ND |
| 207 | 4.2 | 2.4 |
| 208 | ND | ND |
| 209 | ND | ND |
| 210 | 5.0 | 2.3 |
| 211 | 4.5 | 2.3 |
| 212 | 6.8 | 2.0 |
| 213 | 7.4 | ND |
| 214 | 8.3 | ND |
| 215 | 11 | ND |
| 216 | 27 | ND |
| 217 | 26 | ND |
| 218 | 17 | ND |
| 219 | 11 | ND |
| 220 | 4.0 | ND |
| 221 | 5.0 | ND |
| 221a | 10.0 | ND |
| 221b | ND | ND |
| 222 | 2.0, 2.3, 3.5 | ND |
| 223 | 8.5 | 2.1 |
| 224 | ND | ND |
| 225 | ND | ND |
| 226 | ND | ND |
| 227 | 2.2 | ND |
| 228 | 4.6 | ND |
| 229 | 5.3, 6.8 | ND |
| 229a | ND | ND |
| 230 | 5.3 | ND |
| 231 | 6.9 | ND |
| 232 | ND | ND |
| 233 | 8.0 | 2.2 |
| 234 | 8.7 | ND |
| 235 | 5.4 | ND |
| 236 | 113 | ND |
| 237 | 5.0, 6.0 | ND |
| 237b | 30 | ND |
| 237c | ND | ND |
| 238 | 7.3 | ND |
| 238a | 30.7 | ND |
| 238b | ND | ND |
| 238c | ND | ND |
| 239 | 7.8 | ND |
| 240 | 4.2, 4.5 | ND |
| 241 | 6.8 | ND |
| 242 | 3.4 | ND |
| 243 | 8.9 | 2.0 |
| 244 | 14.0 | ND |
| 245 | 5.8 | 2.1 |
| 245a | 5.2, 5.3 | ND |
| 245b | ND | ND |
| 246 | 3.3 | 2.3 |
| 247 | 5.4 | ND |
| 247a | 10.0 | ND |
| 247b | ND | ND |
| 247c | 16.0 | ND |

Note:
ND = not determined

While the invention has been described by reference to exemplary and preferred embodiments and examples, those skilled in the art will recognize that various changes and modifications will become apparent through routine experimentation without departing from the spirit and scope of the invention. The invention should therefore be understood as not being limited by the foregoing detailed description, but as being defined by the appended claims and their equivalents.

What is claimed is:
1. A compound of the formula:

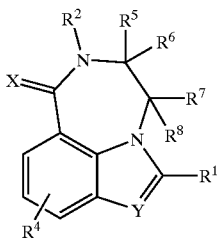

wherein:
X is O or S;
Y is N or $CR^3$, where $R^3$ is: H;
  halogen;
  cyano;
  an optionally substituted alkyl, alkenyl, alkynyl, cycloalkyl, heterocycloalkyl, aryl, or heteroaryl group; or
  —C(W)—$R^{20}$, where W is O or S, and $R^{20}$ is: H; OH; an optionally substituted alkyl, alkenyl, alkynyl, cycloalkyl, heterocycloalkyl, aryl, heteroaryl, O-alkyl, or O-aryl group; or $NR^{27}R^{28}$, where $R^{27}$ and $R^{28}$ are each independently H, OH, or an optionally substituted alkyl, alkenyl, alkynyl, cycloalkyl, heterocycloalkyl, aryl, or heteroaryl group;
  —$CR^{29}$=N—$R^{30}$, where $R^{29}$ is H or an optionally substituted amino, alkyl, alkenyl, alkynyl, cycloalkyl, heterocycloalkyl, aryl, heteroaryl O-alkyl, o-aryl, s-alkyl, or s-aryl group, and $R^{30}$ is H, OH, an optionally substituted alkyl, alkenyl, alkynyl, cycloalkyl, heterocycloalkyl, aryl, heteroaryl, O-alkyl, or O-aryl group, or $NR^{31}R^{32}$, where $R^{31}$ and $R^{32}$ are each independently H, OH, or an optionally substituted alkyl, alkenyl, alkynyl, cycloalkyl, heterocycloalkyl, aryl, or heteroaryl group;
$R^1$ is an unsubstituted, mono- or di-substituted aryl or heteroaryl group;
$R^2$ is H or alkyl;
$R^4$ is H, halogen, or alkyl;
$R^5$, $R^6$, $R^7$, and $R^8$ are each independently selected from:
  H;
  an optionally substituted alkyl, alkenyl, alkynyl, cycloalkyl, heterocycloalkyl, aryl, or heteroaryl group; and
  —C(O)—$R^{50}$, where $R^{50}$ is: H; an optionally substituted alkyl, alkenyl, alkynyl, cycloalkyl, heterocycloalkyl, aryl, or heteroaryl group; or $OR^{51}$ or $NR^{52}R^{53}$, where $R^{51}$, $R^{52}$ and $R^{53}$ are each independently H or an optionally substituted alkyl, alkenyl, alkynyl, cycloalkyl, heterocycloalkyl, aryl, or heteroaryl group;
wherein said substituted alkyl, alkenyl, alkynyl, cycloalkyl, heterocycloalkyl, aryl, heteroaryl, O-alkyl, O-aryl, amino, S-alkyl, and S-aryl groups are substituted with one or more substituents selected from the group consisting of halogen, hydroxy, oxo, acyl, sulfonyl, mercapto, nitro, cyano, amino, alkyl, aryl, heteroaryl, alkoxy, aryloxy, heteroaryloxy, alkylthio, cycloalkyl, heterocycloalkyl, carboxy, carbamoyl, arylthio, and heteroarylthio groups, unsubstituted or substituted with one or more substituents selected from halogen, hydroxy, cyano, nitro, ethers, trifluoromethyl, alkylcarboyl, alkyl, aryl, and amino; and where when Y is $CR^3$, $R^1$, $R^2$, $R^3$, $R^4$, $R^5$, $R^6$, $R^7$, and $R^8$ are not all H;
or a pharmaceutically acceptable salt thereof.

2. A compound of the formula:

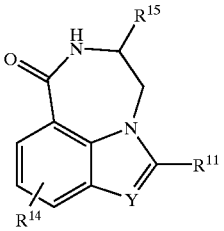

wherein:
Y is N or $CR^3$, where $R^3$ is:
  H;
  halogen;
  cyano;
  an optionally substituted alkyl, alkenyl, alkynyl, cycloalkyl, heterocycloalkyl, aryl, or heteroaryl group; or
  —C(W)—$R^{20}$, where W is O or S, and $R^{20}$ is: H; OH; an optionally substituted alkyl, alkenyl, alkynyl, cycloalkyl, heterocycloalkyl, aryl, heteroaryl, O-alkyl, or O-aryl group; or $NR^{27}R^{28}$, where $R^{27}$ and $R^{28}$ are each independently H, OH, or an optionally substituted alkyl, alkenyl, alkynyl, cycloalkyl, heterocycloalkyl, aryl, or heteroaryl group;
  —CR=N—$R^{30}$, where $R^{29}$ is H or an optionally substituted amino, alkyl, alkenyl, alkynyl, cycloalkyl, heterocycloalkyl, aryl, heteroaryl O-alkyl, o-aryl, s-alkyl, or s-aryl group, and $R^{30}$ is H, OH, an optionally substituted alkyl, alkenyl, alkynyl, cycloalkyl, heterocycloalkyl, aryl, heteroaryl, O-alkyl, or O-aryl group, or $NR^{31}R^{32}$, where $R^{31}$ and $R^{32}$ are each independently H, OH, or an optionally substituted alkyl, alkenyl, alkynyl, cycloalkyl, heterocycloalkyl, aryl, or heteroaryl group;
$R^{11}$ is an aryl or heteroaryl group unsubstituted or substituted with one or more substituents selected from halogen, hydroxy, nitro, amino, alkyl, aryl, heteroaryl, alkoxy, aryloxy, and heteroaryloxy groups, wherein said alkyl, aryl, heteroaryl, alkoxy, aryloxy, and heteroaryloxy groups are unsubstituted or substituted with one or more substituents selected from halogen, hydroxy, lower alkoxy, cyano, nitro, and amino;
$R^{14}$ is H or halogen; and
$R^{15}$ is H, an optionally substituted alkyl, alkenyl, alkynyl, cycloalkyl, heterocycloalkyl, aryl, or heteroaryl group;
wherein said substituted alkyl, alkenyl, alkynyl, cycloalkyl, heterocycloalkyl, aryl, heteroaryl, O-alkyl, O-aryl, amino, S-alkyl, and S-aryl groups are substituted with one or more substituents selected from the group consisting of halogen, hydroxy, oxo, acyl, sulfonyl, mercapto, nitro, cyano, amino, alkyl, aryl, heteroaryl, alkoxy, aryloxy, heteroaryloxy, alkylthio, cycloalkyl, heterocycloalkyl, carboxy, carbamoyl, arylthio, and heteroarylthio groups, unsubstituted or substituted with one or more substituents selected from halogen, hydroxy, cyano, nitro, ethers, trifluoromethyl, alkylcarboyl, alkyl, aryl, and amino; and
or a pharmaceutically acceptable salt thereof.

3. A compound selected from the group consisting of

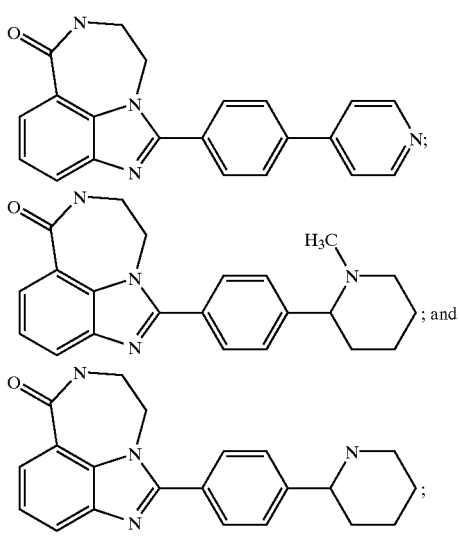

or a pharmaceutically acceptable salt thereof.

4. A compound according to claim 3, wherein the compound is a single stereoisomer.

5. A compound or pharmaceutically acceptable salt according to claim 1, wherein $R^4$ is H or halogen.

6. A compound or pharmaceutically acceptable salt according to claim 1, wherein $R^5$, $R^6$, $R^7$, and $R^8$ are each H.

7. A compound or pharmaceutically acceptable salt according to claim 1, wherein X is oxygen.

8. A compound or pharmaceutically acceptable salt according to claim 2, wherein $R^{11}$ is mono- or di-substituted phenyl.

9. A compound according to claim 1 selected from the group consisting of:

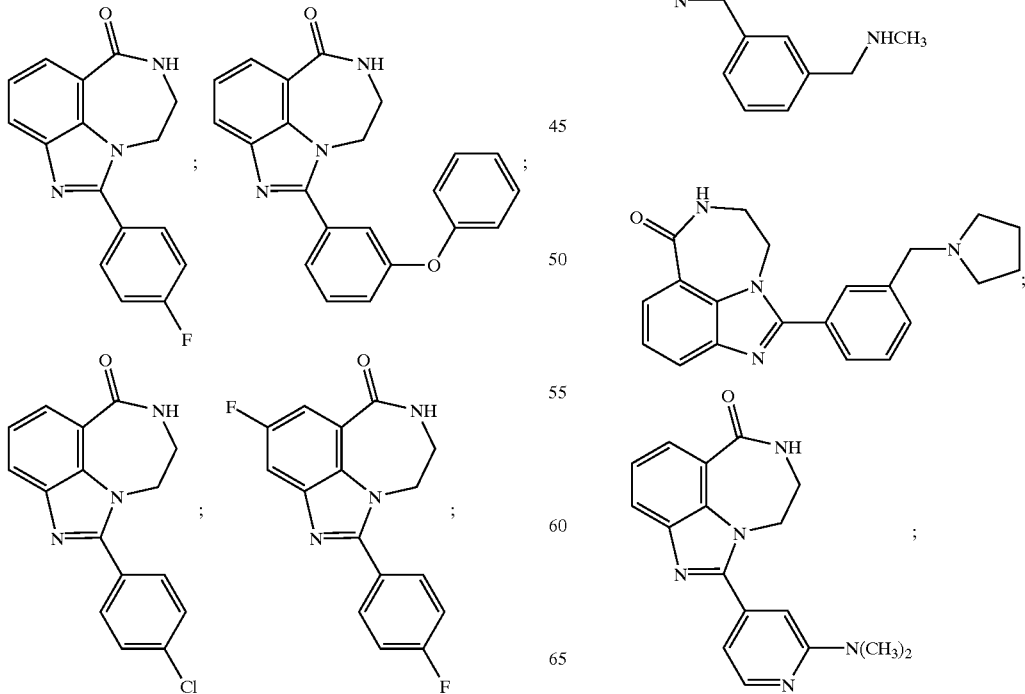

-continued

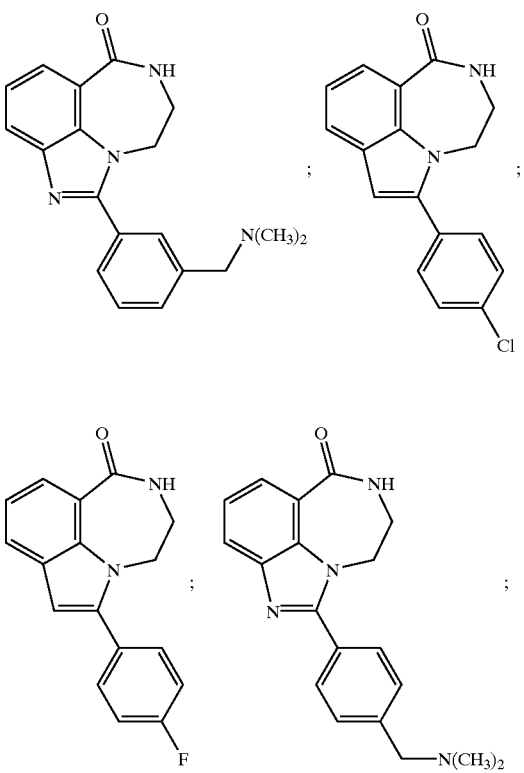

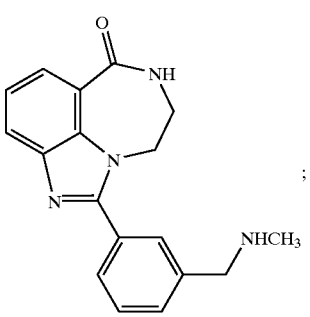

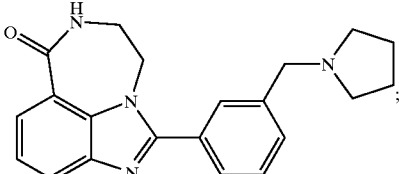

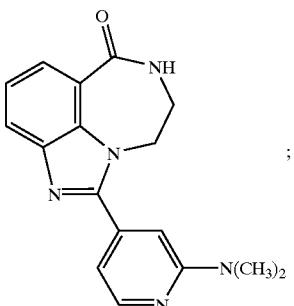

-continued
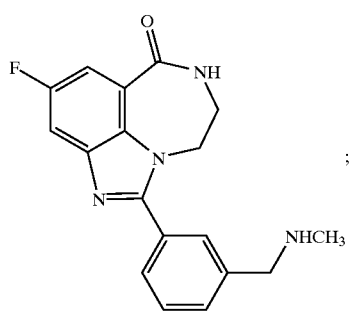
;
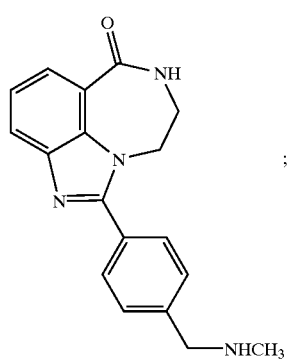
;
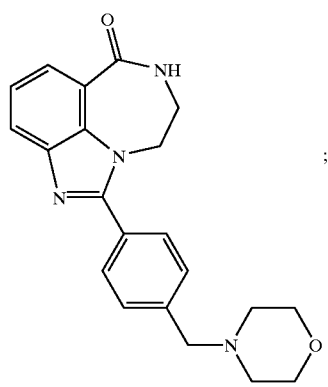
;
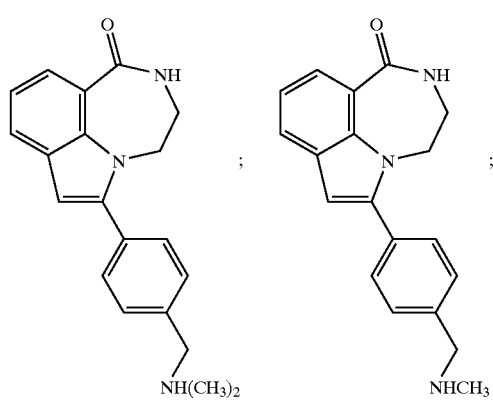
;
-continued
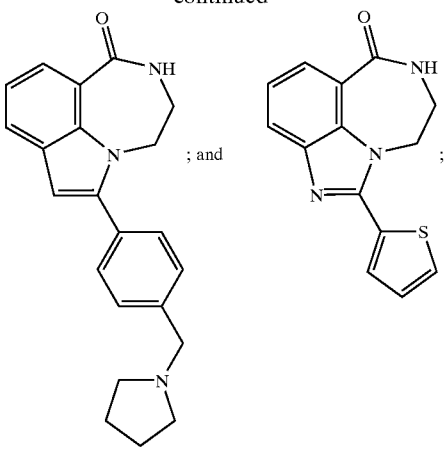
; and
or a pharmaceutically acceptable salt thereof.
10. A compound of claim 1 selected from the group consisting of:
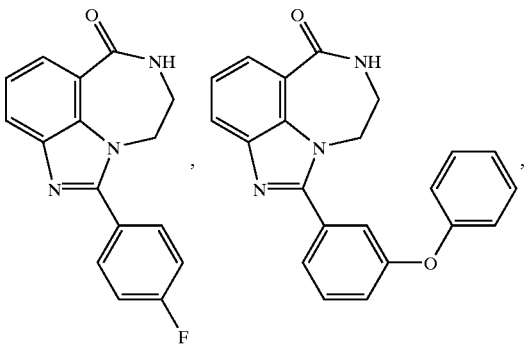
,
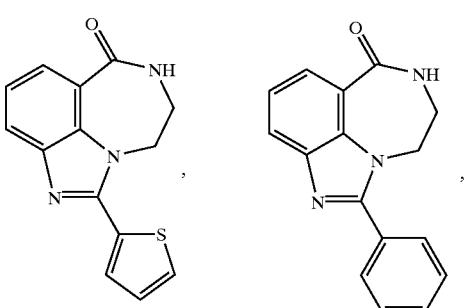
,
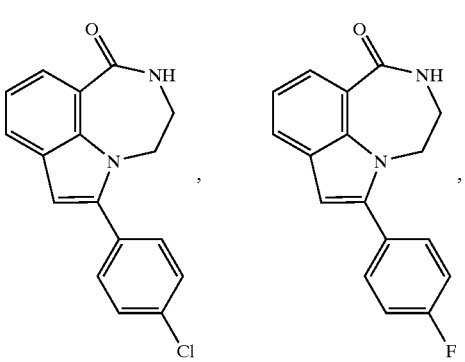
, 213
-continued
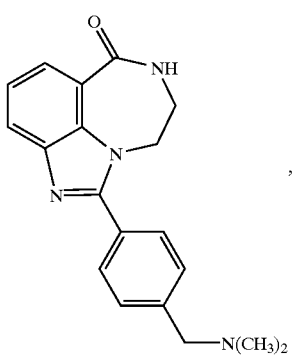
,
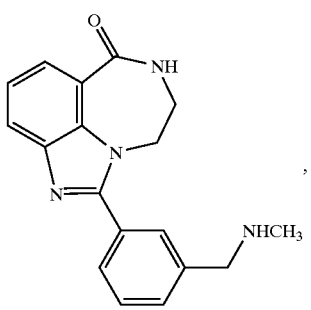
,
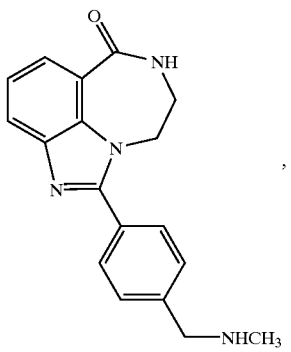
, 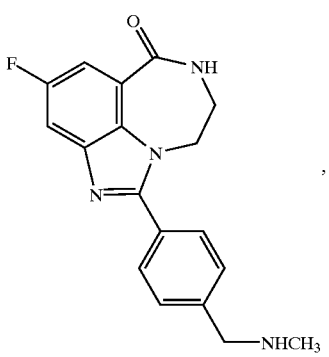
,
214
-continued
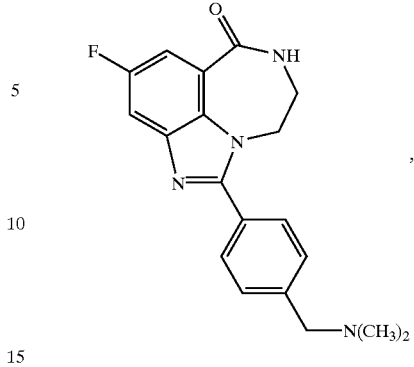
,
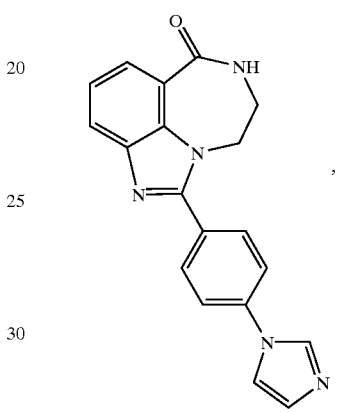
,
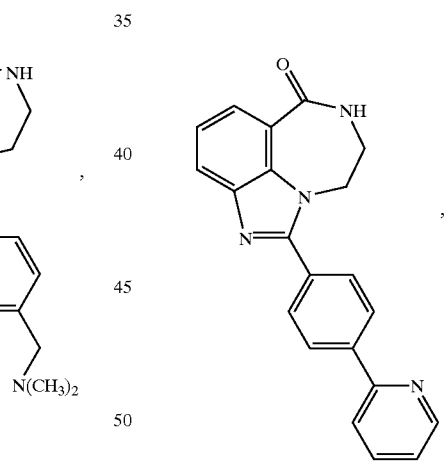
,
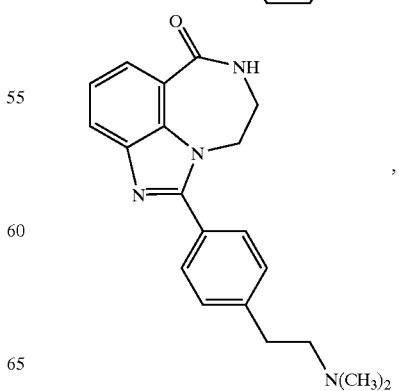
,

215
-continued
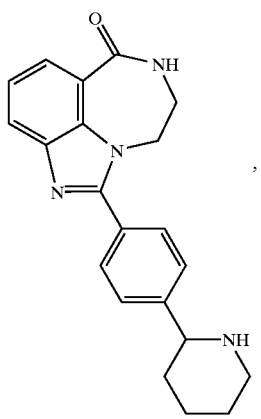,
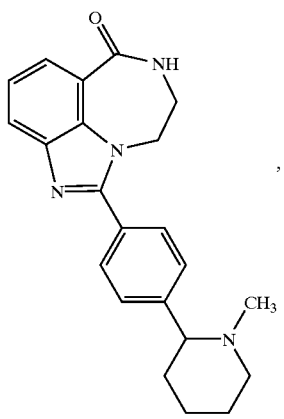,
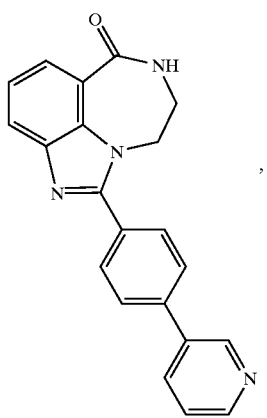,
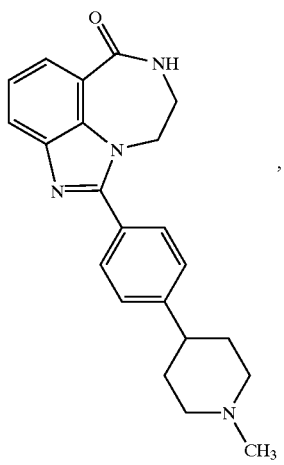,
216
-continued
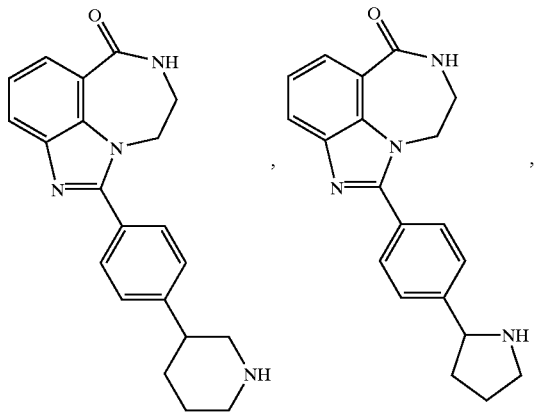,
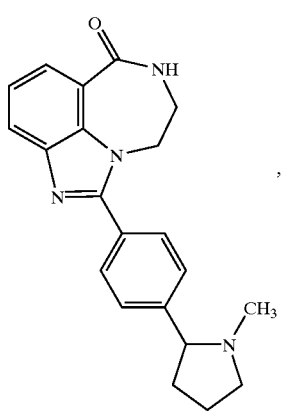,
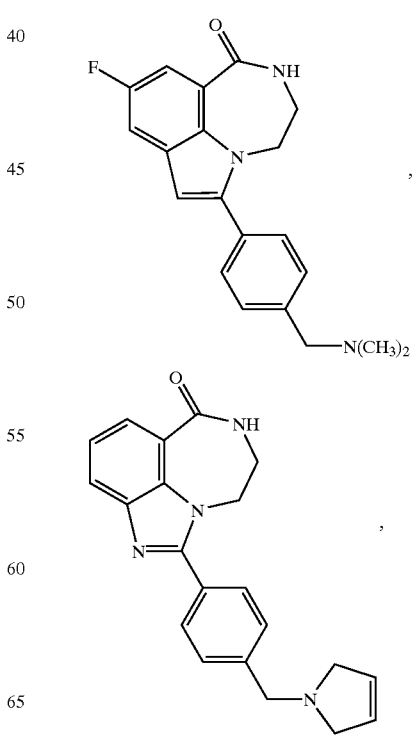,
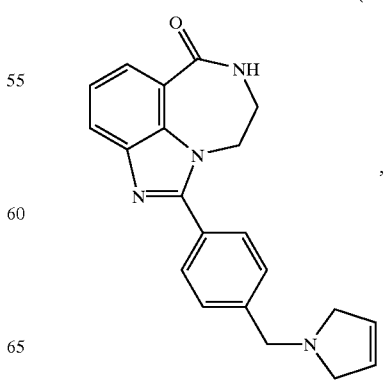,

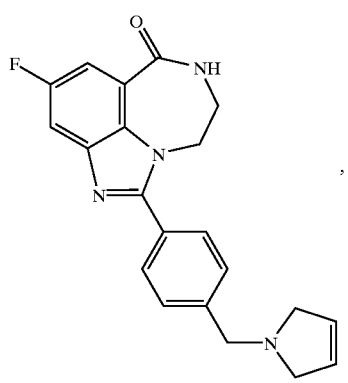,
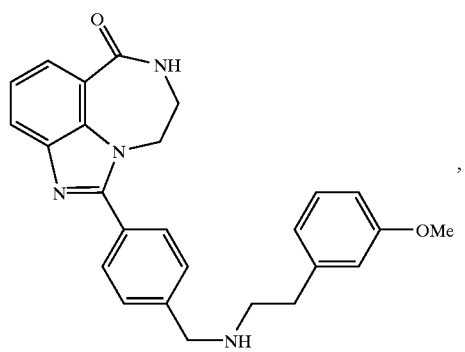,
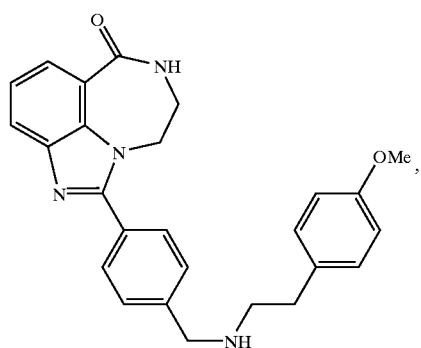,
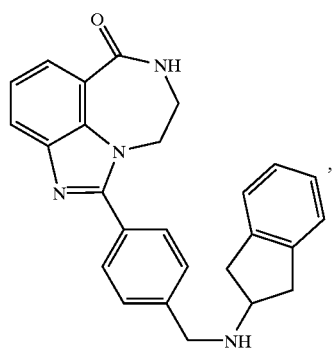,
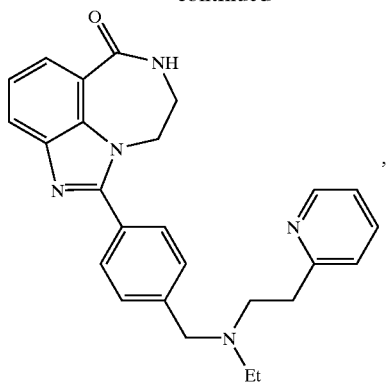,
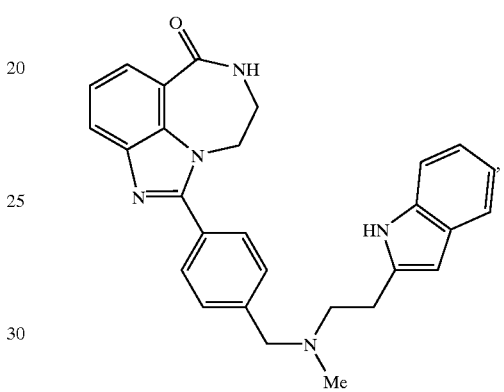,
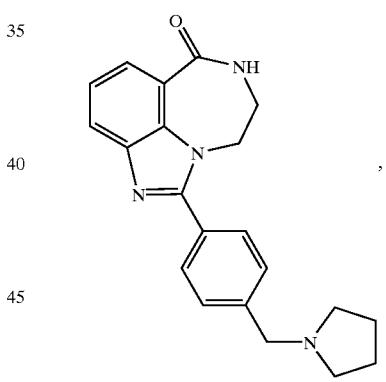,
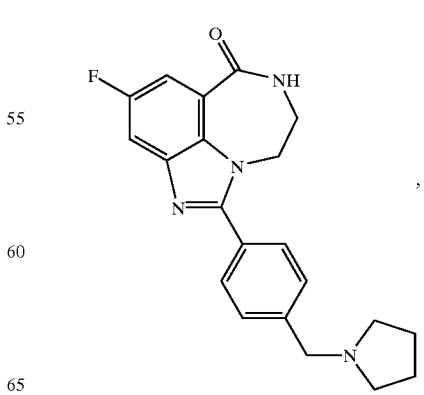, -continued

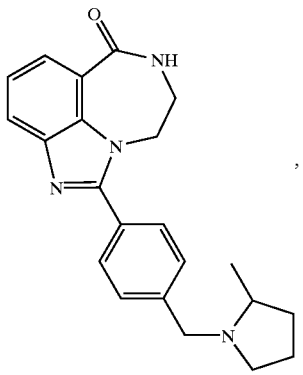

,

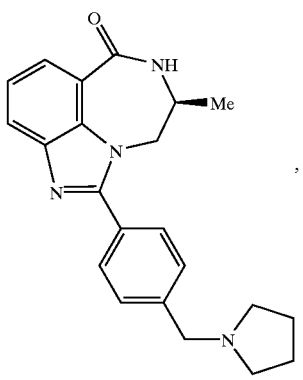

,

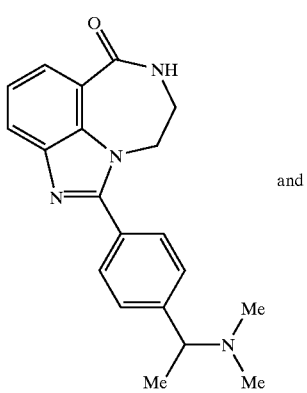

,

-continued

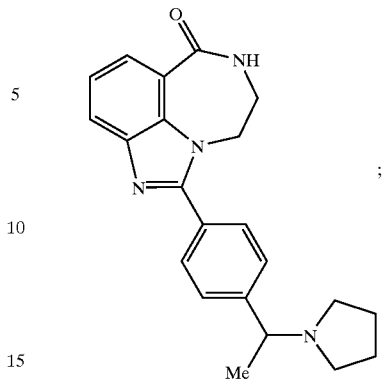

;

or a pharmaceutically acceptable salt thereof.

11. A pharmaceutical composition comprising:

(a) an effective amount of a PARP-inhibiting agent selected from a compound of the formula:

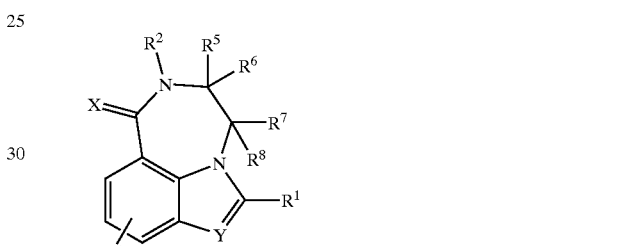

wherein:

X is O or S;

Y is N or $CR^3$, where $R^3$ is:

H;

halogen;

cyano;

an optionally substituted alkyl, alkenyl, alkynyl, cycloalkyl, heterocycloalkyl, aryl, or heteroaryl group; or —C(W)—$R^{20}$, where W is O or S, and $R^{20}$ is: H; OH; an optionally substituted alkyl, alkenyl, alkynyl, cycloalkyl, heterocycloalkyl, aryl, heteroaryl, O-alkyl, or O-aryl group; or $NR^{27}R^{28}$, where $R^{27}$ and $R^{28}$ are each independently H, OH, or an optionally substituted alkyl, alkenyl, alkynyl, cycloalkyl, heterocycloalkyl, aryl, or heteroaryl group;

—$CR^{29}$=N—$R^{30}$, where $R^{29}$ is H or an optionally substituted amino, alkyl, alkenyl, alkynyl, cycloalkyl, heterocycloalkyl, aryl, heteroaryl O-alkyl, o-aryl, s-alkyl, or s-aryl group, and $R^{30}$ is H, OH, an optionally substituted alkyl, alkenyl, alkynyl, cycloalkyl, heterocycloalkyl, aryl, heteroaryl, O-alkyl, or O-aryl group, or $NR^{31}R^{32}$, where $R^{31}$ and $R^{32}$ are each independently H, OH, or an optionally substituted alkyl, alkenyl, alkynyl, cycloalkyl, heterocycloalkyl, aryl, or heteroaryl group;

and $R^1$ is cyano;
a substituted alkyl or an optionally substituted alkenyl, alkynyl, cycloalkyl, heterocycloalkyl, aryl, or heteroaryl group;
$C(O)R^{12}$, where $R^{12}$ is: H; an optionally substituted alkyl, alkenyl, alkynyl, cycloalkyl, heterocycloalkyl, aryl, or heteroaryl group; or $OR^{19}$ or $NR^{21}R^{22}$, where $R^{19}$, $R^{21}$ and $R^{22}$ are each independently H or an optionally substituted alkyl, alkenyl, alkynyl, cycloalkyl, heterocycloalkyl, aryl, or heteroaryl group;
$OR^{13}$, where $R^{13}$ is H or an optionally substituted alkyl, alkenyl, alkynyl, cycloalkyl, heterocycloalkyl, aryl, or heteroaryl group;
$S(O)_nR^{16}$, where n is 0, 1 or 2, and $R^{16}$ is: H; an optionally substituted alkyl, alkenyl, alkynyl, cycloalkyl, heterocycloalkyl, aryl, or heteroaryl group; or $NR^{23}R^{24}$, where $R^{23}$ and $R^{24}$ are each independently H or an optionally substituted alkyl, alkenyl, alkynyl, cycloalkyl, heterocycloalkyl, aryl, or heteroaryl group; or
$NR^{17}R^{18}$, where $R^{17}$ and $R^{18}$ are each independently: H; an optionally substituted alkyl, alkenyl, alkynyl, cycloalkyl, heterocycloalkyl, aryl, or heteroaryl group; $C(O)R^{201}$, where $R^{201}$ is H, an optionally substituted alkyl, alkenyl, alkynyl, cycloalkyl, heterocycloalkyl, aryl, heteroaryl, O-alkyl, or O-aryl group, or $NR^{27}R^{28}$, where $R^{27}$ and $R^{28}$ are each independently H, OH, an optionally substituted alkyl, alkenyl, alkynyl, cycloalkyl, heterocycloalkyl, aryl, or heteroaryl group or $S(O)_2NR^{25}N^{26}$, where $R^{25}$ and $R^{26}$ are each independently H or an optionally substituted alkyl, alkenyl, alkynyl, cycloalkyl, heterocycloalkyl, aryl, or heteroaryl group;
$R^2$ is H or alkyl;
$R^4$ is H or alkyl;
$R^5$, $R^6$, $R^7$, and $R^8$ are each independently selected from:
H;
an optionally substituted alkyl, alkenyl, alkynyl, cycloalkyl, heterocycloalkyl, aryl, or heteroaryl group; and
—C(O)—$R^{50}$, where $R^{50}$ is: H; an optionally substituted alkyl, alkenyl, alkynyl, cycloalkyl, heterocycloalkyl, aryl, or heteroaryl group; or $OR^{51}$ or $NR^{52}R^{53}$, where $R^{51}$, $R^{52}$ and $R^{53}$ are each independently H or an optionally substituted alkyl, alkenyl, alkynyl, cycloalkyl, heterocycloalkyl, aryl, or heteroaryl group;
wherein said substituted alkyl, alkenyl, alkynyl, cycloalkyl, heterocycloalkyl, aryl, heteroaryl, O-alkyl, O-aryl, amino, S-alkyl, and S-aryl groups are substituted with one or more substituents selected from the group consisting of halogen, hydroxy, oxo, acyl, sulfonyl, mercapto, nitro, cyano, amino, alkyl, aryl, heteroaryl, alkoxy, aryloxy, heteroaryloxy, alkylthio, cycloalkyl, heterocycloalkyl, carboxy, carbamoyl, arylthio, and heteroarylthio groups, unsubstituted or substituted with one or more substituents selected from halogen, hydroxy, cyano, nitro, ethers, trifluoromethyl, alkylcarboyl, alkyl, aryl, and amino; and
where when Y is $CR^3$, $R^1$, $R^2$, $R^3$, $R^4$, $R^5$, $R^6$, $R^7$, and $R^8$ are not all H;
or a pharmaceutically acceptable salt thereof; and
(b) a pharmaceutically acceptable carrier for said PARP-inhibiting agent.

12. A compound according to claim 1 having the formula:

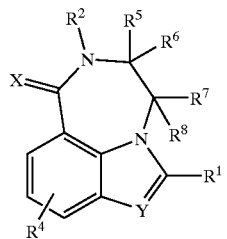

wherein:
X is O or S;
Y is N or $CR^3$, where $R^3$ is:
H;
halogen;
cyano;
an optionally substituted alkyl, alkenyl, alkynyl, cycloalkyl, heterocycloalkyl, aryl, or heteroaryl group; or
—C(W)—$R^{20}$, where W is O or S, and $R^{20}$ is: H; OH; an optionally substituted alkyl, alkenyl, alkynyl, cycloalkyl, heterocycloalkyl, aryl, heteroaryl, O-alkyl, or O-aryl group; or $NR^{27}R^{28}$, where $R^{27}$ and R28 are each independently H, OH, or an optionally substituted alkyl, alkenyl, alkynyl, cycloalkyl, heterocycloalkyl, aryl, or heteroaryl group;
—$CR^9$=N—$R^{30}$, where $R^{29}$ is H or an optionally substituted amino, alkyl, alkenyl, alkynyl, cycloalkyl, heterocycloalkyl, aryl, or heteroaryl group, and $R^{30}$ is H, OH, an optionally substituted alkyl, alkenyl, alkynyl, cycloalkyl, heterocycloalkyl, aryl, heteroaryl, O-alkyl, or O-aryl group, or $NR^{31}R^{32}$, where $R^{31}$ and $R^{32}$ are each independently H, OH, or an optionally substituted alkyl, alkenyl, alkynyl, cycloalkyl, heterocycloalkyl, aryl, or heteroaryl group;
$R^1$ is cyano;
a substituted alkyl or an optionally substituted alkenyl, alkynyl, cycloalkyl, heterocycloalkyl, aryl, or heteroaryl group;
$C(O)R^{12}$, where $R^{12}$ is: H; an optionally substituted alkyl, alkenyl, alkynyl, cycloalkyl, heterocycloalkyl, aryl, or heteroaryl group; or $OR^{19}$ or $NR^{21}R^{22}$, where $R^{19}$, $R^{21}$ and $R^{22}$ are each independently H or an optionally substituted alkyl, alkenyl, alkynyl, cycloalkyl, heterocycloalkyl, aryl, or heteroaryl group;
$OR^{13}$, where $R^{13}$ is H or an optionally substituted alkyl, alkenyl, alkynyl, cycloalkyl, heterocycloalkyl, aryl, or heteroaryl group;
$S(O)_nR^{16}$, where n is 0, 1 or 2, and $R^{16}$ is: H; an optionally substituted alkyl, alkenyl, alkynyl, cycloalkyl,heterocycloalkyl, aryl, or heteroaryl group; or $NR^{23}R^{24}$ where $R^{23}$ and $R^{24}$ are each independently H or an optionally substituted alkyl, alkenyl, alkynyl, cycloalkyl, heterocycloalkyl, aryl, or heteroaryl group; or
$NR^{17}R^{18}$, where $R^{17}$ and $R^{18}$ are each independently: H; an optionally substituted alkyl, alkenyl, alkynyl, cycloalkyl, heterocycloalkyl, aryl, or heteroaryl group; or $S(O)_2NR^{25}N^{26}$, where $R^{25}$ and $R^{26}$ are each independently H or an optionally substituted alkyl, alkenyl, alkynyl, cycloalkyl, heterocycloalkyl, aryl, or heteroaryl group;

$R^2$ is H or alkyl;

$R^4$ is H or alkyl;

$R^5$, $R^6$, $R^7$, and $R^8$ are each independently selected from:
H;
an optionally substituted alkyl, alkenyl, alkynyl, cycloalkyl, heterocycloalkyl, aryl, or heteroaryl group; and
—C(O)—$R^{50}$, where $R^{50}$ is: H; an optionally substituted alkyl, alkenyl, alkynyl, cycloalkyl, heterocycloalkyl, aryl, or heteroaryl group; or $OR^{51}$ or $NR^{52}R^{53}$, where $R^{51}$, $R^{52}$ and $R^{53}$ are each independently H or an optionally substituted alkyl, alkenyl, alkynyl, cycloalkyl, heterocycloalkyl, aryl, or heteroaryl group;

wherein said substituted alkyl, alkenyl, alkynyl, cycloalkyl, heterocycloalkyl, aryl, heteroaryl, O-alkyl, O-aryl, amino, S-alkyl, and S-aryl groups are substituted with one or more substituents selected from the group consisting of halogen, hydroxy, oxo, acyl, sulfonyl, mercapto, nitro, cyano, amino, alkyl, aryl, heteroaryl, alkoxy, aryloxy, heteroaryloxy, alkylthio, cycloalkyl, heterocycloalkyl, carboxy, carbamoyl, arylthio, and heteroarylthio groups, unsubstituted or substituted with one or more substituents selected from halogen, hydroxy, cyano, nitro, ethers, trifluoromethyl, alkylcarboyl, alkyl, aryl, and amino; and where when Y is $CR^3$, $R^1$, $R^2$, $R^3$, $R^4$, $R^5$, $R^6$, $R^7$, and $R^8$ are not all H;

or a pharmaceutically acceptable salt thereof.

13. A compound of the formula:

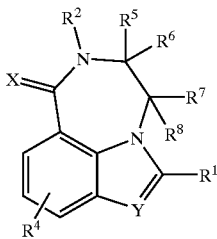

wherein:

X is O or S;

Y is N or $CR^3$, where $R^3$ is:
H;
halogen;
cyano;
an optionally substituted alkyl, alkenyl, alkynyl, cycloalkyl, heterocycloalkyl, aryl, or heteroaryl group; or
—C(W)—$R^{20}$, where W is O or S, and $R^{20}$ is: H; OH; an optionally substituted alkyl, alkenyl, alkynyl, cycloalkyl, heterocycloalkyl, aryl, heteroaryl, O-alkyl, or O-aryl group; or $NR^{27}R^{28}$, where $R^{27}$ and $R^{28}$ are each independently H, OH, or an optionally substituted alkyl, alkenyl, alkynyl, cycloalkyl, heterocycloalkyl, aryl, or heteroaryl group;
—$CR^{29}$=N—$R^{30}$, where $R^{29}$ is H or an optionally substituted amino, alkyl, alkenyl, alkynyl, cycloalkyl, heterocycloalkyl, aryl, heteroaryl O-alkyl, o-aryl, s-alkyl, or s-aryl group, and $R^{30}$ is H, OH, an optionally substituted alkyl, alkenyl, alkynyl, cycloalkyl, heterocycloalkyl, aryl, heteroaryl, O-alkyl, or O-aryl group, or $NR^{31}R^{32}$, where $R^{31}$ and $R^{32}$ are each independently H, OH, or an optionally substituted alkyl, alkenyl, alkynyl, cycloalkyl, heterocycloalkyl, aryl, or heteroaryl group;

$R^1$ is cyano;
a substituted alkyl or an optionally substituted alkenyl, alkynyl, cycloalkyl, heterocycloalkyl, aryl, or heteroaryl group;
$C(O)R^{12}$, where $R^{12}$ is: H; an optionally substituted alkyl, alkenyl, alkynyl, cycloalkyl, heterocycloalkyl, aryl, or heteroaryl group; or $OR^{19}$ or $NR^{21}R^{22}$, where $R^{19}$, $R^{21}$ and $R^{22}$ are each independently H or an optionally substituted alkyl, alkenyl, alkynyl, cycloalkyl, heterocycloalkyl, aryl, or heteroaryl group;
$OR^{13}$, where $R^{13}$ is H or an optionally substituted alkyl, alkenyl, alkynyl, cycloalkyl, heterocycloalkyl, aryl, or heteroaryl group;
$S(O)_nR^{16}$, where n is 0, 1 or 2, and $R^{16}$ is: H; an optionally substituted alkyl, alkenyl, alkynyl, cycloalkyl, heterocycloalkyl, aryl, or heteroaryl group; or $NR^{23}R^{24}$, where $R^{23}$ and $R^{24}$ are each independently H or an optionally substituted alkyl, alkenyl, alkynyl, cycloalkyl, heterocycloalkyl, aryl, or heteroaryl group; or
$NR^{17}R^{18}$, where $R^{17}$ and $R^{18}$ are each independently: H; an optionally substituted alkyl, alkenyl, alkynyl, cycloalkyl, heterocycloalkyl, aryl, or heteroaryl group; $C(O)R^{201}$, where $R^{201}$ is H, an optionally substituted alkyl, alkenyl, alkynyl, cycloalkyl, heterocycloalkyl, aryl, heteroaryl, O-alkyl, or O-aryl group, or $NR^{27}R^{28}$, where $R^{27}$ and $R^{28}$ are each independently H, OH, an optionally substituted alkyl, alkenyl, alkynyl, cycloalkyl, heterocycloalkyl, aryl; or heteroaryl group or $S(O)_2NR^{25}N^{26}$, where $R^{25}$ and $R^{26}$ are each independently H or an optionally substituted alkyl, alkenyl, alkynyl, cycloalkyl, heterocycloalkyl, aryl, or heteroaryl group;

$R^2$ is H or alkyl;

$R^4$ is H or alkyl;

$R^5$, $R^6$, $R^7$, and $R^8$ are each independently selected from:
H;
an optionally substituted alkyl, alkenyl, alkynyl, cycloalkyl, heterocycloalkyl, aryl, or heteroaryl group; and
—C(O)—$R^{50}$, where $R^{50}$ is: H; an optionally substituted alkyl, alkenyl, alkynyl, cycloalkyl, heterocycloalkyl, aryl, or heteroaryl group; or $OR^{51}$ or $NR^{52}R^{53}$, where $R^{51}$, $R^{52}$ and $R^{53}$ are each independently H or an optionally substituted alkyl, alkenyl, alkynyl, cycloalkyl, heterocycloalkyl, aryl, or heteroaryl group;

wherein said substituted alkyl, alkenyl, alkynyl, cycloalkyl, heterocycloalkyl, aryl, heteroaryl, O-alkyl, O-aryl, amino, S-alkyl, and S-aryl groups are substituted with one or more substituents selected from the group consisting of halogen, hydroxy, oxo, acyl, sulfonyl, mercapto, nitro, cyano, amino, alkyl, aryl, heteroaryl, alkoxy, aryloxy, heteroaryloxy, alkylthio, cycloalkyl, heterocycloalkyl, carboxy, carbamoyl, arylthio, and heteroarylthio groups, unsubstituted or substituted with one or more substituents selected from halogen, hydroxy, cyano, nitro, ethers, trifluoromethyl, alkylcarboyl, alkyl, aryl, and amino; and where when Y is $CR^3$, $R^1$, $R^2$, $R^3$, $R^4$, $R^5$, $R^6$, $R^7$, and $R^8$ are not all H;

or a pharmaceutically acceptable salt thereof.

* * * * *